(12) United States Patent
Harrison et al.

(10) Patent No.: US 7,566,735 B2
(45) Date of Patent: Jul. 28, 2009

(54) COMPOUNDS WHICH POTENTIATE AMPA RECEPTOR AND USES THEREOF IN MEDICINE

(75) Inventors: Stephen Harrison, Stevenage (GB); Kevin Michael Thewlis, Harlow (GB); Simon Edward Ward, Harlow (GB)

(73) Assignee: Glaxo Group Limited, Middlesex (GB)

( * ) Notice: Subject to any disclaimer, the term of this patent is extended or adjusted under 35 U.S.C. 154(b) by 99 days.

(21) Appl. No.: 11/687,729

(22) Filed: Mar. 19, 2007

(65) Prior Publication Data

US 2008/0045532 A1 Feb. 21, 2008

(30) Foreign Application Priority Data

Mar. 20, 2006 (GB) .................................. 0605589.1
Oct. 27, 2006 (GB) .................................. 0621438.1

(51) Int. Cl.
 *A61K 31/415* (2006.01)
 *A61K 31/535* (2006.01)
(52) U.S. Cl. ...................... 514/403; 514/406; 514/236.5
(58) Field of Classification Search ................. 514/397, 514/403, 406, 236.5
 See application file for complete search history.

(56) References Cited

FOREIGN PATENT DOCUMENTS

| JP | 2001 220390 A | 8/2001 |
|---|---|---|
| WO | WO 2006/015828 | 2/2006 |

OTHER PUBLICATIONS

Lyga, John W., et al: "Synthesis, Mechanism of Action, and QSAR of Herbicidal 3-Substituted-2-ARYL-4,5,6,7-Tetrahydroind azoles." Pesticide Science, 42(1), 29-36 CODEN:PSSCBG; ISSN: 0031-613X, 1994, XP002430700 Compound 6b.

*Primary Examiner*—Jennifer Myong M Kim
(74) *Attorney, Agent, or Firm*—James M. Kanagy; Edward Gimmi; Charles M. Kinzig

(57) ABSTRACT

Compounds of formula (I) and salts are provided:

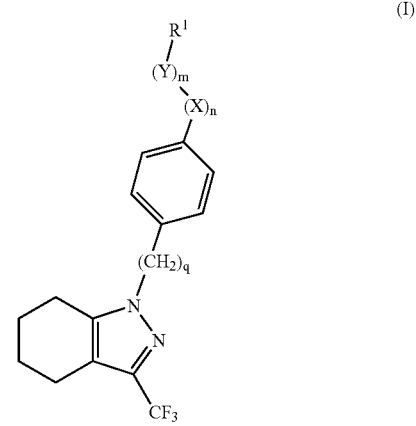

along with pharmaceutical compositions, uses in medicine, e.g., treating disease or condition mediated by a reduction or imbalance in glutamate receptor function, such as schizophrenia or cognition impairment.

4 Claims, No Drawings

COMPOUNDS WHICH POTENTIATE AMPA RECEPTOR AND USES THEREOF IN MEDICINE

This invention relates to novel compounds which potentiate the glutamate receptor. The invention also relates to the use of the compounds in treating diseases and conditions mediated by potentiation of the glutamate receptor, compositions containing the derivatives and processes for their preparation.

Glutamate receptors, which mediate the majority of fast excitatory neurotransmission in the mammalian central nervous system (CNS), are activated by the excitatory amino acid, L-glutamate (for review see Watkins J C, Krogsgaard-Larsen P, Honore T (1990) Trends Pharmacol Sci 11: 25-33).

Glutamate receptors can be divided into two distinct families. The G-protein or second messenger-linked "metabotropic" glutamate receptor family which can be subdivided into three groups (Group I, mGlu1 and mGlu5; Group II, mGlu2 and mGlu3; Group III, mGlu4, mGlu6, mGlu7, mGlu8) based on sequence homology and intracellular transduction mechanisms (for review see Conn P J and Pinn J P (1997) Ann Rev Pharmacol Toxicol 37: 205-237). The "ionotropic" glutamate receptor family, which directly couple to ligand-gated cation channels, can be subdivided into at least three subtypes based on depolarizing activation by selective agonists, N-methyl-D-aspartate (NMDA), α-amino-3-hydroxy-5-methylisoxazole-4-propionic acid (AMPA) and kainic acid (KA) (for review see Dingledine R, Borges K, Bowie, Traynelis S (1999) 51: 7-61).

Native AMPA receptors (AMPAR) exist as heterotetramers consisting of combinations of four different protein subunits (GluR1-4) (for review see Bettler B and Muller C (1995) 34: 123-139.). Receptor subunit diversity is increased further as each subunit can undergo alternative splicing of a 38 amino acid sequence in the extracellular region just before the fourth membrane spanning domain M4. Such editing results in so-called 'flip' and 'flop' receptor isoforms which differ in kinetic and pharmacological properties (Sommer B, Keinanen K, Verdoon T A, Wisden W, Burnashev N, Herb A, Kohler M, Takagi T, Sakmann B, Seeburg P H (1990) Science 249: 1580-1585).

Additionally, post-transcriptional editing of GluR2 mRNA changes a neutral glutamine to a positively charged arginine within M2. In normal humans >99% GluR2 is edited in this way. AMPAR containing such edited GluR2 subunit exhibit low calcium permeability (Burnachev N, Monyer H, Seeburg P H, Sakmann B (1992) Neuron 8: 189-198). There is a suggestion, however, that the number of AMPAR with high calcium permeability is elevated in certain disease-associated conditions (Weiss J H, and Sensi S L (2000) Trends in Neurosci 23: 365-371).

AMPAR depolarization removes voltage dependent $Mg^{2+}$ block of NMDA receptors which in turn leads to NMDA receptor activation, an integral stage in the induction of Long Term Potentiation ("LTP") (Bliss T V P, Collingridge G L (1993) Nature 361: 31-9). LTP is a physiological measure of increased synaptic strength following a repetitive stimulus or activity, such as occurs during learning.

It has been reported that direct activation of glutamate receptors by agonists, in conditions where glutamate receptor function is reduced, increases the risk of excitotoxicity and additional neuronal damage. AMPAR positive allosteric modulators do not activate the receptor directly. However, when the ligand (L-glutamate or AMPA) is present AMPAR modulators increase receptor activity. Thus, AMPA receptor modulators enhance synaptic function when glutamate is released and is able to bind at post-synaptic receptor sites.

Compounds which act as AMPAR positive allosteric modulators have been shown to increase ligand affinity for the receptor (Arai A, Guidotti A, Costa E, Lynch G (1996) Neuroreport. 7: 2211-5.); reduce receptor desensitization and reduce receptor deactivation (Arai A C, Kessler M, Rogers G, Lynch G (2000) 58: 802-813) and facilitate the induction of LTP both in vitro (Arai A, Guidotti A, Costa E, Lynch G (1996) 7: 2211-5.) and in vivo (Staubli U, Perez Y, Xu F, Rogers G, Ingvar M, Stone-Elander S, Lynch G (1994) Proc Natl Acad Sci 91: 11158-11162). Such compounds also enhance the learning and performance of various cognitive tasks in rodent (Zivkovic I, Thompson D M, Bertolino M, Uzunov D, DiBella M, Costa E, Guidotti A (1995) JPET 272: 300-309, Lebrun C, Pilliere E, Lestage P (2000) Eu J Pharmacol 401: 205-212), sub-human primate (Thompson D M, Guidotti A, DiBella M, Costa E (1995) Proc Natl Acad Sci 92: 7667-7671) and man (Ingvar M, Ambros-Ingerson J, Davis M, Granger R, Kessler M, Rogers G A, Schehr R S, Lynch G (1997) Exp Neurol 146: 553-559). The efficacy of various AMPAR positive allosteric modulators in pre-clinical and clinical models of psychiatric disorders, such as schizophrenia, have been investigated (Morrow J A, Maclean J K F, Jamieson C (2006) Current Opinion in Drug Discovery and Development 9(5) 571-579)

Compounds which act as AMPAR positive allosteric modulators are known, for example in international patent application WO2006/015828. JP2001-22-390 discloses the compound 4-methyl-N-[4-[4,5,6,7-tetrahydro-3-(trifluoromethyl)-1H-indazol-1-yl]phenyl]-1,2,3-thiadiazole-5-carboxamide and salts thereof as a calcium channel inhibitor. We have discovered novel compounds which potentiate the AMPA receptor.

In the first aspect, the present invention provides a compound of formula (I), or a salt, or solvate thereof:

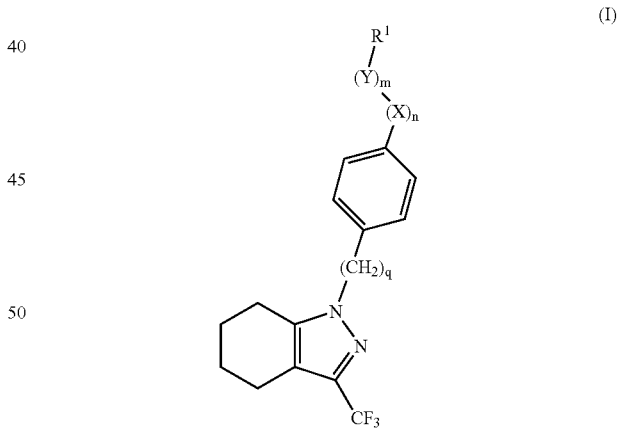

wherein:
q is 0 or 1;
n is 0, 1, or 2;
X is $CR^6R^7$, where $R^6$ and $R^7$ are each independently selected from the group consisting of hydrogen, methyl and fluoro, but $R^6$ and $R^7$ are not both simultaneously methyl; or, when n is 1, $R^6$ and $R^7$ together with the carbon atom to which they are attached, form a 3-membered carbocyclic ring;
Y is selected from the group consisting of CO, $NR^8CO$, SO, $SO_2$ and $NR^8SO_2$;

$R^8$ is selected from the group consisting of hydrogen, $C_{1-4}$alkyl and $C_{2-4}$alkenyl;

m is 0 or 1; and a) when n is 0 and m=1, then $R^1$ is selected from the group consisting of (i) $C_{1-4}$alkyl, (ii) a C-linked 5-membered aromatic heterocyclic group optionally substituted with methyl, (iii) $NHR^2$ and (iv) $NR^{2'}R^3$, wherein:
- $R^2$ is selected from the group consisting of $C_{1-6}$straight chain alkyl, $C_{4-6}$branched chain alkyl and a group —$(CH_2)_pZ$ wherein p is 1, 2 or 3;
- Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$alkyl; wherein when Y is CO, $R^2$ is not $(CH_2)_2$pyrrolidinyl;
- $R^{2'}$ is selected from the group consisting of methyl and ethyl;
- $R^3$ is selected from the group consisting of $C_{1-6}$alkyl and a group —$(CH_2)_pZ'$ wherein p is 1, 2 or 3;
- Z' is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl; or
- $R^{2'}$ and $R^3$, together with the nitrogen atom to which they are attached, form:
  (i) a 4 or 5-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto; or
  (ii) a 6-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto;

b) when n and m are both simultaneously 0, $R^1$ is selected from the group consisting of:
- $C_{1-6}$alkoxy;
- a monocyclic saturated or partially unsaturated 5- or 6-membered heterocyclic group, attached through a carbon atom and optionally substituted by one, two or three groups independently selected from the group consisting of $C_{1-4}$alkyl, $C(O)C_{1-4}$alkyl, halo$C_{1-4}$alkyl, halo and keto;
- N-linked pyrrolidinyl, optionally substituted with one, two or three groups independently selected from the group consisting of $C_{1-4}$alkyl, $C(O)C_{1-4}$alkyl, halo$C_{1-4}$alkyl, halo and keto; and
- oxazolyl or imidazolyl, both being optionally substituted by $C_{1-4}$alkyl;

c) when n is 1 or 2, and m is 1, $R^1$ is selected from the group consisting of $C_{1-4}$alkyl, benzyl, cyclopropyl, thienyl, and $NR^9R^{10}$ wherein:
- $R^9$ is selected from the group consisting of hydrogen and $C_{1-4}$alkyl, and $R^{10}$ is selected from the group consisting of $C_{1-6}$ straight chain alkyl, $C_{3-6}$cycloalkyl and —$(CH_2)_pZ$ wherein p is 1, 2 or 3;
- Z is a phenyl or a 5- or 6-membered heterocyclic group, the phenyl or heterocyclic group being optionally substituted by one, two or three groups independently selected from the group consisting of halo and $C_{1-4}$alkyl; or
- $R^9$ and $R^{10}$, together with the nitrogen atom to which they are attached, form a 5-membered aromatic or non-aromatic heterocyclic group or a 6-membered non-aromatic heterocyclic group, any of the rings being optionally substituted by one, two or three groups independently selected from the group consisting of $C_{1-4}$alkyl, halo, phenyl and (in the case of a non-aromatic ring) keto; and d) when n is 1 or 2, and m is 0, $R^1$ is selected from the group consisting of cyano, hydroxy, $NH_2$, a C-linked 5-membered aromatic heterocyclic group optionally substituted with one, two or three groups independently selected from the group consisting of $C_{1-6}$alkyl and $C_{3-6}$cycloalkyl, and $NR^{11}R^{12}$ in which:
- $R^{11}$ is hydrogen and $R^{12}$ is selected from the group consisting of $SO_2C_{1-4}$alkyl, $SO_2C_{3-6}$cycloalkyl, $C(O)C_{1-4}$alkyl, and $C(O)C_{2-4}$alkenyl; or $R^{11}$ is selected from the group consisting of $C_{1-4}$alkyl and $C_{2-4}$alkenyl, and $R^{12}$ is selected from the group consisting of $SO_2C_{1-4}$alkyl, $SO_2C_{3-6}$cycloalkyl, $C(O)C_{1-4}$alkyl, $C(O)$phenyl and $C(O)C_{2-4}$alkenyl or
- $R^{11}$ and $R^{12}$, together with the nitrogen atom to which they are attached, form a group selected from the group consisting of:
  (i) a 5-membered aromatic heterocyclic group which is optionally substituted by one or two groups independently selected from the group consisting of $C_{1-4}$alkyl, halo, halo$C_{1-4}$alkyl, hydroxy, $C_{3-6}$cycloalkyl and $C_{1-4}$alkoxy; and
  (ii) imidazolyl substituted by phenyl;
  (iii) a 5-membered non-aromatic heterocyclic group which is substituted by one, two or three groups independently selected from the group consisting of keto, hydroxy and $C_{1-4}$alkoxy; and
  (iv) a 6-membered non-aromatic heterocyclic group, which is optionally substituted by one, two or three groups independently selected from the group consisting of keto, hydroxy and $C_{1-4}$alkoxy;

excluding 4-methyl-N-[4-[4,5,6,7-tetrahydro-3-(trifluoromethyl)-1H-indazol-1-yl]phenyl]-1,2,3-thiadiazole-5-carboxamide and salts thereof.

The term "halo" refers to fluoro, chloro, bromo or iodo.

The term "$C_{1-6}$alkyl" refers to an alkyl group having from one to six carbon atoms; and the term "$C_{1-4}$alkyl" refers to an alkyl group having from one to four carbon atoms. Unless otherwise indicated, $C_{1-4}$alkyl or $C_{1-6}$alkyl may be a straight chain or branched alkyl group. For example, a $C_{1-4}$alkyl group may be selected from the group consisting of methyl, ethyl, n-propyl, i-propyl, n-butyl, i-butyl or t-butyl. A $C_{1-6}$alkyl group may be selected from the group consisting of a $C_{1-4}$alkyl group, sec-pentyl, n-pentyl, isopentyl, tert-pentyl and hexyl. For example, $C_{1-4}$alkyl is methyl. The term "$C_{1-6}$ straight chain alkyl" means that the $C_{1-6}$alkyl group is in a straight chain, for example methyl, ethyl, propyl, butyl, pentyl and hexyl. The term "$C_{4-6}$ branched chain alkyl" means that the $C_{4-6}$alkyl group is in a branched chain, for example t-butyl. "Me" means methyl. "Et" means ethyl.

"Ph" means phenyl.

The term "$C_{1-4}$alkoxy" refers to the group —O—$C_{1-4}$alkyl wherein $C_{1-4}$alkyl is as defined above.

The term "$C_{2-4}$alkenyl" herein refers to a linear or branched hydrocarbon group containing one or more carbon-carbon double bonds and having from 2 to 4 carbon atoms. Examples of such groups include ethenyl, propenyl and butenyl.

The term "$C_{3-6}$cycloalkyl" refers to a cycloalkyl group consisting of from 3 to 6 carbon atoms, ie cyclopropanyl, cyclobutanyl, cyclopentanyl and cyclohexanyl.

The term "halo$C_{1-4}$alkyl" refers to a $C_{1-4}$alkyl group as defined above which is substituted with any number of fluorine, chlorine, bromine, or iodine atoms, including with mixtures of those atoms. A halo$C_{1-4}$alkyl group may, for example contain 1, 2 or 3 halogen atoms. For example, a halo$C_{1-4}$alkyl group may have all hydrogen atoms replaced with halogen atoms. Examples of halo$C_{1-4}$alkyl groups include fluoromethyl, difluoromethyl and trifluoromethyl.

The term "3-membered carbocyclic ring" as it appears in the definition of $R^6$ and $R^7$, refers to the following group formed by $R^6$ and $R^7$:

The term "C-linked 5-membered aromatic heterocyclic group" as it appears in the definition of $R^1$ when n is 0 and m is 1 refers to a C-linked aromatic heterocyclic group which contains one, two or three heteroatoms selected from the group consisting of nitrogen, oxygen and sulphur. Examples include pyrrolyl, pyrrolinyl, pyrazolinyl, oxazolyl, isoxazoyl, imidazolyl, pyrazolyl, thiadiazolyl, oxadiazolyl, isothiazolyl, thiazolyl, triazolyl, furyl and thienyl.

The terms "non-aromatic 5- or 6-membered heterocyclic group" and "aromatic or non-aromatic 5- or 6-membered heterocyclic group" as it appears in the definition of Z and Z' refer to an aromatic or non-aromatic 5- or 6-membered group which contains one, two or three heteroatoms independently selected from the group consisting of nitrogen, oxygen and sulfur. Examples of aromatic groups include: pyrrolyl, pyrazolinyl, oxazolyl, isoxazoyl, imidazolyl, pyrazolyl, thiadiazolyl, oxadiazolyl, isothiazolyl, thiazolyl, triazolyl, furyl, thienyl, pyridyl, thiazinyl, pyridazinyl, pyrimidinyl, pyrazinyl and triazinyl. Examples of non-aromatic groups include pyrrolidinyl, pyrrolinyl, imidazolidinyl, pyrazolidinyl, isothiazolyl, thiazolyl, tetrahydrofuranyl, dioxolanyl, piperidyl, piperazinyl, morpholinyl, thiomorpholinyl, tetrahydrothienyl, dioxanyl and dithianyl.

The term "4 or 5-membered non-aromatic heterocyclic group", as it appears in the definition of $R^2$ and $R^3$, refers to a 4- or 5-membered non-aromatic ring formed by $R^2$ and $R^3$, together with the nitrogen to which $R^2$ and $R^3$ are attached, which ring may contain one, two or three additional heteroatoms independently selected from the group consisting of nitrogen, oxygen and sulfur. Examples include azetidinyl, pyrrolidinyl imidazolidinyl, pyrazolidinyl, isothiazolyl and thiazolyl.

The term "6-membered non-aromatic heterocyclic group", as it appears in the definition of $R^2$ and $R^3$, refers to a 6-membered non-aromatic ring formed by $R^2$ and $R^3$, together with the nitrogen to which $R^2$ and $R^3$ are attached, which ring may contain one, two or three additional heteroatoms independently selected from the group consisting of nitrogen, oxygen and sulfur. Examples include morpholinyl, thiomorpholinyl, piperidinyl and piperazinyl.

"CO" and "C(=O)" are interchangeable and represent a carbonyl group. The term "keto" refers to the group =O.

The term "monocyclic saturated or partially unsaturated 5- or 6-membered heterocyclic group, attached through a carbon atom", as it appears in the definition of $R^1$ when n and m are both 0, refers to a 5- or 6-membered ring which is attached through a carbon atom and which contains one, two or three heteroatoms independently selected from the group consisting of nitrogen, oxygen and sulfur. Examples include pyrrolidinyl, pyrrolinyl, imidazolinyl, imidazolidinyl, piperidyl and morpholinyl.

The term "5-membered aromatic or non-aromatic heterocyclic group", as it appears in the definition of $R^9$ and $R^{10}$, refers to a 5-membered aromatic ring or a 5-membered non-aromatic ring, formed by $R^9$ and $R^{10}$, together with the nitrogen to which $R^9$ and $R^{10}$ are attached, which ring may include one, two or three further heteroatoms selected from the group consisting of nitrogen, oxygen and sulphur. In one embodiment, the heterocyclic group contains zero, one or two further heteroatoms selected from the group consisting of nitrogen, oxygen and sulphur. Examples include pyrrolidinyl, imidazolidinyl, pyrazolidinyl, isothiazolyl, thiazolyl, pyrrolyl, pyrazolinyl, isoxazoyl, imidazolyl, pyrazolyl, thiadiazolyl, oxadiazolyl, isothiazolyl, thiazolyl and triazolyl.

The term "6-membered non-aromatic heterocyclic group" as it appears in the definition of $R^9$ and $R^{10}$, refers to a 6-membered non-aromatic ring, formed by $R^9$ and $R^{10}$, together with the nitrogen to which $R^9$ and $R^{10}$ are attached, which ring may include one or more further heteroatoms selected from the group consisting of nitrogen, oxygen and sulphur. In one embodiment, the heterocyclic group contains zero, one, two or three further heteroatoms selected from the group consisting of nitrogen, oxygen and sulphur. Examples include piperidyl, piperazinyl, morpholinyl and thiomorpholinyl.

The term "C-linked 5-membered aromatic heterocyclic group" as it appears in the definition of $R^1$ when n is 1 or 2 and m is 0, refers to a C-linked aromatic heterocyclic group which contains one, two or three heteroatoms selected from the group consisting of nitrogen, oxygen and sulphur. Examples include pyrrolyl, pyrrolinyl, pyrazolinyl, oxazolyl, isoxazoyl, imidazolyl, pyrazolyl, thiadiazolyl, oxadiazolyl, isothiazolyl, thiazolyl, triazolyl, furyl and thienyl.

The term "5-membered aromatic heterocyclic group" as it appears in the definition of $R^{11}$ and $R^{12}$ when n is 1 or 2, m is 0, and $R^1$ is $NR^{11}R^{12}$, refers to a 5-membered aromatic heterocyclic group, formed by $R^{10}$ and $R^{11}$, together with the nitrogen to which $R^{10}$ and $R^{11}$ are attached, which ring may contain one, two or three further heteroatoms selected from the group consisting of nitrogen, oxygen and sulphur. Examples include pyrrolyl, pyrrolinyl, pyrazolinyl, oxazolyl, isoxazoyl, imidazolyl, pyrazolyl, thiadiazolyl, oxadiazolyl, isothiazolyl, thiazolyl and triazolyl.

The term "5-membered non-aromatic heterocyclic group" as it appears in the definition of $R^{11}$ and $R^{12}$ when n is 1 or 2, m is 0, and $R^1$ is $NR^{11}R^{12}$, refers to a 5-membered non-aromatic heterocyclic group, formed by $R^{10}$ and $R^{11}$, together with the nitrogen to which $R^{10}$ and $R^{11}$ are attached, which ring may contain one, two or three further heteroatoms selected from the group consisting of nitrogen, oxygen and sulphur. Examples include pyrrolidinyl, thiazolidinyl, imidazolidinyl, pyrazolidinyl and isothiazolidinyl.

The term "6-membered non-aromatic heterocyclic group" as it appears in the definition of $R^{11}$ and $R^{12}$ when n is 1 or 2, m is 0, and $R^1$ is $NR^{11}R^{12}$, refers to a 6-membered non-aromatic heterocyclic group, formed by $R^{10}$ and $R^{11}$, together with the nitrogen to which $R^{10}$ and $R^{11}$ are attached, which ring may contain one, two or three further heteroatoms selected from the group consisting of nitrogen, oxygen and sulphur. Examples include piperidyl, piperazinyl, morpholinyl and thiomorpholinyl.

Examples of compounds of formula (I) include
1. N,N-dimethyl-4-[3-(trifluoromethyl)-4,5,6,7-tetrahydro-1H-indazol-1-yl]benzamide (Example 1)
2. 1-[4-(1-pyrrolidinylcarbonyl)phenyl]-3-(trifluoromethyl)-4,5,6,7-tetrahydro-1H-indazole (Example 2)
3. N-methyl-N-(phenylmethyl)-4-[3-(trifluoromethyl)-4,5,6,7-tetrahydro-1H-indazol-1-yl]benzamide (Example 3)
4. N-ethyl-N-methyl-4-[3-(trifluoromethyl)-4,5,6,7-tetrahydro-1H-indazol-1-yl]benzamide (Example 4)
5. N-butyl-N-methyl-4-[3-(trifluoromethyl)-4,5,6,7-tetrahydro-1H-indazol-1-yl]benzamide (Example 5)
6. N-methyl-N-(2-phenylethyl)-4-[3-(trifluoromethyl)-4,5,6,7-tetrahydro-1H-indazol-1-yl]benzamide (Example 6)
7. N,N-dimethyl-4-[3-(trifluoromethyl)-4,5,6,7-tetrahydro-1H-indazol-1-yl]benzenesulfonamide (Example 7)
8. 1-{4-[3-(trifluoromethyl)-4,5,6,7-tetrahydro-1H-indazol-1-yl]phenyl}ethanone (Example 8)
9. 1-{4-[3-(trifluoromethyl)-4,5,6,7-tetrahydro-1H-indazol-1-yl]phenyl}-1-propanone (Example 9)
10. 1-[4-(methylsulfonyl)phenyl]-3-(trifluoromethyl)-4,5,6,7-tetrahydro-1H-indazole (Example 10)
11. 1-{4-[3-(trifluoromethyl)-4,5,6,7-tetrahydro-1H-indazol-1-yl]phenyl}-2-propanone (Example 11)
12. N,N-dimethyl-2-{4-[3-(trifluoromethyl)-4,5,6,7-tetrahydro-1H-indazol-1-yl]phenyl}acetamide (Example 12)
13. 1-{4-[2-oxo-2-(1-pyrrolidinyl)ethyl]phenyl}-3-(trifluoromethyl)-4,5,6,7-tetrahydro-1H-indazole (Example 13)
14. N-ethyl-N-methyl-2-{4-[3-(trifluoromethyl)-4,5,6,7-tetrahydro-1H-indazol-1-yl]phenyl}acetamide (Example 14)
15. N-methyl-N-(phenylmethyl)-2-{4-[3-(trifluoromethyl)-4,5,6,7-tetrahydro-1H-indazol-1-yl]phenyl}acetamide (Example 15)
16. N-butyl-N-methyl-2-{4-[3-(trifluoromethyl)-4,5,6,7-tetrahydro-1H-indazol-1-yl]phenyl}acetamide (Example 16)
17. N-methyl-N-(2-phenylethyl)-2-{4-[3-(trifluoromethyl)-4,5,6,7-tetrahydro-1H-indazol-1-yl]phenyl}acetamide (Example 17)
18. 1-{[4-(1-pyrrolidinylcarbonyl)phenyl]methyl}-3-(trifluoromethyl)-4,5,6,7-tetrahydro-1H-indazole (Example 18)
19. 1-{4-[1-methyl-2-oxo-2-(1-pyrrolidinyl)ethyl]phenyl}-3-(trifluoromethyl)-4,5,6,7-tetrahydro-1H-indazole (Example 19)
20. N,N-dimethyl-3-{4-[3-(trifluoromethyl)-4,5,6,7-tetrahydro-1H-indazol-1-yl]phenyl}propanamide (Example 20)
21. 1-{4-[3-oxo-3-(1-pyrrolidinyl)propyl]phenyl}-3-(trifluoromethyl)-4,5,6,7-tetrahydro-1H-indazole (Example 21)
22. 1-{4-[1-(1-pyrrolidinylcarbonyl)cyclopropyl]phenyl}-3-(trifluoromethyl)-4,5,6,7-tetrahydro-1H-indazole (Example 22)
23. 1-{4-[2-oxo-2-(1-piperidinyl)ethyl]phenyl}-3-(trifluoromethyl)-4,5,6,7-tetrahydro-1H-indazole (Example 23)
24. 1-{4-[2-(3,3-difluoro-1-pyrrolidinyl)-2-oxoethyl]phenyl}-3-(trifluoromethyl)-4,5,6,7-tetrahydro-1H-indazole (Example 24)
25. N-methyl-N-propyl-2-{4-[3-(trifluoromethyl)-4,5,6,7-tetrahydro-1H-indazol-1-yl]phenyl}acetamide (Example 25)
26. N-cyclopentyl-2-{4-[3-(trifluoromethyl)-4,5,6,7-tetrahydro-1H-indazol-1-yl]phenyl}acetamide (Example 26)
27. N-methyl-N-(2-thienylmethyl)-2-{4-[3-(trifluoromethyl)-4,5,6,7-tetrahydro-1H-indazol-1-yl]phenyl}acetamide (Example 27)
28. {4-[3-(trifluoromethyl)-4,5,6,7-tetrahydro-1H-indazol-1-yl]phenyl}acetonitrile (Example 28)
29. {4-[3-(trifluoromethyl)-4,5,6,7-tetrahydro-1H-indazol-1-yl]phenyl}methanol (Example 29)
30. N-methyl-N-({4-[3-(trifluoromethyl)-4,5,6,7-tetrahydro-1H-indazol-1-yl]phenyl}methyl)acetamide (Example 30)
31. 1-({4-[3-(trifluoromethyl)-4,5,6,7-tetrahydro-1H-indazol-1-yl]phenyl}methyl)-2-pyrrolidinone (Example 31)
32. N-methyl-N-({4-[3-(trifluoromethyl)-4,5,6,7-tetrahydro-1H-indazol-1-yl]phenyl}methyl)propanamide (Example 32)
33. N-ethyl-N-({4-[3-(trifluoromethyl)-4,5,6,7-tetrahydro-1H-indazol-1-yl]phenyl}methyl)acetamide (Example 33)
34. 1-({4-[3-(trifluoromethyl)-4,5,6,7-tetrahydro-1H-indazol-1-yl]phenyl}methyl)-2-piperidinone (Example 34)
35. 1-methyl-5-{4-[3-(trifluoromethyl)-4,5,6,7-tetrahydro-1H-indazol-1-yl]phenyl}-2-pyrrolidinone (Example 35)
36. N-[3-(1H-imidazol-1-yl)propyl]-N-methyl-4-[3-(trifluoromethyl)-4,5,6,7-tetrahydro-1H-indazol-1-yl]benzamide (Example 36)
37. N-methyl-N-[2-(2-thienyl)ethyl]-4-[3-(trifluoromethyl)-4,5,6,7-tetrahydro-1H-indazol-1-yl]benzamide (Example 37)
38. N-methyl-N-[2-(1H-1,2,4-triazol-1-yl)ethyl]-4-[3-(trifluoromethyl)-4,5,6,7-tetrahydro-1H-indazol-1-yl]benzamide (Example 38)
39. N-methyl-N-(1,3-thiazol-2-ylmethyl)-4-[3-(trifluoromethyl)-4,5,6,7-tetrahydro-1H-indazol-1-yl]benzamide (Example 39)
40. N-methyl-N-[2-(1-methyl-1H-pyrrol-2-yl)ethyl]-4-[3-(trifluoromethyl)-4,5,6,7-tetrahydro-1H-indazol-1-yl]benzamide (Example 40)
41. N-methyl-N-(2-thienylmethyl)-4-[3-(trifluoromethyl)-4,5,6,7-tetrahydro-1H-indazol-1-yl]benzamide (Example 41)
42. N-methyl-N-(3-pyridinylmethyl)-4-[3-(trifluoromethyl)-4,5,6,7-tetrahydro-1H-indazol-1-yl]benzamide (Example 42)
43. N-(2-furanylmethyl)-N-methyl-4-[3-(trifluoromethyl)-4,5,6,7-tetrahydro-1H-indazol-1-yl]benzamide (Example 43)
44. N-[(4-fluorophenyl)methyl]-N-methyl-4-[3-(trifluoromethyl)-4,5,6,7-tetrahydro-1H-indazol-1-yl]benzamide (Example 44)
45. 1-[4-(4-morpholinylcarbonyl)phenyl]-3-(trifluoromethyl)-4,5,6,7-tetrahydro-1H-indazole (Example 45)
46. N-({4-[3-(trifluoromethyl)-4,5,6,7-tetrahydro-1H-indazol-1-yl]phenyl}methyl)methanesulfonamide (Example 46)
47. 1-{4-[1-fluoro-2-oxo-2-(1-pyrrolidinyl)ethyl]phenyl}-3-(trifluoromethyl)-4,5,6,7-tetrahydro-1H-indazole
48. 1-{4-[1,1-difluoro-2-oxo-2-(1-pyrrolidinyl)ethyl]phenyl}-3-(trifluoromethyl)-4,5,6,7-tetrahydro-1H-indazole
49. N-methyl-N-({4-[3-(trifluoromethyl)-4,5,6,7-tetrahydro-1H-indazol-1-yl]phenyl}methyl)methanesulfonamide
50. 1-(4-{[3-(trifluoromethyl)-4,5,6,7-tetrahydro-1H-indazol-1-yl]methyl}phenyl)-2-pyrrolidinone
51. N-methyl-N-({4-[3-(trifluoromethyl)-4,5,6,7-tetrahydro-1H-indazol-1-yl]phenyl}methyl)-1-pyrrolidinecarboxamide
52. 5-{4-[3-(trifluoromethyl)-4,5,6,7-tetrahydro-1H-indazol-1-yl]phenyl}-2-pyrrolidinone
53. N-(1-{4-[3-(trifluoromethyl)-4,5,6,7-tetrahydro-1H-indazol-1-yl]phenyl}ethyl)acetamide 54. N-methyl-N-(1-{4-[3-(trifluoromethyl)-4,5,6,7-tetrahydro-1H-indazol-1-yl]phenyl}ethyl)acetamide
55. 1-[4-(1-acetyl-2-pyrrolidinyl)phenyl]-3-(trifluoromethyl)-4,5,6,7-tetrahydro-1H-indazole
56. 1-(2-{4-[3-(trifluoromethyl)-4,5,6,7-tetrahydro-1H-indazol-1-yl]phenyl}ethyl)-2-pyrrolidinone
57. 1-{4-[(1,1-dioxido-2-isothiazolidinyl)methyl]phenyl}-3-(trifluoromethyl)-4,5,6,7-tetrahydro-1H-indazole
58. 2-methyl-N-({4-[3-(trifluoromethyl)-4,5,6,7-tetrahydro-1H-indazol-1-yl]phenyl}methyl)propanamide
59. N-({4-[3-(trifluoromethyl)-4,5,6,7-tetrahydro-1H-indazol-1-yl]phenyl}methyl)butanamide
60. N-({4-[3-(trifluoromethyl)-4,5,6,7-tetrahydro-1H-indazol-1-yl]phenyl}methyl)-2-thiophenecarboxamide
61. N-({4-[3-(trifluoromethyl)-4,5,6,7-tetrahydro-1H-indazol-1-yl]phenyl}methyl)propanamide
62. N-({4-[3-(trifluoromethyl)-4,5,6,7-tetrahydro-1H-indazol-1-yl]phenyl}methyl)acetamide
63. N-methyl-2-phenyl-N-({4-[3-(trifluoromethyl)-4,5,6,7-tetrahydro-1H-indazol-1-yl]phenyl}methyl)acetamide
64. N-(2-hydroxyethyl)-N-methyl-4-[3-(trifluoromethyl)-4,5,6,7-tetrahydro-1H-indazol-1-yl]benzamide
65. N-methyl-N-[2-(methyloxy)ethyl]-4-[3-(trifluoromethyl)-4,5,6,7-tetrahydro-1H-indazol-1-yl]benzamide
66. N-methyl-N-[2-(methylamino)ethyl]-4-[3-(trifluoromethyl)-4,5,6,7-tetrahydro-1H-indazol-1-yl]benzamide
67. 1-({4-[3-(trifluoromethyl)-4,5,6,7-tetrahydro-1H-indazol-1-yl]phenyl}carbonyl)-3-pyrrolidinol
68. N-methyl-1-({4-[3-(trifluoromethyl)-4,5,6,7-tetrahydro-1H-indazol-1-yl]phenyl}carbonyl)-3-pyrrolidinamine
69. 1-[4-(1-azetidinylcarbonyl)phenyl]-3-(trifluoromethyl)-4,5,6,7-tetrahydro-1H-indazole
70. 1-({4-[3-(trifluoromethyl)-4,5,6,7-tetrahydro-1H-indazol-1-yl]phenyl}carbonyl)-3-azetidinol
71. (3,3-difluorocyclobutyl){4-[3-(trifluoromethyl)-4,5,6,7-tetrahydro-1H-indazol-1-yl]phenyl}methanone
72. 1-[4-(1H-imidazol-1-yl)phenyl]-3-(trifluoromethyl)-4,5,6,7-tetrahydro-1H-indazole
73. N-({4-[3-(trifluoromethyl)-4,5,6,7-tetrahydro-1H-indazol-1-yl]phenyl}methyl)-2-propenamide
74. N-(1-methylethenyl)-N-({4-[3-(trifluoromethyl)-4,5,6,7-tetrahydro-1H-indazol-1-yl]phenyl}methyl)-2-propenamide
75. N-methyl-N-({4-[3-(trifluoromethyl)-4,5,6,7-tetrahydro-1H-indazol-1-yl]phenyl}methyl)-2-propenamide
76. 1-{4-[(3-methyl-1,2,4-oxadiazol-5-yl)methyl]phenyl}-3-(trifluoromethyl)-4,5,6,7-tetrahydro-1H-indazole
77. 1-{4-[(3-cyclopropyl-1,2,4-oxadiazol-5-yl)methyl]phenyl}-3-(trifluoromethyl)-4,5,6,7-tetrahydro-1H-indazole
78. N-ethyl-4-[3-(trifluoromethyl)-4,5,6,7-tetrahydro-1H-indazol-1-yl]benzamide
79. N-methyl-N-(1-methylethyl)-4-[3-(trifluoromethyl)-4,5,6,7-tetrahydro-1H-indazol-1-yl]benzamide
80. 1-[4-(1-piperidinylcarbonyl)phenyl]-3-(trifluoromethyl)-4,5,6,7-tetrahydro-1H-indazole
81. N,N-diethyl-4-[3-(trifluoromethyl)-4,5,6,7-tetrahydro-1H-indazol-1-yl]benzamide
82. N-methyl-4-[3-(trifluoromethyl)-4,5,6,7-tetrahydro-1H-indazol-1-yl]benzamide
83. 1-{4-[2-oxo-2-(2-phenyl-1-pyrrolidinyl)ethyl]phenyl}-3-(trifluoromethyl)-4,5,6,7-tetrahydro-1H-indazole
84. N-methyl-N-({4-[3-(trifluoromethyl)-4,5,6,7-tetrahydro-1H-indazol-1-yl]phenyl}methyl)benzamide
85. 1-[4-(1,3-oxazol-5-yl)phenyl]-3-(trifluoromethyl)-4,5,6,7-tetrahydro-1H-indazole
86. 1-[4-(propyloxy)phenyl]-3-(trifluoromethyl)-4,5,6,7-tetrahydro-1H-indazole
87. 1-[4-(1-methyl-1H-imidazol-4-yl)phenyl]-3-(trifluoromethyl)-4,5,6,7-tetrahydro-1H-indazole
88. N-({4-[3-(trifluoromethyl)-4,5,6,7-tetrahydro-1H-indazol-1-yl]phenyl}methyl)-2-propanesulfonamide
89. N-({4-[3-(trifluoromethyl)-4,5,6,7-tetrahydro-1H-indazol-1-yl]phenyl}methyl)cyclopropanesulfonamide
90. N-({4-[3-(trifluoromethyl)-4,5,6,7-tetrahydro-1H-indazol-1-yl]phenyl}methyl)cyclopentanesulfonamide
91. 1-[4-(1-pyrrolidinylsulfonyl)phenyl]-3-(trifluoromethyl)-4,5,6,7-tetrahydro-1H-indazole
92. N-(2-methylpropyl)-4-[3-(trifluoromethyl)-4,5,6,7-tetrahydro-1H-indazol-1-yl]benzenesulfonamide
93. 1-[4-(4-morpholinylsulfonyl)phenyl]-3-(trifluoromethyl)-4,5,6,7-tetrahydro-1H-indazole
94. N-[2-(methyloxy)ethyl]-4-[3-(trifluoromethyl)-4,5,6,7-tetrahydro-1H-indazol-1-yl]benzenesulfonamide
95. N-[2-(1-pyrrolidinyl)ethyl]-4-[3-(trifluoromethyl)-4,5,6,7-tetrahydro-1H-indazol-1-yl]benzenesulfonamide
96. N-(tetrahydro-2-furanylmethyl)-4-[3-(trifluoromethyl)-4,5,6,7-tetrahydro-1H-indazol-1-yl]benzenesulfonamide
97. 1-[4-(1H-imidazol-1-ylmethyl)phenyl]-3-(trifluoromethyl)-4,5,6,7-tetrahydro-1H-indazole
98. 1-[4-(1H-1,2,4-triazol-1-ylmethyl)phenyl]-3-(trifluoromethyl)-4,5,6,7-tetrahydro-1H-indazole
99. 1-[4-(1H-pyrazol-1-ylmethyl)phenyl]-3-(trifluoromethyl)-4,5,6,7-tetrahydro-1H-indazole
100. 1-[4-(1H-1,2,3-triazol-1-ylmethyl)phenyl]-3-(trifluoromethyl)-4,5,6,7-tetrahydro-1H-indazole
101. 1-[4-(2H-1,2,3-triazol-2-ylmethyl)phenyl]-3-(trifluoromethyl)-4,5,6,7-tetrahydro-1H-indazole
102. 1-{4-[(4-methyl-1H-pyrazol-1-yl)methyl]phenyl}-3-(trifluoromethyl)-4,5,6,7-tetrahydro-1H-indazole
103. 1-{4-[(3,5-dimethyl-1H-pyrazol-1-yl)methyl]phenyl}-3-(trifluoromethyl)-4,5,6,7-tetrahydro-1H-indazole
104. 3-(trifluoromethyl)-1-(4-{[3-(trifluoromethyl)-1H-pyrazol-1-yl]methyl}phenyl)-4,5,6,7-tetrahydro-1H-indazole
105. 3-(trifluoromethyl)-1-(4-{[5-(trifluoromethyl)-1H-pyrazol-1-yl]methyl}phenyl)-4,5,6,7-tetrahydro-1H-indazole
106. 1-(4-{[5-methyl-3-(trifluoromethyl)-1H-pyrazol-1-yl]methyl}phenyl)-3-(trifluoromethyl)-4,5,6,7-tetrahydro-1H-indazole
107. 1-(4-{[3-methyl-5-(trifluoromethyl)-1H-pyrazol-1-yl]methyl}phenyl)-3-(trifluoromethyl)-4,5,6,7-tetrahydro-1H-indazole
108. 1-{4-[(2-methyl-1H-imidazol-1-yl)methyl]phenyl}-3-(trifluoromethyl)-4,5,6,7-tetrahydro-1H-indazole
109. 1-(4-{[2-(1-methylethyl)-1H-imidazol-1-yl]methyl}phenyl)-3-(trifluoromethyl)-4,5,6,7-tetrahydro-1H-indazole
110. 1-{4-[(4-phenyl-1H-imidazol-1-yl)methyl]phenyl}-3-(trifluoromethyl)-4,5,6,7-tetrahydro-1H-indazole
111. 1-{4-[(4-bromo-1H-pyrazol-1-yl)methyl]phenyl}-3-(trifluoromethyl)-4,5,6,7-tetrahydro-1H-indazole
112. N-methyl-1H-imidazol-2-yl){4-[3-(trifluoromethyl)-4,5,6,7-tetrahydro-1H-indazol-1-yl]phenyl}methanone
113. N-methyl-N-{4-[3-(trifluoromethyl)-4,5,6,7-tetrahydro-1H-indazol-1-yl]phenyl}-1-pyrrolidinecarboxamide and salts and solvates thereof.

In one embodiment, the compound is selected from the group consisting of:

Examples of compounds of formula (I) include N,N-dimethyl-4-[3-(trifluoromethyl)-4,5,6,7-tetrahydro-1H-indazol-1-yl]benzamide (Example 1)

1-[4-(1-pyrrolidinylcarbonyl)phenyl]-3-(trifluoromethyl)-4,5,6,7-tetrahydro-1H-indazole (Example 2)
N-methyl-N-(phenylmethyl)-4-[3-(trifluoromethyl)-4,5,6,7-tetrahydro-1H-indazol-1-yl]benzamide (Example 3)
N-ethyl-N-methyl-4-[3-(trifluoromethyl)-4,5,6,7-tetrahydro-1H-indazol-1-yl]benzamide (Example 4)
N-butyl-N-methyl-4-[3-(trifluoromethyl)-4,5,6,7-tetrahydro-1H-indazol-1-yl]benzamide (Example 5)
N-methyl-N-(2-phenylethyl)-4-[3-(trifluoromethyl)-4,5,6,7-tetrahydro-1H-indazol-1-yl]benzamide (Example 6)
N,N-dimethyl-4-[3-(trifluoromethyl)-4,5,6,7-tetrahydro-1H-indazol-1-yl]benzenesulfonamide (Example 7)
1-{4-[3-(trifluoromethyl)-4,5,6,7-tetrahydro-1H-indazol-1-yl]phenyl}ethanone (Example 8)
1-{4-[3-(trifluoromethyl)-4,5,6,7-tetrahydro-1H-indazol-1-yl]phenyl}-1-propanone (Example 9)
1-[4-(methylsulfonyl)phenyl]-3-(trifluoromethyl)-4,5,6,7-tetrahydro-1H-indazole (Example 10)
1-{4-[3-(trifluoromethyl)-4,5,6,7-tetrahydro-1H-indazol-1-yl]phenyl}-2-propanone (Example 11)
N,N-dimethyl-2-{4-[3-(trifluoromethyl)-4,5,6,7-tetrahydro-1H-indazol-1-yl]phenyl}acetamide (Example 12)
1-{4-[2-oxo-2-(1-pyrrolidinyl)ethyl]phenyl}-3-(trifluoromethyl)-4,5,6,7-tetrahydro-1H-indazole (Example 13)
N-ethyl-N-methyl-2-{4-[3-(trifluoromethyl)-4,5,6,7-tetrahydro-1H-indazol-1-yl]phenyl}acetamide (Example 14)
N-methyl-N-(phenylmethyl)-2-{4-[3-(trifluoromethyl)-4,5,6,7-tetrahydro-1H-indazol-1-yl]phenyl}acetamide (Example 15)
N-butyl-N-methyl-2-{4-[3-(trifluoromethyl)-4,5,6,7-tetrahydro-1H-indazol-1-yl]phenyl}acetamide (Example 16)
N-methyl-N-(2-phenylethyl)-2-{4-[3-(trifluoromethyl)-4,5,6,7-tetrahydro-1H-indazol-1-yl]phenyl}acetamide (Example 17)
1-{[4-(1-pyrrolidinylcarbonyl)phenyl]methyl}-3-(trifluoromethyl)-4,5,6,7-tetrahydro-1H-indazole (Example 18)
1-{4-[1-methyl-2-oxo-2-(1-pyrrolidinyl)ethyl]phenyl}-3-(trifluoromethyl)-4,5,6,7-tetrahydro-1H-indazole (Example 19)
N,N-dimethyl-3-{4-[3-(trifluoromethyl)-4,5,6,7-tetrahydro-1H-indazol-1-yl]phenyl}propanamide (Example 20)
1-{4-[3-oxo-3-(1-pyrrolidinyl)propyl]phenyl}-3-(trifluoromethyl)-4,5,6,7-tetrahydro-1H-indazole (Example 21)
1-{4-[1-(1-pyrrolidinylcarbonyl)cyclopropyl]phenyl}-3-(trifluoromethyl)-4,5,6,7-tetrahydro-1H-indazole (Example 22)
1-{4-[2-oxo-2-(1-piperidinyl)ethyl]phenyl}-3-(trifluoromethyl)-4,5,6,7-tetrahydro-1H-indazole (Example 23)
1-{4-[2-(3,3-difluoro-1-pyrrolidinyl)-2-oxoethyl]phenyl}-3-(trifluoromethyl)-4,5,6,7-tetrahydro-1H-indazole (Example 24)
N-methyl-N-propyl-2-{4-[3-(trifluoromethyl)-4,5,6,7-tetrahydro-1H-indazol-1-yl]phenyl}acetamide (Example 25)
N-cyclopentyl-2-{4-[3-(trifluoromethyl)-4,5,6,7-tetrahydro-1H-indazol-1-yl]phenyl}acetamide (Example 26)
N-methyl-N-(2-thienylmethyl)-2-{4-[3-(trifluoromethyl)-4,5,6,7-tetrahydro-1H-indazol-1-yl]phenyl}acetamide (Example 27)
{4-[3-(trifluoromethyl)-4,5,6,7-tetrahydro-1H-indazol-1-yl]phenyl}acetonitrile (Example 28)
{4-[3-(trifluoromethyl)-4,5,6,7-tetrahydro-1H-indazol-1-yl]phenyl}methanol (Example 29)
N-methyl-N-({4-[3-(trifluoromethyl)-4,5,6,7-tetrahydro-1H-indazol-1-yl]phenyl}methyl)acetamide (Example 30)
1-({4-[3-(trifluoromethyl)-4,5,6,7-tetrahydro-1H-indazol-1-yl]phenyl}methyl)-2-pyrrolidinone (Example 31)
N-methyl-N-({4-[3-(trifluoromethyl)-4,5,6,7-tetrahydro-1H-indazol-1-yl]phenyl}methyl)propanamide (Example 32)
N-ethyl-N-({4-[3-(trifluoromethyl)-4,5,6,7-tetrahydro-1H-indazol-1-yl]phenyl}methyl)acetamide (Example 33)
1-({4-[3-(trifluoromethyl)-4,5,6,7-tetrahydro-1H-indazol-1-yl]phenyl}methyl)-2-piperidinone (Example 34)
1-methyl-5-{4-[3-(trifluoromethyl)-4,5,6,7-tetrahydro-1H-indazol-1-yl]phenyl}-2-pyrrolidinone (Example 35)
N-[3-(1H-imidazol-1-yl)propyl]-N-methyl-4-[3-(trifluoromethyl)-4,5,6,7-tetrahydro-1H-indazol-1-yl]benzamide (Example 36)
N-methyl-N-[2-(2-thienyl)ethyl]-4-[3-(trifluoromethyl)-4,5,6,7-tetrahydro-1H-indazol-1-yl]benzamide (Example 37)
N-methyl-N-[2-(1H-1,2,4-triazol-1-yl)ethyl]-4-[3-(trifluoromethyl)-4,5,6,7-tetrahydro-1H-indazol-1-yl]benzamide (Example 38)
N-methyl-N-(1,3-thiazol-2-ylmethyl)-4-[3-(trifluoromethyl)-4,5,6,7-tetrahydro-1H-indazol-1-yl]benzamide (Example 39)
N-methyl-N-[2-(1-methyl-1H-pyrrol-2-yl)ethyl]-4-[3-(trifluoromethyl)-4,5,6,7-tetrahydro-1H-indazol-1-yl]benzamide (Example 40)
N-methyl-N-(2-thienylmethyl)-4-[3-(trifluoromethyl)-4,5,6,7-tetrahydro-1H-indazol-1-yl]benzamide (Example 41)
N-methyl-N-(3-pyridinylmethyl)-4-[3-(trifluoromethyl)-4,5,6,7-tetrahydro-1H-indazol-1-yl]benzamide (Example 42)
N-(2-furanyl methyl)-N-methyl-4-[3-(trifluoromethyl)-4,5,6,7-tetrahydro-1H-indazol-1-yl]benzamide (Example 43) and
N-[(4-fluorophenyl)methyl]-N-methyl-4-[3-(trifluoromethyl)-4,5,6,7-tetrahydro-1H-indazol-1-yl]benzamide (Example 44).

In one embodiment, the compound is selected from the group consisting of:
N,N-dimethyl-4-[3-(trifluoromethyl)-4,5,6,7-tetrahydro-1H-indazol-1-yl]benzamide (Example 1)
1-[4-(1-pyrrolidinylcarbonyl)phenyl]-3-(trifluoromethyl)-4,5,6,7-tetrahydro-1H-indazole (Example 2)
N-methyl-N-(phenylmethyl)-4-[3-(trifluoromethyl)-4,5,6,7-tetrahydro-1H-indazol-1-yl]benzamide (Example 3)
N-ethyl-N-methyl-4-[3-(trifluoromethyl)-4,5,6,7-tetrahydro-1H-indazol-1-yl]benzamide (Example 4)
N-butyl-N-methyl-4-[3-(trifluoromethyl)-4,5,6,7-tetrahydro-1H-indazol-1-yl]benzamide (Example 5)
N-methyl-N-(2-phenylethyl)-4-[3-(trifluoromethyl)-4,5,6,7-tetrahydro-1H-indazol-1-yl]benzamide (Example 6)
N,N-dimethyl-4-[3-(trifluoromethyl)-4,5,6,7-tetrahydro-1H-indazol-1-yl]benzenesulfonamide (Example 7)
1-{4-[3-(trifluoromethyl)-4,5,6,7-tetrahydro-1H-indazol-1-yl]phenyl}ethanone (Example 8)
1-{4-[3-(trifluoromethyl)-4,5,6,7-tetrahydro-1H-indazol-1-yl]phenyl}-1-propanone (Example 9)
1-[4-(methylsulfonyl)phenyl]-3-(trifluoromethyl)-4,5,6,7-tetrahydro-1H-indazole (Example 10)
1-{4-[3-(trifluoromethyl)-4,5,6,7-tetrahydro-1H-indazol-1-yl]phenyl}-2-propanone (Example 11)
N,N-dimethyl-2-{4-[3-(trifluoromethyl)-4,5,6,7-tetrahydro-1H-indazol-1-yl]phenyl}acetamide (Example 12)
1-{4-[2-oxo-2-(1-pyrrolidinyl)ethyl]phenyl}-3-(trifluoromethyl)-4,5,6,7-tetrahydro-1H-indazole (Example 13)
N-ethyl-N-methyl-2-{4-[3-(trifluoromethyl)-4,5,6,7-tetrahydro-1H-indazol-1-yl]phenyl}acetamide (Example 14)
N-methyl-N-(phenylmethyl)-2-{4-[3-(trifluoromethyl)-4,5,6,7-tetrahydro-1H-indazol-1-yl]phenyl}acetamide (Example 15)

N-butyl-N-methyl-2-{4-[3-(trifluoromethyl)-4,5,6,7-tetrahydro-1H-indazol-1-yl]phenyl}acetamide (Example 16)

N-methyl-N-(2-phenylethyl)-2-{4-[3-(trifluoromethyl)-4,5,6,7-tetrahydro-1H-indazol-1-yl]phenyl}acetamide (Example 17)

1-{[4-(1-pyrrolidinylcarbonyl)phenyl]methyl}-3-(trifluoromethyl)-4,5,6,7-tetrahydro-1H-indazole (Example 18)

1-{4-[1-methyl-2-oxo-2-(1-pyrrolidinyl)ethyl]phenyl}-3-(trifluoromethyl)-4,5,6,7-tetrahydro-1H-indazole (Example 19)

N,N-dimethyl-3-{4-[3-(trifluoromethyl)-4,5,6,7-tetrahydro-1H-indazol-1-yl]phenyl}propanamide (Example 20)

1-{4-[3-oxo-3-(1-pyrrolidinyl)propyl]phenyl}-3-(trifluoromethyl)-4,5,6,7-tetrahydro-1H-indazole (Example 21)

1-{4-[1-(1-pyrrolidinylcarbonyl)cyclopropyl]phenyl}-3-(trifluoromethyl)-4,5,6,7-tetrahydro-1H-indazole (Example 22)

1-{4-[2-oxo-2-(1-piperidinyl)ethyl]phenyl}-3-(trifluoromethyl)-4,5,6,7-tetrahydro-1H-indazole (Example 23)

1-{4-[2-(3,3-difluoro-1-pyrrolidinyl)-2-oxoethyl]phenyl}-3-(trifluoromethyl)-4,5,6,7-tetrahydro-1H-indazole (Example 24)

N-methyl-N-propyl-2-{4-[3-(trifluoromethyl)-4,5,6,7-tetrahydro-1H-indazol-1-yl]phenyl}acetamide (Example 25)

N-cyclopentyl-2-{4-[3-(trifluoromethyl)-4,5,6,7-tetrahydro-1H-indazol-1-yl]phenyl}acetamide (Example 26)

N-methyl-N-(2-thienylmethyl)-2-{4-[3-(trifluoromethyl)-4,5,6,7-tetrahydro-1H-indazol-1-yl]phenyl}acetamide (Example 27)

{4-[3-(trifluoromethyl)-4,5,6,7-tetrahydro-1H-indazol-1-yl]phenyl}acetonitrile (Example 28)

{4-[3-(trifluoromethyl)-4,5,6,7-tetrahydro-1H-indazol-1-yl]phenyl}methanol (Example 29)

N-methyl-N-({4-[3-(trifluoromethyl)-4,5,6,7-tetrahydro-1H-indazol-1-yl]phenyl}methyl)acetamide (Example 30)

1-({4-[3-(trifluoromethyl)-4,5,6,7-tetrahydro-1H-indazol-1-yl]phenyl}methyl)-2-pyrrolidinone (Example 31)

N-methyl-N-({4-[3-(trifluoromethyl)-4,5,6,7-tetrahydro-1H-indazol-1-yl]phenyl}methyl)propanamide (Example 32)

N-ethyl-N-({4-[3-(trifluoromethyl)-4,5,6,7-tetrahydro-1H-indazol-1-yl]phenyl}methyl)acetamide (Example 33)

1-({4-[3-(trifluoromethyl)-4,5,6,7-tetrahydro-1H-indazol-1-yl]phenyl}methyl)-2-piperidinone (Example 34)

1-methyl-5-{4-[3-(trifluoromethyl)-4,5,6,7-tetrahydro-1H-indazol-1-yl]phenyl}-2-pyrrolidinone (Example 35)

N-[3-(1H-imidazol-1-yl)propyl]-N-methyl-4-[3-(trifluoromethyl)-4,5,6,7-tetrahydro-1H-indazol-1-yl]benzamide (Example 36)

N-methyl-N-[2-(2-thienyl)ethyl]-4-[3-(trifluoromethyl)-4,5,6,7-tetrahydro-1H-indazol-1-yl]benzamide (Example 37)

N-methyl-N-[2-(1H-1,2,4-triazol-1-yl)ethyl]-4-[3-(trifluoromethyl)-4,5,6,7-tetrahydro-1H-indazol-1-yl]benzamide (Example 38)

N-methyl-N-(1,3-thiazol-2-ylmethyl)-4-[3-(trifluoromethyl)-4,5,6,7-tetrahydro-1H-indazol-1-yl]benzamide (Example 39)

N-methyl-N-[2-(1-methyl-1H-pyrrol-2-yl)ethyl]-4-[3-(trifluoromethyl)-4,5,6,7-tetrahydro-1H-indazol-1-yl]benzamide (Example 40)

N-methyl-N-(2-thienylmethyl)-4-[3-(trifluoromethyl)-4,5,6,7-tetrahydro-1H-indazol-1-yl]benzamide (Example 41)

N-methyl-N-(3-pyridinylmethyl)-4-[3-(trifluoromethyl)-4,5,6,7-tetrahydro-1H-indazol-1-yl]benzamide (Example 42)

N-(2-furanyl methyl)-N-methyl-4-[3-(trifluoromethyl)-4,5,6,7-tetrahydro-1H-indazol-1-yl]benzamide (Example 43)

N-[(4-fluorophenyl)methyl]-N-methyl-4-[3-(trifluoromethyl)-4,5,6,7-tetrahydro-1H-indazol-1-yl]benzamide (Example 44)

1-[4-(4-morpholinylcarbonyl)phenyl]-3-(trifluoromethyl)-4,5,6,7-tetrahydro-1H-indazole (Example 45)

N-({4-[3-(trifluoromethyl)-4,5,6,7-tetrahydro-1H-indazol-1-yl]phenyl}methyl)methanesulfonamide (Example 46)

and salts and solvates thereof.

In one embodiment, the compound is selected from the group consisting of:

1. 1-{4-[1-fluoro-2-oxo-2-(1-pyrrolidinyl)ethyl]phenyl}-3-(trifluoromethyl)-4,5,6,7-tetrahydro-1H-indazole
2. 1-{4-[1,1-difluoro-2-oxo-2-(1-pyrrolidinyl)ethyl]phenyl}-3-(trifluoromethyl)-4,5,6,7-tetrahydro-1H-indazole
3. N-methyl-N-({4-[3-(trifluoromethyl)-4,5,6,7-tetrahydro-1H-indazol-1-yl]phenyl}methyl)methanesulfonamide
4. 1-(4-{[3-(trifluoromethyl)-4,5,6,7-tetrahydro-1H-indazol-1-yl]methyl}phenyl)-2-pyrrolidinone
5. N-methyl-N-({4-[3-(trifluoromethyl)-4,5,6,7-tetrahydro-1H-indazol-1-yl]phenyl}methyl)-1-pyrrolidinecarboxamide
6. 5-{4-[3-(trifluoromethyl)-4,5,6,7-tetrahydro-1H-indazol-1-yl]phenyl}-2-pyrrolidinone
7. N-(1-{4-[3-(trifluoromethyl)-4,5,6,7-tetrahydro-1H-indazol-1-yl]phenyl}ethyl)acetamide
8. N-methyl-N-(1-{4-[3-(trifluoromethyl)-4,5,6,7-tetrahydro-1H-indazol-1-yl]phenyl}ethyl)acetamide
9. 1-[4-(1-acetyl-2-pyrrolidinyl)phenyl]-3-(trifluoromethyl)-4,5,6,7-tetrahydro-1H-indazole
10. 1-(2-{4-[3-(trifluoromethyl)-4,5,6,7-tetrahydro-1H-indazol-1-yl]phenyl}ethyl)-2-pyrrolidinone
11. 1-{4-[(1,1-dioxido-2-isothiazolidinyl)methyl]phenyl}-3-(trifluoromethyl)-4,5,6,7-tetrahydro-1H-indazole
12. 2-methyl-N-({4-[3-(trifluoromethyl)-4,5,6,7-tetrahydro-1H-indazol-1-yl]phenyl}methyl)propanamide
13. N-({4-[3-(trifluoromethyl)-4,5,6,7-tetrahydro-1H-indazol-1-yl]phenyl}methyl)butanamide
14. N-({4-[3-(trifluoromethyl)-4,5,6,7-tetrahydro-1H-indazol-1-yl]phenyl}methyl)-2-thiophenecarboxamide
15. N-({4-[3-(trifluoromethyl)-4,5,6,7-tetrahydro-1H-indazol-1-yl]phenyl}methyl)propanamide
16. N-({4-[3-(trifluoromethyl)-4,5,6,7-tetrahydro-1H-indazol-1-yl]phenyl}methyl)acetamide
17. N-methyl-2-phenyl-N-({4-[3-(trifluoromethyl)-4,5,6,7-tetrahydro-1H-indazol-1-yl]phenyl}methyl)acetamide
18. N-(2-hydroxyethyl)-N-methyl-4-[3-(trifluoromethyl)-4,5,6,7-tetrahydro-1H-indazol-1-yl]benzamide
19. N-methyl-N-[2-(methyloxy)ethyl]-4-[3-(trifluoromethyl)-4,5,6,7-tetrahydro-1H-indazol-1-yl]benzamide
20. N-methyl-N-[2-(methylamino)ethyl]-4-[3-(trifluoromethyl)-4,5,6,7-tetrahydro-1H-indazol-1-yl]benzamide
21. 1-({4-[3-(trifluoromethyl)-4,5,6,7-tetrahydro-1H-indazol-1-yl]phenyl}carbonyl)-3-pyrrolidinol
22. N-methyl-1-({4-[3-(trifluoromethyl)-4,5,6,7-tetrahydro-1H-indazol-1-yl]phenyl}carbonyl)-3-pyrrolidinamine
23. 1-[4-(1-azetidinylcarbonyl)phenyl]-3-(trifluoromethyl)-4,5,6,7-tetrahydro-1H-indazole
24. 1-({4-[3-(trifluoromethyl)-4,5,6,7-tetrahydro-1H-indazol-1-yl]phenyl}carbonyl)-3-azetidinol
25. (3,3-difluorocyclobutyl){4-[3-(trifluoromethyl)-4,5,6,7-tetrahydro-1H-indazol-1-yl]phenyl}methanone
26. 1-[4-(1H-imidazol-1-yl)phenyl]-3-(trifluoromethyl)-4,5,6,7-tetrahydro-1H-indazole
27. N-({4-[3-(trifluoromethyl)-4,5,6,7-tetrahydro-1H-indazol-1-yl]phenyl}methyl)-2-propenamide 28. N-(1-methylethenyl)-N-({4-[3-(trifluoromethyl)-4,5,6,7-tetrahydro-1H-indazol-1-yl]phenyl}methyl)-2-propenamide
29. N-methyl-N-({4-[3-(trifluoromethyl)-4,5,6,7-tetrahydro-1H-indazol-1-yl]phenyl}methyl)-2-propenamide
30. 1-{4-[(3-methyl-1,2,4-oxadiazol-5-yl)methyl]phenyl}-3-(trifluoromethyl)-4,5,6,7-tetrahydro-1H-indazole
31. 1-{4-[(3-cyclopropyl-1,2,4-oxadiazol-5-yl)methyl]phenyl}-3-(trifluoromethyl)-4,5,6,7-tetrahydro-1H-indazole
32. N-ethyl-4-[3-(trifluoromethyl)-4,5,6,7-tetrahydro-1H-indazol-1-yl]benzamide
33. N-methyl-N-(1-methylethyl)-4-[3-(trifluoromethyl)-4,5,6,7-tetrahydro-1H-indazol-1-yl]benzamide
34. 1-[4-(1-piperidinylcarbonyl)phenyl]-3-(trifluoromethyl)-4,5,6,7-tetrahydro-1H-indazole
35. N,N-diethyl-4-[3-(trifluoromethyl)-4,5,6,7-tetrahydro-1H-indazol-1-yl]benzamide
36. N-methyl-4-[3-(trifluoromethyl)-4,5,6,7-tetrahydro-1H-indazol-1-yl]benzamide
37. 1-{4-[2-oxo-2-(2-phenyl-1-pyrrolidinyl)ethyl]phenyl}-3-(trifluoromethyl)-4,5,6,7-tetrahydro-1H-indazole
38. N-methyl-N-({4-[3-(trifluoromethyl)-4,5,6,7-tetrahydro-1H-indazol-1-yl]phenyl}methyl)benzamide
39. 1-[4-(1,3-oxazol-5-yl)phenyl]-3-(trifluoromethyl)-4,5,6,7-tetrahydro-1H-indazole
40. 1-[4-(propyloxy)phenyl]-3-(trifluoromethyl)-4,5,6,7-tetrahydro-1H-indazole
41. 1-[4-(1-methyl-1H-imidazol-4-yl)phenyl]-3-(trifluoromethyl)-4,5,6,7-tetrahydro-1H-indazole
42. N-({4-[3-(trifluoromethyl)-4,5,6,7-tetrahydro-1H-indazol-1-yl]phenyl}methyl)-2-propanesulfonamide
43. N-({4-[3-(trifluoromethyl)-4,5,6,7-tetrahydro-1H-indazol-1-yl]phenyl}methyl)cyclopropanesulfonamide
44. N-({4-[3-(trifluoromethyl)-4,5,6,7-tetrahydro-1H-indazol-1-yl]phenyl}methyl)cyclopentanesulfonamide
45. 1-[4-(1-pyrrolidinylsulfonyl)phenyl]-3-(trifluoromethyl)-4,5,6,7-tetrahydro-1H-indazole
46. N-(2-methylpropyl)-4-[3-(trifluoromethyl)-4,5,6,7-tetrahydro-1H-indazol-1-yl]benzenesulfonamide
47. 1-[4-(4-morpholinylsulfonyl)phenyl]-3-(trifluoromethyl)-4,5,6,7-tetrahydro-1H-indazole
48. N-[2-(methyloxy)ethyl]-4-[3-(trifluoromethyl)-4,5,6,7-tetrahydro-1H-indazol-1-yl]benzenesulfonamide
49. N-[2-(1-pyrrolidinyl)ethyl]-4-[3-(trifluoromethyl)-4,5,6,7-tetrahydro-1H-indazol-1-yl]benzenesulfonamide
50. N-(tetrahydro-2-furanylmethyl)-4-[3-(trifluoromethyl)-4,5,6,7-tetrahydro-1H-indazol-1-yl]benzenesulfonamide
51. 1-[4-(1H-imidazol-1-ylmethyl)phenyl]-3-(trifluoromethyl)-4,5,6,7-tetrahydro-1H-indazole
52. 1-[4-(1H-1,2,4-triazol-1-ylmethyl)phenyl]-3-(trifluoromethyl)-4,5,6,7-tetrahydro-1H-indazole
53. 1-[4-(1H-pyrazol-1-ylmethyl)phenyl]-3-(trifluoromethyl)-4,5,6,7-tetrahydro-1H-indazole
54. 1-[4-(1H-1,2,3-triazol-1-ylmethyl)phenyl]-3-(trifluoromethyl)-4,5,6,7-tetrahydro-1H-indazole
55. 1-[4-(2H-1,2,3-triazol-2-ylmethyl)phenyl]-3-(trifluoromethyl)-4,5,6,7-tetrahydro-1H-indazole
56. 1-{4-[(4-methyl-1H-pyrazol-1-yl)methyl]phenyl}-3-(trifluoromethyl)-4,5,6,7-tetrahydro-1H-indazole
57. 1-{4-[(3,5-dimethyl-1H-pyrazol-1-yl)methyl]phenyl}-3-(trifluoromethyl)-4,5,6,7-tetrahydro-1H-indazole
58. 3-(trifluoromethyl)-1-(4-{[3-(trifluoromethyl)-1H-pyrazol-1-yl]methyl}phenyl)-4,5,6,7-tetrahydro-1H-indazole
59. 3-(trifluoromethyl)-1-(4-{[5-(trifluoromethyl)-1H-pyrazol-1-yl]methyl}phenyl)-4,5,6,7-tetrahydro-1H-indazole
60. 1-(4-{[5-methyl-3-(trifluoromethyl)-1H-pyrazol-1-yl]methyl}phenyl)-3-(trifluoromethyl)-4,5,6,7-tetrahydro-1H-indazole
61. 1-(4-{[3-methyl-5-(trifluoromethyl)-1H-pyrazol-1-yl]methyl}phenyl)-3-(trifluoromethyl)-4,5,6,7-tetrahydro-1H-indazole
62. 1-{4-[(2-methyl-1H-imidazol-1-yl)methyl]phenyl}-3-(trifluoromethyl)-4,5,6,7-tetrahydro-1H-indazole
63. 1-(4-{[2-(1-methylethyl)-1H-imidazol-1-yl]methyl}phenyl)-3-(trifluoromethyl)-4,5,6,7-tetrahydro-1H-indazole
64. 1-{4-[(4-phenyl-1H-imidazol-1-yl)methyl]phenyl}-3-(trifluoromethyl)-4,5,6,7-tetrahydro-1H-indazole
65. 1-{4-[(4-bromo-1H-pyrazol-1-yl)methyl]phenyl}-3-(trifluoromethyl)-4,5,6,7-tetrahydro-1H-indazole
66. N-methyl-1H-imidazol-2-yl){4-[3-(trifluoromethyl)-4,5,6,7-tetrahydro-1H-indazol-1-yl]phenyl}methanone
67. N-methyl-N-{4-[3-(trifluoromethyl)-4,5,6,7-tetrahydro-1H-indazol-1-yl]phenyl}-1-pyrrolidinecarboxamide and salts and solvates thereof.

The present invention also provides a compound of formula (A), or a salt, or solvate thereof:

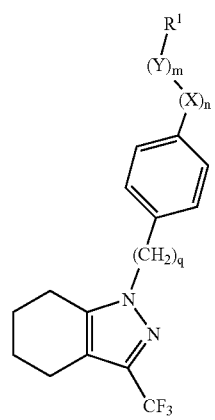

(A)

wherein:
q is 0 or 1;
n is 0, 1, or 2;
X is $CR^6R^7$, where $R^6$ and $R^7$ are each independently selected from the group consisting of hydrogen, methyl and fluoro, but $R^6$ and $R^7$ are not both simultaneously methyl; or, when n is 1, $R^6$ and $R^7$ together with the carbon atom to which they are attached, form a 3-membered carbocyclic ring;
Y is selected from the group consisting of CO, $NR^8CO$, SO, $SO_2$ and $NR^8SO_2$;
$R^8$ is selected from the group consisting of hydrogen, $C_{2-4}$alkenyl and $C_{1-4}$alkyl;
m is 0 or 1; and
a) when n is 0 and m=1, then $R^1$ is selected from the group consisting of (i) $C_{1-4}$alkyl, (ii) a C-linked 5-membered aromatic heterocyclic group optionally substituted with methyl, (iii) $NHR^2$ and (iv) $NR^2R^3$, wherein:
$R^2$ is selected from the group consisting of $C_{1-6}$straight chain alkyl, $C_{4-6}$branched chain alkyl and a group $-(CH_2)_pZ$ wherein p is 1, 2 or 3;
Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$alkyl; wherein when Y is CO, $R^2$ is not $(CH_2)_2$pyrrolidinyl;

$R^{2'}$ is selected from the group consisting of methyl and ethyl;

$R^3$ is selected from the group consisting of $C_{1-4}$alkyl and a group —$(CH_2)_pZ'$ wherein p is 1, 2 or 3;

Z' is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl; or $R^{2'}$ and $R^3$, together with the nitrogen atom to which they are attached, form:
  (i) a 4 or 5-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto; or
  (ii) a 6-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto;

b) when n and m are both simultaneously 0, $R^1$ is selected from the group consisting of:
$C_{1-6}$alkoxy;
a monocyclic saturated or partially unsaturated 5- or 6-membered heterocyclic group, attached through a carbon atom and optionally substituted by one, two or three groups independently selected from the group consisting of $C_{1-4}$alkyl, $C(O)C_{1-4}$alkyl, halo$C_{1-4}$alkyl, halo and keto;
N-linked pyrrolidinyl, optionally substituted with one, two or three groups independently selected from the group consisting of $C_{1-4}$alkyl, $C(O)C_{1-4}$alkyl, halo $C_{1-4}$alkyl, halo and keto; and
oxazolyl or imidazolyl, both being optionally substituted by $C_{1-4}$alkyl;

c) when n is 1 or 2, and m is 1, $R^1$ is selected from the group consisting of $C_{1-4}$alkyl, benzyl, cyclopropyl, thienyl, and $NR^9R^{10}$ wherein:

$R^9$ is selected from the group consisting of hydrogen and $C_{1-4}$alkyl, and $R^{10}$ is selected from the group consisting of $C_{1-6}$ straight chain alkyl, $C_{3-6}$cycloalkyl and —$(CH_2)_pZ$ wherein p is 1, 2 or 3;

Z is a phenyl or a 5- or 6-membered heterocyclic group, the phenyl or heterocyclic group being optionally substituted by one, two or three groups independently selected from the group consisting of halo and $C_{1-4}$alkyl; or $R^9$ and $R^{10}$, together with the nitrogen atom to which they are attached, form a 5-membered aromatic or non-aromatic heterocyclic group or a 6-membered non-aromatic heterocyclic group, any of the rings being optionally substituted by one, two or three groups independently selected from the group consisting of $C_{1-4}$alkyl, halo, phenyl and (in the case of a non-aromatic ring) keto; and d) when n is 1 or 2, and m is 0, $R^1$ is selected from the group consisting of cyano, hydroxy, $NH_2$, a C-linked 5-membered aromatic heterocyclic group optionally substituted with one, two or three groups independently selected from the group consisting of $C_{1-6}$alkyl and $C_{3-6}$cycloalkyl, and $NR^{11}R^{12}$ in which:

$R^{11}$ is hydrogen and $R^{12}$ is selected from the group consisting of $SO_2C_{1-4}$alkyl, $SO_2C_{3-6}$cycloalkyl, $C(O)C_{1-4}$alkyl, and $C(O)C_{2-4}$alkenyl; or $R^{11}$ is selected from the group consisting of $C_{1-4}$alkyl and $C_{2-4}$alkenyl, and $R^{12}$ is selected from the group consisting of $SO_2C_{1-4}$alkyl, $SO_2C_{3-6}$cycloalkyl, $C(O)C_{1-4}$alkyl, $C(O)$phenyl and $C(O)C_{2-4}$alkenyl or $R^{11}$ and $R^{12}$, together with the nitrogen atom to which they are attached, form a group selected from the group consisting of:
  (i) a 5-membered aromatic heterocyclic group which is optionally substituted by one or two groups independently selected from the group consisting of $C_{1-4}$alkyl, halo, halo$C_{1-4}$alkyl, hydroxy, $C_{3-6}$cycloalkyl and $C_{1-4}$alkoxy; and
  (ii) imidazolyl substituted by phenyl;
  (iii) a 5-membered non-aromatic heterocyclic group which is substituted by one, two or three groups independently selected from the group consisting of keto, hydroxy and $C_{1-4}$alkoxy; and
  (iv) a 6-membered non-aromatic heterocyclic group, which is optionally substituted by one, two or three groups independently selected from the group consisting of keto, hydroxy and $C_{1-4}$alkoxy;

with the proviso that the compound is not 4-methyl-N-[4-[4,5,6,7-tetrahydro-3-(trifluoromethyl)-1H-indazol-1-yl]phenyl]-1,2,3-thiadiazole-5-carboxamide and salts thereof, or a compound in which simultaneously n=0, m=1, q=0, Y=CO and $R^1$ is selected from the group consisting of: $NMe_2$, pyrrolidinyl, $NMeCH_2Ph$, morpholinyl, piperidyl, NHEt, $NEt_2$, NHMe, $NHCH_2$-tetrahydrofuran-2-yl, $NH(CH_2)_2Ph$, $NH(CH_2)Ph$, NHtBu, $NHCH_2$-furan-2-yl and $NH(CH_2)_3OMe$.

Examples of compounds of formula (A) include:
N,N-dimethyl-4-[3-(trifluoromethyl)-4,5,6,7-tetrahydro-1H-indazol-1-yl]benzamide (Example 1)
N-ethyl-N-methyl-4-[3-(trifluoromethyl)-4,5,6,7-tetrahydro-1H-indazol-1-yl]benzamide (Example 4)
N-butyl-N-methyl-4-[3-(trifluoromethyl)-4,5,6,7-tetrahydro-1H-indazol-1-yl]benzamide (Example 5)
N-methyl-N-(2-phenylethyl)-4-[3-(trifluoromethyl)-4,5,6,7-tetrahydro-1H-indazol-1-yl]benzamide (Example 6)
N,N-dimethyl-4-[3-(trifluoromethyl)-4,5,6,7-tetrahydro-1H-indazol-1-yl]benzenesulfonamide (Example 7)
1-{4-[3-(trifluoromethyl)-4,5,6,7-tetrahydro-1H-indazol-1-yl]phenyl}ethanone (Example 8)
1-{4-[3-(trifluoromethyl)-4,5,6,7-tetrahydro-1H-indazol-1-yl]phenyl}-1-propanone (Example 9)
1-[4-(methylsulfonyl)phenyl]-3-(trifluoromethyl)-4,5,6,7-tetrahydro-1H-indazole (Example 10)
1-{4-[3-(trifluoromethyl)-4,5,6,7-tetrahydro-1H-indazol-1-yl]phenyl}-2-propanone (Example 11)
N,N-dimethyl-2-{4-[3-(trifluoromethyl)-4,5,6,7-tetrahydro-1H-indazol-1-yl]phenyl}acetamide (Example 12)
1-{4-[2-oxo-2-(1-pyrrolidinyl)ethyl]phenyl}-3-(trifluoromethyl)-4,5,6,7-tetrahydro-1H-indazole (Example 13)
N-ethyl-N-methyl-2-{4-[3-(trifluoromethyl)-4,5,6,7-tetrahydro-1H-indazol-1-yl]phenyl}acetamide (Example 14)
N-methyl-N-(phenylmethyl)-2-{4-[3-(trifluoromethyl)-4,5,6,7-tetrahydro-1H-indazol-1-yl]phenyl}acetamide (Example 15)
N-butyl-N-methyl-2-{4-[3-(trifluoromethyl)-4,5,6,7-tetrahydro-1H-indazol-1-yl]phenyl}acetamide (Example 16)

N-methyl-N-(2-phenylethyl)-2-{4-[3-(trifluoromethyl)-4,5,6,7-tetrahydro-1H-indazol-1-yl]phenyl}acetamide (Example 17)

1-{[4-(1-pyrrolidinylcarbonyl)phenyl]methyl}-3-(trifluoromethyl)-4,5,6,7-tetrahydro-1H-indazole (Example 18)

1-{4-[1-methyl-2-oxo-2-(1-pyrrolidinyl)ethyl]phenyl}-3-(trifluoromethyl)-4,5,6,7-tetrahydro-1H-indazole (Example 19)

N,N-dimethyl-3-{4-[3-(trifluoromethyl)-4,5,6,7-tetrahydro-1H-indazol-1-yl]phenyl}propanamide (Example 20)

1-{4-[3-oxo-3-(1-pyrrolidinyl)propyl]phenyl}-3-(trifluoromethyl)-4,5,6,7-tetrahydro-1H-indazole (Example 21)

1-{4-[1-(1-pyrrolidinylcarbonyl)cyclopropyl]phenyl}-3-(trifluoromethyl)-4,5,6,7-tetrahydro-1H-indazole (Example 22)

1-{4-[2-oxo-2-(1-piperidinyl)ethyl]phenyl}-3-(trifluoromethyl)-4,5,6,7-tetrahydro-1H-indazole (Example 23)

1-{4-[2-(3,3-difluoro-1-pyrrolidinyl)-2-oxoethyl]phenyl}-3-(trifluoromethyl)-4,5,6,7-tetrahydro-1H-indazole (Example 24)

N-methyl-N-propyl-2-{4-[3-(trifluoromethyl)-4,5,6,7-tetrahydro-1H-indazol-1-yl]phenyl}acetamide (Example 25)

N-cyclopentyl-2-{4-[3-(trifluoromethyl)-4,5,6,7-tetrahydro-1H-indazol-1-yl]phenyl}acetamide (Example 26)

N-methyl-N-(2-thienylmethyl)-2-{4-[3-(trifluoromethyl)-4,5,6,7-tetrahydro-1H-indazol-1-yl]phenyl}acetamide (Example 27)

{4-[3-(trifluoromethyl)-4,5,6,7-tetrahydro-1H-indazol-1-yl]phenyl}acetonitrile (Example 28)

{4-[3-(trifluoromethyl)-4,5,6,7-tetrahydro-1H-indazol-1-yl]phenyl}methanol (Example 29)

N-methyl-N-({4-[3-(trifluoromethyl)-4,5,6,7-tetrahydro-1H-indazol-1-yl]phenyl}methyl)acetamide (Example 30)

1-({4-[3-(trifluoromethyl)-4,5,6,7-tetrahydro-1H-indazol-1-yl]phenyl}methyl)-2-pyrrolidinone (Example 31)

N-methyl-N-({4-[3-(trifluoromethyl)-4,5,6,7-tetrahydro-1H-indazol-1-yl]phenyl}methyl)propanamide (Example 32)

N-ethyl-N-({4-[3-(trifluoromethyl)-4,5,6,7-tetrahydro-1H-indazol-1-yl]phenyl}methyl)acetamide (Example 33)

1-({4-[3-(trifluoromethyl)-4,5,6,7-tetrahydro-1H-indazol-1-yl]phenyl}methyl)-2-piperidinone (Example 34)

1-methyl-5-{4-[3-(trifluoromethyl)-4,5,6,7-tetrahydro-1H-indazol-1-yl]phenyl}-2-pyrrolidinone (Example 35)

N-[3-(1H-imidazol-1-yl)propyl]-N-methyl-4-[3-(trifluoromethyl)-4,5,6,7-tetrahydro-1H-indazol-1-yl]benzamide (Example 36)

N-methyl-N-[2-(2-thienyl)ethyl]-4-[3-(trifluoromethyl)-4,5,6,7-tetrahydro-1H-indazol-1-yl]benzamide (Example 37)

N-methyl-N-[2-(1H-1,2,4-triazol-1-yl)ethyl]-4-[3-(trifluoromethyl)-4,5,6,7-tetrahydro-1H-indazol-1-yl]benzamide (Example 38)

N-methyl-N-(1,3-thiazol-2-ylmethyl)-4-[3-(trifluoromethyl)-4,5,6,7-tetrahydro-1H-indazol-1-yl]benzamide (Example 39)

N-methyl-N-[2-(1-methyl-1H-pyrrol-2-yl)ethyl]-4-[3-(trifluoromethyl)-4,5,6,7-tetrahydro-1H-indazol-1-yl]benzamide (Example 40)

N-methyl-N-(2-thienylmethyl)-4-[3-(trifluoromethyl)-4,5,6,7-tetrahydro-1H-indazol-1-yl]benzamide (Example 41)

N-methyl-N-(3-pyridinylmethyl)-4-[3-(trifluoromethyl)-4,5,6,7-tetrahydro-1H-indazol-1-yl]benzamide (Example 42)

N-(2-furanyl methyl)-N-methyl-4-[3-(trifluoromethyl)-4,5,6,7-tetrahydro-1H-indazol-1-yl]benzamide (Example 43)

N-[(4-fluorophenyl)methyl]-N-methyl-4-[3-(trifluoromethyl)-4,5,6,7-tetrahydro-1H-indazol-1-yl]benzamide (Example 44)

N-({4-[3-(trifluoromethyl)-4,5,6,7-tetrahydro-1H-indazol-1-yl]phenyl}methyl)methanesulfonamide (Example 46)

1-{4-[1-fluoro-2-oxo-2-(1-pyrrolidinyl)ethyl]phenyl}-3-(trifluoromethyl)-4,5,6,7-tetrahydro-1H-indazole 1-{4-[,1-difluoro-2-oxo-2-(1-pyrrolidinyl)ethyl]phenyl}-3-(trifluoromethyl)-4,5,6,7-tetrahydro-1H-indazole N-methyl-N-({4-[3-(trifluoromethyl)-4,5,6,7-tetrahydro-1H-indazol-1-yl]phenyl}methyl)methanesulfonamide 1-(4-{[3-(trifluoromethyl)-4,5,6,7-tetrahydro-1H-indazol-1-yl]methyl}phenyl)-2-pyrrolidinone N-methyl-N-({4-[3-(trifluoromethyl)-4,5,6,7-tetrahydro-1H-indazol-1-yl]phenyl}methyl)-1-pyrrolidinecarboxamide 5-{4-[3-(trifluoromethyl)-4,5,6,7-tetrahydro-1H-indazol-1-yl]phenyl}-2-pyrrolidinone N-(1-{4-[3-(trifluoromethyl)-4,5,6,7-tetrahydro-1H-indazol-1-yl]phenyl}ethyl)acetamide N-methyl-N-(1-{4-[3-(trifluoromethyl)-4,5,6,7-tetrahydro-1H-indazol-1-yl]phenyl}ethyl)acetamide 1-[4-(1-acetyl-2-pyrrolidinyl)phenyl]-3-(trifluoromethyl)-4,5,6,7-tetrahydro-1H-indazole 1-(2-{4-[3-(trifluoromethyl)-4,5,6,7-tetrahydro-1H-indazol-1-yl]phenyl}ethyl)-2-pyrrolidinone 1-{4-[(1,1-dioxido-2-isothiazolidinyl)methyl]phenyl}-3-(trifluoromethyl)-4,5,6,7-tetrahydro-1H-indazole 2-methyl-N-({4-[3-(trifluoromethyl)-4,5,6,7-tetrahydro-1H-indazol-1-yl]phenyl}methyl)propanamide N-({4-[3-(trifluoromethyl)-4,5,6,7-tetrahydro-1H-indazol-1-yl]phenyl}methyl)butanamide N-({4-[3-(trifluoromethyl)-4,5,6,7-tetrahydro-1H-indazol-1-yl]phenyl}methyl)-2-thiophenecarboxamide N-({4-[3-(trifluoromethyl)-4,5,6,7-tetrahydro-1H-indazol-1-yl]phenyl}methyl)propanamide N-({4-[3-(trifluoromethyl)-4,5,6,7-tetrahydro-1H-indazol-1-yl]phenyl}methyl)acetamide N-methyl-2-phenyl-N-({4-[3-(trifluoromethyl)-4,5,6,7-tetrahydro-1H-indazol-1-yl]phenyl}methyl)acetamide N-(2-hydroxyethyl)-N-methyl-4-[3-(trifluoromethyl)-4,5,6,7-tetrahydro-1H-indazol-1-yl]benzamide N-methyl-N-[2-(methyloxy)ethyl]-4-[3-(trifluoromethyl)-4,5,6,7-tetrahydro-1H-indazol-1-yl]benzamide N-methyl-N-[2-(methylamino)ethyl]-4-[3-(trifluoromethyl)-4,5,6,7-tetrahydro-1H-indazol-1-yl]benzamide 1-({4-[3-(trifluoromethyl)-4,5,6,7-tetrahydro-1H-indazol-1-yl]phenyl}carbonyl)-3-pyrrolidinol N-methyl-1-({4-[3-(trifluoromethyl)-4,5,6,7-tetrahydro-1H-indazol-1-yl]phenyl}carbonyl)-3-pyrrolidinamine 1-[4-(1-azetidinylcarbonyl)phenyl]-3-(trifluoromethyl)-4,5,6,7-tetrahydro-1H-indazole 1-({4-[3-(trifluoromethyl)-4,5,6,7-tetrahydro-1H-indazol-1-yl]phenyl}carbonyl)-3-azetidinol (3,3-difluorocyclobutyl){4-[3-(trifluoromethyl)-4,5,6,7-tetrahydro-1H-indazol-1-yl]phenyl}methanone 1-[4-(1H-imidazol-1-yl)phenyl]-3-(trifluoromethyl)-4,5,6,7-tetrahydro-1H-indazole N-({4-[3-(trifluoromethyl)-4,5,6,7-tetrahydro-1H-indazol-1-yl]phenyl}methyl)-2-propenamide N-(1-methylethenyl)-N-({4-[3-(trifluoromethyl)-4,5,6,7-tetrahydro-1H-indazol-1-yl]phenyl}methyl)-2-propenamide N-methyl-N-({4-[3-(trifluoromethyl)-4,5,6,7-tetrahydro-1H-indazol-1-yl]phenyl}methyl)-2-propenamide 1-{4-[(3-methyl-1,2,4-oxadiazol-5-yl)methyl]phenyl}-3-(trifluoromethyl)-4,5,6,7-tetrahydro-1H-indazole 1-{4-[(3-cyclopropyl-1,2,4-oxadiazol-5-yl)methyl]phenyl}-3-(trifluoromethyl)-4,5,6,7-tetrahydro-1H-indazole
N-methyl-N-(1-methylethyl)-4-[3-(trifluoromethyl)-4,5,6,7-tetrahydro-1H-indazol-1-yl]benzamide
1-{4-[2-oxo-2-(2-phenyl-1-pyrrolidinyl)ethyl]phenyl}-3-(trifluoromethyl)-4,5,6,7-tetrahydro-1H-indazole
N-methyl-N-({4-[3-(trifluoromethyl)-4,5,6,7-tetrahydro-1H-indazol-1-yl]phenyl}methyl)benzamide
1-[4-(1,3-oxazol-5-yl)phenyl]-3-(trifluoromethyl)-4,5,6,7-tetrahydro-1H-indazole
1-[4-(propyloxy)phenyl]-3-(trifluoromethyl)-4,5,6,7-tetrahydro-1H-indazole
1-[4-(1-methyl-1H-imidazol-4-yl)phenyl]-3-(trifluoromethyl)-4,5,6,7-tetrahydro-1H-indazole
N-({4-[3-(trifluoromethyl)-4,5,6,7-tetrahydro-1H-indazol-1-yl]phenyl}methyl)-2-propanesulfonamide
N-({4-[3-(trifluoromethyl)-4,5,6,7-tetrahydro-1H-indazol-1-yl]phenyl}methyl)cyclopropanesulfonamide
N-({4-[3-(trifluoromethyl)-4,5,6,7-tetrahydro-1H-indazol-1-yl]phenyl}methyl)cyclopentanesulfonamide
1-[4-(1-pyrrolidinylsulfonyl)phenyl]-3-(trifluoromethyl)-4,5,6,7-tetrahydro-1H-indazole
N-(2-methylpropyl)-4-[3-(trifluoromethyl)-4,5,6,7-tetrahydro-1H-indazol-1-yl]benzenesulfonamide
1-[4-(4-morpholinylsulfonyl)phenyl]-3-(trifluoromethyl)-4,5,6,7-tetrahydro-1H-indazole
N-[2-(methyloxy)ethyl]-4-[3-(trifluoromethyl)-4,5,6,7-tetrahydro-1H-indazol-1-yl]benzenesulfonamide
N-[2-(1-pyrrolidinyl)ethyl]-4-[3-(trifluoromethyl)-4,5,6,7-tetrahydro-1H-indazol-1-yl]benzenesulfonamide
N-(tetrahydro-2-furanylmethyl)-4-[3-(trifluoromethyl)-4,5,6,7-tetrahydro-1H-indazol-1-yl]benzenesulfonamide
1-[4-(1H-imidazol-1-ylmethyl)phenyl]-3-(trifluoromethyl)-4,5,6,7-tetrahydro-1H-indazole
1-[4-(1H-1,2,4-triazol-1-ylmethyl)phenyl]-3-(trifluoromethyl)-4,5,6,7-tetrahydro-1H-indazole
1-[4-(1H-pyrazol-1-ylmethyl)phenyl]-3-(trifluoromethyl)-4,5,6,7-tetrahydro-1H-indazole
1-[4-(1H-1,2,3-triazol-1-ylmethyl)phenyl]-3-(trifluoromethyl)-4,5,6,7-tetrahydro-1H-indazole
1-[4-(2H-1,2,3-triazol-2-ylmethyl)phenyl]-3-(trifluoromethyl)-4,5,6,7-tetrahydro-1H-indazole
1-{4-[(4-methyl-1H-pyrazol-1-yl)methyl]phenyl}-3-(trifluoromethyl)-4,5,6,7-tetrahydro-1H-indazole
1-{4-[(3,5-dimethyl-1H-pyrazol-1-yl)methyl]phenyl}-3-(trifluoromethyl)-4,5,6,7-tetrahydro-1H-indazole
3-(trifluoromethyl)-1-(4-{[3-(trifluoromethyl)-1H-pyrazol-1-yl]methyl}phenyl)-4,5,6,7-tetrahydro-1H-indazole
3-(trifluoromethyl)-1-(4-{[5-(trifluoromethyl)-1H-pyrazol-1-yl]methyl}phenyl)-4,5,6,7-tetrahydro-1H-indazole
1-(4-{[5-methyl-3-(trifluoromethyl)-1H-pyrazol-1-yl]methyl}phenyl)-3-(trifluoromethyl)-4,5,6,7-tetrahydro-1H-indazole
1-(4-{[3-methyl-5-(trifluoromethyl)-1H-pyrazol-1-yl]methyl}phenyl)-3-(trifluoromethyl)-4,5,6,7-tetrahydro-1H-indazole
1-{4-[(2-methyl-1H-imidazol-1-yl)methyl]phenyl}-3-(trifluoromethyl)-4,5,6,7-tetrahydro-1H-indazole
1-(4-{[2-(1-methylethyl)-1H-imidazol-1-yl]methyl}phenyl)-3-(trifluoromethyl)-4,5,6,7-tetrahydro-1H-indazole
1-{4-[(4-phenyl-1H-imidazol-1-yl)methyl]phenyl}-3-(trifluoromethyl)-4,5,6,7-tetrahydro-1H-indazole
1-{4-[(4-bromo-1H-pyrazol-1-yl)methyl]phenyl}-3-(trifluoromethyl)-4,5,6,7-tetrahydro-1H-indazole
N-methyl-1H-imidazol-2-yl){4-[3-(trifluoromethyl)-4,5,6,7-tetrahydro-1H-indazol-1-yl]phenyl}methanone and
N-methyl-N-{4-[3-(trifluoromethyl)-4,5,6,7-tetrahydro-1H-indazol-1-yl]phenyl}-1-pyrrolidinecarboxamide.

In one embodiment, a compound of formula (I) is a compound in which n=0 and m=1, that is to say a compound of formula (Ia), in which q, Y and $R^1$ are as set out for formula (I) above, excluding 4-methyl-N-[4-[4,5,6,7-tetrahydro-3-(trifluoromethyl)-1H-indazol-1-yl]phenyl]-1,2,3-thiadiazole-5-carboxamide and salts and solvates thereof:

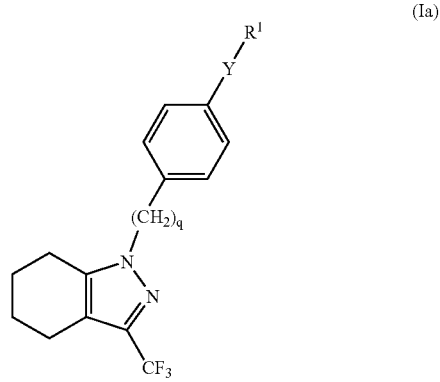

(Ia)

In one embodiment, in formula (Ia), q is 0.

In one embodiment, in formula (Ia), Y is selected from the group consisting of CO, $SO_2$ and NMeCO. In one embodiment, Y is CO or $SO_2$. In a further embodiment, Y is CO.

In one embodiment, in formula (Ia), $R^1$ is $C_{1-4}$alkyl.

In one embodiment, in formula (Ia), $R^1$ is a C-linked 5-membered aromatic heterocyclic group optionally substituted by methyl. In one embodiment, in formula (Ia), $R^1$ is selected from the group consisting of pyrrolyl, pyrrolinyl, pyrazolinyl, oxazolyl, isoxazoyl, imidazolyl, pyrazolyl, oxadiazolyl, isothiazolyl, thiazolyl, triazolyl, furyl and thienyl, each group being optionally substituted by methyl. In one embodiment, in formula (Ia), $R^1$ is imidazolyl optionally substituted with methyl.

In one embodiment, in formula (Ia), $R^1$ is a group $NHR^2$ wherein $R^2$ is selected from the group consisting of $C_{1-6}$straight chain alkyl and $C_{4-6}$branched chain alkyl.

In one embodiment, in formula (Ia), $R^1$ is a group $NHR^2$ wherein $R^2$ is selected from the group consisting of methyl and ethyl.

In one embodiment, in formula (Ia), $R^1$ is a group $NHR^2$ wherein $R^2$ is a group —$(CH_2)_pZ$ wherein p is 1, 2 or 3, and Z is selected from the group consisting of hydroxy, methoxy and NHMe.

In one embodiment, in formula (Ia), $R^1$ is a group $NHR^2$ wherein $R^2$ is a group —$(CH_2)_pZ$ wherein p is 1, 2 or 3, and Z is selected from the group consisting of phenyl, imidazolyl, thienyl, triazolyl, thiazolyl, pyrrolyl, pyridyl, furanyl, pyrrolidynl and tetrahydrofuranyl, each group being optionally substituted by one or two groups independently selected from the group consisting of halo, $C_{1-4}$alkyl and halo$C_{1-4}$alkyl; wherein when Y is CO, $R^2$ is not $(CH_2)_2$pyrrolidinyl.

In one embodiment, in formula (Ia), $R^1$ is $NR^{2'}R^3$, wherein $R^2$ is selected from the group consisting of methyl and ethyl; and $R^3$ is $C_{1-6}$alkyl.

In one embodiment, in formula (Ia), $R^1$ is $NR^{2'}R^3$, wherein $R^2$ is selected from the group consisting of methyl and ethyl; and $R^3$ is selected from the group consisting of methyl, ethyl, propyl, isopropyl, butyl and t-butyl.

In one embodiment, in formula (Ia), $R^1$ is $NR^{2'}R^3$, wherein $R^2$ is selected from the group consisting of methyl and ethyl and $R^3$ is a group —$(CH_2)_pZ'$ wherein p is 1, 2 or 3 and $Z'$ is hydroxy, methoxy or NHMe.

In one embodiment, in formula (Ia), $R^1$ is $NR^{2'}R^3$, wherein $R^2$ is selected from the group consisting of methyl and ethyl and $R^3$ is a group —$(CH_2)_pZ'$ wherein p is 1, 2 or 3 and $Z'$ is selected from the group consisting of phenyl, imidazolyl, thienyl, triazolyl, thiazolyl, pyrrolyl, pyridyl, furanyl, pyrrolidinyl and tetrahydrofuranyl, each group being optionally substituted by one or two groups independently selected from the group consisting of halo, $C_{1-4}$alkyl and halo$C_{1-4}$alkyl.

In one embodiment, in formula (Ia), $R^1$ is $NR^{2'}R^3$, and $R^{2'}$ and $R^3$, together with the nitrogen atom to which they are attached, form:
 a 4 or 5-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto.

In one embodiment, in formula (Ia), $R^1$ is $NR^{2'}R^3$, and $R^{2'}$ and $R^3$, together with the nitrogen atom to which they are attached, form:
 pyrrolidinyl or azetidinyl, both of which is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto.

In one embodiment, in formula (Ia), $R^1$ is $NR^{2'}R^3$, and $R^{2'}$ and $R^3$, together with the nitrogen atom to which they are attached, form:
 pyrrolidinyl or azetidinyl, both of which is optionally substituted by one or two groups independently selected from the group consisting of hydroxy, NMe and fluoro.

In one embodiment, in formula (Ia), $R^1$ is $NR^{2'}R^3$, and $R^{2'}$ and $R^3$, together with the nitrogen atom to which they are attached, form:
 a 6-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto.

In one embodiment, in formula (Ia), $R^1$ is $NR^{2'}R^3$, and $R^{2'}$ and $R^3$, together with the nitrogen atom to which they are attached, form:
 piperidyl, morpholinyl or piperazinyl, any of which is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto.

In one embodiment, in formula (Ia), $R^1$ is $NR^{2'}R^3$, and $R^{2'}$ and $R^3$, together with the nitrogen atom to which they are attached, form:
 piperidyl, morpholinyl or piperazinyl, any of which is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto.

In a further embodiment, $R^2$ and $R^3$ together with the nitrogen atom to which they are attached form a pyrrolidinyl ring, which may be substituted with one or more groups selected from halo, $C_{1-4}$alkyl, halo$C_{1-4}$alkyl, or keto. In an embodiment, $R^2$ and $R^3$ together with the nitrogen atom to which they are attached form a pyrrolidinonyl ring or a pyrrolidinyl ring.

In one embodiment, in formula (Ia), Y is CO, and $R^1$ is selected from the group consisting of (i) $C_{1-4}$alkyl and (ii) a C-linked 5-membered aromatic heterocyclic group optionally substituted with methyl.

In one embodiment, in formula (Ia), Y is CO, and $R^1$ is selected from the group consisting of methyl, ethyl, and imidazolyl optionally substituted with one methyl.

In one embodiment, in formula (Ia), Y is CO, and $R^1$ is selected from the group consisting of $NHR^2$ and $NR^{2'}R^3$, wherein:
 $R^2$ is selected from the group consisting of $C_{1-6}$straight chain alkyl, $C_{4-6}$branched chain alkyl and a group —$(CH_2)_pZ$ wherein p is 1, 2 or 3;
 Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$alkyl;
 $R^{2'}$ is selected from the group consisting of methyl and ethyl;
 $R^3$ is selected from the group consisting of $C_{1-6}$alkyl and a group —$(CH_2)_pZ'$ wherein p is 1, 2 or 3;
 $Z'$ is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl.

In one embodiment, in formula (Ia), Y is CO, and $R^1$ is a group $NHR^2$ wherein:
 $R^2$ is selected from the group consisting of $C_{1-6}$straight chain alkyl and $C_{4-6}$branched chain alkyl.

In one embodiment, in formula (Ia), Y is CO, and $R^1$ is a group $NHR^2$ wherein:
 $R^2$ is selected from the group consisting of methyl and ethyl.

In one embodiment, in formula (Ia), Y is CO, and $R^1$ is a group $NHR^2$ wherein:
 $R^2$ is a group —$(CH_2)_pZ$ wherein p is 1, 2 or 3 and Z is hydroxy, methoxy, or NHMe.

In one embodiment, in formula (Ia), Y is CO, and $R^1$ is a group $NHR^2$ wherein:
 $R^2$ is a group —$(CH_2)_pZ$ wherein p is 1, 2 or 3 and Z is selected from the group consisting of phenyl, imidazolyl, thienyl, triazolyl, thiazolyl, pyrrolyl, pyridyl, furanyl and tetrahydrofuranyl, each group being optionally substituted by one or two groups independently selected from the group consisting of halo, $C_{1-4}$alkyl and halo$C_{1-4}$alkyl.

In one embodiment, in formula (Ia), Y is CO, and $R^1$ is $NR^{2'}R^3$, wherein:
 $R^{2'}$ is selected from the group consisting of methyl and ethyl; and
 $R^3$ is $C_{1-6}$alkyl.

In one embodiment, in formula (Ia), Y is CO, and $R^1$ is $NR^{2'}R^3$, wherein:
 $R^{2'}$ is selected from the group consisting of methyl and ethyl;
 $R^3$ is a group —$(CH_2)_pZ'$ wherein p is 1, 2 or 3 and $Z'$ is hydroxy, methoxy or NHMe.

In one embodiment, in formula (Ia), Y is CO, and $R^1$ is $NR^{2'}R^3$, wherein:
 $R^{2'}$ is selected from the group consisting of methyl and ethyl;

$R^3$ is a group —$(CH_2)_pZ'$ wherein p is 1, 2 or 3 and $Z'$ is selected from the group consisting of phenyl, imidazolyl, thienyl, triazolyl, thiazolyl, pyrrolyl, pyridyl, furanyl, pyrrolidynl and tetrahydrofuranyl, each group being optionally substituted by one or two groups independently selected from the group consisting of halo, $C_{1-4}$alkyl and halo$C_{1-4}$alkyl.

In one embodiment, in formula (Ia), Y is CO, $R^1$ is $NR^{2'}R^3$, and $R^{2'}$ and $R^3$, together with the nitrogen atom to which they are attached, form:

a 4 or 5-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto.

In one embodiment, in formula (Ia), Y is CO, $R^1$ is $NR^{2'}R^3$, and $R^{2'}$ and $R^3$, together with the nitrogen atom to which they are attached, form:

pyrrolidinyl or azetidinyl, both of which is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkylhalo$C_{1-4}$alkyl, and keto.

In one embodiment, in formula (Ia), Y is CO, $R^1$ is $NR^{2'}R^3$, and $R^{2'}$ and $R^3$, together with the nitrogen atom to which they are attached, form:

pyrrolidinyl or azetidinyl, both of which is optionally substituted by one or two groups independently selected from the group consisting of hydroxy, NMe and fluoro.

In one embodiment, in formula (Ia), Y is CO, $R^1$ is $NR^{2'}R^3$, and $R^{2'}$ and $R^3$, together with the nitrogen atom to which they are attached, form:

a 6-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto.

In one embodiment, in formula (Ia), Y is CO, $R^1$ is $NR^{2'}R^3$, and $R^{2'}$ and $R^3$, together with the nitrogen atom to which they are attached, form:

piperidyl, morpholinyl or piperazinyl, any of which is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto.

In one embodiment, in formula (Ia), Y is CO, $R^1$ is $NR^{2'}R^3$, and $R^{2'}$ and $R^3$, together with the nitrogen atom to which they are attached, form:

piperidyl, morpholinyl or piperazinyl, any of which is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto.

In one embodiment, in formula (Ia), Y is $NR^8CO$, SO, $SO_2$ or $NR^8SO_2$, and $R^1$ is $C_{1-4}$alkyl.

In one embodiment, formula (Ia), Y is $NR^8CO$, SO, $SO_2$ or $NR^8SO_2$, and $R^1$ is methyl.

In one embodiment, formula (Ia), Y is $NR^8CO$, SO, $SO_2$ or $NR^8SO_2$, and $R^1$ is a group $NHR^2$, wherein $R^2$ is selected from the group consisting of $C_{1-6}$straight chain alkyl and $C_{4-6}$branched chain alkyl.

In one embodiment, formula (Ia), Y is $NR^8CO$, SO, $SO_2$ or $NR^8SO_2$, and $R^1$ is a group $NHR^2$, wherein $R^2$ is t-butyl.

In one embodiment, formula (Ia), Y is $NR^8CO$, SO, $SO_2$ or $NR^8SO_2$, and $R^1$ is a group $NHR^2$, wherein $R^2$ is a group —$(CH_2)_pZ$ wherein p is 1, 2 or 3 and Z is hydroxy, methoxy or NHMe.

In one embodiment, formula (Ia), Y is $NR^8CO$, SO, $SO_2$ or $NR^8SO_2$, and $R^1$ is a group $NHR^2$, wherein $R^2$ is a group —$(CH_2)_pZ$ wherein p is 1, 2 or 3 and Z is phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$alkyl.

In one embodiment, formula (Ia), Y is $NR^8CO$, SO, $SO_2$ or $NR^8SO_2$, and $R^1$ is a group $NHR^2$, wherein $R^2$ is a group —$(CH_2)_pZ$ wherein p is 1, 2 or 3 and Z is pyrrolidinyl or tetrahydrofuranyl.

In one embodiment, in formula (Ia), Y is $NR^8CO$, SO, $SO_2$ or $NR^8SO_2$, and $R^1$ is $NR^{2'}R^3$, wherein $R^{2'}$ is selected from the group consisting of methyl and ethyl; and $R^3$ is $C_{1-6}$alkyl.

In one embodiment, in formula (Ia), Y is $NR^8CO$, SO, $SO_2$ or $NR^8SO_2$, and $R^1$ is $NR^{2'}R^3$, wherein $R^{2'}$ is selected from the group consisting of methyl and ethyl; and $R^3$ is selected from the group consisting of methyl and ethyl.

In one embodiment, in formula (Ia), Y is $NR^8CO$, SO, $SO_2$ or $NR^8SO_2$, and $R^1$ is $NR^{2'}R^3$, wherein:

$R^{2'}$ is selected from the group consisting of methyl and ethyl;

$R^3$ is a group —$(CH_2)_pZ'$ wherein p is 1, 2 or 3;

$Z'$ is hydroxy, methoxy or NHMe.

In one embodiment, in formula (Ia), Y is $NR^8CO$, SO, $SO_2$ or $NR^8SO_2$, and $R^1$ is $NR^{2'}R^3$, wherein:

$R^{2'}$ is selected from the group consisting of methyl and ethyl;

$Z'$ is phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl. In one embodiment, in formula (Ia), $R^1$ is $NR^{2'}R^3$, wherein:

$R^{2'}$ and $R^3$, together with the nitrogen atom to which they are attached, form azetidinyl, pyrrolidinyl, morpholinyl or piperidyl, each group being optionally substituted by one or two groups independently selected from the group consisting of halo, hydroxy, NHMe, $C_{1-4}$alkyl, halo$C_{1-4}$alkyl and keto.

In one embodiment, a compound of formula (I) is a compound in which n=0 and m=0, that is to say a compound of formula (Ib), in which q, and $R^1$ are as set out for formula (I) above:

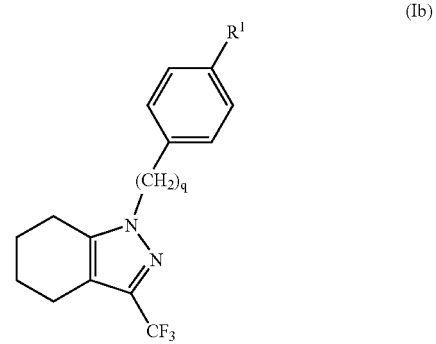

(Ib)

In one embodiment, in formula (Ib), q is 0.

In one embodiment, in formula (Ib), $R^1$ is $C_{1-6}$alkoxy. In one embodiment, $R^1$ is methoxy, ethoxy or propoxy.

In one embodiment, in formula (Ib), $R^1$ is N- or C-linked pyrrolidinyl, optionally substituted by one or two groups selected from the group consisting of $C_{1-4}$alkyl, $C(O)C_{1-4}$alkyl and keto. In one embodiment, $R^1$ is a 2-pyrrolidinonyl attached through a nitrogen or a carbon atom, or a N-methyl 2-pyrrolidinonyl group attached through a carbon atom.

In one embodiment, in formula (Ib), $R^1$ is oxazolyl or imidazolyl, both being optionally substituted by a methyl.

In one embodiment, a compound of formula (I) is a compound in which n=1 or 2 and m=1, that is to say a compound of formula (Ic), in which q, Y and $R^1$ are as set out for formula (I) above:

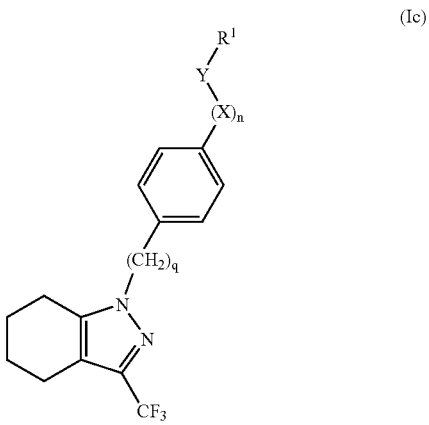

(Ic)

In one embodiment, in formula (Ic), q is 0.

In one embodiment, in formula (Ic), Y is selected from the group consisting of CO, $NR^8SO_2$ and $NR^8CO$, wherein $R^8$ is hydrogen or $C_{1-2}$alkyl. In one embodiment, Y is selected from the group consisting of CO, NHCO, NMeCO, NEtCO, $NHSO_2$ and $NMeSO_2$.

In one embodiment, in formula (Ic), X is selected from the group consisting of $CH_2$, CHMe, $CF_2$ and $CR^6R^7$, wherein $R^6$ and $R^7$, together with the carbon atom to which they are attached, form a 3-membered carbocyclic ring. In one embodiment, X is $CH_2$.

In one embodiment, in formula (Ic), $R^1$ is selected from the group consisting of $C_{1-4}$alkyl, benzyl, cyclopropyl and thienyl.

In one embodiment, in formula (Ic), $R^1$ is $NR^9R^{10}$ wherein: $R^9$ is selected from the group consisting of hydrogen and $C_{1-4}$alkyl, and $R^{10}$ is selected from the group consisting of $C_{1-6}$ straight chain alkyl, $C_{3-6}$cycloalkyl and $—(CH_2)_pZ$ wherein p is 1, 2 or 3 and Z is a phenyl or a 5- or 6-membered heterocyclic group, the phenyl or heterocyclic group being optionally substituted by one, two or three groups independently selected from the group consisting of halo and $C_{1-4}$alkyl.

In one embodiment, in formula (Ic), $R^1$ is $NR^9R^{10}$ wherein: $R^9$ is selected from the group consisting of hydrogen and methyl, and $R^{10}$ is selected from the group consisting of $C_{1-6}$ straight chain alkyl, $C_{3-6}$cycloalkyl and $—(CH_2)_pZ$ wherein p is 1, 2 or 3; and Z is phenyl or thienyl.

In one embodiment, in formula (Ic), $R^1$ is $NR^9R^{10}$ wherein: $R^9$ and $R^{10}$, together with the nitrogen atom to which they are attached, form a 5- or 6-membered non-aromatic heterocyclic group being optionally substituted by one, two or three groups independently selected from the group consisting of $C_{1-4}$alkyl, halo, phenyl and keto.

In one embodiment, in formula (Ic), $R^1$ is $NR^9R^{10}$ wherein: $R^9$ and $R^{10}$, together with the nitrogen atom to which they are attached, form a pyrrolidinyl or piperidyl ring, both ring being optionally substituted by one or two groups independently selected from the group consisting of $C_{1-4}$alkyl, halo, phenyl and keto.

In one embodiment, in formula (Ic), $R^1$ is $NR^9R^{10}$ wherein: $R^9$ and $R^{10}$, together with the nitrogen atom to which they are attached, form a pyrrolidinyl or piperidyl ring, both ring being optionally substituted by one or two fluoro.

In one embodiment, a compound of formula (I) is a compound in which n=1 or 2 and m=0, that is to say a compound of formula (Id), in which q, n, X and R' are as set out for formula (I) above:

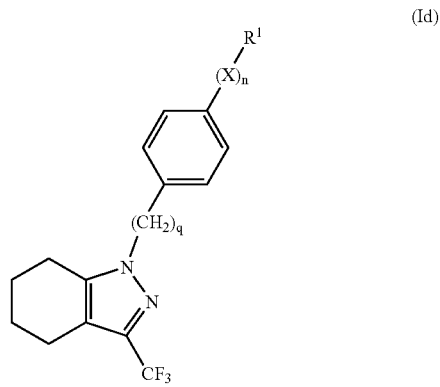

(Id)

In one embodiment, in formula (Id), q is 0.

In one embodiment, in formula (Id), a compound of formula (Id) is a compound in which X is selected from the group consisting of $CH_2$, CHMe and (when n=1) $CR^6R^7$, where $R^6$ and $R^7$, together with the carbon atom to which they are attached, form a 3-membered carbocyclic ring. In one embodiment, X is $CH_2$.

In one embodiment, in formula (Id), n is 1.

In one embodiment, in formula (Id), $R^1$ is selected from the group consisting of cyano and hydroxy.

In one embodiment, in formula (Id), $R^1$ is a C-linked 5-membered aromatic heterocyclic group optionally substituted by one, two or three groups independently selected from the group consisting of $C_{1-6}$alkyl and $C_{3-6}$cycloalkyl. In one embodiment, $R^1$ is oxadiazolyl optionally substituted by one or two groups independently selected from the group consisting of $C_{1-6}$alkyl and $C_{3-6}$cycloalkyl. In one embodiment, $R^1$ is oxadiazolyl substituted by a methyl or cyclopropyl.

In one embodiment, in formula (Id), $R^1$ is a group $NHR^{12}$ in which:
$R^{12}$ is selected from the group consisting of $SO_2C_{3-6}$cycloalkyl and $C(O)C_{2-4}$alkenyl.

In one embodiment, in formula (Id), $R^1$ is a group $NHR^{12}$ in which:
$R^{12}$ is selected from $CO(CH=CH_2)$ and $SO_2$-cyclopentanyl.

In one embodiment, in formula (Id), $R^1$ is a group $NR^{11}R^{12}$ in which:
$R^{11}$ is selected from the group consisting of $C_{1-4}$alkyl and $C_{2-4}$alkenyl, and $R^{12}$ is selected from the group consisting of $C(O)C_{1-4}$alkyl, C(O)phenyl and $C(O)C_{2-4}$alkenyl.

In one embodiment, in formula (Id), $R^1$ is a group $NR^{11}R^{12}$ in which:

$R^{11}$ is selected from the group consisting of $C_{1-4}$alkyl and $C_{2-4}$alkenyl, and $R^{12}$ is selected from the group consisting of COMe, C(O)phenyl and C(O)(CH=CH$_2$).

In one embodiment, in formula (Id), $R^1$ is a group $NR^{11}R^{12}$ in which:
$R^{11}$ and $R^{12}$, together with the nitrogen atom to which they are attached, form a group selected from the group consisting of:
pyrazolyl, imidazolyl and triazolyl, each being optionally substituted by one or two groups independently selected from the group consisting of $C_{1-4}$alkyl, halo and halo$C_{1-4}$alkyl; and
imidazolyl substituted by phenyl; and
pyrrolidinyl or isothiazolidinyl, each substituted by one or two keto, hydroxy and $C_{1-4}$alkoxy; and
piperidyl, optionally substituted by one or two groups independently selected from the group consisting of keto, hydroxy and $C_{1-4}$alkoxy.

In one embodiment, in formula (Id), $R^1$ is a group $NR^{11}R^{12}$ in which:
$R^{11}$ and $R^{12}$, together with the nitrogen atom to which they are attached, form a group selected from the group consisting of:
(i) pyrazolyl, imidazolyl and triazolyl, each being optionally substituted by one or two groups independently selected from the group consisting of methyl, isopropyl, halo and CF$_3$; and
(ii) imidazolyl substituted by phenyl; and
(iii) pyrrolidinyl or isothiazolidinyl, each substituted by one or two keto; and
(iv) piperidyl, optionally substituted by a keto.

In one embodiment, the present invention provides a compound of formula (Ie) or a salt or solvate thereof:

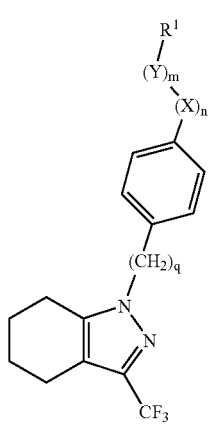

(Ie)

wherein:
q is 0 or 1;
n is 0, 1, or 2;
X is CR$^6$R$^7$, where R$^6$ and R$^7$ are each independently selected from the group consisting of hydrogen, methyl and fluoro, but R$^6$ and R$^7$ are not both simultaneously methyl; or, when n is 1, R$^6$ and R$^7$ together with the carbon atom to which they are attached, form a 3-membered carbocyclic ring;
Y is selected from the group consisting of CO, NR$^8$CO, SO, SO$_2$ and NR$^8$SO$_2$;
R$^8$ is selected from the group consisting of hydrogen, $C_{2-4}$alkenyl and $C_{1-4}$alkyl;
m is 0 or 1; and a) when n is 0 and m=1, then $R^1$ is selected from the group consisting of (i) $C_{1-4}$alkyl, (ii) imidazolyl optionally substituted with methyl, and, (iii) NHR$^2$ and (iv) NR$^2$R$^3$, wherein:
$R^2$ is selected from the group consisting of $C_{1-6}$straight chain alkyl, $C_{4-6}$branched chain alkyl and a group —(CH$_2$)$_p$Z wherein p is 1, 2 or 3;
Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$ alkyl; wherein when Y is CO, $R^2$ is not (CH$_2$)$_2$pyrrolidinyl;
$R^{2'}$ is selected from the group consisting of methyl and ethyl;
$R^3$ is selected from the group consisting of $C_{1-6}$alkyl and a group —(CH$_2$)$_p$Z' wherein p is 1, 2 or 3;
Z' is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl;
$R^{2'}$ and $R^3$, together with the nitrogen atom to which they are attached, form:
(i) a 4 or 5-membered non-aromatic heterocyclic group, which ring is optionally substituted by one, two or three groups independently selected from the group consisting of halo, hydroxy, NR$^{13}$R$^{14}$ (wherein R$^{13}$ and R$^{14}$ are independently selected from the group consisting of hydrogen and $C_{1-4}$alkyl), halo$C_{1-4}$alkyl, and keto; or
(ii) a 6-membered non-aromatic heterocyclic group, which ring is optionally substituted by one, two or three groups independently selected from the group consisting of halo, hydroxy, NR$^{13}$R$^{14}$ (wherein R$^{13}$ and R$^{14}$ are independently selected from the group consisting of hydrogen and $C_{1-4}$alkyl), $C_{2-4}$alkyl, halo$C_{1-4}$alkyl and keto;
b) when n and m are both simultaneously 0, $R^1$ is selected from the group consisting of:
$C_{1-6}$alkoxy;
a monocyclic saturated or partially unsaturated 5- or 6-membered heterocyclic group, attached through a carbon atom and optionally substituted by one, two or three groups independently selected from the group consisting of $C_{1-4}$alkyl, C(O)$C_{1-4}$alkyl, halo$C_{1-4}$ alkyl, halo and keto;
N-linked pyrrolidinyl, optionally substituted with one, two or three groups independently selected from the group consisting of $C_{1-4}$alkyl, C(O)$C_{1-4}$alkyl, halo $C_{1-4}$alkyl, halo and keto; and
oxazolyl or imidazolyl, both being optionally substituted by $C_{1-4}$alkyl;
c) when n is 1 or 2, and m is 1, $R^1$ is selected from the group consisting of $C_{1-4}$alkyl, benzyl, cyclopropyl, thienyl, and NR$^9$R$^{10}$ wherein:
$R^9$ is selected from the group consisting of hydrogen and $C_{1-4}$alkyl, and $R^{10}$ is selected from the group consisting of $C_{1-6}$ straight chain alkyl, $C_{3-6}$cycloalkyl and —(CH$_2$)$_p$Z wherein p is 1, 2 or 3;
Z is a phenyl or a 5- or 6-membered heterocyclic group, the phenyl or heterocyclic group being optionally substituted by one, two or three groups independently selected from the group consisting of halo and $C_{1-4}$alkyl; or R⁹ and R¹⁰, together with the nitrogen atom to which they are attached, form a 5-membered aromatic or non-aromatic heterocyclic group or a 6-membered non-aromatic heterocyclic group, any of the rings being optionally substituted by one, two or three groups independently selected from the group consisting of $C_{1-4}$alkyl, halo, phenyl and (in the case of a non-aromatic ring) keto; and d) when n is 1 or 2, and m is 0, $R^1$ is selected from the group consisting of cyano, hydroxy, $NH_2$, a C-linked 5-membered aromatic heterocyclic group optionally substituted with one, two or three groups independently selected from the group consisting of $C_{1-6}$alkyl and $C_{3-6}$cycloalkyl, and $NR^{11}R^{12}$ in which:

$R^{11}$ is hydrogen and $R^{12}$ is selected from the group consisting of $SO_2C_{1-4}$alkyl, $SO_2C_{3-6}$cycloalkyl, $C(O)C_{1-4}$alkyl, and $C(O)C_{2-4}$alkenyl; or $R^{11}$ is selected from the group consisting of $C_{1-4}$alkyl and $C_{2-4}$alkenyl, and $R^{12}$ is selected from the group consisting of $SO_2C_{1-4}$alkyl, $SO_2C_{3-6}$cycloalkyl, $C(O)C_{1-4}$alkyl, $C(O)$phenyl and $C(O)C_{2-4}$alkenyl or $R^{11}$ and $R^{12}$, together with the nitrogen atom to which they are attached, form a group selected from the group consisting of:
(i) a 5-membered aromatic heterocyclic group which is optionally substituted by one or two groups independently selected from the group consisting of $C_{1-4}$alkyl, halo, halo$C_{1-4}$alkyl, hydroxy, $C_{3-6}$cycloalkyl and $C_{1-4}$alkoxy; and
(ii) imidazolyl substituted by phenyl;
(iii) a 5-membered non-aromatic heterocyclic group which is substituted by one, two or three groups independently selected from the group consisting of keto, hydroxy and $C_{1-4}$alkoxy; and
(iv) a 6-membered non-aromatic heterocyclic group, which is optionally substituted by one, two or three groups independently selected from the group consisting of keto, hydroxy and $C_{1-4}$alkoxy.

In one embodiment, in formula (Ie) above, the compound is not a compound in which simultaneously n=0, m=1, q=0, Y=CO and $R^1$ is selected from the group consisting of: $NMe_2$, pyrrolidinyl, $NMeCH_2Ph$, morpholinyl, piperidyl, NHEt, $NEt_2$, NHMe, $NHCH_2$-tetrahydrofuran-2-yl, $NH(CH_2)_2Ph$, $NH(CH_2)Ph$, NHtBu, $NHCH_2$-furan-2-yl and $NH(CH_2)_3OMe$.

In one embodiment, the present invention provides a compound of formula (If) or a salt or solvate thereof:

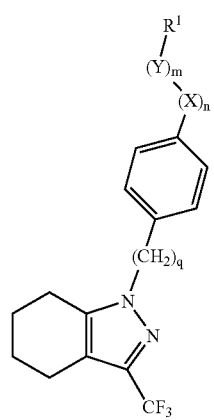

(If)

wherein:
q is 0 or 1;
n is 0, 1, or 2;
X is $CR^6R^7$, where $R^6$ and $R^7$ are each independently selected from the group consisting of hydrogen, methyl and fluoro, but $R^6$ and $R^7$ are not both simultaneously methyl; or, when n is 1, $R^6$ and $R^7$ together with the carbon atom to which they are attached, form a 3-membered carbocyclic ring;
Y is selected from the group consisting of CO, $NR^8CO$, SO, $SO_2$ and $NR^8SO_2$;
$R^8$ is selected from the group consisting of hydrogen, $C_{2-4}$alkenyl and $C_{1-4}$alkyl;
m is 0 or 1; and
(a)(i) when n is 0 and m=1 and Y is CO, then $R^1$ is selected from the group consisting of (i) $C_{1-4}$alkyl, (ii) a C-linked 5-membered aromatic heterocyclic group optionally substituted with methyl, (iii) $NHR^2$ and (iv) $NR^2R^3$, wherein:
$R^2$ is selected from the group consisting of $C_{1-6}$straight chain alkyl, $C_{4-6}$branched chain alkyl and a group $—(CH_2)_pZ$ wherein p is 1, 2 or 3;
Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$alkyl;
$R^{2'}$ is selected from the group consisting of methyl and ethyl;
$R^3$ is selected from the group consisting of $C_{1-6}$alkyl and a group $—(CH_2)_pZ'$ wherein p is 1, 2 or 3;
Z' is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl; or
$R^{2'}$ and $R^3$, together with the nitrogen atom to which they are attached, form:
(i) a 4 or 5-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto; or
(ii) a 6-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto;
(a)(ii) when n is 0 and m=1 and Y is $NR^8CO$, SO, $SO_2$ or $NR^8SO_2$, then $R^1$ is selected from the group consisting of (i) $C_{1-4}$alkyl, (ii) $NHR^2$ and (iii) $NR^2R^3$, wherein:
$R^2$ is selected from the group consisting of $C_{1-6}$straight chain alkyl, $C_{4-6}$branched chain alkyl and a group $—(CH_2)_pZ$ wherein p is 1, 2 or 3;
Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$alkyl;

R$^{2'}$ is selected from the group consisting of methyl and ethyl;

R$^3$ is selected from the group consisting of C$_{1-6}$alkyl and a group —(CH$_2$)$_p$Z' wherein p is 1, 2 or 3;

Z' is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, C$_{1-4}$alkyl and haloC$_{1-4}$alkyl; or R$^{2'}$ and R$^3$, together with the nitrogen atom to which they are attached, form:
  (i) a 4 or 5-membered non-aromatic heterocyclic group, which ring is optionally substituted by one, two or three groups independently selected from the group consisting of halo, hydroxy, NR$^{13}$R$^{14}$ (wherein R$^{13}$ and R$^{14}$ are independently selected from the group consisting of hydrogen and C$_{1-4}$alkyl), haloC$_{1-4}$alkyl, and keto; or
  (ii) a 6-membered non-aromatic heterocyclic group, which ring is optionally substituted by one, two or three groups independently selected from the group consisting of halo, hydroxy, NR$^{13}$R$^{14}$ (wherein R$^{13}$ and R$^{14}$ are independently selected from the group consisting of hydrogen and C$_{1-4}$alkyl), C$_{2-4}$alkyl, haloC$_{1-4}$alkyl and keto;

b) when n and m are both simultaneously 0, R$^1$ is selected from the group consisting of:
  C$_{1-6}$alkoxy;
  a monocyclic saturated or partially unsaturated 5- or 6-membered heterocyclic group, attached through a carbon atom and optionally substituted by one, two or three groups independently selected from the group consisting of C$_{1-4}$alkyl, C(O)C$_{1-4}$alkyl, haloC$_{1-4}$alkyl, halo and keto;
  N-linked pyrrolidinyl, optionally substituted with one, two or three groups independently selected from the group consisting of C$_{1-4}$alkyl, C(O)C$_{1-4}$alkyl, halo C$_{1-4}$alkyl, halo and keto; and
  oxazolyl or imidazolyl, both being optionally substituted by C$_{1-4}$alkyl;

c) when n is 1 or 2, and m is 1, R$^1$ is selected from the group consisting of C$_{1-4}$alkyl, benzyl, cyclopropyl, thienyl, and NR$^9$R$^{10}$ wherein:
  R$^9$ is selected from the group consisting of hydrogen and C$_{1-4}$alkyl, and R$^{10}$ is selected from the group consisting of C$_{1-6}$ straight chain alkyl, C$_{3-6}$cycloalkyl and —(CH$_2$)$_p$Z wherein p is 1, 2 or 3;
  Z is a phenyl or a 5- or 6-membered heterocyclic group, the phenyl or heterocyclic group being optionally substituted by one, two or three groups independently selected from the group consisting of halo and C$_{1-4}$alkyl; or
  R$^9$ and R$^{10}$, together with the nitrogen atom to which they are attached, form a 5-membered aromatic or non-aromatic heterocyclic group or a 6-membered non-aromatic heterocyclic group, any of the rings being optionally substituted by one, two or three groups independently selected from the group consisting of C$_{1-4}$alkyl, halo, phenyl and (in the case of a non-aromatic ring) keto; and d) when n is 1 or 2, and m is 0, R$^1$ is selected from the group consisting of cyano, hydroxy, NH$_2$, a C-linked 5-membered aromatic heterocyclic group optionally substituted with one, two or three groups independently selected from the group consisting of C$_{1-6}$alkyl and C$_{3-6}$cycloalkyl, and NR$^{11}$R$^{12}$ in which:

R$^{11}$ is hydrogen and R$^{12}$ is selected from the group consisting of SO$_2$C$_{1-4}$alkyl, SO$_2$C$_{3-6}$cycloalkyl, C(O)C$_{1-4}$alkyl, and C(O)C$_{2-4}$alkenyl; or R$^{11}$ is selected from the group consisting of C$_{1-4}$alkyl and C$_{2-4}$alkenyl, and R$^{12}$ is selected from the group consisting of SO$_2$C$_{1-4}$alkyl, SO$_2$C$_{3-6}$cycloalkyl, C(O)C$_{1-4}$alkyl, C(O)phenyl and C(O)C$_{2-4}$alkenyl or R$^{11}$ and R$^{12}$, together with the nitrogen atom to which they are attached, form a group selected from the group consisting of:
  (i) a 5-membered aromatic heterocyclic group which is optionally substituted by one or two groups independently selected from the group consisting of C$_{1-4}$alkyl, halo, haloC$_{1-4}$alkyl, hydroxy, C$_{3-6}$cycloalkyl and C$_{1-4}$alkoxy; and
  (ii) imidazolyl substituted by phenyl;
  (iii) a 5-membered non-aromatic heterocyclic group which is substituted by one, two or three groups independently selected from the group consisting of keto, hydroxy and C$_{1-4}$alkoxy; and
  (iv) a 6-membered non-aromatic heterocyclic group, which is optionally substituted by one, two or three groups independently selected from the group consisting of keto, hydroxy and C$_{1-4}$alkoxy.

In one embodiment, in formula (If) above, the compound is not a compound in which simultaneously n=0, m=1, q=0, Y=CO and R$^1$ is selected from the group consisting of: NMe$_2$, pyrrolidinyl, NMeCH$_2$Ph, morpholinyl, piperidyl, NHEt, NEt$_2$, NHMe, NHCH$_2$-tetrahydrofuran-2-yl, NH(CH$_2$)$_2$Ph, NH(CH$_2$)Ph, NHtBu, NHCH$_2$-furan-2-yl and NH(CH$_2$)$_3$OMe.

The present invention also provides a compound of formula (I'), or a salt, or solvate thereof:

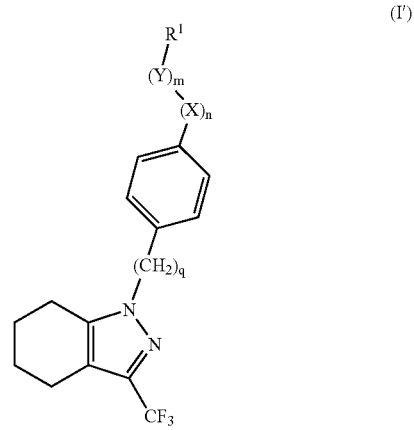

(I')

wherein:
  q is 0 or 1
  n=0, 1, or 2;
  X is CR$^6$R$^7$, where R$^6$ and R$^7$ are each independently selected from H, Me and F, but R$^6$ and R$^7$ are not both simultaneously Me; or, when n=1, R$^6$ and R$^7$ together with the carbon atom to which they are attached, form a 3-membered carbocyclic ring.
  Y is selected from the group consisting of CO, NR$^8$CO, SO, SO$_2$ and NR$^8$SO$_2$
  R$^8$ is selected from H and C$_{1-4}$ alkyl
  m=0 or 1,
  and a) when n is 0 and m=1, then:
- $R^1$ is selected from the group consisting of $C_{1-4}$ alkyl, and $NR^2R^3$ in which
- $R^2$ is $CH_3$ and $R^3$ is selected from $C_{1-6}$ straight chain alkyl, $C(O)C_{1-4}$alkyl and $-(CH_2)_pZ$ where p=1, 2 or 3;
- Z is a phenyl or a 5- or 6-membered heterocyclic group, the phenyl or heterocyclic group optionally being substituted with one or more groups selected from halo, $C_{1-4}$alkyl and halo$C_{1-4}$alkyl; or
- $R^2$ and $R^3$ together with the nitrogen atom to which they are attached form a 5-membered non-aromatic heterocyclic ring, which ring may be substituted with one or more groups selected from halo, $C_{1-4}$alkyl, halo$C_{1-4}$alkyl, and keto;

b) when n and m are both simultaneously 0,
- $R^1$ is a monocyclic saturated or partially unsaturated 5- or 6-membered heterocyclic ring, attached through a carbon atom and optionally substituted with one or more groups selected from $C_{1-4}$alkyl, $C(O)C_{1-4}$alkyl, halo $C_{1-4}$alkyl, halo and keto;

c) when n is 1 or 2, and m is 1,
- $R^1$ is selected from the group consisting of $C_{1-4}$ alkyl and $NR^9R^{10}$ in which
- $R^9$ is selected from hydrogen and $C_{1-4}$alkyl, and $R^{10}$ is selected from $C_{1-6}$ straight chain alkyl, $C_{3-6}$cycloalkyl, $C(O)C_{1-4}$alkyl and $-(CH_2)_pZ$ where p=1, 2 or 3;
- Z is a phenyl or a 5- or 6-membered heterocyclic group, the phenyl or heterocyclic group optionally being substituted with one or more groups selected from halo and $C_{1-4}$alkyl; or
- $R^9$ and $R^{10}$ together with the nitrogen atom to which they are attached form a 5-membered aromatic or non-aromatic heterocyclic ring or a 6-membered non-aromatic heterocyclic ring, either of which may include one or more further heteroatoms selected from N, O or S, and may be substituted with one or more groups selected from $C_{1-4}$alkyl, halo, and (in the case of a non-aromatic ring) keto; and d) when n is 1 or 2, and m is 0,
- $R^1$ is selected from the group consisting of cyano, OH, $NH_2$ and $NR^{11}R^{12}$ in which
- $R^{11}$ is selected from H and $C_{1-4}$alkyl, and $R^{12}$ is selected from $SO_2C_{1-4}$alkyl and $C(O)C_{1-4}$alkyl; or
- $R^{11}$ and $R^{12}$ together with the nitrogen atom to which they are attached form a group selected from a 5-membered aromatic heterocyclic ring, a 5-membered non-aromatic heterocyclic ring and a 6-membered non-aromatic heterocyclic ring, any of which may include one or more further heteroatoms selected from N, O or S, and wherein the 5-membered aromatic heterocyclic ring is optionally substituted with one or more groups selected from $C_{1-4}$alkyl, halo, halo$C_{1-4}$alkyl, hydroxy and $C_{1-4}$alkoxy; the 5-membered non-aromatic heterocyclic ring is substituted with one or more groups selected from keto, hydroxy and $C_{1-4}$alkoxy; and the 6-membered non-aromatic heterocyclic ring is optionally substituted with one or more groups selected from keto, hydroxy and $C_{1-4}$alkoxy;

with the proviso that the compound is not:
- the compound in which simultaneously n=0, m=0, q=0, and $R^1=NH_2$.
- a compound in which simultaneously n=0, m=1, q=0, Y=CO and $R^1$ is selected from NMeCH$_2$Ph, piperidinyl, pyrrolidinyl, $NH_2$, N-methylpiperizinyl, $NMe_2$ and morpholinyl.

Any statements above regarding embodiments of compounds of any of formula (I), (Ia), (Ib), (Ic), (Id), (Ie) and (If) above apply equally to each other and to compounds of formula (A), (B) and (B').

For the avoidance of doubt, unless otherwise indicated, the term substituted means substituted by one or more defined groups. In the case where groups may be selected from a number of alternative groups, the selected groups may be the same or different.

For the avoidance of doubt, the term independently means that where more than one substituent is selected from a number of possible substituents, those substituents may be the same or different.

It will be appreciated that the present invention is intended to include compounds having any combination of the groups listed hereinbefore.

In one embodiment the salt or solvate of the compound of formula (I) is a pharmaceutically acceptable salt or solvate. In one embodiment, the invention provides a compound of formula (I), a pharmaceutically acceptable salt or solvate thereof.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a pharmaceutically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, (1S)-(−)-10-camphorsulphonic, (1S)-(+)-10-camphorsulphonic, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example naphthalene-1,5-disulphonic, naphthalene-1,3-disulphonic, benzenesulfonic, and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations. The salts may have any suitable stoichiometry. For example, a salt may have 1:1 or 2:1 stoichiometry. Non-integral stoichiometry ratios are also possible.

Furthermore, some of the crystalline forms of the compounds of formula (I) may exist as polymorphs, which are included in the present invention.

Furthermore, some of the crystalline forms of the compounds of structure (I) may exist as polymorphs, which are included in the present invention. Some of the compounds of this invention may be crystallised or recrystallised from solvents such as aqueous and organic solvents. In such cases solvates may be formed. This invention includes within its scope stoichiometric solvates as well as compounds containing variable amounts of solvent, where non-stoichiometric solvates may be produced by processes such as lyophilisation. In one embodiment, the compounds of the present invention are provided in the form of stoichiometric and non-stoichiometric hydrates.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may be administered as prodrugs. Examples of pro-drug forms for certain compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Examples of prodrugs for certain compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Certain compounds of formula (I) are capable of existing in stereoisomeric forms (e.g. geometric (or "cis-trans") isomers, diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. The present invention includes within its scope all such isomers, including mixtures. It will be appreciated, in common with most biologically active molecules that the level of biological activity may vary between the enantiomers of a given molecule.

In one embodiment a compound of the invention in chiral form has at least 80% e.e. In another embodiment, a compound of the invention in chiral form has at least 90% e.e., for example at least 95% e.e. In another embodiment the isomers correspond to at least 98% e.e, for example at least 99% e.e.

Since the compounds of the invention are intended for use in pharmaceutical compositions it will readily be understood that they are each optionally provided in substantially pure form, for example at least 60% pure, for example at least 75% pure or at least 85%, or at least 98% pure (% are on a weight for weight basis). Impure preparations of the compounds may be used for preparing the more pure forms used in the pharmaceutical compositions; these less pure preparations of the compounds should contain at least 1%, or at least 5% or from 10 to 59% of a compound of the invention.

Compounds of the invention may be prepared in a variety of ways. These processes form further aspects of the invention.

The present invention also provides a process for the manufacture of a compound of formula (I) or a salt or solvate thereof, which process comprises coupling a compound of formula (II):

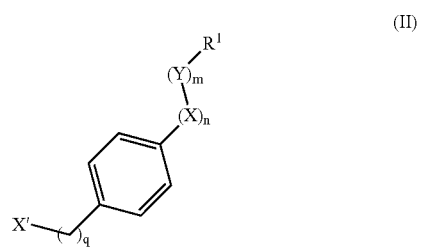

wherein X' is a leaving group and X, Y, q, m, n and $R^1$ are as defined for formula (I), with 3-(trifluoromethyl)-4,5,6,7-tetrahydro-1H-indazole:

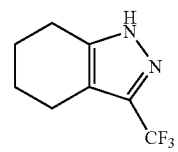

and thereafter optionally:
  removing any protecting groups; and/or
  converting a compound of formula (I) or a salt or solvate thereof to another compound of formula (I) or a salt or solvate thereof.

In the above reaction, for compounds of formula (I) wherein q is 0, X' may be for example a halogen such as bromine or iodine. Typical reaction conditions for compounds of formula (I) wherein q is 0 comprise heating a compound of formula (II), 3-(trifluoromethyl)-4,5,6,7-tetrahydro-1H-indazole, a base (such as potassium carbonate or cesium carbonate), copper (I) iodide or copper (I) oxide with N,N-dimethylglycine at 190 degc in a microwave reactor or with conventional heating at 130 degc in dimethylsulfoxide or trans-1,2-diaminocyclohexane in 1,4-dioxane at 180 degc in a microwave reactor, or (1R,2R)-N,N'-dimethyl-1,2-cyclohexanediamine in toluene at 130 degc in a microwave reactor. In one embodiment, $(X)_n(Y)_mR^1$ is an acid, amide, ester, sulphonamide, ketone, urea, sulfone, alcohol, nitrile or a heterocyclic group. 3-(Trifluoromethyl)-4,5,6,7-tetrahydro-1H-indazole is commercially available. Compounds of formula (II) are commercially available or may be prepared as described herein or by conventional chemistry.

In the above reaction, for compounds of formula (I) wherein q is 1, X' may be for example a halogen such as bromine. Typical reaction conditions for compounds of formula (I) wherein q is 1 comprise stirring a mixture of 3-(trifluoromethyl)-4,5,6,7-tetrahydro-1H-indazole and a compound of formula (II) in dimethylformamide with potassium carbonate at room temperature for 16 hours. Compounds of formula (II) are commercially available or may be prepared as described herein or by conventional chemistry. 3-(Trifluoromethyl)-4,5,6,7-tetrahydro-1H-indazole) is commercially available.

A compound of formula (XIV) (ie a compound of formula (II) wherein X, n and $R^1$ are as defined for formula (I)) can be prepared from a compound of formula (XIII) (wherein X, n and $R^1$ are as defined for formula (I)) by iodination according to reaction scheme 2. Typical conditions comprise heating a mixture of a compound of formula (XIII), iodine, periodic acid, water and concentrated sulphuric acid in acetic acid at 60 degc for approximately 6 hours. In one embodiment, X is a methylene or methyl substituted methylene, and $R^1$ is $NR^9R^{10}$ wherein $R^9$ and $R^{10}$ are aliphatic and may be the same or different, or are linked to form a ring. Compounds of formula (XIII) are commercially available or may be prepared using conventional chemistry.

Scheme 2

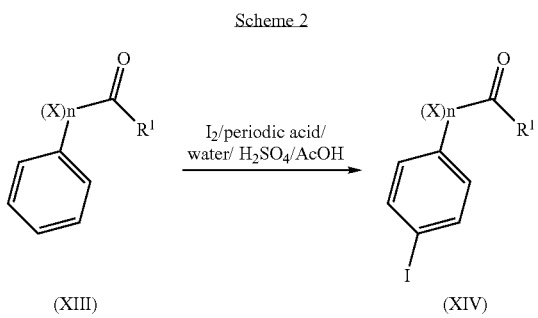

(XIII)     (XIV)

A compound of formula (XVII), which is useful for the preparation of a compound of formula (II), can be prepared from a compound of formula (XV) by acylation or sulphonylation using a reagent of formula (XVI) according to reaction scheme 3. Typical conditions comprise addition of reagent (XVI) to a cooled solution of (XV) in dichloromethane in the presence of a suitable base such as triethylamine or 1,8-diazabicyclo[5.4.0]undec-7-ene. In one embodiment, X is a carbonyl or sulphonyl, R/Ar is aliphatic or aromatic, and R' and R" are aliphatic (or one may be hydrogen) and may be the same or different, or are linked to form a ring. Compounds of formula (XV) are commercially available. Compounds of formula (XVI) are commercially available or may be prepared analogously to as set out above in Scheme 11 below.

Scheme 3

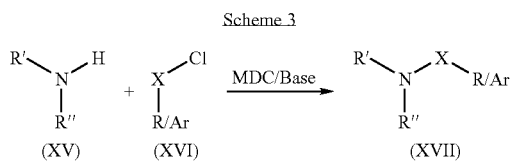

(XV)     (XVI)     (XVII)

A compound of formula (XIX), which is useful for the preparation of a compound of formula (II), can be prepared by coupling a compound of formula (XVIII) with a secondary amine according to reaction scheme 4. Typical coupling conditions comprise treatment of a compound of formula (XVII) with 1,1'-carbonyldiimidazole in dichloromethane, followed by addition of the secondary amine after a short stirring period at ambient temperature (a base such as triethylamine or diisopropylamine is also added should the amine be available as an acid salt). In one embodiment, R/Ar is aliphatic or aromatic, and R' and R" are aliphatic and may be the same or different, or are linked to form a ring. Compounds of formula (XVIII) are commercially available.

Scheme 4

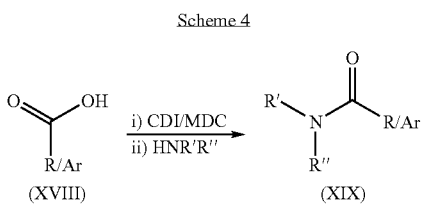

(XVIII)     (XIX)

A compound of formula (XXI), which is useful for the preparation of a compound of formula (II), can be prepared by alkylation of a secondary amide or urea of formula (XX) with an alkylhalide according to reaction scheme 5. Typical alkylation conditions comprise treatment of a compound of formula (XX) with a suitable base such as sodium hydride (available as a 60% suspension in mineral oil) in dimethylformamide, followed by the addition of the alkylating agent. In one embodiment, R' and R" are aliphatic (in the case of amides) and may be the same or different, or are linked to form a ring, or R' is aromatic and R" is an amine connected through the nitrogen (in the case of ureas).

Scheme 5

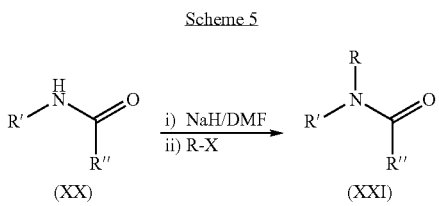

(XX)     (XXI)

A compound of formula (XXXVI), which is useful for the preparation of a compound of formula (II), can be prepared by acylation of a secondary amine with a compound of formula (XXXV) according to reaction scheme 6. Typical reaction conditions comprise addition of the secondary amine to a solution of a compound of formula (XXXV) and a suitable base such as triethylamine and stirring at room temperature. In one embodiment, R' and R" are aliphatic and may be the same or different, or are linked to form a ring, and R/Ar is aliphatic or aromatic. Compounds of formula (XXXV) are commercially available.

Scheme 6

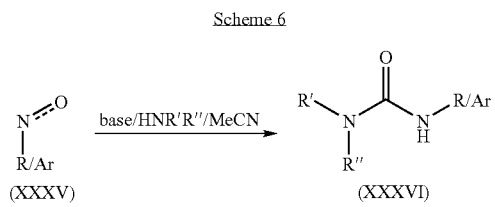

(XXXV)     (XXXVI)

A compound of formula (XLII), which is useful for the preparation of a compound of formula (II), can be prepared by acylation then alkylation of a compound of formula (XL) using 4-chlorobutyryl chloride or 3-chloropropanesulfonyl chloride according to reaction scheme 7. Typical conditions comprise treating a solution of a compound of formula (XL) and a suitable base such as triethylamine in dimethylformamide with 4-chlorobutyryl chloride or 3-chloropropanesulfonyl chloride, followed by the addition of excess sodium hydride (60% suspension in mineral oil) and stirring at room temperature until complete cyclisation. In one embodiment, R/Ar is aliphatic or aromatic, and X is a carbonyl or sulfonyl.

Compounds of formula (XL) are commercially available. Compounds of formula (XLI) are commercially available.

Scheme 7

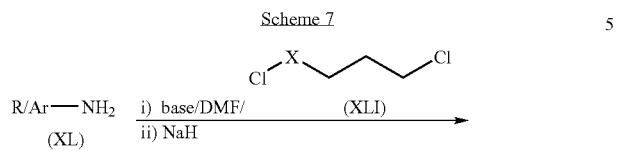

A compound of formula (IV) (ie a compound of formula (I) in which n=0, 1 or 2, X=CH$_2$, Y=CO, m=1 and R$^1$=NR$^2$R$^3$ or R$^1$=NR$^9$R$^{10}$ wherein R$^2$, R$^3$, R$^9$ and R$^{10}$ are as defined for formula (I)) can be prepared by coupling a compound of formula (V) with a secondary amine according to reaction scheme 8. Typical coupling conditions comprise treatment of a compound of formula (V) with 1,1'-carbonyldiimidazole in dichloromethane, followed by addition of the secondary amine after a 15 minute stirring period at ambient temperature. In one embodiment, R$^2$ and R$^3$, or R$^9$ and R$^{10}$, are aliphatic (or one is hydrogen) and may be the same or different, or are linked to form a ring.

Scheme 8

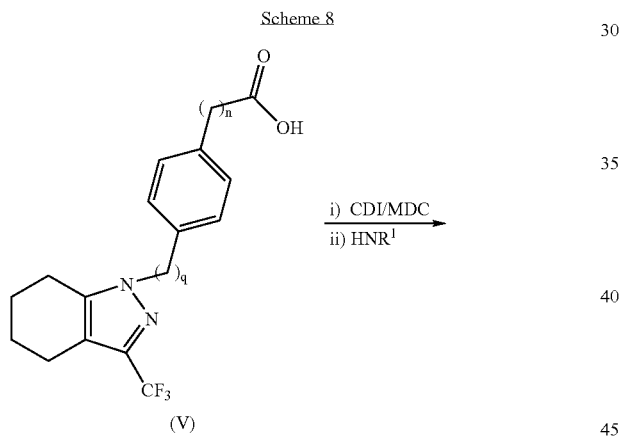

A compound of formula (V), wherein q and n are as defined for formula (I), can be prepared from an ester of formula (X) (wherein q and n are as defined for formula (I) and R=alkyl for example C$_{1-6}$alkyl) according to reaction Scheme 9. Typical reaction conditions comprise heating a solution of the ester of formula (X) and sodium hydroxide in a 1:1 mix of water and ethanol at reflux for 1 hour. Compounds of formula (X) can be prepared in a manner similar to that described above for compounds of formula (I), ie reacting a compound of formula (II) with 3-(trifluoromethyl)-4,5,6,7-tetrahydro-1H-indazole).

Scheme 9

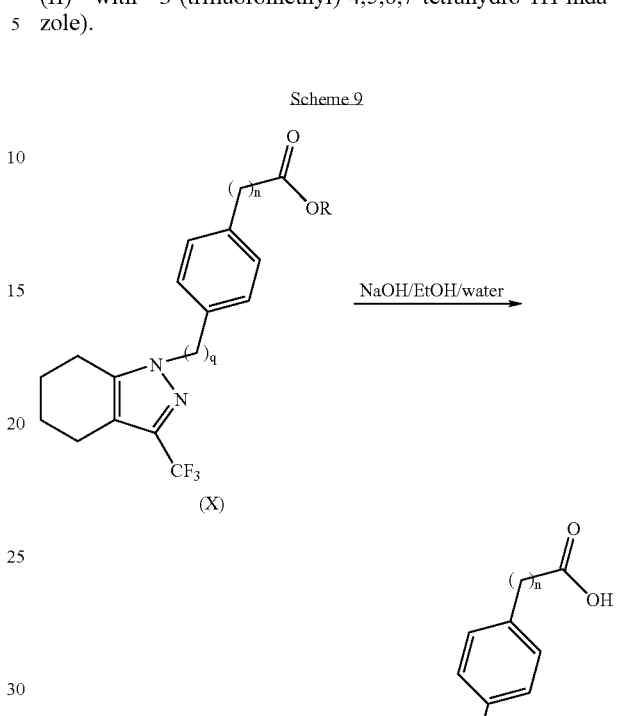

A compound of formula (VI) (ie a compound of formula (I) in which q=0, X=CH$_2$, n=1 or 2, Y=NR$^8$CO, m=1 and R$^1$ and R$^8$ are as defined for formula (I)) can be prepared by acylation of a secondary amide of formula (VIII) with an alkylhalide compound of formula (VII) according to reaction scheme 10. Typical alkylation conditions comprise treatment of a compound of formula (VIII) with a suitable base such as sodium hydride (available as a 60% suspension in mineral oil) in dimethylformamide, followed by the addition of the alkylating agent (VII). In one embodiment, R$^1$ and R$^8$ are aliphatic and may be the same or different, or are linked to form a ring. Compounds of formula (VIII) are commercially available.

Scheme 10

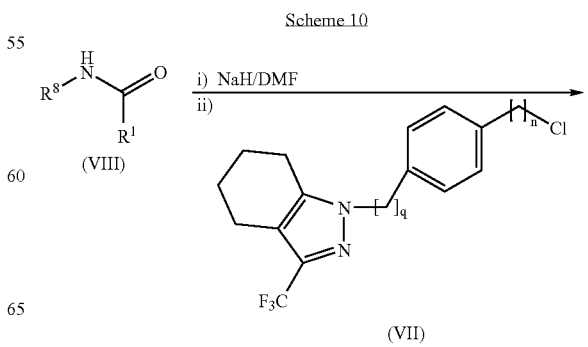

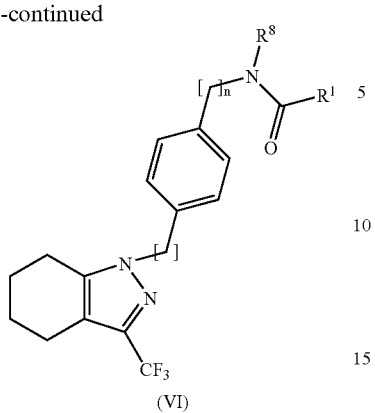

(VI)

A compound of formula (VII) can be prepared from a benzylic alcohol of formula (IX) according to reaction scheme 11. Typical reaction conditions comprise treatment of a compound of formula (IX) in dichloromethane with a suitable base such as triethylamine, followed by the addition of methanesulfonyl chloride and stirring at room temperature for 18 h hours. Compounds of formula (IX) can be prepared in a manner similar to that described above for compounds of formula (I), ie reacting a compound of formula (II) with 3-(trifluoromethyl)-4,5,6,7-tetrahydro-1H-indazole).

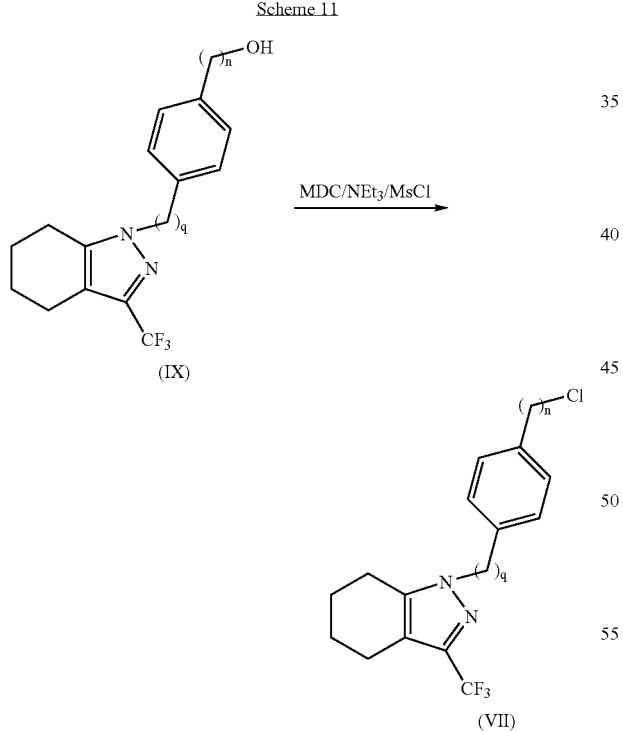

A compound of formula (XII) (ie a compound of formula (I) in which q=1, n=0, Y=CO, m=1 and $R^1$=$NR^2R^3$ wherein $R^2$ and $R^3$ together with the nitrogen atom to which they are attached form a 4, 5 or 6-membered non-aromatic heterocyclic group as defined for formula (I) and indicated as "G" in Scheme 12 below) can be prepared by alkylation of 3-(trifluoromethyl)-4,5,6,7-tetrahydro-1H-indazole with an alkyl-halide compound of formula (XI) according to reaction scheme 12. Typical alkylation conditions comprise heating a mixture of 3-(trifluoromethyl)-4,5,6,7-tetrahydro-1H-indazole and (XI) in dimethylformamide with potassium carbonate at 140 degc in a microwave reactor for 10 minutes. Compounds of formula (XI) are commercially available or may be prepared from the corresponding acid in a manner similar to that set out in Scheme 8.

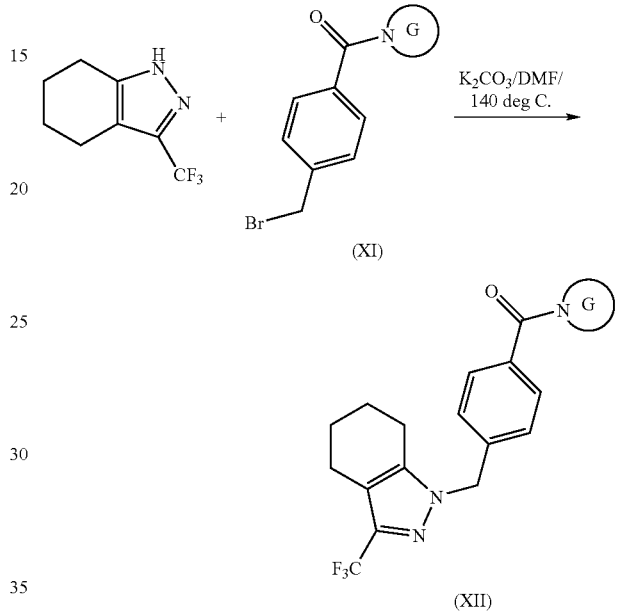

A compound of formula (XXIII) can be prepared from a benzonitrile of formula (XXII) according to reaction scheme 13. Typical reaction conditions comprise treatment of a solution of lithium aluminium hydride in tetrahydrofuran with a compound of formula (XXII) in tetrahydrofuran with cooling, followed by stirring at room temperature for 1.5 h hours. Compounds of formula (XXII) can be prepared in a manner similar to that described above for compounds of formula (I), ie reacting a compound of formula (II) with 3-(trifluoromethyl)-4,5,6,7-tetrahydro-1H-indazole).

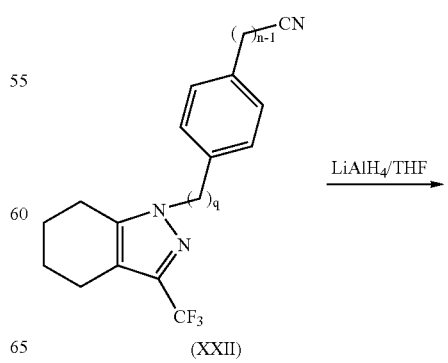

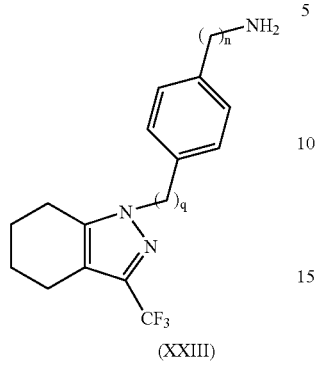

(XXIII)

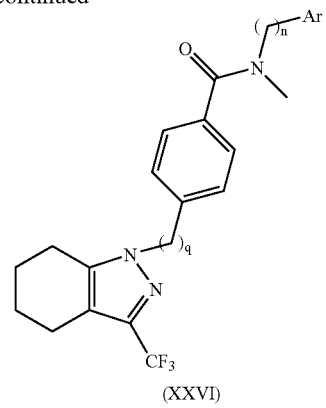

(XXVI)

A compound of formula (XXVI) (i.e. a compound of formula (I) where n=0, m=1, Y=CO and $R^1$=NMe($CH_2$)p-Ar wherein p is 1, 2 or 3 and Ar is phenyl or 5- or 6-membered heterocyclic group, as defined for formula (I)) can be prepared by coupling a compound of formula (XXIV) with a secondary amine according to reaction scheme 14. Typical coupling conditions comprise treatment of polymer supported 1-ethyl-3-(dimethylaminopropyl)carbodiimide with a solution of 1-hydroxy-7-azabezotriazole in tetrahydrofuran:dichloromethane (1:1) followed by the addition of the benzoic acid (XXIV) in N-methyl-2-pyrrolidinone:tetrahydrofuran (1:3), followed by the addition of the amine (XXV) in dichloromethane and allowed to mix for 60 hours. In one embodiment, Ar is aromatic or heterocyclic and n is 1, 2 or 3. Compounds of formula (XXIV) can be prepared in a manner similar to that described above for compounds of formula (I), ie reacting a compound of formula (II) with 3-(trifluoromethyl)-4,5,6,7-tetrahydro-1H-indazole). Compounds of formula (XXV) are commercially available. Compounds of formula (XXIV) can be prepared in a manner similar to that described above for compounds of formula (I).

A compound of formula (XXVII) (i.e. a compound of formula (I) wherein n=1 or 2, m=0, X=$CH_2$ and $R^1$=$NHR^{12'}$ wherein $R^{12'}$ is $SO_2C_{1-4}$alkyl, $SO_2C_{3-6}$cycloalkyl, $C(O)C_{1-4}$alkyl, C(O)phenyl or $C(O)C_{2-4}$alkenyl) can be prepared from a compound of formula (XXIII) by acylation or sulphonylation using a reagent of formula (XVI) according to reaction scheme 15. Typical conditions comprise addition of reagent (XVI) to a solution of (XXIII) in dichloromethane or 5-10% dimethylformamide in dichloromethane in the presence of a suitable base such as triethylamine. Compounds of formula (XVI) are commercially available.

Scheme 15

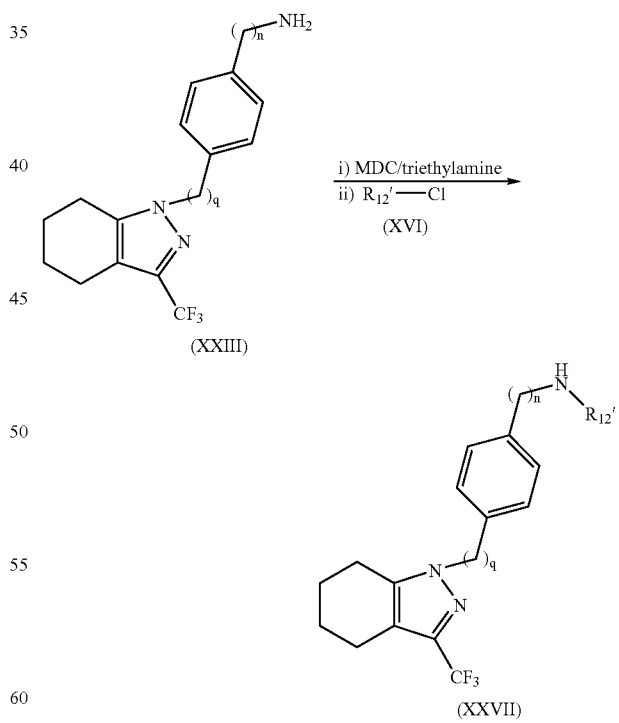

(XXVII)

Scheme 14

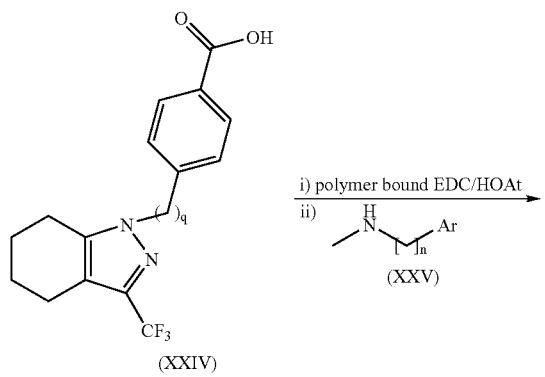

(XXIV)

A compound of formula (XXX) (ie a compound of formula (I) wherein q=0, n=1, m=1, Y=CO, X=$CR^6R^7$ wherein $R^6$ is fluorine and $R^7$ is hydrogen or fluorine, $R^1$=$NR^9R^{10}$ wherein $R^9$ and $R^{10}$ form a 5-membered aromatic or non-aromatic heterocyclic group or a 6-membered non-aromatic heterocyclic group, as defined for formula (I)) can be prepared from a compound of formula (XXVIII) by fluorination using a reagent of formula (XXIX) according to reaction scheme 16. Typical conditions comprise addition of a tetrahydrofuran solution of a compound of formula (XXVIII) to a solution of lithium diisopropylamide in tetrahydrofuran at −78 degC followed 1 hour later by the addition of the fluorinating agent (XXIX) in tetrahydrofuran, then stirring at ambient temperature, giving a mix of R=H and R=F. The compound of formula (XXVIII) can be prepared in a manner similar to that described above for compounds of formula (I), ie reacting a compound of formula (II) with 3-(trifluoromethyl)-4,5,6,7-tetrahydro-1H-indazole). The compound of formula (XXIX) is commercially available.

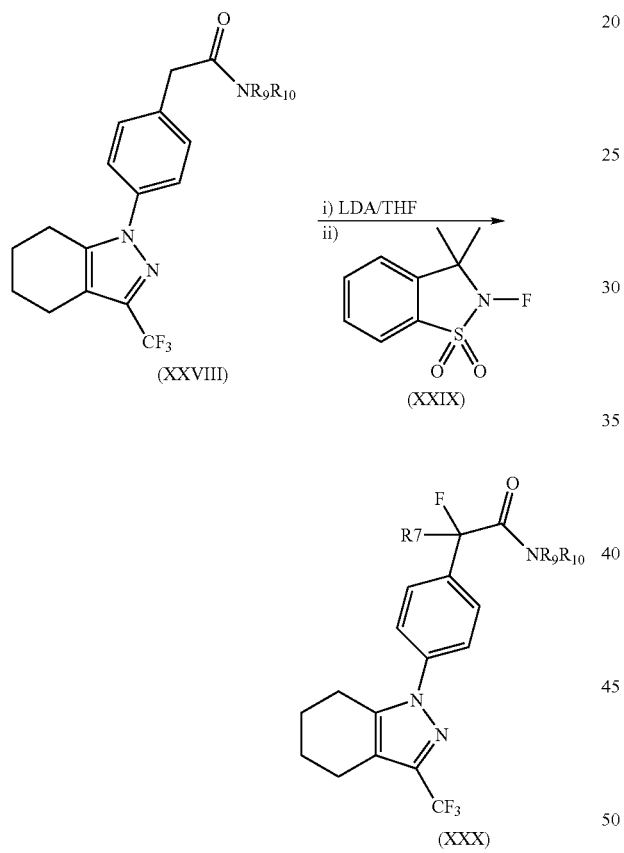

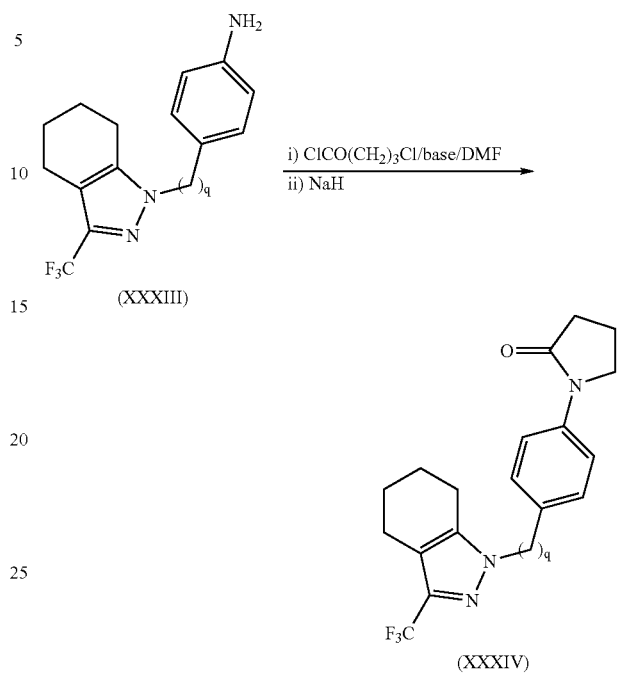

A compound of formula (XXXIII) can be prepared by reduction of the compound of formula (XXXII) using sodium borohydride according to scheme 18. Typical conditions comprise addition of a compound of formula (XXXII) in methanol to a suspension of 10% palladium on charcoal and sodium borohydride in water and stirring at room temperature for 1 hour.

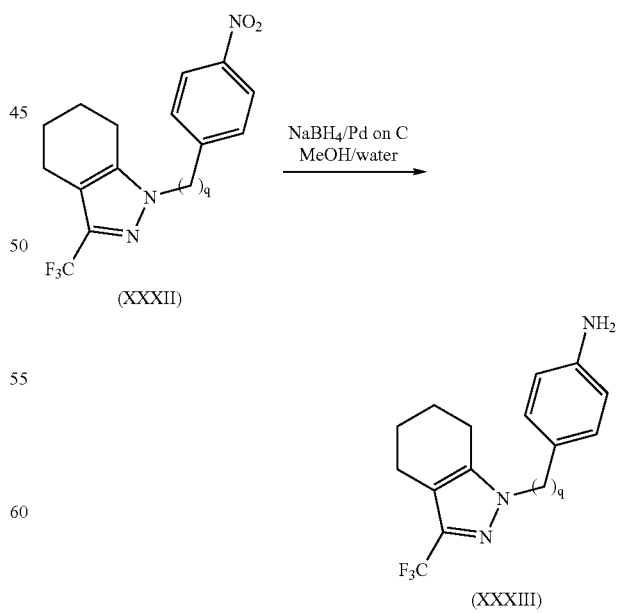

A compound of formula (XXXIV) (ie a compound of formula (I) wherein q is 0 or 1, m and n are both 0 and $R^1$ is optionally substituted N-linked pyrrolidinyl substituted with one keto) can be prepared by acylation then alkylation of a compound of formula (XXXIII) using 4-chlorobutyryl chloride according to reaction scheme 17. Typical conditions comprise treating a solution of a compound of formula (XXXIII) and a suitable base such as diisopropylethylamine in dimethylformamide with 4-chlorobutyryl chloride, followed by the addition of excess sodium hydride (60% suspension in mineral oil) and stirring at room temperature.

A compound of formula (XXXIX) (ie a compound of formula (I) wherein m is 0, n=1 or 2, $R^1$ is 1,2,4-oxadiazol-5-yl and R is $C_{1-6}$alkyl or $C_{3-6}$cycloalkyl) can be prepared upon reaction of a compound of formula (XXXVII) with an amidoxime of formula (XXXVIII) according to reaction scheme 19. Typical conditions comprise addition of 1-ethyl-3-(dimethylaminopropyl)carbodiimide hydrochloride to a slurry of the acid (XXXVII) and 1-hydroxybenzotriazole in acetonitrile, followed by the addition of the appropriate amidoxime after 30 minutes, and then heating at reflux. Compounds of formula (XXXVIII) are commercially available. Compounds of formula (XXXVII) can be prepared in a manner similar to that described above for compounds of formula (V) in Scheme 9.

Scheme 19

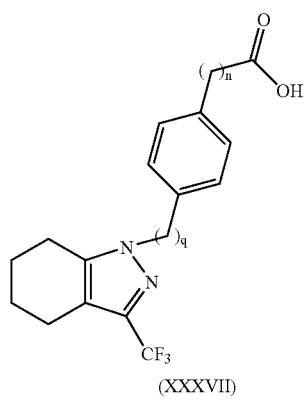

(XXXVII)

EDC/HOBt/MeCN
(XXXVIII)

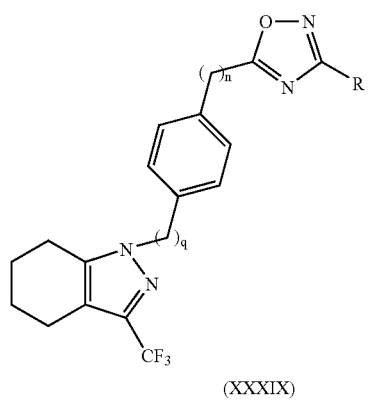

(XXXIX)

A compound of formula (XLV) (ie a compound of formula (I) wherein q=0, n=0, m=1, Y=CO and $R^1$ is a C-linked 5-membered aromatic heterocyclic group optionally substituted by methyl) can be prepared in 3 stages from 3-(trifluoromethyl)-4,5,6,7-tetrahydro-1H-indazole, 4-bromoiodobenzene and a compound of formula (XLIV) according to reaction scheme 20. Typical reaction conditions comprise heating compound A with 4-bromoiodobenzene in the presence of a base (such as potassium carbonate), copper (I) iodide and N,N-dimethylglycine with conventional heating at 130 degC in dimethylsulfoxide. The product is isolated then treated with n-butyllithium in tetrahydrofuran at −78 degC, followed by the treatment with a compound of formula (XLIV). 3-(Trifluoromethyl)-4,5,6,7-tetrahydro-1H-indazole and bromoiodobenzene are commercially available.

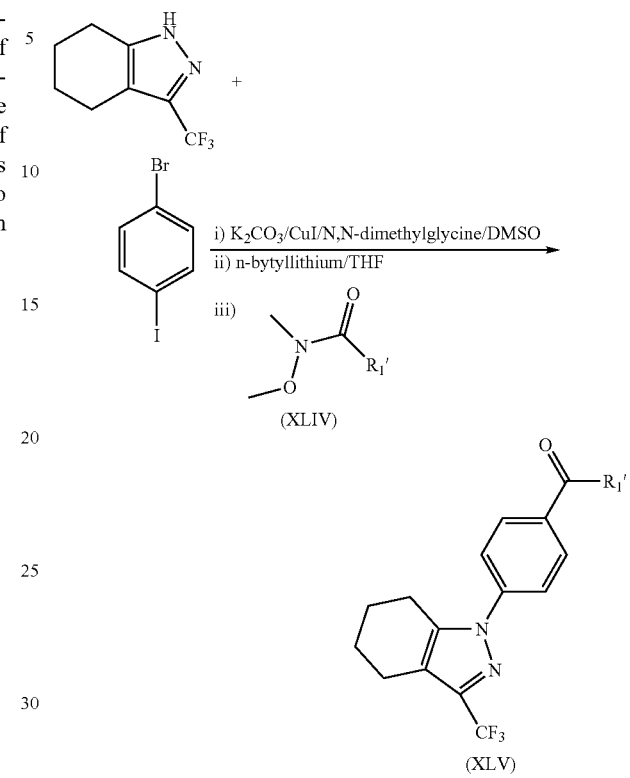

Scheme 20

A compound of formula (XLIV) can be prepared by the acylation of a compound of formula (XLIII) (wherein R1' is a C-linked 5-membered aromatic heterocyclic group optionally substituted with methyl) with N,O-dimethylhydroxylamine hydrochloride according to reaction scheme 21. Typical acylation conditions comprise the addition of HATU (O-(7-azabenzotriazol-1-yl)-N,N,N',N'-tetramethyluronium hexafluorophosphate) to a solution of the compound of formula (XLIII), with N,O-dimethylhydroxylamine hydrochloride and diisopropylamine (DIPEA) in dimethylformamide and stirring at room temperature for 17 hours. The compound of formula (XLIII) is commercially available.

Scheme 21

A compound of formula (XLVI) (wherein q is as defined for formula (I), n=0, m=1, Y=NHCO and $R^2R^3$ form a 4, 5 or 6-membered non-aromatic heterocyclic group optionally substituted as defined for formula (I)), can be prepared from a compound of formula (XXIV) via a Curtius rearrangement and subsequent reaction with a compound $HNR^2R^3$, according to reaction scheme 22. For example, $HNR^2R^3$ may be pyrrolidine. Typical reaction conditions comprise addition of diphenylphosphoryl azide (DPPA) to a mixture of a compound of formula (XXIV) and diisopropylethylamine (DI- PEA) in 1,4-dioxane. After 2 hours of stirring at reflux the mix is treated with the HNR²R³ compound, and reflux continued for a further hour. Compounds of formula (XXIV) can be prepared in a manner similar to that described above for compounds of formula (I), ie reacting a compound of formula (II) with 3-(trifluoromethyl)-4,5,6,7-tetrahydro-1H-indazole).

imidazolyl, triazolyl or pyrazolyl derivative. Compounds of formula (XLVII) are commercially available. The compound of formula (VII) can be prepared in a manner similar to that described above in Scheme 11.

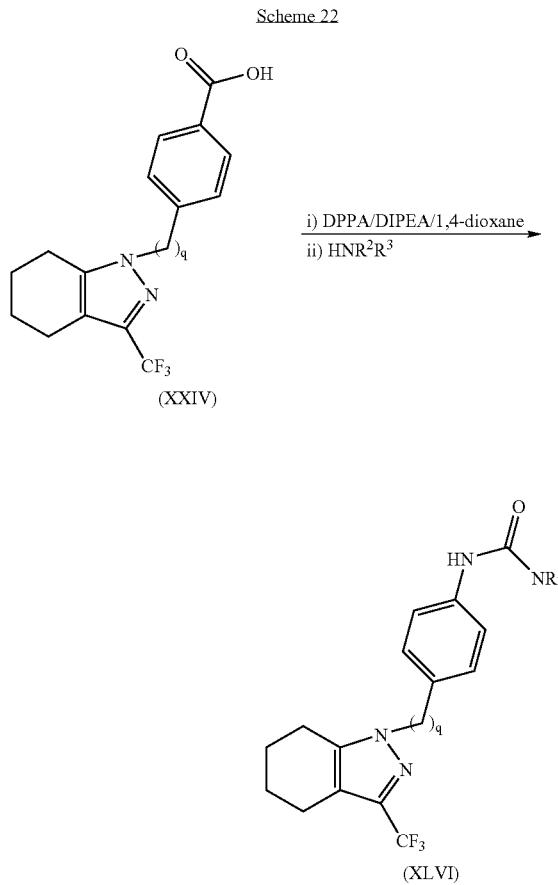

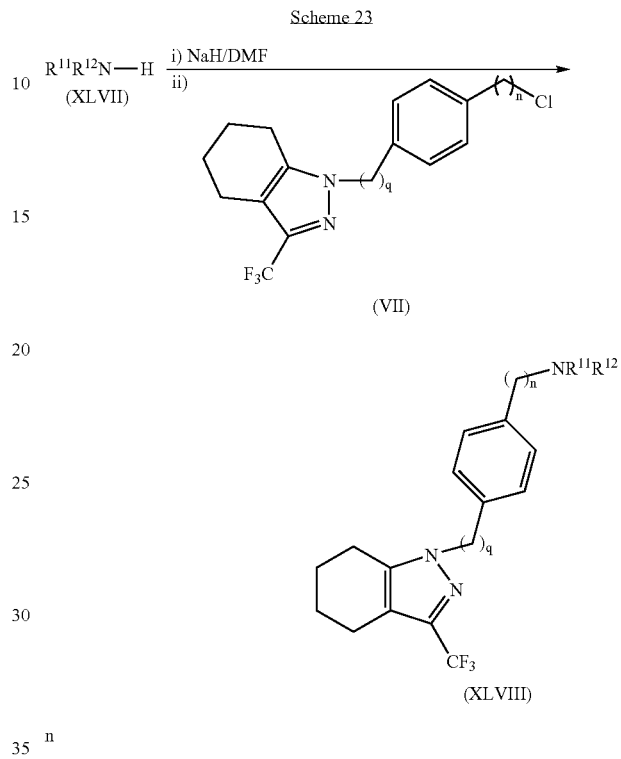

A compound of formula (XLVIII) (wherein q is as defined for formula (I), n=1 or 2, m=0 and R¹ is a group NR¹¹R¹² wherein R¹¹ and R¹² form a 5-membered aromatic heterocyclic group optionally substituted by one or two groups independently selected from the group consisting of $C_{1-4}$alkyl, halo, halo$C_{1-4}$alkyl, hydroxy, $C_{3-6}$cycloalkyl and $C_{1-4}$alkoxy; or imidazolyl substituted by phenyl, or a 5- or 6-membered non-aromatic heterocyclic group which is substituted by at least one keto, and optionally by one or two other groups independently selected from the group consisting of keto, hydroxy and $C_{1-4}$alkoxy) can be prepared by the alkylation of a heterocyclic group of formula (XLVII) (wherein R¹¹ and R¹² are as defined for formula (XLVIII)), with the benzyl chloride compound of formula (VII) according to reaction scheme 23. Typical alkylation conditions comprise treatment of a compound of formula (XLVII) with a suitable base such as sodium hydride (available as a 60% suspension in mineral oil) in dimethylformamide, followed by the addition of the alkylating agent (VII). In one embodiment, NR¹¹R¹² is an Further details for the preparation of compounds of formula (I) are found in the Examples section hereinafter.

The compounds of the invention may be prepared singly or as compound libraries comprising at least 2, for example 5 to 1,000 compounds, for example 10 to 100 compounds. Libraries of compounds of the invention may be prepared by a combinatorial 'split and mix' approach or by multiple parallel synthesis using either solution phase or solid phase chemistry, by procedures known to those skilled in the art. Thus according to a further aspect there is provided a compound library comprising at least 2 compounds of the invention.

The compounds of the present invention potentiate the AMPA receptor. Compounds which potentiate the AMPA receptor are potentially useful for treating diseases and conditions which are mediated by the potentiation of the glutamate receptor.

Thus the present invention provides a compound of formula (I) or a salt or solvate thereof, excluding 4-methyl-N-[4-[4,5,6,7-tetrahydro-3-(trifluoromethyl)-1H-indazol-1-yl]phenyl]-1,2,3-thiadiazole-5-carboxamide and salts thereof for use as a medicament.

In one embodiment, the compound of formula (I) is a compound selected from the group consisting of formula (Ia) (excluding 4-methyl-N-[4-[4,5,6,7-tetrahydro-3-(trifluoromethyl)-1H-indazol-1-yl]phenyl]-1,2,3-thiadiazole-5-carboxamide and salts thereof), (Ib), (Ic), (Id), (Ie) and (If).

In one embodiment, there is provided a compound of formula (Ig) or a salt or solvate thereof for use in medicine:

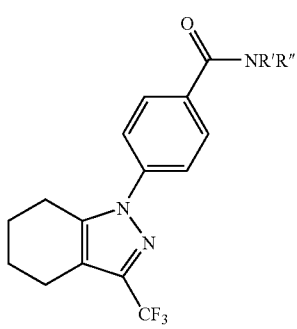

(Ig)

wherein R' and R", together with the nitrogen atom to which they are attached, form a pyrrolidinyl or morpholinyl.

The present invention also provides a compound of formula (Ih) for use in medicine:

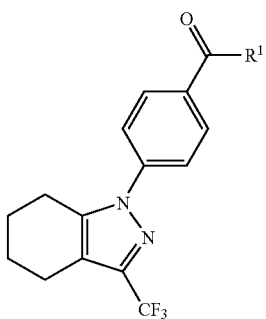

(Ih)

in which $R^1$ is a group $NR^2R^3$ in which $R^2$ and $R^3$ together with the nitrogen atom to which they are attached form a 5-membered non-aromatic heterocyclic ring, which may be substituted with one or more groups selected from halo, $C_{1-4}$alkyl, halo$C_{1-4}$alkyl, and keto. In one embodiment, $R^2$ and $R^3$ together with the nitrogen atom to which they are attached form a pyrrolidinyl ring, which may be substituted with one or more groups selected from halo, $C_{1-4}$alkyl, halo$C_{1-4}$alkyl and keto.

The present invention also provides a salt or a solvate of a compound of formula (Ih) as defined above for use in medicine.

The present invention also provides a pharmaceutical composition comprising a compound of formula (I) or a salt or solvate thereof, excluding 4-methyl-N-[4-[4,5,6,7-tetrahydro-3-(trifluoromethyl)-1H-indazol-1-yl]phenyl]-1,2,3-thiadiazole-5-carboxamide and salts thereof, and at least one carrier, diluent or excipient.

In one embodiment, the compound of formula (I) is selected from the group consisting of a compound of formula (Ia) (excluding 4-methyl-N-[4-[4,5,6,7-tetrahydro-3-(trifluoromethyl)-1H-indazol-1-yl]phenyl]-1,2,3-thiadiazole-5-carboxamide and salts thereof), (Ib), (Ic), (Id), (Ie), (If), (Ig) and (Ih).

The present invention also provides a compound of formula (Ii) or a salt or solvate thereof for use in the treatment of a disease or a condition which is mediated by the glutamate receptor:

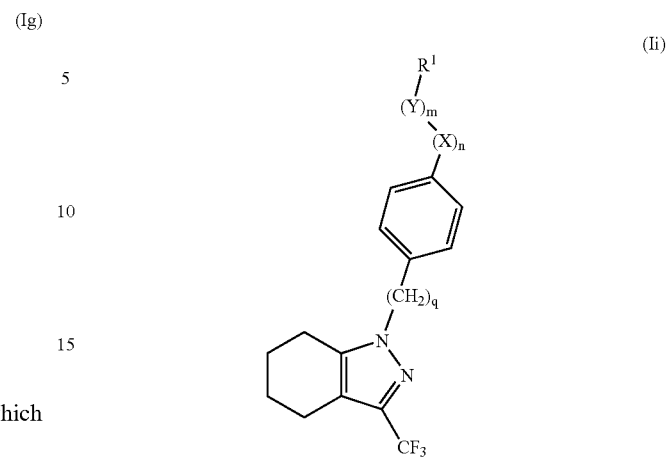

(Ii)

wherein:
  q is 0 or 1;
  n is 0, 1, or 2;
  X is $CR^6R^7$, where $R^6$ and $R^7$ are each independently selected from the group consisting of hydrogen, methyl and fluoro, but $R^6$ and $R^7$ are not both simultaneously methyl; or, when n is 1, $R^6$ and $R^7$ together with the carbon atom to which they are attached, form a 3-membered carbocyclic ring;
  Y is selected from the group consisting of CO, $NR^8CO$, SO, $SO_2$ and $NR^8SO_2$;
  $R^8$ is selected from the group consisting of hydrogen, $C_{2-4}$alkenyl and $C_{1-4}$alkyl;
  m is 0 or 1; and
  a) when n is 0 and m=1, then $R^1$ is selected from the group consisting of (i) $C_{1-4}$alkyl, (ii) a C-linked 5-membered aromatic heterocyclic group optionally substituted with methyl, (iii) $NHR^2$ and (iv) $NR^{2'}R^3$, wherein:
    $R^2$ is selected from the group consisting of $C_{1-6}$straight chain alkyl, $C_{4-6}$branched chain alkyl and a group —$(CH_2)_pZ$ wherein p is 1, 2 or 3;
    Z is hydroxy, methoxy, NHMe, phenyl or a 5- or 6-membered non-aromatic heterocyclic group, the phenyl or heterocyclic group being optionally substituted by one, two or three groups independently selected from the group consisting of halo, $C_{1-4}$alkyl and halo$C_{1-4}$ alkyl; wherein when Y is CO, $R^2$ is not $(CH_2)_2$pyrrolidinyl;
    $R^{2'}$ is selected from the group consisting of methyl and ethyl;
    $R^3$ is selected from the group consisting of $C_{1-6}$alkyl and a group —$(CH_2)_pZ'$ wherein p is 1, 2 or 3;
    $Z'$ is hydroxy, methoxy, NHMe, phenyl or a 5- or 6-membered non-aromatic or aromatic heterocyclic group, the phenyl or heterocyclic group being optionally substituted by one, two or three groups independently selected from the group consisting of halo, $C_{1-4}$alkyl and halo$C_{1-4}$alkyl; or
    $R^{2'}$ and $R^3$, together with the nitrogen atom to which they are attached, form:
      (i) a 4 or 5-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), halo$C_{1-4}$alkyl, and keto; or (ii) a 6-membered non-aromatic heterocyclic group, which ring is optionally substituted by one, two or three groups independently selected from the group consisting of halo, hydroxy, $NR^{13}R^{14}$ (wherein $R^{13}$ and $R^{14}$ are independently selected from the group consisting of hydrogen and $C_{1-4}$alkyl), $C_{2-4}$alkyl, halo$C_{1-4}$alkyl and keto;

b) when n and m are both simultaneously 0, $R^1$ is selected from the group consisting of:

$C_{1-6}$alkoxy;

a monocyclic saturated or partially unsaturated 5- or 6-membered heterocyclic group, attached through a carbon atom and optionally substituted by one, two or three groups independently selected from the group consisting of $C_{1-4}$alkyl, $C(O)C_{1-4}$alkyl, halo$C_{1-4}$ alkyl, halo and keto;

N-linked pyrrolidinyl, optionally substituted with one, two or three groups independently selected from the group consisting of $C_{1-4}$alkyl, $C(O)C_{1-4}$alkyl, halo $C_{1-4}$alkyl, halo and keto; and oxazolyl or imidazolyl, both being optionally substituted by $C_{1-4}$alkyl;

c) when n is 1 or 2, and m is 1, $R^1$ is selected from the group consisting of $C_{1-4}$alkyl, benzyl, cyclopropyl, thienyl, and $NR^9R^{10}$ wherein:

$R^9$ is selected from the group consisting of hydrogen and $C_{1-4}$alkyl, and $R^{10}$ is selected from the group consisting of $C_{1-6}$ straight chain alkyl, $C_{3-6}$cycloalkyl and $—(CH_2)_pZ$ wherein p is 1, 2 or 3;

Z is a phenyl or a 5- or 6-membered heterocyclic group, the phenyl or heterocyclic group being optionally substituted by one, two or three groups independently selected from the group consisting of halo and $C_{1-4}$alkyl; or $R^9$ and $R^{10}$, together with the nitrogen atom to which they are attached, form a 5-membered aromatic or non-aromatic heterocyclic group or a 6-membered non-aromatic heterocyclic group, any of the rings being optionally substituted by one, two or three groups independently selected from the group consisting of $C_{1-4}$alkyl, halo, phenyl and (in the case of a non-aromatic ring) keto; and d) when n is 1 or 2, and m is 0, $R^1$ is selected from the group consisting of cyano, hydroxy, $NH_2$, a C-linked 5-membered aromatic heterocyclic group optionally substituted with one, two or three groups independently selected from the group consisting of $C_{1-6}$alkyl and $C_{3-6}$cycloalkyl, and $NR^{11}R^{12}$ in which:

$R^{11}$ is hydrogen and $R^{12}$ is selected from the group consisting of $SO_2C_{1-4}$alkyl, $SO_2C_{3-6}$cycloalkyl, $C(O)C_{1-4}$alkyl, and $C(O)C_{2-4}$alkenyl; or $R^{11}$ is selected from the group consisting of $C_{1-4}$alkyl and $C_{2-4}$alkenyl, and $R^{12}$ is selected from the group consisting of $SO_2C_{1-4}$alkyl, $SO_2C_{3-6}$cycloalkyl, $C(O)C_{1-4}$alkyl, $C(O)$phenyl and $C(O)C_{2-4}$alkenyl or $R^{11}$ and $R^{12}$, together with the nitrogen atom to which they are attached, form a group selected from the group consisting of:

(i) a 5-membered aromatic heterocyclic group which is optionally substituted by one or two groups independently selected from the group consisting of $C_{1-4}$alkyl, halo, halo$C_{1-4}$alkyl, hydroxy, $C_{3-6}$cycloalkyl and $C_{1-4}$alkoxy; and (ii) imidazolyl substituted by phenyl;

(iii) a 5-membered non-aromatic heterocyclic group which is substituted by one, two or three groups independently selected from the group consisting of keto, hydroxy and $C_{1-4}$alkoxy; and (iv) a 6-membered non-aromatic heterocyclic group, which is optionally substituted by one, two or three groups independently selected from the group consisting of keto, hydroxy and $C_{1-4}$alkoxy.

The present invention also provides a compound of formula (J) or a salt or solvate thereof for use as a medicament:

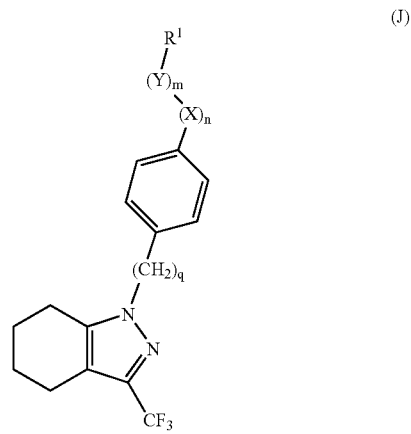

(J)

wherein:

q is 0 or 1 n=0, 1, or 2;

X is $CR^6R^7$, where $R^6$ and $R^7$ are each independently selected from H, Me and F, but $R^6$ and $R^7$ are not both simultaneously Me; or, when n=1, $R^6$ and $R^7$ together with the carbon atom to which they are attached, form a 3-membered carbocyclic ring.

Y is selected from the group consisting of CO, $NR^8CO$, SO, $SO_2$ and $NR^8SO_2$ $R^8$ is selected from H and $C_{1-4}$ alkyl m=0 or 1 and a) when n is 0 and m=1, then:

$R^1$ is selected from the group consisting of $C_{1-4}$ alkyl, and $NR^2R^3$ in which:

$R^2$ is $CH_3$ and $R^3$ is selected from $C_{1-6}$ straight chain alkyl, $C(O)C_{1-4}$alkyl and $—(CH_2)_pZ$ where p=1, 2 or 3;

Z is a phenyl or a 5- or 6-membered heterocyclic group, the phenyl or heterocyclic group optionally being substituted with one or more groups selected from halo, $C_{1-4}$alkyl and halo$C_{1-4}$alkyl; or $R^2$ and $R^3$ together with the nitrogen atom to which they are attached form a 5-membered non-aromatic heterocyclic ring, which ring may be substituted with one or more groups selected from halo, $C_{1-4}$alkyl, halo$C_{1-4}$alkyl, and keto;

b) when n and m are both simultaneously 0, $R^1$ is a monocyclic saturated or partially unsaturated 5- or 6-membered heterocyclic ring, attached through a carbon atom and optionally substituted with one or more groups selected from $C_{1-4}$alkyl, $C(O)C_{1-4}$alkyl, halo $C_{1-4}$alkyl, halo and keto;

c) when n is 1 or 2, and m is 1, $R^1$ is selected from the group consisting of $C_{1-4}$ alkyl and $NR^9R^{10}$ in which:

$R^9$ is selected from hydrogen and $C_{1-4}$alkyl, and $R^{10}$ is selected from $C_{1-6}$ straight chain alkyl, $C_{3-6}$cycloalkyl, $C(O)C_{1-4}$alkyl and $-(CH_2)_pZ$ where p=1, 2 or 3;

Z is a phenyl or a 5- or 6-membered heterocyclic group, the phenyl or heterocyclic group optionally being substituted with one or more groups selected from halo and $C_{1-4}$alkyl; or $R^9$ and $R^{10}$ together with the nitrogen atom to which they are attached form a 5-membered aromatic or non-aromatic heterocyclic ring or a 6-membered non-aromatic heterocyclic ring, either of which may include one or more further heteroatoms selected from N, O or S, and may be substituted with one or more groups selected from $C_{1-4}$alkyl, halo, and (in the case of a non-aromatic ring) keto; and d) when n is 1 or 2, and m is 0, $R^1$ is selected from the group consisting of cyano, OH, $NH_2$ and $NR^{11}R^{12}$ in which $R^{11}$ is selected from H and $C_{1-4}$alkyl, and $R^{12}$ is selected from $SO_2C_{1-4}$alkyl and $C(O)C_{1-4}$alkyl; or $R^{11}$ and $R^{12}$ together with the nitrogen atom to which they are attached form a group selected from a 5-membered aromatic heterocyclic ring, a 5-membered non-aromatic heterocyclic ring and a 6-membered non-aromatic heterocyclic ring, any of which may include one or more further heteroatoms selected from N, O or S, and wherein the 5-membered aromatic heterocyclic ring is optionally substituted with one or more groups selected from $C_{1-4}$alkyl, halo, halo$C_{1-4}$alkyl, hydroxy and $C_{1-4}$alkoxy; the 5-membered non-aromatic heterocyclic ring is substituted with one or more groups selected from keto, hydroxy and $C_{1-4}$alkoxy; and the 6-membered non-aromatic heterocyclic ring is optionally substituted with one or more groups selected from keto, hydroxy and $C_{1-4}$alkoxy.

Any statements above regarding embodiments of compounds of any of formula (I), (A), (Ia), (Ib), (Ic), (Id), (Ie), (If) above apply to compounds of formula (Ig), formula (Ih) and formula (Ii).

Examples of compounds for use as a medicament as described herein, or for a composition as described herein, or for use in the treatment of a disease or a condition which is mediated by the glutamate receptor as described herein, include:

1. N,N-dimethyl-4-[3-(trifluoromethyl)-4,5,6,7-tetrahydro-1H-indazol-1-yl]benzamide (Example 1)
2. 1-[4-(1-pyrrolidinylcarbonyl)phenyl]-3-(trifluoromethyl)-4,5,6,7-tetrahydro-1H-indazole (Example 2)
3. N-methyl-N-(phenylmethyl)-4-[3-(trifluoromethyl)-4,5,6,7-tetrahydro-1H-indazol-1-yl]benzamide (Example 3)
4. N-ethyl-N-methyl-4-[3-(trifluoromethyl)-4,5,6,7-tetrahydro-1H-indazol-1-yl]benzamide (Example 4)
5. N-butyl-N-methyl-4-[3-(trifluoromethyl)-4,5,6,7-tetrahydro-1H-indazol-1-yl]benzamide (Example 5)
6. N-methyl-N-(2-phenylethyl)-4-[3-(trifluoromethyl)-4,5,6,7-tetrahydro-1H-indazol-1-yl]benzamide (Example 6)
7. N,N-dimethyl-4-[3-(trifluoromethyl)-4,5,6,7-tetrahydro-1H-indazol-1-yl]benzenesulfonamide (Example 7)
8. 1-{4-[3-(trifluoromethyl)-4,5,6,7-tetrahydro-1H-indazol-1-yl]phenyl}ethanone (Example 8)
9. 1-{4-[3-(trifluoromethyl)-4,5,6,7-tetrahydro-1H-indazol-1-yl]phenyl}-1-propanone (Example 9)
10. 1-[4-(methylsulfonyl)phenyl]-3-(trifluoromethyl)-4,5,6,7-tetrahydro-1H-indazole (Example 10)
11. 1-{4-[3-(trifluoromethyl)-4,5,6,7-tetrahydro-1H-indazol-1-yl]phenyl}-2-propanone (Example 11)
12. N,N-dimethyl-2-{4-[3-(trifluoromethyl)-4,5,6,7-tetrahydro-1H-indazol-1-yl]phenyl}acetamide (Example 12)
13. 1-{4-[2-oxo-2-(1-pyrrolidinyl)ethyl]phenyl}-3-(trifluoromethyl)-4,5,6,7-tetrahydro-1H-indazole (Example 13)
14. N-ethyl-N-methyl-2-{4-[3-(trifluoromethyl)-4,5,6,7-tetrahydro-1H-indazol-1-yl]phenyl}acetamide (Example 14)
15. N-methyl-N-(phenylmethyl)-2-{4-[3-(trifluoromethyl)-4,5,6,7-tetrahydro-1H-indazol-1-yl]phenyl}acetamide (Example 15)
16. N-butyl-N-methyl-2-{4-[3-(trifluoromethyl)-4,5,6,7-tetrahydro-1H-indazol-1-yl]phenyl}acetamide (Example 16)
17. N-methyl-N-(2-phenylethyl)-2-{4-[3-(trifluoro methyl)-4,5,6,7-tetrahydro-1H-indazol-1-yl]phenyl}acetamide (Example 17)
18. 1-{[4-(1-pyrrolidinylcarbonyl)phenyl]methyl}-3-(trifluoromethyl)-4,5,6,7-tetrahydro-1H-indazole (Example 18)
19. 1-{4-[1-methyl-2-oxo-2-(1-pyrrolidinyl)ethyl]phenyl}-3-(trifluoromethyl)-4,5,6,7-tetrahydro-1H-indazole (Example 19)
20. N,N-dimethyl-3-{4-[3-(trifluoromethyl)-4,5,6,7-tetrahydro-1H-indazol-1-yl]phenyl}propanamide (Example 20)
21. 1-{4-[3-oxo-3-(1-pyrrolidinyl)propyl]phenyl}-3-(trifluoromethyl)-4,5,6,7-tetrahydro-1H-indazole (Example 21)
22. 1-{4-[1-(1-pyrrolidinylcarbonyl)cyclopropyl]phenyl}-3-(trifluoromethyl)-4,5,6,7-tetrahydro-1H-indazole (Example 22)
23. 1-{4-[2-oxo-2-(1-piperidinyl)ethyl]phenyl}-3-(trifluoromethyl)-4,5,6,7-tetrahydro-1H-indazole (Example 23)
24. 1-{4-[2-(3,3-difluoro-1-pyrrolidinyl)-2-oxoethyl]phenyl}-3-(trifluoromethyl)-4,5,6,7-tetrahydro-1H-indazole (Example 24)
25. N-methyl-N-propyl-2-{4-[3-(trifluoromethyl)-4,5,6,7-tetrahydro-1H-indazol-1-yl]phenyl}acetamide (Example 25)
26. N-cyclopentyl-2-{4-[3-(trifluoromethyl)-4,5,6,7-tetrahydro-1H-indazol-1-yl]phenyl}acetamide (Example 26)
27. N-methyl-N-(2-thienylmethyl)-2-{4-[3-(trifluoromethyl)-4,5,6,7-tetrahydro-1H-indazol-1-yl]phenyl}acetamide (Example 27)
28. {4-[3-(trifluoromethyl)-4,5,6,7-tetrahydro-1H-indazol-1-yl]phenyl}acetonitrile (Example 28)
29. {4-[3-(trifluoromethyl)-4,5,6,7-tetrahydro-1H-indazol-1-yl]phenyl}methanol (Example 29)
30. N-methyl-N-({4-[3-(trifluoromethyl)-4,5,6,7-tetrahydro-1H-indazol-1-yl]phenyl}methyl)acetamide (Example 30)
31. 1-({4-[3-(trifluoromethyl)-4,5,6,7-tetrahydro-1H-indazol-1-yl]phenyl}methyl)-2-pyrrolidinone (Example 31)
32. N-methyl-N-({4-[3-(trifluoromethyl)-4,5,6,7-tetrahydro-1H-indazol-1-yl]phenyl}methyl)propanamide (Example 32)
33. N-ethyl-N-({4-[3-(trifluoromethyl)-4,5,6,7-tetrahydro-1H-indazol-1-yl]phenyl}methyl)acetamide (Example 33)
34. 1-({4-[3-(trifluoromethyl)-4,5,6,7-tetrahydro-1H-indazol-1-yl]phenyl}methyl)-2-piperidinone (Example 34)
35. 1-methyl-5-{4-[3-(trifluoromethyl)-4,5,6,7-tetrahydro-1H-indazol-1-yl]phenyl}-2-pyrrolidinone (Example 35)
36. N-[3-(1H-imidazol-1-yl)propyl]-N-methyl-4-[3-(trifluoromethyl)-4,5,6,7-tetrahydro-1H-indazol-1-yl]benzamide (Example 36)
37. N-methyl-N-[2-(2-thienyl)ethyl]-4-[3-(trifluoromethyl)-4,5,6,7-tetrahydro-1H-indazol-1-yl]benzamide (Example 37)

38. N-methyl-N-[2-(1H-1,2,4-triazol-1-yl)ethyl]-4-[3-(trifluoromethyl)-4,5,6,7-tetrahydro-1H-indazol-1-yl]benzamide (Example 38)
39. N-methyl-N-(1,3-thiazol-2-ylmethyl)-4-[3-(trifluoromethyl)-4,5,6,7-tetrahydro-1H-indazol-1-yl]benzamide (Example 39)
40. N-methyl-N-[2-(1-methyl-1H-pyrrol-2-yl)ethyl]-4-[3-(trifluoromethyl)-4,5,6,7-tetrahydro-1H-indazol-1-yl]benzamide (Example 40)
41. N-methyl-N-(2-thienylmethyl)-4-[3-(trifluoromethyl)-4,5,6,7-tetrahydro-1H-indazol-1-yl]benzamide (Example 41)
42. N-methyl-N-(3-pyridinylmethyl)-4-[3-(trifluoromethyl)-4,5,6,7-tetrahydro-1H-indazol-1-yl]benzamide (Example 42)
43. N-(2-furanylmethyl)-N-methyl-4-[3-(trifluoromethyl)-4,5,6,7-tetrahydro-1H-indazol-1-yl]benzamide (Example 43)
44. N-[(4-fluorophenyl)methyl]-N-methyl-4-[3-(trifluoromethyl)-4,5,6,7-tetrahydro-1H-indazol-1-yl]benzamide (Example 44)
45. 1-[4-(4-morpholinylcarbonyl)phenyl]-3-(trifluoromethyl)-4,5,6,7-tetrahydro-1H-indazole (Example 45)
46. N-({4-[3-(trifluoromethyl)-4,5,6,7-tetrahydro-1H-indazol-1-yl]phenyl}methyl)methanesulfonamide (Example 46)
47. 1-{4-[1-fluoro-2-oxo-2-(1-pyrrolidinyl)ethyl]phenyl}-3-(trifluoromethyl)-4,5,6,7-tetrahydro-1H-indazole
48. 1-{4-[1,1-difluoro-2-oxo-2-(1-pyrrolidinyl)ethyl]phenyl}-3-(trifluoromethyl)-4,5,6,7-tetrahydro-1H-indazole
49. N-methyl-N-({4-[3-(trifluoromethyl)-4,5,6,7-tetrahydro-1H-indazol-1-yl]phenyl}methyl)methanesulfonamide
50. 1-(4-{[3-(trifluoromethyl)-4,5,6,7-tetrahydro-1H-indazol-1-yl]methyl}phenyl)-2-pyrrolidinone
51. N-methyl-N-({4-[3-(trifluoromethyl)-4,5,6,7-tetrahydro-1H-indazol-1-yl]phenyl}methyl)-1-pyrrolidinecarboxamide
52. 5-{4-[3-(trifluoromethyl)-4,5,6,7-tetrahydro-1H-indazol-1-yl]phenyl}-2-pyrrolidinone
53. N-(1-{4-[3-(trifluoromethyl)-4,5,6,7-tetrahydro-1H-indazol-1-yl]phenyl}ethyl)acetamide
54. N-methyl-N-(1-{4-[3-(trifluoromethyl)-4,5,6,7-tetrahydro-1H-indazol-1-yl]phenyl}ethyl)acetamide
55. 1-[4-(1-acetyl-2-pyrrolidinyl)phenyl]-3-(trifluoromethyl)-4,5,6,7-tetrahydro-1H-indazole
56. 1-(2-{4-[3-(trifluoromethyl)-4,5,6,7-tetrahydro-1H-indazol-1-yl]phenyl}ethyl)-2-pyrrolidinone
57. 1-{4-[(1,1-dioxido-2-isothiazolidinyl)methyl]phenyl}-3-(trifluoromethyl)-4,5,6,7-tetrahydro-1H-indazole
58. 2-methyl-N-({4-[3-(trifluoromethyl)-4,5,6,7-tetrahydro-1H-indazol-1-yl]phenyl}methyl)propanamide
59. N-({4-[3-(trifluoromethyl)-4,5,6,7-tetrahydro-1H-indazol-1-yl]phenyl}methyl)butanamide
60. N-({4-[3-(trifluoromethyl)-4,5,6,7-tetrahydro-1H-indazol-1-yl]phenyl}methyl)-2-thiophenecarboxamide
61. N-({4-[3-(trifluoromethyl)-4,5,6,7-tetrahydro-1H-indazol-1-yl]phenyl}methyl)propanamide
62. N-({4-[3-(trifluoromethyl)-4,5,6,7-tetrahydro-1H-indazol-1-yl]phenyl}methyl)acetamide
63. N-methyl-2-phenyl-N-({4-[3-(trifluoromethyl)-4,5,6,7-tetrahydro-1H-indazol-1-yl]phenyl}methyl)acetamide
64. N-(2-hydroxyethyl)-N-methyl-4-[3-(trifluoromethyl)-4,5,6,7-tetrahydro-1H-indazol-1-yl]benzamide
65. N-methyl-N-[2-(methyloxy)ethyl]-4-[3-(trifluoromethyl)-4,5,6,7-tetrahydro-1H-indazol-1-yl]benzamide
66. N-methyl-N-[2-(methylamino)ethyl]-4-[3-(trifluoromethyl)-4,5,6,7-tetrahydro-1H-indazol-1-yl]benzamide
67. 1-({4-[3-(trifluoromethyl)-4,5,6,7-tetrahydro-1H-indazol-1-yl]phenyl}carbonyl)-3-pyrrolidinol
68. N-methyl-1-({4-[3-(trifluoromethyl)-4,5,6,7-tetrahydro-1H-indazol-1-yl]phenyl}carbonyl)-3-pyrrolidinamine
69. 1-[4-(1-azetidinylcarbonyl)phenyl]-3-(trifluoromethyl)-4,5,6,7-tetrahydro-1H-indazole
70. 1-({4-[3-(trifluoromethyl)-4,5,6,7-tetrahydro-1H-indazol-1-yl]phenyl}carbonyl)-3-azetidinol
71. (3,3-difluorocyclobutyl){4-[3-(trifluoromethyl)-4,5,6,7-tetrahydro-1H-indazol-1-yl]phenyl}methanone
72. 1-[4-(1H-imidazol-1-yl)phenyl]-3-(trifluoromethyl)-4,5,6,7-tetrahydro-1H-indazole
73. N-({4-[3-(trifluoromethyl)-4,5,6,7-tetrahydro-1H-indazol-1-yl]phenyl}methyl)-2-propenamide
74. N-(1-methylethenyl)-N-({4-[3-(trifluoromethyl)-4,5,6,7-tetrahydro-1H-indazol-1-yl]phenyl}methyl)-2-propenamide
75. N-methyl-N-({4-[3-(trifluoromethyl)-4,5,6,7-tetrahydro-1H-indazol-1-yl]phenyl}methyl)-2-propenamide
76. 1-{4-[(3-methyl-1,2,4-oxadiazol-5-yl)methyl]phenyl}-3-(trifluoromethyl)-4,5,6,7-tetrahydro-1H-indazole
77. 1-{4-[(3-cyclopropyl-1,2,4-oxadiazol-5-yl)methyl]phenyl}-3-(trifluoromethyl)-4,5,6,7-tetrahydro-1H-indazole
78. N-ethyl-4-[3-(trifluoromethyl)-4,5,6,7-tetrahydro-1H-indazol-1-yl]benzamide
79. N-methyl-N-(1-methylethyl)-4-[3-(trifluoromethyl)-4,5,6,7-tetrahydro-1H-indazol-1-yl]benzamide
80. 1-[4-(1-piperidinylcarbonyl)phenyl]-3-(trifluoromethyl)-4,5,6,7-tetrahydro-1H-indazole
81. N,N-diethyl-4-[3-(trifluoromethyl)-4,5,6,7-tetrahydro-1H-indazol-1-yl]benzamide
82. N-methyl-4-[3-(trifluoromethyl)-4,5,6,7-tetrahydro-1H-indazol-1-yl]benzamide
83. 1-{4-[2-oxo-2-(2-phenyl-1-pyrrolidinyl)ethyl]phenyl}-3-(trifluoromethyl)-4,5,6,7-tetrahydro-1H-indazole
84. N-methyl-N-({4-[3-(trifluoromethyl)-4,5,6,7-tetrahydro-1H-indazol-1-yl]phenyl}methyl)benzamide
85. 1-[4-(1,3-oxazol-5-yl)phenyl]-3-(trifluoromethyl)-4,5,6,7-tetrahydro-1H-indazole
86. 1-[4-(propyloxy)phenyl]-3-(trifluoromethyl)-4,5,6,7-tetrahydro-1H-indazole
87. 1-[4-(1-methyl-1H-imidazol-4-yl)phenyl]-3-(trifluoromethyl)-4,5,6,7-tetrahydro-1H-indazole
88. N-({4-[3-(trifluoromethyl)-4,5,6,7-tetrahydro-1H-indazol-1-yl]phenyl}methyl)-2-propanesulfonamide
89. N-({4-[3-(trifluoromethyl)-4,5,6,7-tetrahydro-1H-indazol-1-yl]phenyl}methyl)cyclopropanesulfonamide
90. N-({4-[3-(trifluoromethyl)-4,5,6,7-tetrahydro-1H-indazol-1-yl]phenyl}methyl)cyclopentanesulfonamide
91. 1-[4-(1-pyrrolidinylsulfonyl)phenyl]-3-(trifluoromethyl)-4,5,6,7-tetrahydro-1H-indazole
92. N-(2-methylpropyl)-4-[3-(trifluoromethyl)-4,5,6,7-tetrahydro-1H-indazol-1-yl]benzenesulfonamide
93. 1-[4-(4-morpholinylsulfonyl)phenyl]-3-(trifluoromethyl)-4,5,6,7-tetrahydro-1H-indazole
94. N-[2-(methyloxy)ethyl]-4-[3-(trifluoromethyl)-4,5,6,7-tetrahydro-1H-indazol-1-yl]benzenesulfonamide
95. N-[2-(1-pyrrolidinyl)ethyl]-4-[3-(trifluoromethyl)-4,5,6,7-tetrahydro-1H-indazol-1-yl]benzenesulfonamide
96. N-(tetrahydro-2-furanylmethyl)-4-[3-(trifluoromethyl)-4,5,6,7-tetrahydro-1H-indazol-1-yl]benzenesulfonamide
97. 1-[4-(1H-imidazol-1-ylmethyl)phenyl]-3-(trifluoromethyl)-4,5,6,7-tetrahydro-1H-indazole
98. 1-[4-(1H-1,2,4-triazol-1-ylmethyl)phenyl]-3-(trifluoromethyl)-4,5,6,7-tetrahydro-1H-indazole 99. 1-[4-(1H-pyrazol-1-ylmethyl)phenyl]-3-(trifluoromethyl)-4,5,6,7-tetrahydro-1H-indazole
100. 1-[4-(1H-1,2,3-triazol-1-ylmethyl)phenyl]-3-(trifluoromethyl)-4,5,6,7-tetrahydro-1H-indazole
101. 1-[4-(2H-1,2,3-triazol-2-ylmethyl)phenyl]-3-(trifluoromethyl)-4,5,6,7-tetrahydro-1H-indazole
102. 1-{4-[(4-methyl-1H-pyrazol-1-yl)methyl]phenyl}-3-(trifluoromethyl)-4,5,6,7-tetrahydro-1H-indazole
103. 1-{4-[(3,5-dimethyl-1H-pyrazol-1-yl)methyl]phenyl}-3-(trifluoromethyl)-4,5,6,7-tetrahydro-1H-indazole
104. 3-(trifluoromethyl)-1-(4-{[3-(trifluoromethyl)-1H-pyrazol-1-yl]methyl}phenyl)-4,5,6,7-tetrahydro-1H-indazole
105. 3-(trifluoromethyl)-1-(4-{[5-(trifluoromethyl)-1H-pyrazol-1-yl]methyl}phenyl)-4,5,6,7-tetrahydro-1H-indazole
106. 1-(4-{[5-methyl-3-(trifluoromethyl)-1H-pyrazol-1-yl]methyl}phenyl)-3-(trifluoromethyl)-4,5,6,7-tetrahydro-1H-indazole
107. 1-(4-{[3-methyl-5-(trifluoromethyl)-1H-pyrazol-1-yl]methyl}phenyl)-3-(trifluoromethyl)-4,5,6,7-tetrahydro-1H-indazole
108. 1-{4-[(2-methyl-1H-imidazol-1-yl)methyl]phenyl}-3-(trifluoromethyl)-4,5,6,7-tetrahydro-1H-indazole
109. 1-(4-{[2-(1-methylethyl)-1H-imidazol-1-yl]methyl}phenyl)-3-(trifluoromethyl)-4,5,6,7-tetrahydro-1H-indazole
110. 1-{4-[(4-phenyl-1H-imidazol-1-yl)methyl]phenyl}-3-(trifluoromethyl)-4,5,6,7-tetrahydro-1H-indazole
111. 1-{4-[(4-bromo-1H-pyrazol-1-yl)methyl]phenyl}-3-(trifluoromethyl)-4,5,6,7-tetrahydro-1H-indazole
112. N-methyl-1H-imidazol-2-yl){4-[3-(trifluoromethyl)-4,5,6,7-tetrahydro-1H-indazol-1-yl]phenyl}methanone
113. N-methyl-N-{4-[3-(trifluoromethyl)-4,5,6,7-tetrahydro-1H-indazol-1-yl]phenyl}-1-pyrrolidinecarboxamide and salts and solvates thereof.

It will be appreciated that the invention includes the following further aspects. Hereinafter, the term "a compound of the invention" refers to compounds of formula (II), their salts and their solvates as defined in any aspect of the invention (except Intermediate compounds in chemical processes). The embodiments described in respect of the first aspect apply equally to each of these further aspects:

i) the use of a compound of formula (II) or a salt or solvate thereof in the manufacture of a medicament for treating a disease or condition mediated by a reduction or imbalance in glutamate receptor function in a mammal;

ii) a compound of formula (II) or a salt or solvate thereof for use in treating a disease or condition mediated by a reduction or imbalance in glutamate receptor function in a mammal;

iii) a method of treatment of a disease or condition mediated by a reduction or imbalance in glutamate receptor function in a mammal comprising administering an effective amount of a compound of formula (II) or a salt or solvate thereof;

iv) a combination product of a compound of formula (II) or a salt or solvate thereof with an antipsychotic;

v) a pharmaceutical composition comprising a combination product as defined in vi) above and at least one carrier, diluent or excipient;

vi) the use of a combination product as defined in vi) above in the manufacture of a medicament for treating a disease or condition mediated by a reduction or imbalance in glutamate receptor function in a mammal;

vii) a combination product as defined in vi) above for use in treating a disease or condition mediated by a reduction or imbalance in glutamate receptor function in a mammal;

viii) a combination product as defined in vi) above for use as a medicament;

ix) a method of treatment of a disease or condition mediated by a reduction or imbalance in glutamate receptor function in a mammal comprising administering an effective amount of a combination product as defined in vi) above.

In the case of aspects ii), iii), iv), vii), viii), ix) and x), relevant diseases or conditions are: psychosis and psychotic disorders (including schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism, delerium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease); substance related disorders (including alcohol-related disorders and nicotine-related disorders); cognitive impairment (e.g. the treatment of impairment of cognitive functions including attention, orientation, memory (i.e. memory disorders, amnesia, amnesic disorders and age-associated memory impairment) and language function, and including cognitive impairment as a result of stroke, Alzheimer's disease, Aids-related dementia or other dementia states, as well as other acute or sub-acute conditions that may cause cognitive decline such as delirium or depression (pseudodementia states) trauma, aging, stroke, neurodegeneration, drug-induced states, neurotoxic agents), mild cognitive impairment, age related cognitive impairment, autism related cognitive impairment, Down's syndrome, cognitive deficit related to psychosis, post-electroconvulsive treatment related cognitive disorders; anxiety disorders (including generalised anxiety disorder, social anxiety disorder, agitation, tension, social or emotional withdrawal in psychotic patients, panic disorder, and obsessive compulsive disorder); neurodegenerative diseases (such as Alzheimer's disease, amyotrophic lateral sclerosis, motor neurone disease and other motor disorders such as Parkinson's disease (including relief from locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture), dementia in Parkinson's disease, dementia in Huntington's disease, neuroleptic-induced Parkinsonism and tardive dyskinesias, neurodegeneration following stroke, cardiac arrest, pulmonary bypass, traumatic brain injury, spinal cord injury or the like, and demyelinating diseases such as multiple sclerosis and amyotrophic lateral sclerosis); depression (which term includes bipolar (manic) depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression, and depressive disorders resulting from a general medical condition including, but not limited to, myocardial infarction, diabetes, miscarriage or abortion); post-traumatic stress syndrome; attention deficit disorder; attention deficit hyperactivity disorder; drug-induced (phencyclidine, ketamine and other dissociative anaesthetics, amphetamine and other psychostimulants and cocaine) disorders; Huntingdon's chorea; tardive dyskinesia;

dystonia; myoclonus; spasticity; obesity; stroke; sexual dysfunction; sleep disorders and some forms of epilepsy.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Compounds of the invention may also be of use in the treatment of the following disorders:—

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

Within the context of the present invention, the term "cognitive impairment" includes for example the treatment of impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

In one embodiment, the present invention provides a compound of the invention for use in treating schizophrenia or impairment of cognition.

In one embodiment, the present invention provides a use of a compound of the invention in the manufacture of a medicament for treating schizophrenia or impairment of cognition.

In one embodiment, the present invention provides a method of treatment of schizophrenia or impairment of cognition.

It is to be understood that the term "a disease or condition mediated by a reduction or imbalance in glutamate receptor function in a mammal" encompasses "a disease or condition caused by a reduction or imbalance in glutamate receptor function in a mammal".

The compounds of the invention may be used in combination with one or more of the following agents to treat psychotic disorders: i) antipsychotics (such as olanzapine, risperidone, clozapine, ziprazidone, talnetant); ii) drugs for extrapyramidal side effects, for example anticholinergics (such as benztropine, biperiden, procyclidine, trihexyphenidyl), antihistamines (such as diphenhydramine), dopaminergics (such as amantadine); iii) antidepressants; iv) anxiolytics; v) cognitive enhancers for example cholinesterase inhibitors (such as tacrine, donepezil, rivastigmine, galantamine).

The compounds of the invention may be used in combination with antidepressants to treat depression and mood disorders.

The compounds of the invention may be used in combination with one or more of the following agents to treat bipolar disease: i) mood stabilisers; ii) antipsychotics; iii) antidepressants.

The compounds of the invention may be used in combination with one or more of the following agents to treat anxiety disorders: i) anxiolytics; ii) antidepressants.

The compounds of the invention may be used in combination with one or more of the following agents to improve nicotine withdrawal and reduce nicotine craving: i) nicotine replacement therapy, for example a sublingual formulation of nicotine beta-cyclodextrin and nicotine patches; ii) drugs for treating nicotine addition, for example bupropion.

The compounds of the invention may be used in combination with one or more of the following agents to improve alcohol withdrawal and reduce alcohol craving: i) NMDA receptor antagonists for example acamprosate; ii) GABA receptor agonists for example tetrabamate; iii) Opioid receptor antagonists for example naltrexone.

The compounds of the invention may be used in combination with one or more of the following agents to improve opiate withdrawal and reduce opiate craving: i) opioid mu receptor agonist/opioid kappa receptor antagonist for example buprenorphine; ii) opioid receptor antagonists for example naltrexone; iii) vasodilatory antihypertensives for example lofexidine.

The compounds of the invention may be used in combination with one or more of the following agents to treat sleeping disorders: i) benzodiazepines for example temazepam, lormetazepam, estazolam, triazolam; ii) non-benzodiazepine hypnotics for example zolpidem, zopiclone, zaleplon, indiplon; iii) barbiturates for example aprobarbital, butabarbital, pentobarbital, secobarbita, phenobarbital; iv) antidepressants; v) other sedative-hypnotics for example chloral hydrate, chlormethiazole.

The compounds of the invention may be used in combination with one or more of the following agents to treat anorexia: i) appetite stimulants for example cyproheptidine; ii) antidepressants; iii) antipsychotics; iv) zinc; v) premenstrual agents for example pyridoxine and progesterones.

The compounds of the invention may be used in combination with one or more of the following agents to treat bulimia: i) antidepressants; ii) opioid receptor antagonists; iii) antiemetics for example ondansetron; iv) testosterone receptor antagonists for example flutamide; v) mood stabilisers; vi) zinc; vii) premenstrual agents.

The compounds of the invention may be used in combination with one or more of the following agents to treat autism: i) antipsychotics; ii) antidepressants; iii) anxiolytics; iv) stimulants for example methylphenidate, amphetamine formulations, pemoline.

The compounds of the invention may be used in combination with one or more of the following agents to treat Attention Deficit Hyperactivity Disorder: i) stimulants for example methylphenidate, amphetamine formulations, pemoline; ii) non-stimulants for example norepinephrine reuptake inhibitors (such as atomoxetine), alpha 2 adrenoceptor agonists (such as clonidine), antidepressants, modafinil, cholinesterase inhibitors (such as galantamine and donezepil).

The compounds of the invention may be used in combination with one or more of the following agents to treat personality disorders: i) antipsychotics; ii) antidepressants; iii) mood stabilisers; iv) anxiolytics.

The compounds of the invention may be used in combination with one or more of the following agents to treat male sexual dysfunction: i) phosphodiesterase V inhibitors, for example vardenafil, sildenafil; ii) dopamine agonists/dopamine transport inhibitors for example apomorphine, buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine; vii) 5-HT1A agonists, for example flibanserine.

The compounds of the invention may be used in combination with one or more of the following agents to treat female sexual dysfunction: i) the same agents specified for male sexual dysfunction, ii) an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone, amisulpride, ziprazidone and talnetant).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration to mammals including humans. The compositions may be formulated for administration by any route. The compositions may be formulated for oral, topical, or parenteral administration, and may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, for example water. The compound, depending on the vehicle and concentration used, can be either suspended or dissolved in the vehicle. In preparing solutions the compound can be dissolved in water for injection and filter sterilised before filling into a suitable vial or ampoule and sealing.

Agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. A surfactant or wetting agent may be included in the composition to facilitate uniform distribution of the compound.

The compositions may contain from 0.1% by weight, for example from 10-60% by weight, of the active material, depending on the method of administration. Where the compositions comprise dosage units, each unit may, for example contain from 0.1 to 20 mg of the active ingredient. For example, such a unit may contain from 1 to 10 mg. The dosage as employed for adult human treatment may, for example, range from 2 to 50 mg per day, for instance 5 to 20 mg per day depending on the route and frequency of administration (though in some instances, a dosage of 50 mg to 100 mg per day may be appropriate). Based on a 75 kg individual, such a dosage corresponds to 0.027 to 0.667 mg/kg per day. Suitably the dosage is from 0.05 to 0.3 mg/kg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of a compound of the invention given per day for a defined number of days, can be ascertained by those skilled in the art using conventional course of treatment determination tests.

It is to be understood that "treatment" as used herein includes prophylaxis as well as alleviation of established symptoms. In one embodiment, the mammal to be treated is a human.

The invention is illustrated by the Examples described below.

Starting materials were obtained from commercial suppliers and used without further purification unless otherwise stated. Flash chromatography was carried out using pre-packed Isolute Flash™ or Biotage™ silica-gel columns as the stationary phase and analytical grade solvents as the eluent.

NMR spectra were obtained at 298K, at the frequency stated using either a Bruker™ DPX400 or an Oxford Instruments™ 250 MHz machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

Total ion current traces were obtained for electrospray positive and negative ionisation (ES+/ES−) and atmospheric pressure chemical positive and negative ionisation (AP+/AP−).

All quoted retention times are as measured using LC/MS (Liquid Chromatography/Mass Spectrometry). Where appropriate, these retention times were used as a guide for purification using mass-directed auto-preparation (MDAP), which refers to purification by HPLC, wherein fraction collection is triggered by detection of the programmed mass ion for the compound of interest.

Unless otherwise stated, all compounds with chiral centre(s) are racemic.

LC/MS Conditions for Examples 1-35 and 45-113

| Column: | Waters Atlantis, 4.6 mm × 50 mm. The stationary phase particle size is 3 um. |
|---|---|
| Solvents: | A: Aqueous solvent = Water + 0.05% Formic Acid; B: Organic solvent = Acetonitrile + 0.05% Formic Acid |
| Methods: | The generic method used has a 5 minute runtime. |

| Time/min | % B |
|---|---|
| 0 | 3 |
| 0.1 | 3 |
| 4 | 97 |
| 4.8 | 97 |
| 4.9 | 3 |
| 5.0 | 3 |

| Flow rate: | 3 ml/min |
|---|---|
| Injection volume: | 5 ul |
| Column temperature: | 30 deg C. |
| UV wavelength range: | 220-330 nm |

LC/MS Conditions for Examples 36-44

| Column: | Waters Atlantis, 4.6 mm × 20 mm. The stationary phase particle size is 3 um. |
|---|---|
| Solvents: | A: Aqueous solvent = Water + 0.1% Formic Acid; B: Organic solvent = Acetonitrile + 0.1% Formic Acid |
| Methods: | The generic method has a 5.5 minute runtime using the following gradient programme. |

| Time/min | % B |
|---|---|
| 0 | 3 |
| 0.7 | 3 |
| 4.5 | 100 |
| 5.3 | 100 |
| 5.4 | 3 |
| 5.5 | 3 |

| Flow rate: | 1 ml/mins |
|---|---|
| Injection volume: | 2 ul full loop injection |
| Column temperature: | ambient |
| UV wavelength range: | 210-350 nm |

MDAP Conditions for Examples 1-35 and 45-113

Column: Waters Atlantis, 19 mm×100 mm (small scale) and 30 mm×100 mm (large scale). Stationary phase particle size=5 um.

Solvents: A: Aqueous solvent=Water+0.1% Formic Acid; B: Organic solvent=Acetonitrile+0.1% Formic Acid. Make up solvent=Methanol:Water 80:20. Needle rinse solvent=Methanol Methods: There are five methods used depending on the analytical retention time of the compound of interest. They have a 13.5-minute runtime, which comprises of a 10-minute gradient followed by a 3.5 minute column flush and re-equilibration step.

Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow rate: 20 mls/min (Small Scale) or 40 mls/min (Large Scale).

MDAP Conditions for Example 36-44

Column: Waters Atlantis, 19 mm×100 mm with particle size 5 mm.

Solvents: A: Aqueous solvent=Water+0.1% Trifluoroacetic Acid; B: Organic solvent=Acetonitrile+0.1% Trifluoroacetic Acid; Make up solvent=Methanol:Water 80:20+0.1% Formic Acid; Needle rinse solvent=Methanol Methods: There are five methods used depending on the analytical retention time of the compound of interest. They have a 20 minute runtime, which comprises of a 15.5 minute gradient followed by a 3.5 minute column flush and re-equilibration step.

Method 1.8-2.1=0-30% B
Method 2.1-2.6=10-45% B
Method 2.6-3.1=15-65% B
Method 3.1-4.1=30-75% B
Method >4.1=50-100% B (in 14 minutes followed by 5 minutes flush and re-equilibration)

Flow rate: 20 mls/min
Injection volume: 500 ul partial loop injection.
Column temperature: ambient Abbreviations

| DCM | Dichloromethane |
|---|---|
| TEA | Triethylamine |
| TMS-Cl- | Trimethylsilyl chloride |
| DME | Dimethyl ether |
| ss | saturated solution |
| TFA | Trifluoroacetic acid |
| DAD | Diode Array Detector |
| CD | Circular dichroism |
| a/a % | percentage by area unde the curve |
| LC/Mass Spec | Liquid Chromatography/Mass Spectrometry |
| NMR | Nuclear Magnetic Resonance |
| SCX | Chromatography column supplied by Varian ™ |
| THF | Tetrahydrofuran |
| DMSO | Dimethylsulfoxide |
| DMF | Dimethylformamide |
| DCM/MDC | Dichloromethane/Methylene dichloride |
| CDI | 1,1'-Carbonyldiimidazole |
| LDA | Lithium diisopropylamide |
| EDC | 1-ethyl-3-(dimethylaminopropyl)carbodiimide |
| MsCl | Methanesulfonyl chloride |
| AcOH | Acetic acid |
| HOAt | 1-hydroxy-7-azabenzotriazole |
| HOBt | 1-hydroxybenzotriazole |
| Pd on C | Palladium on Charcoal |
| MeCN | Acetonitrile |

In the procedures that follow, reference to an Intermediate or Example by number is typically provided. This is provided merely for assistance to the skilled chemist to identify the starting material used. The starting material may not necessarily have been prepared from the batch referred to. All reactions were either carried out under argon or may be carried out under argon.

Intermediates

Description 1

4-iodo-N,N-dimethylbenzamide

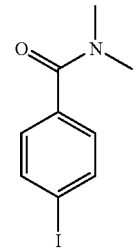

A suspension of dimethylamine hydrochloride (2.45 g, 30 mmol) in dichloromethane (150 ml) was cooled in an ice/methanol bath and then treated with triethylamine (6.0 g, 59 mmol) followed by 4-iodobenzoyl chloride (8.0 g, 30 mmol) portionwise with stirring under an atmosphere of argon. The reaction mixture was allowed to stir at room temperature for 30 minutes before the solution was washed with water (2×100 ml). The organic layer was separated, dried over sodium sulphate, and evaporated under reduced pressure to give the title compound as a light beige coloured solid (7.73 g, 94%).

LC/mass spec (ES): Found 276 (ES+), retention time 2.30 mins. $C_9H_{10}INO$ requires 275.

$^1$H-NMR (400 MHz, CDCl$_3$): 2.97 (3H, s), 3.11 (3H, m), 7.16 (2H, m), 7.75 (2H, m).

Description 2

4-iodo-N,N-dimethylbenzenesulfonamide

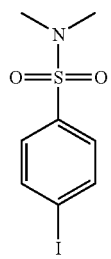

The title compound was prepared from pipsyl chloride and dimethylamine hydrochloride using a similar procedure to that used for Description 1.

LC/mass spec (ES): Found 312 (ES+), retention time 2.86 mins. $C_8H_{10}INO_2S$ requires 311.

$^1$H-NMR (400 MHz, CDCl$_3$): 2.70 (6H, m), 7.49 (2H, d, J=8 Hz), 7.91 (2H, d, J=8 Hz).

Description 3

2-(4-bromophenyl)-N,N-dimethylacetamide

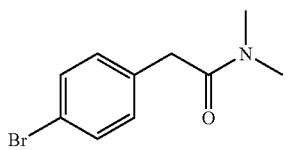

A solution of 4-bromophenylacetic acid (960 mg, 4.49 mmol) in dichloromethane (30 ml) was treated in one portion with solid 1,1'-carbonyldiimidazole (730 mg, 4.5 mmol) at 20° C. with stirring under argon. This mixture was allowed to stir at room temperature for 15 minutes. Triethylamine (0.63 ml) was then added followed by dimethylamine hydrochloride (367 mg, 4.5 mmol) and the stirring continued for 1 hour. Most of the solvent was removed under reduced pressure and the residue added to a 20 g isolute silica sep-pak column and eluted from 0-50% ethyl acetate in petroleum ether to give the title compound as a colourless solid (689 mg, 64%).

LC/mass spec (ES): Found 242 (ES+), retention time 2.36 mins. $C_{10}H_{12}^{79}BrNO$ requires 241.

$^1$H-NMR (400 MHz, CDCl$_3$): 2.97 (3H, s), 3.00 (3H, s), 3.66 (2H, s), 7.12 (2H, m), 7.44 (2H, m).

Description 4

Methyl 4-[3-(trifluoromethyl)-4,5,6,7-tetrahydro-1H-indazol-1-yl]benzoate

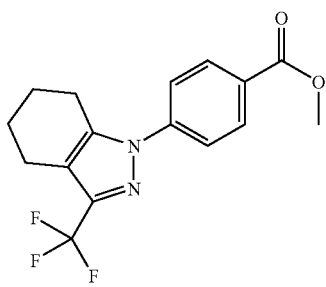

A mixture of methyl 4-iodobenzoate (1.40 g, 5.34 mmol), 3-(trifluoromethyl)-4,5,6,7-tetrahydro-1H-indazole (1.22 g, 6.42 mmol), copper (I) iodide (1 mol %, 10 mg, 0.05 mmol), trans-1,2-diaminocyclohexane (10 mol %, 62 mg, 0.54 mmol) and potassium carbonate (1.56 g, 11.3 mmol) in 1,4-dioxane (8 ml) was stirred at 180° C. in a microwave reactor for 45 minutes, then fresh copper (I) iodide (1 mol %, 10 mg, 0.05 mmol) and trans-1,2-diaminocyclohexane (10 mol %, 62 mg, 0.54 mmol) were added and the reaction stirred at 180° C. in a microwave reactor for 1 h 45 minutes. The reaction mix was cooled and added to a 50 g pre-packed silica column which was then eluted from 0-50% ethyl acetate in petroleum ether to give a crop of the title compound as a brown oil (630 mg, 36%).

LC/mass spec (ES): Found 325 (ES+), retention time 3.78 mins. $C_{16}H_{15}F_3N_2O_2$ requires 324.

$^1$H-NMR (400 MHz, CDCl$_3$): 1.83 (4H, m), 2.68 (4H, m), 3.95 (3H, s), 7.61 (2H, m), 8.15 (2H, m).

Description 5

4-[3-(trifluoromethyl)-4,5,6,7-tetrahydro-1H-indazol-1-yl]benzoic acid

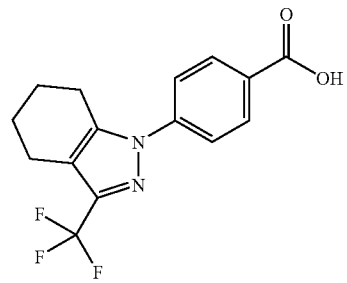

A mixture of methyl 4-[3-(trifluoromethyl)-4,5,6,7-tetrahydro-1H-indazol-1-yl]benzoate (600 mg, 1.85 mmol), sodium hydroxide (81 mg, 2.0 mmol), in ethanol (4 ml) and water (4 ml) was stirred at reflux for 1 hour. The reaction mix was allowed to cool and the ethanol was removed under reduced pressure and the residue was partitioned between diethyl ether (10 ml) and water (10 ml). The aqueous layer was separated and made acidic with 2N HCl, then extracted with dichloromethane. The organic layer was dried over sodium sulphate and evaporated under reduced pressure to give the title compound as a beige solid (222 mg, 39%)

LC/mass spec (ES): Found 311 (ES+), retention time 3.24 mins. $C_{15}H_{13}F_3N_2O_2$ requires 310.

$^1$H-NMR (400 MHz, CDCl$_3$): 1.85 (4H, m), 2.68 (2H, m), 2.79 (2H, m), 7.67 (2H, m), 8.21 (2H, m).

Description 5a

4-[3-(trifluoromethyl)-4,5,6,7-tetrahydro-1H-indazol-1-yl]benzoic acid

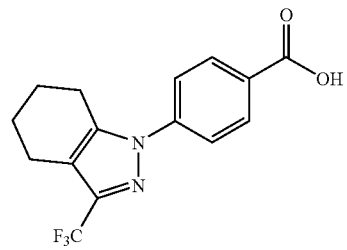

A mixture of 3-(trifluoromethyl)-4,5,6,7-tetrahydro-1H-indazole (950 mg, 5.0 mmol), 4-iodobenzoic acid (1.24 g, 5.0 mmol), N,N-dimethylglycine (20 mol %, 103 mg, 1.0 mmol), copper (I) iodide (10 mol %, 95 mg, 0.5 mmol) and potassium carbonate (1.45 g, 10.5 mmol) in dimethylsulfoxide (15 ml) was stirred at 130° C. in an oil bath under argon for 3.25 hours. The reaction mix was then filtered under vacuum and the filtrate separated between ethyl acetate and water. The aqueous layer was retained and acidified to approximately Ph2 using 5M aqueous HCl. The aqueous fraction was then washed 3 times with ethyl acetate. The organic layers were combined and dried over sodium sulphate, and the solvent was removed by rotary evaporation to give the title compound as a brown solid (1.62 g, 100%).

¹H-NMR (400 MHz, MeOD): 1.86 (4H, m), 2.66 (2H, m), 2.81 (2H, m), 7.68 (2H, d, J=9 Hz), 8.18 (2H, d, J=9 Hz).

Description 6

Ethyl {4-[3-(trifluoromethyl)-4,5,6,7-tetrahydro-1H-indazol-1-yl]phenyl}acetate

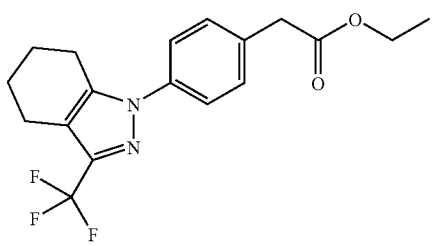

A mixture of ethyl-4-bromophenylacetate (875 mg, 3.60 mmol), 3-(trifluoromethyl)-4,5,6,7-tetrahydro-1H-indazole (570 mg, 3.00 mmol), potassium carbonate (842 mg, 6.10 mmol), copper (I) iodide (5 mol %, 29 mg, 0.15 mmol), and (1R,2R)-N,N'-dimethyl-1,2-cyclohexanediamine (20 mol %, 85 mg, 0.60 mmol) in toluene (2 ml) was stirred under an atmosphere of argon at 130° C. in a microwave reactor for 1 h. Further copper (I) iodide (10 mg, 0.05 mmol), and (1R, 2R)-N,N'-dimethyl-1,2-cyclohexanediamine (30 mg, 0.21 mmol) was added and heating continued at 130° C. for a total of 4 h. The reaction mix was cooled and added to a 20 g pre-packed silica column and eluted with 0-20% ethyl acetate in petroleum ether to give the title compound as a brown oil (0.92 g, 87%).

LC/mass spec (ES): Found 353 (ES+), retention time 3.70 mins. $C_{18}H_{19}F_3N_2O_2$ requires 352.

¹H-NMR (400 MHz, CDCl₃): 1.26 (3H, m), 1.81 (4H, m), 2.69 (4H, m), 3.66 (2H, s), 4.15 (2H, m), 7.38 (2H, m), 7.45 (2H, m).

Description 7

{4-[3-(trifluoromethyl)-4,5,6,7-tetrahydro-1H-indazol-1-yl]phenyl}acetic acid

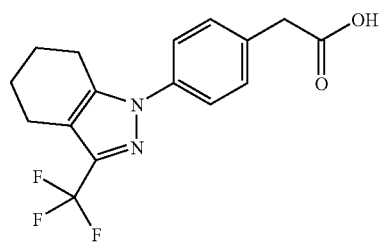

A mixture of ethyl {4-[3-(trifluoromethyl)-4,5,6,7-tetrahydro-1H-indazol-1-yl]phenyl}acetate (0.92 g, 2.61 mmol), sodium hydroxide (114 mg, 2.85 mmol), in ethanol (10 ml) and water (10 ml) was stirred at reflux for 1 hour. The reaction mix was allowed to cool and the ethanol was removed under reduced pressure and the residue was made acidic with 5N HCl, then extracted into dichloromethane. The organic layer was added to a 5 g pre-packed column and eluted from 0-100% ethyl acetate in petroleum ether to give the title compound as a pale yellow solid (0.42 g, 50%).

LC/mass spec (ES): Found 325 (ES+), retention time 3.00 mins. $C_{16}H_{15}F_3N_2O_2$ requires 324.

¹H-NMR (400 MHz, DMSO D6): 1.75 (4H, m), 2.60 (2H, m), 2.73 (2H, m), 3.67 (2H, s) 7.43 (2H, d, J=8 Hz), 7.51 (2H, m), 12.43 (1H, bs).

Description 8

1-{[4-(bromomethyl)phenyl]carbonyl}pyrrolidine

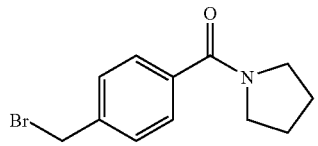

A solution of 4-(bromomethyl)benzoic acid (2.43 g, 11.3 mmol) in dichloromethane (40 ml) was treated in one portion with solid 1,1'-carbonyldiimidazole (1.83 g, 11.3 mmol). This mixture was allowed to stir at room temperature for 15 minutes. Pyrrolidine (0.8 g, 11.3 mmol) was then added and the stirring continued for 1 hour at room temperature. The reaction mixture was partitioned between dichloromethane and saturated sodium bicarbonate solution. The organic layer was dried over sodium sulphate and evaporated in vaccuo (i.e under reduced pressure) to give a yellow oil which was added to a 20 g pre-packed silica column and eluted from 20-50% ethyl acetate in petroleum ether to give the title compound as a colourless solid (0.5 g, 17%).

LC/mass spec (ES): Found 268 (ES+), retention time 2.46 mins. $C_{12}H_{14}{}^{79}BrNO$ requires 267.

¹H-NMR (400 MHz, CDCl₃): 1.88 (2H, m), 1.97 (2H, m), 3.43 (2H, t, J=7 Hz), 3.65 (2H, t, J=7 Hz), 4.50 (2H, s), 7.42 (2H, dd, J=7 Hz & 2 Hz), 7.50 (2H, dd, J=7 Hz & 2 Hz).

Description 9

1-[2-(4-bromophenyl)propanoyl]pyrrolidine

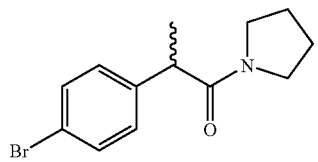

A solution of 2-(4-bromophenyl)propanoic acid (215 mg, 0.94 mmol) in dichloromethane (4 ml) was treated in one portion with solid 1,1'-carbonyldiimidazole (152 g, 0.94 mmol). This mixture was allowed to stir at room temperature for 15 minutes. Pyrrolidine (67 mg, 0.94 mmol) was then added and the stirring continued for 1 hour at room temperature. Most of the solvent was removed under reduced pressure and the residue added to a 5 g pre-packed silica column and eluted from 0-50% ethyl acetate in petroleum ether to give the title compound as a colourless solid (189 mg, 71%).

LC/mass spec (ES): Found 282 (ES+), retention time 2.78 mins. $C_{13}H_{16}{}^{79}BrNO$ requires 281.

$^1$H-NMR (400 MHz, CDCl$_3$): 1.43 (3H, d, J=7 Hz), 1.75-1.93 (4H, m), 3.16 (1H, m), 3.37-3.56 (3H, m), 3.70 (1H, m), 7.19 (2H, m), 7.43 (2H, m).

Description 10

1-[(1-phenylcyclopropyl)carbonyl]pyrrolidine

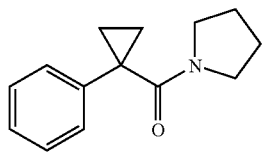

The title compound was prepared from 1-phenylcyclopropanecarboxylic acid and pyrrolidine using a similar procedure to that described for Description 8.

LC/mass spec (ES): Found 216 (ES+), retention time 2.45 mins. $C_{14}H_{17}NO$ requires 215.

$^1$H-NMR (400 MHz, CDCl$_3$): 1.14 (2H, m), 1.44 (2H, m), 1.72-1.81 (4H, m), 3.17 (2H, m), 3.49 (2H, m), 7.19 (3H, m), 7.29 (2H, m).

Description 11

1-{[1-(4-iodophenyl)cyclopropyl]carbonyl}pyrrolidine

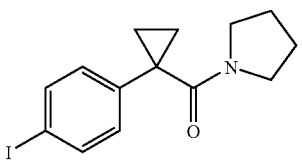

1-[(1-phenylcyclopropyl)carbonyl]pyrrolidine (0.75 g, 3.49 mmol) was dissolved in glacial acetic acid (14 ml) and treated successively with concentrated sulfuric acid (0.4 ml), water (1.5 ml), periodic acid (184 mg, 0.8 mmol), and iodine (379 mg, 1.49 mmol). This mixture was then stirred at 60° C. for 6 hours and then allowed to cool to room temperature. The reaction mixture was poured into a 10% aqueous solution of sodium metabisulfite and extracted into ethyl acetate. The organic layer was separated and dried over anhydrous sodium sulphate and evaporated under reduced pressure to give a yellow oil (1.45 g) which was added to a 20 g pre-packed silica column and eluted from 0-50% ethyl acetate in petroleum ether to give the title compound as a yellow oil (0.62 g, 52%).

LC/mass spec (ES): Found 342 (ES+), retention time 2.94 mins. $C_{14}H_{16}INO$ requires 341.

$^1$H-NMR (400 MHz, CDCl$_3$): 1.13 (2H, m), 1.43 (2H, m), 1.72-1.82 (4H, m), 3.17 (2H, m), 3.49 (2H, m), 6.95 (2H, m), 7.61 (2H, m).

Description 12

3-(4-bromophenyl)-N,N-dimethylpropanamide

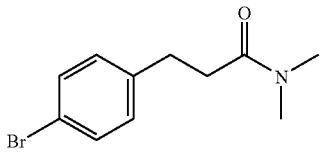

A solution of 3-(4-bromophenyl)propionic acid (1.0 g, 4.37 mmol) in dichloromethane (30 ml) was treated in one portion with solid 1,1'-carbonyldiimidazole (707 mg, 4.36 mmol). This mixture was allowed to stir at room temperature for 15 minutes. Dimethylamine hydrochloride (360 mg, 4.42 mmol) was then added followed by diisopropylethylamine (0.76 ml, 4.4 mmol) and the stirring continued for 1 hour at room temperature. The reaction mixture was partitioned between dichloromethane and saturated sodium bicarbonate solution. The organic layer was dried over sodium sulphate and evaporated under reduced pressure to give the title compound as a colourless oil (972 mg, 87%).

LC/mass spec (ES): Found 256 (ES+), retention time 2.61 mins. $C_{11}H_{14}{}^{79}BrNO$ requires 255.

$^1$H-NMR (400 MHz, CDCl$_3$): 2.59 (2H, t, J=8 Hz), 2.93 (8H, m), 7.11 (2H, m), 7.40 (2H, m).

Description 13

1-[3-(4-bromophenyl)propanoyl]pyrrolidine

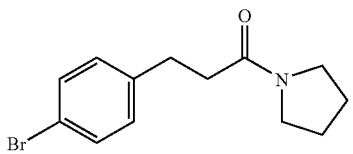

The title compound was prepared from 3-(4-bromophenyl)propanoic acid and pyrrolidine using a similar procedure to that described for Description 8, but without chromatographic purification.

LC/mass spec (ES): Found 282 (ES+), retention time 2.76 mins. $C_{13}H_{16}{}^{79}BrNO$ requires 281. $^1$H-NMR (400 MHz, CDCl$_3$): 1.79-1.94 (4H, m), 2.53 (2H, t, J=8 Hz), 2.94 (2H, t, J=8 Hz), 3.30 (2H, t, J=7 Hz), 3.46 (2H, t, J=7 Hz), 7.11 (2H, m), 7.40 (2H, m).

Description 14

N-[(4-bromophenyl)methyl]-N-methylacetamide

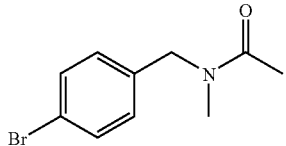

A solution of triethylamine (0.22 ml, 1.6 mmol) in dichloromethane (10 ml) was treated with acetyl chloride (0.08 ml, 1.10 mmol), followed by 4-bromo-N-methylbenzylamine (210 mg, 1.05 mmol). This mixture was then stirred under an atmosphere of argon for 10 minutes. The reaction mixture was washed twice with water and the organic layer was separated and dried over sodium sulphate, and the solvent removed via rotary evaporation to give a yellow oil which was purified on a 5 g sep-pak column eluting from 0-100% ethyl acetate in petroleum ether to give the title compound as a yellow oil.

LC/mass spec (ES): Found 242 (ES+), retention time 2.39 mins. $C_{10}H_{12}{}^{79}BrNO$ requires 241.

$^1$H-NMR (400 MHz, CDCl$_3$): 2.14 (3H, m), 2.90 (3H, m), 4.54 (2H, m), 7.13 (2H, m), 7.47 (2H, m).

Description 15

1-[(4-iodophenyl)methyl]-2-pyrrolidinone

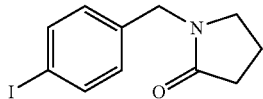

A solution of 2-pyrrolidinone (850 mg, 10 mmol) in dimethylformamide (40 ml) was cooled in an ice/methanol bath with stirring under an atmosphere of argon. Then a solid suspension of sodium hydride (60% in mineral oil, 440 mg, 11 mmol) was added portionwise over 10 minutes. The reaction mix was allowed to stir with cooling for 30 minutes, then 4-iodobenzyl bromide (2.97 g, 10 mmol) was added portionwise over 10 minutes. The whole mix was allowed to warm slowly up to room temperature then stirred for a further 2 hours. The reaction mixture was partitioned between ethyl acetate (100 ml), and water (200 ml), the organic layer was removed and reduced to minimum volume under reduced pressure. The residue was purified by column chromatography on a 20 g pre-packed silica column eluting from 0-100% ethyl acetate in petroleum ether to give the title compound as a yellow solid (2.97 g, 99%).

LC/mass spec (ES): Found 302 (ES+), retention time 2.59 mins. $C_{11}H_{12}INO$ requires 301.

$^1$H-NMR (400 MHz, CDCl$_3$): 2.01 (2H, m), 2.44 (2H, t, J=8 Hz), 3.25 (2H, t, J=7 Hz), 4.39 (2H, s), 7.00 (2H, d, J=8 Hz), 7.66 (2H, m).

Description 16

5-(4-bromophenyl)-1-methyl-2-pyrrolidinone

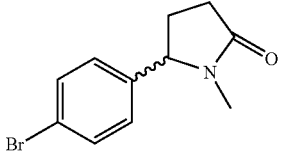

A solution of 5-(4-bromophenyl)-2-pyrrolidinone (preparation described in WO00/21958) (200 mg, 0.83 mmol) in dimethylformamide (5 ml) was treated with a solid suspension of sodium hydride (60% in mineral oil, 35 mg, 0.88 mmol). The reaction mix was allowed to stir for 20 minutes, then methyl iodide (124 mg, 0.88 mmol) was added and the whole mix stirred for a further 18 hours. The reaction mixture was quenched with a few drops of water then partitioned between dichloromethane (15 ml), and water (60 ml), the organic layer was removed and washed with water again (2×10 ml), then reduced to minimum volume under reduced pressure to give the title compound as a brown oil (141 mg, 67%).

LC/mass spec (ES): Found 254 (ES+), retention time 2.41 mins. $C_{11}H_{12}{}^{79}BrNO$ requires 253.

$^1$H-NMR (400 MHz, CDCl$_3$): 1.85 (1H, m), 2.40-2.62 (3H, m), 2.67 (3H, s), 4.48 (1H, m), 7.08 (2H, m), 7.52 (2H, m).

Description 17

1-[4-(chloromethyl)phenyl]-3-(trifluoromethyl)-4,5,6,7-tetrahydro-1H-indazole

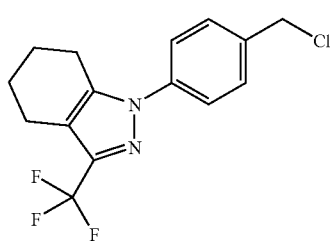

To a solution of {4-[3-(trifluoromethyl)-4,5,6,7-tetrahydro-1H-indazol-1-yl]phenyl}methanol (Example 30, 1.23 g, 4.16 mmol) in dichloromethane (20 ml) under an atmosphere of argon was added triethylamine (0.75 ml, 5.4 mmol) and the mixture stirred at room temperature for 10 minutes. Methanesulfonyl chloride (0.42 ml, 5.4 mmol) was added dropwise over 5 minutes and the whole mix stirred at room temperature for 18 hours. The reaction mixture was then washed twice with water followed by saturated sodium bicarbonate. The organic layer dried over sodium sulphate and the solvent removed by rotary evaporation to give the title compound as a brown oil (1.24 g, 94%)

LC/mass spec (ES): Found 315 (ES+), retention time 3.74 mins. $C_{15}H_{14}{}^{35}ClF_3N_2$ requires 314. $^1$H-NMR (400 MHz, CDCl$_3$): 1.83 (4H, m), 2.70 (4H, m), 4.63 (2H, s), 7.51 (4H, m).

Description 18

4-[(4-iodophenyl)carbonyl]morpholine

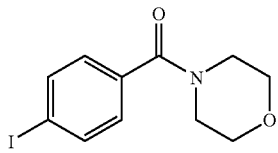

A solution of morpholine (653 mg, 7.5 mmol) in dichloromethane (40 ml) was cooled in an ice/methanol bath and then treated with stirring under argon with triethylamine (7.5 mmol, 1.05 ml) followed by the portionwise addition of 4-iodobenzoyl chloride (2.0 g, 7.5 mmol). The reaction mix was allowed to stir at room temperature for 0.5 h before the solution was washed with water (2×20 ml). The organic layer was dried over sodium sulphate and evaporated under reduced pressure to give the title compound as a yellow solid (2.4 g, 100%).

LC/Mass Spec (ES): Found 318 (ES+), retention time 2.36 mins. $C_{11}H_{12}INO_2$ requires 317.

1H-NMR (400 MHz, $CDCl_3$): 3.32-3.94 (8H, m), 7.15 (2H, m), 7.77 (2H, m).

Description 19

4-[3-(trifluoromethyl)-4,5,6,7-tetrahydro-1H-indazol-1-yl]benzonitrile

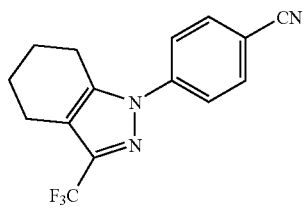

A mixture of 4-iodobenzonitrile (2.41 g, 10.5 mmol), 3-(trifluoromethyl)-4,5,6,7-tetrahydro-1H-indazole (2.0 g, 10.5 mmol), copper (I) oxide (20 mol %, 2.1 mmol, 300 mg), N,N-dimethylglycine (10.5 mmol, 1.082 g), and cesium carbonate (21 mmol, 6.84 g) in dimethylsulfoxide (5 ml) was heated in an oil bath at 130° C. under argon for 4 h. The reaction mixture was diluted with ethyl acetate. Solid filtered off through kieselguhr. The filtrate was partitioned between ethyl acetate and water. The organic layer was separated and dried over sodium sulphate. The solvent was removed by rotary evaporation and triturated with diethyl ether to give the title compound as a light brown solid (1.812 g, 59.5%).

LC/Mass Spec (ES): Found 292 (ES+), retention time 3.43 mins. $C_{15}H_{12}F_3N_3$ requires 291.

1H-NMR (400 MHz, DMSO): 1.76 (4H, m), 2.60 (2H, m), 2.82 (2H, m), 7.82 (2H, m), 8.10 (2H, m).

Description 20

({4-[3-(trifluoromethyl)-4,5,6,7-tetrahydro-1H-indazol-1-yl]phenyl}methyl)amine

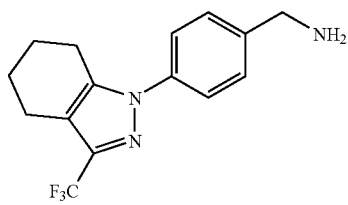

Lithium aluminium hydride (12.44 ml, 2 M in THF solution, 24.88 mmol) and THF (30 ml) were stirred in an ice bath under argon. A solution of 4-[3-(trifluoromethyl)-4,5,6,7-tetrahydro-1H-indazol-1-yl]benzonitrile (1.812 g, 6.22 mmol) in THF (30 ml) was added dropwise over 15 mins. Then the ice bath was removed and the reaction mixture was allowed to stir at room temperature for 1.5 hrs. Then the reaction mixture was cooled using an ice bath and quenched with water dropwise, solvent was removed under vacuo (i.e reduced pressure). Residual material was diluted with DCM and water. Insoluble solid filtered off and organic layer separated, washed with brine, dried over sodium sulphate. The solvent was removed by rotary evaporation. The desired product was isolated using a 25 g SCX column initially washed with DCM (30 ml), DCM/MeOH (60 ml), MeOH (30 ml) and then the desired product was eluted with 1M ammonia in MeOH (25 ml). Solvent evaporated off under reduced pressure to give the title compound as a brown oil (1.563 g, 85%).

LC/Mass Spec (ES): Found 279 (M-16, ES+), retention time 2.16 mins. $C_{15}H_{16}F_3N_3$ requires 295. 1H-NMR (400 MHz, CDCl3): 1.82 (4H, m), 2.68 (4H, m), 3.93 (2H, s), 7.43 (4H, m).

Description 21

1-[(4-nitrophenyl)methyl]-3-(trifluoromethyl)-4,5,6,7-tetrahydro-1H-indazole

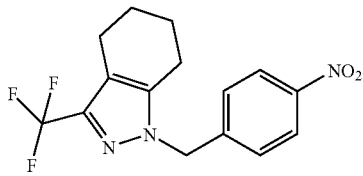

A solution of 3-(trifluoromethyl)-4,5,6,7-tetrahydro-1H-indazole (380 mg, 2 mmol) in anhydrous DMF (10 ml) was treated with potassium carbonate (552 mg, 4 mmol) followed by 4-nitrobenzyl chloride (343 mg, 2 mmol) and the whole mix stirred under argon for 16 h at room temperature. The reaction mixture was separated between water (20 ml) and ethyl acetate (20 ml). The organic layer was washed again with a water/brine mix (1:1) (10 ml) then dried over sodium sulphate and the solvent removed under reduced pressure to give a yellow oil (751 mg) which was chromatographed on a 5 g pre-packed silica column eluting from 0-20% ethyl acetate in petroleum ether to give the title compound as a yellow oil (416 mg, 64%).

LC/Mass Spec (ES): Found 326 (ES+), retention time 3.44 mins. $C_{15}H_{14}F_3N_3O_2$ requires 325.

Description 22

4-{[3-(trifluoromethyl)-4,5,6,7-tetrahydro-1H-indazol-1-yl]methyl}aniline

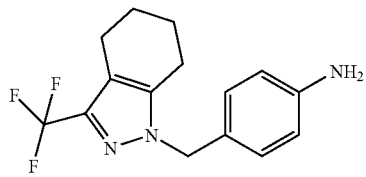

A solution of 1-[(4-nitrophenyl)methyl]-3-(trifluoromethyl)-4,5,6,7-tetrahydro-1H-indazole (410 mg, 1.26 mmol) in methanol (3 ml) was added dropwise to a stirred suspension of 10% palladium on charcoal in water (1.3 ml) containing sodium borohydride (95 mg, 2.50 mmol), under argon with cooling. The resulting mix was stirred at room temperature for 1 hour. The reaction mix was filtered and then acidified using 2M HCl to destroy any excess sodium borohydride, and then basified again using 2M aqueous sodium hydroxide. The mix was partitioned between ethyl acetate and water. The organic layer was dried over sodium sulphate and the solvent removed under reduced pressure to give a yellow oil, which was chromatographed on a 5 g pre-packed silica column eluting from 0-20% ethyl acetate in petroleum ether to give the title compound as a yellow oil (166 mg, 43%).

LC/Mass Spec (ES): Found 296 (ES+), retention time 2.70 mins. $C_{15}H_{16}F_3N_3$ requires 295.

$^1$H-NMR (400 MHz, CDCl$_3$): 1.64-1.88 (4H, m), 2.43-2.68 (4H, m), 3.68 (2H, bs), 5.12 (2H, s), 6.62 (2H, m), 6.98 (2H, m).

Description 23

N-[(4-bromophenyl)methyl]-1-pyrrolidinecarboxamide

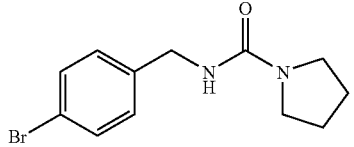

A solution of 4-bromobenzylisocyanate (408 mg, 1.92 mmol) in acetonitrile (15 ml) was treated with triethylamine (390 mg, 3.86 mmol) followed by pyrrolidine (137 mg, 1.93 mmol) at room temperature with stirring under argon. The reaction was stirred at 20° C. for 30 minutes and then partitioned between ethyl acetate (10 ml) and water (20 ml). The organic layer was dried over sodium sulphate and evaporated under reduced pressure to give the title compound as a colourless solid (542 mg, 99%).

LC/Mass Spec (ES): Found 283 (ES+), retention time 2.42 mins. $C_{12}H_{15}^{79}BrN_2O$ requires 282. $^1$H-NMR (400 MHz, CDCl$_3$): 1.91 (4H, m), 3.45 (4H, m), 4.49 (2H, m), 4.51 (1H, m), 7.21 (2H, m), 7.44 (2H, m).

Description 24

N-[(4-bromophenyl)methyl]-N-methyl-1-pyrrolidinecarboxamide

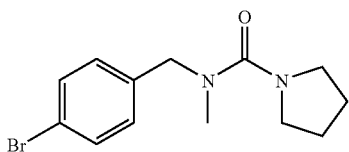

N-[(4-bromophenyl)methyl]-1-pyrrolidinecarboxamide (230 mg, 0.81 mmol), was dissolved in dimethylformamide (2 ml) and treated at room temperature with a 60% sodium hydride suspension in mineral oil (33 mg, 0.83 mmol). This mix was stirred for 15 minutes before being treated with iodomethane (116 mg, 0.82 mmol). The resulting mix was stirred at 20° C. for a total of 16.5 hours. The reaction was quenched with water (4 ml) and extracted into ethyl acetate (4 ml). The organic layer was dried over sodium sulphate and the solvent removed under reduced pressure to give the title compound as a colourless oil (250 mg, crude). LC/Mass Spec (ES): Found 297 (ES+), retention time 2.90 mins. $C_{13}H_{17}^{79}BrN_2O$ requires 296.

Description 25

N-[1-(4-bromophenyl)ethyl]acetamide

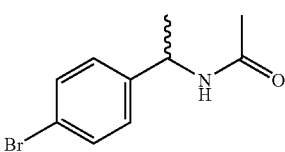

To a solution of 4-bromo-methylbenzylamine (2.0 g, 10 mmol) and triethylamine (2 g, 20 mmol, 2.8 ml), in dichloromethane (40 ml) was added acetyl chloride (0.86 g, 11 mmol, 0.78 ml) dropwise with stirring under an atmosphere of argon, and the whole mix stirred at 20° C. for 0.5 hours. The reaction mixture was washed twice with water (30 ml each) and the organic layer dried over sodium sulphate and the solvent removed under reduced pressure to give the title compound as a yellow solid (2.27 g, 94%).

LC/Mass Spec (ES): Found 242 (ES+), retention time 2.24 mins. $C_{10}H_{12}^{79}BrNO$ requires 241.

$^1$H-NMR (400 MHz, CDCl$_3$): 1.46 (3H, d, J=7 Hz), 1.99 (3H, s), 5.08 (1H, m), 5.67 (1H, M), 7.19 (2H, m), 7.46 (2H, m).

Description 26

N-[1-(4-bromophenyl)ethyl]-N-methylacetamide

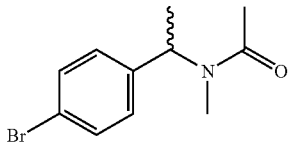

The title compound was prepared from N-[1-(4-bromophenyl)ethyl]acetamide and iodomethane in a manner similar to that described for description 24.

LC/Mass Spec (ES): Found 257 (ES+), retention time 2.53 mins. $C_{11}H_{14}{}^{79}BrNO$ requires 256.

Description 27

1-acetyl-2-(4-bromophenyl)pyrrolidine

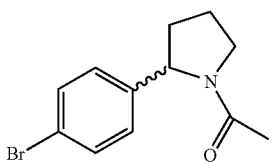

The title compound was prepared from 2-(4-bromophenyl)pyrrolidine and acetyl chloride using a similar procedure to that described in description 25.

LC/Mass Spec (ES): Found 268 (ES+), retention time 2.59 mins. $C_{12}H_{14}{}^{79}BrNO$ requires 267.

Description 28

2-[(4-bromophenyl)methyl]isothiazolidine 1,1-dioxide

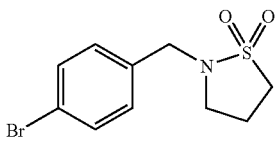

A solution of 4-bromobenzylamine (1.85 g, 10 mmol) and triethylamine (2 g, 20 mmol) in dimethylformamide (30 ml) was treated with 3-chloropropanesulfonyl chloride (1.78 g, 10 mmol) by dropwise addition over 10 minutes with stirring under argon. This mix was stirred for 30 minutes before being treated with a 60% suspension of sodium hydride in mineral oil (1.2 g, 30 mmol of NaH) portionwise and the whole mix stirred at room temperature for 3 days. The reaction mixture was partitioned between water (50 ml) and dichloromethane (30 ml). The organic layer was dried over sodium sulphate and reduced to minimum volume by rotary evaporation. The residue was added to a 20 g pre-packed silica column and eluted from 0-50% ethyl acetate in petroleum ether to give the title compound as a yellow oil (2.72 g, 94%).

LC/Mass Spec (ES): Found 290 (ES+), retention time 2.68 mins. $C_{10}H_{12}{}^{79}BrNO_2S$ requires 289. $^1$H-NMR (400 MHz, CDCl$_3$): 2.32 (2H, m), 3.11 (2H, m), 3.21 (2H, m), 3.13 (2H, s), 7.24 (2H, m), 7.49 (2H, m).

Description 29

1-[2-(4-bromophenyl)ethyl]-2-pyrrolidinone

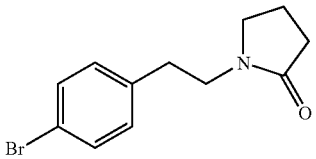

The title compound was prepared from 4-bromophenethylamine and 4-chlorobutyryl chloride using a similar procedure to that described for Description 28.

LC/Mass Spec (ES): Found 268 (ES+), retention time 2.50 mins. $C_{12}H_{14}{}^{79}BrNO$ requires 267. $^1$H-NMR (400 MHz, CDCl$_3$): 1.96 (2H, m), 2.35 (2H, t, J=8 Hz), 2.80 (2H, t, J=7 Hz), 3.26 (2H, m), 3.51 (2H, m), 7.10 (2H, m), 7.42 (2H, m).

Description 30

4-iodo-N-(2-methylpropyl)benzenesulfonamide

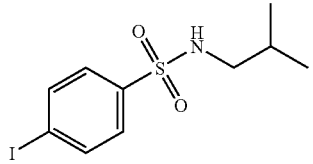

A solution of (2-methylpropyl)amine (121 mg, 1.65 mmol) and triethylamine (0.35 ml, 2.47 mmol) in DCM (10 ml) was treated with 4-iodobenzenesulfonyl chloride (500 mg, 1.65 mmol) by dropwise addition over 10 minutes with stirring under argon. The reaction mixture was stirred at room temperature for 16 hr. Then the reaction mixture was washed with water (10 ml), separated the organic layer, dried with sodium sulphate. Solvent was removed by rotary evaporation to give the title compound as a white solid (517 mg, 92%).

LC/Mass Spec (ES): Found 340 (ES+), retention time 3.14 mins. C10H14INO2S requires 339. $^1$H-NMR (400 MHz, CDCl3): 0.88 (6H, m), 1.72 (1H, m), 2.78 (2H, m), 4.41 (1H, m) 7.56 (2H, m), 7.88 (2H, m).

Description 31

1-[(4-iodophenyl)sulfonyl]pyrrolidine

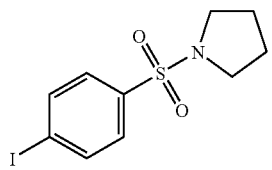

The title compound was prepared from 4-iodobenzenesulfonyl chloride and pyrrolidine using a similar procedure to that described for Description 30.

LC/Mass Spec (ES): Found 338 (ES+), retention time 2.95 mins. C10H12INO2S requires 337. ¹H-NMR (400 MHz, CDCl3): 1.76 (4H, m), 3.21 (4H, m), 7.53 (2H, m), 7.88 (2H, m).

Description 32

4-[(4-iodophenyl)sulfonyl]morpholine

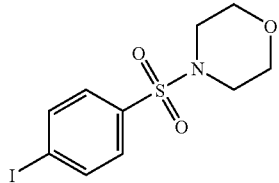

The title compound was prepared from morpholine and 4-iodobenzenesulfonyl chloride using a similar procedure to that described for Description 30.

LC/Mass Spec (ES): Found 354 (ES+), retention time 2.83 mins. C10H12INO3S requires 353. ¹H-NMR (400 MHz, CDCl3): 3.00 (4H, m), 3.75 (4H, m), 7.46 (2H, m), 7.92 (2H, m).

Description 33

4-iodo-N-[2-(methyloxy)ethyl]benzenesulfonamide

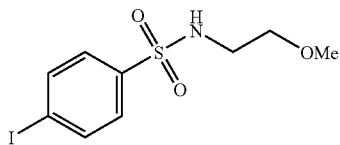

The title compound was prepared from [2-(methyloxy)ethyl]amine and 4-iodobenzenesulfonyl chloride using a similar procedure to that described for Description 30.

LC/Mass Spec (ES): Found 342 (ES+), retention time 2.61 mins. C9H12INO3S requires 341. ¹H-NMR (400 MHz, CDCl3): 3.10 (2H, m), 3.27 (3H, s), 3.40 (2H, m), 4.86 (1H, m), 7.56 (2H, m), 7.87 (2H, m).

Description 34

4-iodo-N-[2-(1-pyrrolidinyl)ethyl]benzenesulfonamide

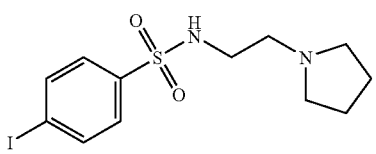

The title compound was prepared from [2-(1-pyrrolidinyl)ethyl]amine and 4-iodobenzenesulfonyl chloride using a similar procedure to that described for Description 30.

LC/Mass Spec (ES): Found 381 (ES+), retention time 1.69 mins. C12H17IN2O2S requires 380.

Description 35

4-iodo-N-(tetrahydro-2-furanylmethyl)benzenesulfonamide

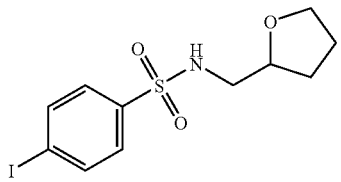

The title compound was prepared from (tetrahydro-2-furanylmethyl)amine and 4-iodobenzenesulfonyl chloride using a similar procedure to that described for Description 30.

LC/Mass Spec (ES): Found 368 (ES+), retention time 2.70 mins. C11H14INO3S requires 367. ¹H-NMR (400 MHz, CDCl3): 1.60 (1H, m), 1.83-2.0 (3H, m), 2.88 (1H, m), 3.13 (1H, m), 3.70 (1H, m), 3.77 (1H, m), 3.93 (1H, m), 4.83 (1H, m), 7.55 (2H, m), 7.86 (2H, m).

Description 36

N,1-dimethyl-N-(methyloxy)-1H-imidazole-2-carboxamide

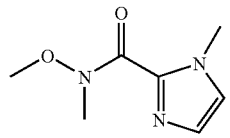

HATU (O-(7-azabenzotriazol-1-yl)-N,N,N',N'-tetramethyluronium hexafluorophosphate) (1.75 g; 4.60 mmol) was added in on portion to a stirring solution of 1-methyl-1H-imidazole-2-carboxylic acid (509 mg; 4.04 mmol), N,O-dimethylhydroxylamine hydrochloride (391 mg; 4.01 mmol), and diisopropylethylamine (2.0 mL; 11.9 mmol) in anhydrous DMF (14 mL). The mixture was stirred at room temperature for 17 hours and partitioned between ethyl acetate (100 mL) and water (100 mL). The organic phase was dried (MgSO₄) and concentrated in vacuo, giving a colourless oil (1.45 g). This was purified by column chromatography, giving the title compound as a colourless oil (494 mg; 73%).

¹H-NMR (400 MHz, CDCl₃): 3.57 (3H, br s), 3.86 (3H, s), 3.91 (3H, s), 6.97 (1H, d, J=1 Hz), 7.07 (1H, d, J=1 Hz).

Description 37

N-{4-[3-(trifluoromethyl)-4,5,6,7-tetrahydro-1H-indazol-1-yl]phenyl}-1-pyrrolidinecarboxamide

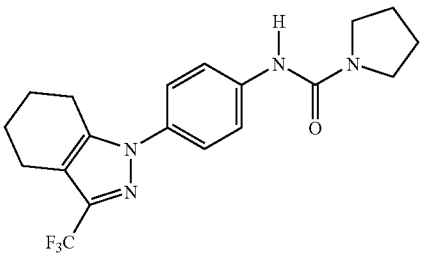

Diphenylphosphoryl azide (290 µL; 1.36 mmol) was added in one portion to a stirring mixture of 4-[3-(trifluoromethyl)-4,5,6,7-tetrahydro-1H-indazol-1-yl]benzoic acid (195 mg; 0.63 mmol) and diisopropylethylamine (220 µL; 1.29 mmol) in 1,4-dioxane (2.2 mL). The mixture was heated at reflux for 2 hours, pyrrolidine (100 µL; 1.21 mmol) was added in on portion, and the reaction heated at reflux for a further 1 hour.

Concentration in vacuo, followed by column chromatography gave the title compound (38 mg; 16%).

LC/Mass Spec (ES): found 379 (ES+), retention time 3.18 mins. $C_{19}H_{21}F_3N_4O$ requires 378. $^1$H-NMR (400 MHz, CDCl$_3$): 1.67-1.77 (4H, m), 1.83-2.03 (4H, m), 2.68-2.77 (4H, m), 3.40-3.54 (4H, m), 6.34 (1H, s), 7.34-7.40 (2H, m), 7.50-7.55 (2H, m).

EXAMPLE 1

N,N-dimethyl-4-[3-(trifluoromethyl)-4,5,6,7-tetrahydro-1H-indazol-1-yl]benzamide

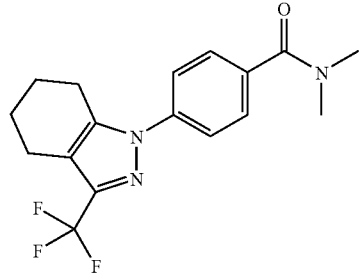

A mixture of 4-iodo-N,N-dimethylbenzamide (100 mg, 0.36 mmol), 3-(trifluoromethyl)-4,5,6,7-tetrahydro-1H-indazole (83 mg, 0.44 mmol), copper (I) iodide (1 mol %, 0.7 mg, 0.0036 mmol), trans-1,2-diaminocyclohexane (10 mol %, 4 mg, 0.036 mmol) and potassium carbonate (105 mg, 0.76 mmol) in 1,4-dioxane (0.5 ml) was stirred at 180° C. in a microwave reactor for 15 minutes, then fresh copper (I) iodide (1 mol %, 0.7 mg, 0.0036 mmol) and trans-1,2-diaminocyclohexane (10 mol %, 4 mg, 0.036 mmol) were added and the reaction stirred at 180° C. in a microwave reactor for 20 minutes. Then fresh copper (I) iodide (1 mol %, 0.7 mg, 0.0036 mmol) and trans-1,2-diaminocyclohexane (10 mol %, 4 mg, 0.036 mmol) were added and the reaction stirred at 180° C. in a microwave reactor for 30 minutes. The reaction mix was cooled and added to a 5 g pre-packed silica column which was then eluted from ethyl acetate, the product was further purified by mass directed auto-prep to give a crop of the title compound as a brown oil (53 mg, 43%).

LC/mass spec (ES): Found 338 (ES+), retention time 3.09 mins. $C_{17}H_{18}F_3N_3O$ requires 337. $^1$H-NMR (400 MHz, CDCl$_3$): 1.83 (4H, m), 2.70 (4H, m), 3.00 (3H, s), 3.14 (3H, s), 7.54 (4H, m).

EXAMPLE 2

1-[4-(1-pyrrolidinylcarbonyl)phenyl]-3-(trifluoromethyl)-4,5,6,7-tetrahydro-1H-indazole

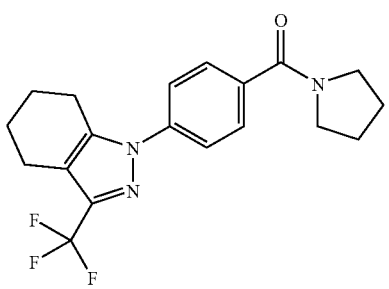

A solution of 4-[3-(trifluoromethyl)-4,5,6,7-tetrahydro-1H-indazol-1-yl]benzoic acid (87 mg, 0.28 mmol) in dichloromethane (3 ml) was treated in one portion with solid 1,1'-carbonyldiimidazole (46 mg, 0.28 mmol). This mixture was allowed to stir at room temperature for 15 minutes. Pyrrolidine (23 mg, 0.32 mmol) was then added and the stirring continued for 1 hour at room temperature. The reaction mixture was then added to a 5 g pre-packed silica column and eluted from 0-50% ethyl acetate in petroleum ether to give the title compound as a yellow oil (51 mg, 50%).

LC/mass spec (ES): Found 364 (ES+), retention time 3.22 mins. $C_{19}H_{20}F_3N_3O$ requires 363. $^1$H-NMR (400 MHz, CDCl$_3$): 1.83 (4H, m), 1.91 (2H, m), 1.98 (2H, m), 2.70 (4H, m), 3.43 (2H, t, J=6 Hz), 3.67 (2H, t, J=6 Hz), 7.53 (2H, m), 7.64 (2H, m).

EXAMPLE 3

N-methyl-N-(phenylmethyl)-4-[3-(trifluoromethyl)-4,5,6,7-tetrahydro-1H-indazol-1-yl]benzamide

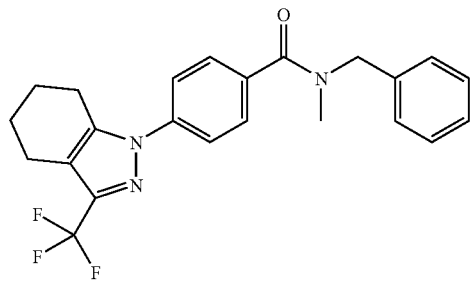

The title compound was prepared from 4-[3-(trifluoromethyl)-4,5,6,7-tetrahydro-1H-indazol-1-yl]benzoic acid and N-methylbenzylamine using a similar procedure to that described for Example 2.

LC/mass spec (ES): Found 414 (ES+), retention time 3.71 mins. $C_{23}H_{22}F_3N_3O$ requires 413. $^1$H-NMR (400 MHz, CDCl$_3$): 1.82 (4H, m), 2.69 (4H, m), 2.88 & 3.07 (3H, s (rotomers)), 4.52 & 4.77 (2H, s (rotomers)), 7.17 (1H, m), 7.34 (4H, m), 7.55 (4H, m).

EXAMPLE 4

N-ethyl-N-methyl-4-[3-(trifluoromethyl)-4,5,6,7-tetrahydro-1H-indazol-1-yl]benzamide

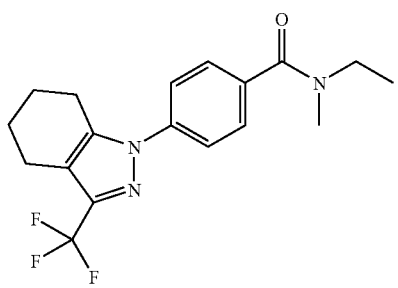

The title compound was prepared from 4-[3-(trifluoromethyl)-4,5,6,7-tetrahydro-1H-indazol-1-yl]benzoic acid and N-ethylmethylamine using a similar procedure to that described for Example 2.

LC/mass spec (ES): Found 352 (ES+), retention time 3.22 mins. $C_{18}H_{20}F_3N_3O$ requires 351. $^1$H-NMR (400 MHz, CDCl$_3$): 1.07-1.28 (3H, m (rotomers)), 1.83 (4H, m), 2.70 (4H, m), 2.96 & 3.09 (3H, m (rotomers)), 3.31 & 3.61 (2H, m (rotomers)), 7.53 (4H, m).

EXAMPLE 5

N-butyl-N-methyl-4-[3-(trifluoromethyl)-4,5,6,7-tetrahydro-1H-indazol-1-yl]benzamide

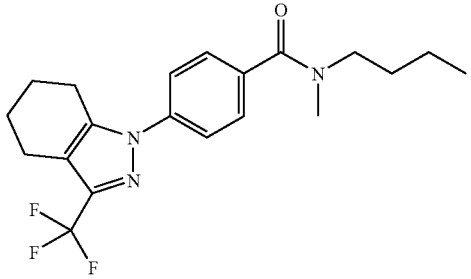

The title compound was prepared from 4-[3-(trifluoromethyl)-4,5,6,7-tetrahydro-1H-indazol-1-yl]benzoic acid and N-methylbutylamine using a similar procedure to that described for Example 2.

LC/mass spec (ES): Found 380 (ES+), retention time 3.54 mins. $C_{20}H_{24}F_3N_3O$ requires 379. $^1$H-NMR (400 MHz, CDCl$_3$): 0.81-1.01 (3H, m (rotomers)), 1.17 & 1.42 (2H, m (rotomers)), 1.53-1.63 (2H, m) 1.83 (4H, m), 2.70 (4H, m), 2.95 & 3.09 (3H, m (rotomers)), 3.24 & 3.55 (2H, m (rotomers)), 7.53 (4H, m).

EXAMPLE 6

N-methyl-N-(2-phenylethyl)-4-[3-(trifluoromethyl)-4,5,6,7-tetrahydro-1H-indazol-1-yl]benzamide

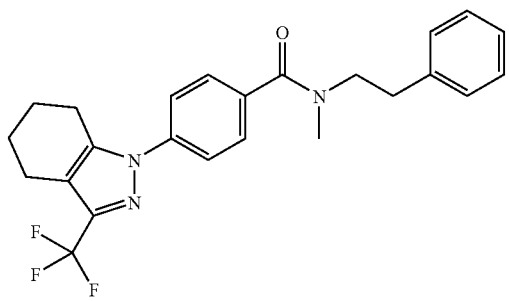

The title compound was prepared from 4-[3-(trifluoromethyl)-4,5,6,7-tetrahydro-1H-indazol-1-yl]benzoic acid and N-methylphenethylamine using a similar procedure to that described for Example 2.

LC/mass spec (ES): Found 428 (ES+), retention time 3.70 mins. $C_{24}H_{24}F_3N_3O$ requires 427. $^1$H-NMR (400 MHz, CDCl$_3$): 1.82 (4H, m), 2.68 (4H, m), 2.83 (3H, s), 3.00 & 3.16 (2H, m (rotomers)), 3.51 & 3.80 (2H, m (rotomers)), 6.98 (1H, m), 7.12 (1H, m), 7.28 (4H, m), 7.43 (2H, m), 7.52 (1H, m).

EXAMPLE 7

N,N-dimethyl-4-[3-(trifluoromethyl)-4,5,6,7-tetrahydro-1H-indazol-1-yl]benzenesulfonamide

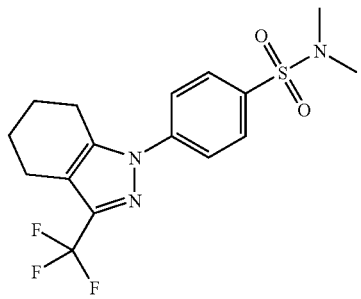

A mixture of 4-iodo-N,N-dimethylbenzenesulfonamide (156 mg, 0.5 mmol), 3-(trifluoromethyl)-4,5,6,7-tetrahydro-1H-indazole (105 mg, 0.55 mmol), copper (I) iodide (1 mol %, 1 mg, 0.005 mmol), trans-1,2-diaminocyclohexane (10 mol %, 6 mg, 0.05 mmol) and potassium carbonate (145 mg, 1.05 mmol) in 1,4-dioxane (1 ml) was stirred at 180° C. in a microwave reactor for 45 minutes. The reaction mix was cooled and added to a 5 g pre-packed silica column which was then eluted from ethyl acetate, the product was further purified by mass directed auto-prep to give a crop of the title compound as a pale beige solid (65 mg, 35%).

LC/mass spec (ES): Found 374 (ES+), retention time 3.55 mins. $C_{16}H_{18}F_3N_3O_2S$ requires 373. $^1$H-NMR (400 MHz, CDCl$_3$): 1.85 (4H, m), 2.70 (2H, m), 2.74 (6H, s), 2.77 (2H, m), 7.72 (2H, m), 7.89 (2H, m).

EXAMPLE 8

1-{4-[3-(trifluoromethyl)-4,5,6,7-tetrahydro-1H-indazol-1-yl]phenyl}ethanone

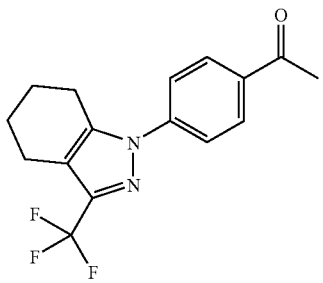

The title compound was prepared from 4-iodoacetophenone and 3-(trifluoromethyl)-4,5,6,7-tetrahydro-1H-indazole using a similar procedure to that described for Example 7.

LC/mass spec (ES): Found 309 (ES+), retention time 3.52 mins. $C_{16}H_{15}F_3N_2O$ requires 308. $^1$H-NMR (400 MHz, CDCl$_3$): 1.84 (4H, m), 2.64 (3H, s), 2.70 (2H, m), 2.77 (2H, m), 7.64 (2H, m), 8.07 (2H, m).

EXAMPLE 9

1-{4-[3-(trifluoromethyl)-4,5,6,7-tetrahydro-1H-indazol-1-yl]phenyl}-1-propanone

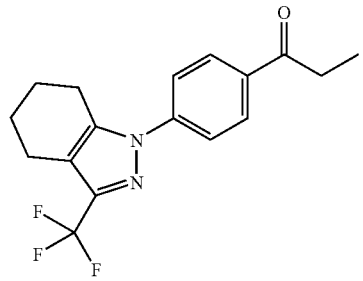

The title compound was prepared from 1-(4-bromophenyl)-1-propanone and 3-(trifluoromethyl)-4,5,6,7-tetrahydro-1H-indazole using a similar procedure to that described for Example 1.

LC/mass spec (ES): Found 323 (ES+), retention time 3.75 mins. $C_{17}H_{17}F_3N_2O$ requires 322. $^1$H-NMR (400 MHz, CDCl$_3$): 1.25 (3H, t, J=7 Hz), 1.84 (4H, m), 2.69 (2H, m), 2.78 (2H, m), 3.04 (2H, quart., J=7 Hz), 7.63 (2H, m), 8.07 (2H, m).

EXAMPLE 10

1-[4-(methylsulfonyl)phenyl]-3-(trifluoromethyl)-4,5,6,7-tetrahydro-1H-indazole

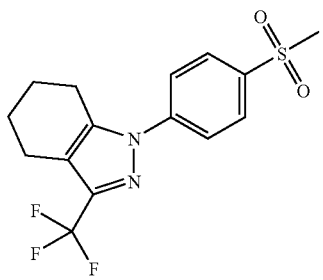

The title compound was prepared from 4-bromophenyl methyl sulfone and 3-(trifluoromethyl)-4,5,6,7-tetrahydro-1H-indazole using a similar procedure to that described for Example 7.

LC/mass spec (ES): Found 345 (ES+), retention time 3.26 mins. $C_{15}H_{15}F_3N_2O_2S$ requires 344. $^1$H-NMR (400 MHz, CDCl$_3$): 1.86 (4H, m), 2.70 (2H, m), 2.80 (2H, m), 3.10 (3H, s), 7.76 (2H, m), 8.06 (2H, m).

EXAMPLE 11

1-{4-[3-(trifluoromethyl)-4,5,6,7-tetrahydro-1H-indazol-1-yl]phenyl}-2-propanone

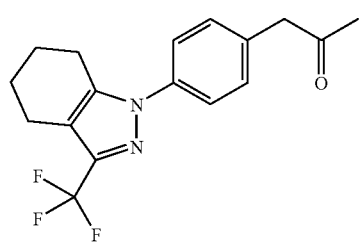

The title compound was prepared from 4-bromophenylacetone and 3-(trifluoromethyl)-4,5,6,7-tetrahydro-1H-indazole using a similar procedure to that described for Example 7.

LC/mass spec (ES): Found 323 (ES+), retention time 3.44 mins. $C_{17}H_{17}F_3N_2O$ requires 322. $^1$H-NMR (400 MHz, CDCl$_3$): 1.82 (4H, m), 2.19 (3H, s), 2.69 (4H, m), 3.76 (2H, s), 7.30 (2H, m), 7.46 (2H, m).

EXAMPLE 12

N,N-dimethyl-2-{4-[3-(trifluoromethyl)-4,5,6,7-tetrahydro-1H-indazol-1-yl]phenyl}acetamide

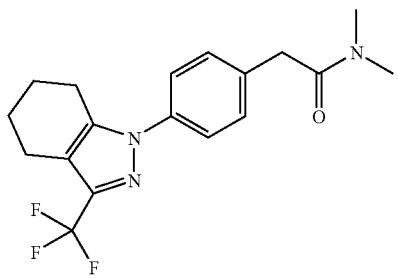

The title compound was prepared from 2-(4-bromophenyl)-N,N-dimethylacetamide and 3-(trifluoromethyl)-4,5,6,7-tetrahydro-1H-indazole using a similar procedure to that described for Example 7.

LC/mass spec (ES): Found 352 (ES+), retention time 3.15 mins. $C_{18}H_{20}F_3N_3O$ requires 351. $^1$H-NMR (400 MHz, CDCl$_3$): 1.81 (4H, m), 2.69 (4H, m), 2.99 (3H, s), 3.02 (3H, s), 3.76 (2H, s), 7.35 (2H, d, J=8 Hz), 7.43 (2H, m).

EXAMPLE 13

1-{4-[2-oxo-2-(1-pyrrolidinyl)ethyl]phenyl}-3-(trifluoromethyl)-4,5,6,7-tetrahydro-1H-indazole

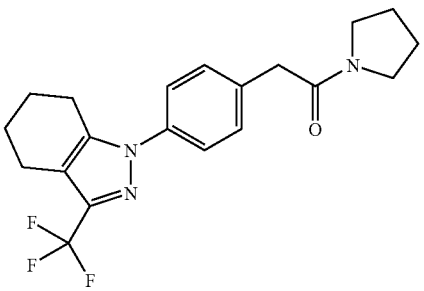

A solution of {4-[3-(trifluoromethyl)-4,5,6,7-tetrahydro-1H-indazol-1-yl]phenyl}acetic acid (113 mg, 0.35 mmol) in dichloromethane (4 ml) in a sarstedt tube was treated in one portion with solid 1,1'-carbonyldiimidazole (60 mg, 0.37 mmol). This mixture was shaken at room temperature for 30 minutes. Pyrrolidine (34 mg, 0.48 mmol) in dichloromethane (2 ml) was then added and the shaking continued for 16 hour at room temperature. The reaction mixture was washed with a mix of saturated sodium bicarbonate solution (4 ml) and brine (2 ml). The organic layer was then added to a 2 g SCX column and eluted with ethyl acetate (25 ml), the solvent removed under reduced pressure and the residue purified by mass directed auto-prep to give the title compound as a yellow oil (30 mg, 23%).

LC/mass spec (ES): Found 378 (ES+), retention time 3.28 mins. $C_{20}H_{22}F_3N_3O$ requires 377. $^1$H-NMR (400 MHz, CDCl$_3$): 1.81 (4H, m), 1.88 (2H, m), 1.96 (2H, m), 2.69 (4H, m), 3.44 (2H, t, J=7 Hz), 3.50 (2H, t, J=7 Hz), 3.71 (2H, s), 7.38 (2H, d, J=8 Hz), 7.43 (2H, m).

EXAMPLE 14

N-ethyl-N-methyl-2-{4-[3-(trifluoromethyl)-4,5,6,7-tetrahydro-1H-indazol-1-yl]phenyl}acetamide

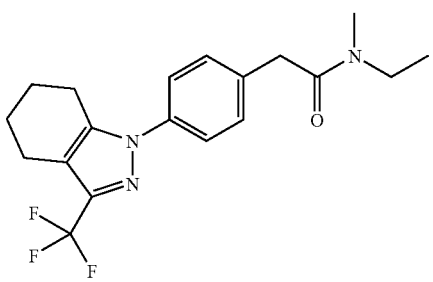

The title compound was prepared from {4-[3-(trifluoromethyl)-4,5,6,7-tetrahydro-1H-indazol-1-yl]phenyl}acetic acid and N-ethylmethylamine using a similar procedure to that described for Example 13, but purified by flash column chromatography eluting from 0-100% ethyl acetate in hexane.

LC/mass spec (ES): Found 366 (ES+), retention time 3.28 mins. $C_{19}H_{22}F_3N_3O$ requires 365. $^1$H-NMR (400 MHz, CDCl$_3$): 1.12 (3H, m), 1.82 (4H, m), 2.68 (4H, m), 2.95 & 2.97 (3H, s (rotomers)), 3.34-3.47 (2H, m (rotomers)), 3.75 (2H, m), 7.36 (2H, m), 7.44 (2H, d, J=8 Hz).

EXAMPLE 15

N-methyl-N-(phenylmethyl)-2-{4-[3-(trifluoromethyl)-4,5,6,7-tetrahydro-1H-indazol-1-yl]phenyl}acetamide

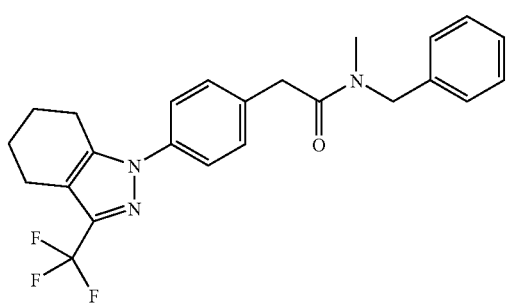

The title compound was prepared from {4-[3-(trifluoromethyl)-4,5,6,7-tetrahydro-1H-indazol-1-yl]phenyl}acetic acid and N-methylbenzylamine using a similar procedure to that described for Example 13, but purified by flash column chromatography eluting from 0-66% ethyl acetate in hexane.

LC/mass spec (ES): Found 428 (ES+), retention time 3.55 mins. $C_{24}H_{24}F_3N_3O$ requires 427. $^1$H-NMR (400 MHz, CDCl$_3$): 1.82 (4H, m), 2.69 (4H, m), 2.93 & 2.99 (3H, s, (rotomers)), 3.78 & 3.82 (2H, s, (rotomers)), 4.55 & 4.62 (2H, s, (rotomers)), 7.12-7.46 (9H, m).

EXAMPLE 16

N-butyl-N-methyl-2-{4-[3-(trifluoromethyl)-4,5,6,7-tetrahydro-1H-indazol-1-yl]phenyl}acetamide

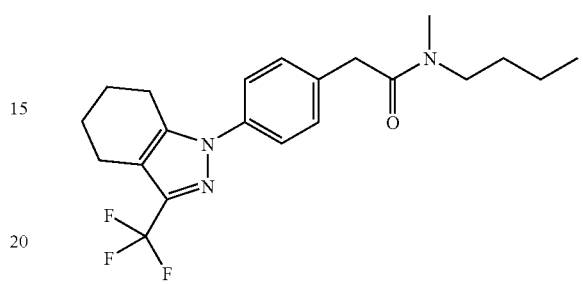

The title compound was prepared from {4-[3-(trifluoromethyl)-4,5,6,7-tetrahydro-1H-indazol-1-yl]phenyl}acetic acid and N-methylbutylamine using a similar procedure to that described for Example 13, but purified by flash column chromatography eluting from 0-66% ethyl acetate in hexane.

LC/mass spec (ES): Found 394 (ES+), retention time 3.63 mins. $C_{21}H_{26}F_3N_3O$ requires 393.

$^1$H-NMR (400 MHz, CDCl$_3$): 0.94 (3H, m), 1.24-1.35 (2H, m), 1.47-1.55 (2H, m), 1.82 (4H, m), 2.68 (4H, m), 2.95 & 2.97 (3H, s (rotomers)), 3.28 & 3.39 (2H, m (rotomers)), 3.75 (2H, m), 7.36 (2H, d, J=8 Hz), 7.43 (2H, d, J=8 Hz)

EXAMPLE 17

N-methyl-N-(2-phenylethyl)-2-{4-[3-(trifluoromethyl)-4,5,6,7-tetrahydro-1H-indazol-1-yl]phenyl}acetamide

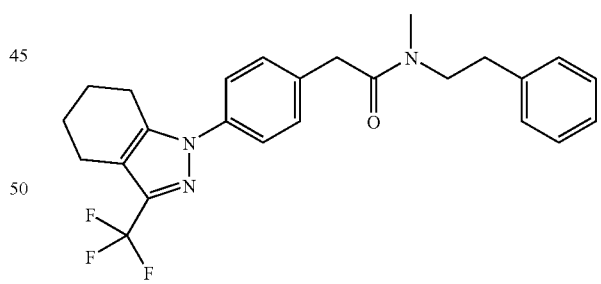

The title compound was prepared from {4-[3-(trifluoromethyl)-4,5,6,7-tetrahydro-1H-indazol-1-yl]phenyl}acetic acid and N-methylphenethylamine using a similar procedure to that described for Example 13, but purified by flash column chromatography eluting from 0-88% ethyl acetate in hexane, followed by mass directed auto-prep.

LC/mass spec (ES): Found 442 (ES+), retention time 3.58 mins. $C_{25}H_{26}F_3N_3O$ requires 441.

$^1$H-NMR (400 MHz, CDCl$_3$): 1.81 (4H, m), 2.68 (4H, m), 2.83 (2H, m), 2.89 & 3.01 (3H, s (rotomers)), 3.41 & 3.73 (2H, s (rotomers)), 3.54 & 3.63 (2H, t, J=7 Hz (rotomers)), 7.17 (3H, m), 7.29 (4H, m), 7.42 (2H, m).

EXAMPLE 18

1-{[4-(1-pyrrolidinylcarbonyl)phenyl]methyl}-3-(trifluoromethyl)-4,5,6,7-tetrahydro-1H-indazole

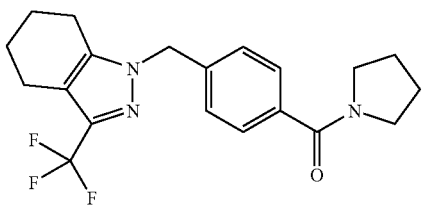

A mixture of 1-{[4-(bromomethyl)phenyl]carbonyl}pyrrolidine (84 mg, 0.31 mmol), 3-(trifluoromethyl)-4,5,6,7-tetrahydro-1H-indazole (60 mg, 0.32 mmol), and potassium carbonate (87 mg, 0.63 mmol) in N,N-dimethylformamide (2 ml) was stirred at 140° C. in a microwave reactor for 10 minutes. The reaction mixture was cooled and partitioned between dichloromethane and water. The organic layer was dried over sodium sulphate and reduced to minimum volume under reduced pressure. The crude product was purified using mass directed auto-prep to give the title compound as a pale yellow oil (63 mg, 54%).

LC/mass spec (ES): Found 378 (ES+), retention time 3.11 mins. $C_{20}H_{22}F_3N_3O$ requires 377.

$^1$H-NMR (400 MHz, CDCl$_3$): 1.69-1.80 (4H, m), 1.87 (2H, m), 1.96 (2H, m), 2.43 (2H, m), 2.60 (2H, m), 3.40 (2H, t, J=7 Hz), 3.64 (2H, t, J=7 Hz), 5.27 (2H, s), 7.13 (2H, d, J=8 Hz), 7.48 (2H, dd, J=6 Hz, & 2 Hz).

EXAMPLE 19

1-{4-[1-methyl-2-oxo-2-(1-pyrrolidinyl)ethyl]phenyl}-3-(trifluoromethyl)-4,5,6,7-tetrahydro-1H-indazole

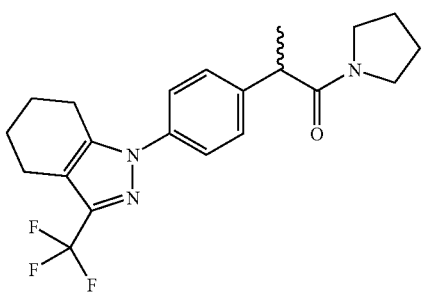

A mixture of 1-[2-(4-bromophenyl)propanoyl]pyrrolidine (140 mg, 0.5 mmol), 3-(trifluoromethyl)-4,5,6,7-tetrahydro-1H-indazole (95 mg, 0.5 mmol), copper (I) iodide (10 mol %, 10 mg, 0.05 mmol), N,N-dimethylglycine (20 mol %, 10 mg, 0.1 mmol) and potassium carbonate (138 mg, 1 mmol) in dimethylsulfoxide (2 ml) was stirred at 190° C. in a microwave reactor for a total of 1.5 h. The reaction mix was cooled and partitioned between ethyl acetate and water. The organic layer was dried over sodium sulphate and the solvent removed under reduced pressure. The resulting product was purified firstly by adding the material in dichloromethane to a 5 g pre-packed silica column and eluting with ethyl acetate, followed by mass directed auto-prep to give a crop of the title compound as a brown oil (8 mg, 4%).

LC/mass spec (ES): Found 392 (ES+), retention time 3.45 mins. $C_{21}H_{24}F_3N_3O$ requires 391.

$^1$H-NMR (400 MHz, CDCl$_3$): 1.47 (3H, d, J=7 Hz), 1.74-1.92 (8H, m), 2.69 (4H, m), 3.17 (1H, m), 3.40-3.57 (3H, m), 3.79 (1H, m), 7.40 (4H, m).

EXAMPLE 20

N,N-dimethyl-3-{4-[3-(trifluoromethyl)-4,5,6,7-tetrahydro-1H-indazol-1-yl]phenyl}propanamide

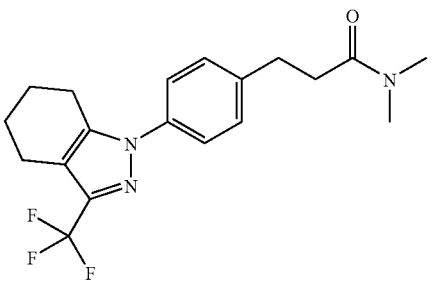

The title compound was prepared from 3-(4-bromophenyl)-N,N-dimethylpropanamide and 3-(trifluoromethyl)-4,5,6,7-tetrahydro-1H-indazole using a similar procedure to that described for Example 1.

LC/mass spec (ES): Found 366 (ES+), retention time 3.23 mins. $C_{19}H_{22}F_3N_3O$ requires 365.

$^1$H-NMR (400 MHz, CDCl$_3$): 1.82 (4H, m), 2.63 (2H, t, J=8 Hz), 2.67 (4H, m), 2.96 (6H, s), 3.02 (2H, t, J=8 Hz), 7.32 (2H, d, J=8 Hz), 7.39 (2H, m).

EXAMPLE 21

1-{4-[3-oxo-3-(1-pyrrolidinyl)propyl]phenyl}-3-(trifluoromethyl)-4,5,6,7-tetrahydro-1H-indazole

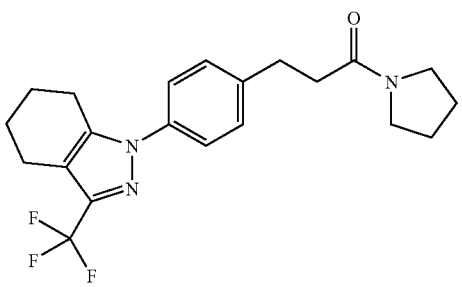

The title compound was prepared from 1-[3-(4-bromophenyl)propanoyl]pyrrolidine and 3-(trifluoromethyl)-4,5,6,7-tetrahydro-1H-indazole using a similar procedure to that described for Example 19.

LC/mass spec (ES): Found 392 (ES+), retention time 3.40 mins. $C_{21}H_{24}F_3N_3O$ requires 391.

$^1$H-NMR (400 MHz, CDCl$_3$): 1.81 (4H, m), 1.85 (2H, m), 1.92 (2H, m), 2.58 (2H, m), 2.64 (4H, m), 3.04 (2H, t, J=8 Hz), 3.33 (2H, t, J=7 Hz), 3.47 (2H, t, J=7 Hz), 7.32 (2H, m), 7.39 (2H, m).

EXAMPLE 22

1-{4-[1-(1-pyrrolidinylcarbonyl)cyclopropyl]phenyl}-3-(trifluoromethyl)-4,5,6,7-tetrahydro-1H-indazole

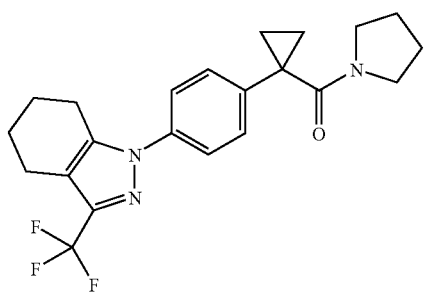

The title compound was prepared from 1-{[1-(4-iodophenyl)cyclopropyl]carbonyl}pyrrolidine and 3-(trifluoromethyl)-4,5,6,7-tetrahydro-1H-indazole using a similar procedure to that described for Example 19.

LC/mass spec (ES): Found 404 (ES+), retention time 3.43 mins. $C_{22}H_{24}F_3N_3O$ requires 403.

$^1$H-NMR (400 MHz, CDCl$_3$): 1.18 (2H, m), 1.48 (2H, m), 1.75-1.83 (8H, m), 2.68 (4H, m), 3.19 (2H, m), 3.49 (2H, m), 7.28 (2H, m), 7.41 (2H, m).

EXAMPLE 23

1-{4-[2-oxo-2-(1-piperidinyl)ethyl]phenyl}-3-(trifluoromethyl)-4,5,6,7-tetrahydro-1H-indazole

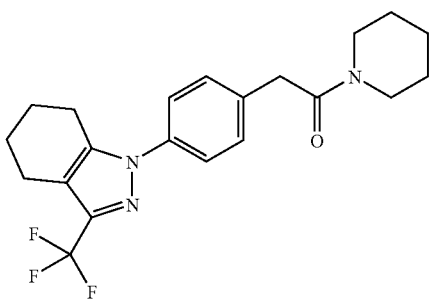

The title compound was prepared from {4-[3-(trifluoromethyl)-4,5,6,7-tetrahydro-1H-indazol-1-yl]phenyl}acetic acid and piperidine using a similar procedure to that described for Example 2, product further purified by mass directed auto-prep.

LC/mass spec (ES): Found 392 (ES+), retention time 3.45 mins. $C_{21}H_{24}F_3N_3O$ requires 391.

$^1$H-NMR (400 MHz, CDCl$_3$): 1.41 (2H, m), 1.53 (2H, m), 1.59 (2H, m), 1.82 (4H, m), 2.68 (4H, m), 3.39 (2H, m), 3.58 (2H, m), 3.77 (2H, s), 7.36 (2H, m), 7.44 (2H, m).

EXAMPLE 24

1-{4-[2-(3,3-difluoro-1-pyrrolidinyl)-2-oxoethyl]phenyl}-3-(trifluoromethyl)-4,5,6,7-tetrahydro-1H-indazole

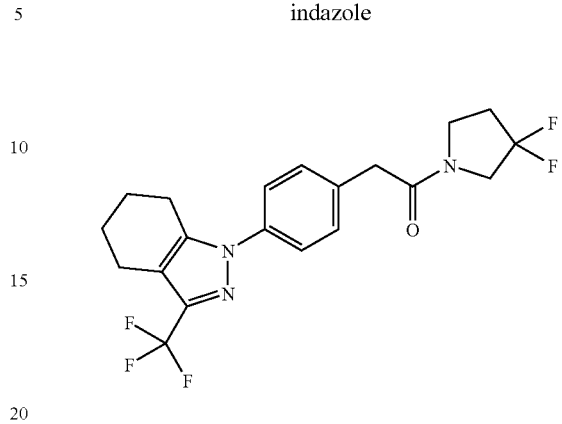

A solution of {4-[3-(trifluoromethyl)-4,5,6,7-tetrahydro-1H-indazol-1-yl]phenyl}acetic acid (65 mg, 0.2 mmol) in dichloromethane (2 ml) was treated in one portion with solid 1,1'-carbonyldiimidazole (33 mg, 0.2 mmol). This mixture was allowed to stir at room temperature for 15 minutes. 3,3-difluoropyrrolidine hydrochloride (29 mg, 0.2 mmol) was then added followed by triethylamine (21 mg, 0.21 mmol) and the stirring continued for 1 hour at room temperature. The reaction mixture was reduced to minimum volume under reduced pressure then purified by mass directed auto-prep to give the title compound as a yellow oil (53 mg, 64%).

LC/mass spec (ES): Found 414 (ES+), retention time 3.34 mins. $C_{20}H_{20}F_5N_3O$ requires 413.

$^1$H-NMR (400 MHz, CDCl$_3$): 1.82 (4H, m), 2.35 (1H, m), 2.43 (1H, m), 2.69 (4H, m), 3.67-3.87 (6H, m), 7.36 (2H, m), 7.46 (2H, m).

EXAMPLE 25

N-methyl-N-propyl-2-{4-[3-(trifluoromethyl)-4,5,6,7-tetrahydro-1H-indazol-1-yl]phenyl}acetamide

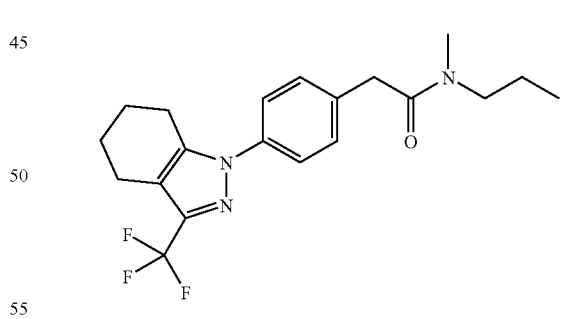

The title compound was prepared from {4-[3-(trifluoromethyl)-4,5,6,7-tetrahydro-1H-indazol-1-yl]phenyl}acetic acid and N-methylpropylamine using a similar procedure to that described for Example 2, product further purified by mass directed auto-prep.

LC/mass spec (ES): Found 380 (ES+), retention time 3.41 mins. $C_{20}H_{24}F_3N_3O$ requires 379.

$^1$H-NMR (400 MHz, CDCl$_3$): 0.89 (3H, m), 1.56 (2H, m), 1.81 (4H, m), 2.68 (4H, m), 2.96 (3H, m), 3.26 (1H, m), 3.36 (1H, m), 3.76 (2H, m), 7.36 (2H, d, J=9 Hz), 7.44 (2H, d, J=8 Hz).

EXAMPLE 26

N-cyclopentyl-2-{4-[3-(trifluoromethyl)-4,5,6,7-tetrahydro-1H-indazol-1-yl]phenyl}acetamide

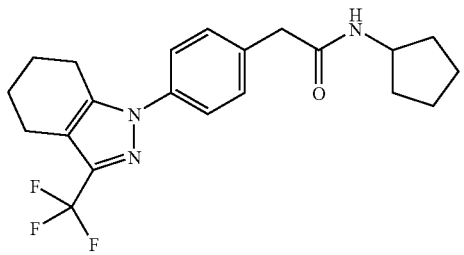

The title compound was prepared from {4-[3-(trifluoromethyl)-4,5,6,7-tetrahydro-1H-indazol-1-yl]phenyl}acetic acid and cyclopentylamine using a similar procedure to that described for Example 2, except product was purified by mass directed auto-prep.

LC/mass spec (ES): Found 392 (ES+), retention time 3.37 mins. $C_{21}H_{24}F_3N_3O$ requires 391.

$^1$H-NMR (400 MHz, CDCl$_3$): 1.26 (2H, m), 1.53-1.63 (4H, m), 1.82 (4H, m), 1.92-2.00 (2H, m), 2.70 (4H, m), 3.58 (2H, s), 4.20 (1H, m), 5.29 (1H, m), 7.36 (2H, d, J=8 Hz), 7.48 (2H, m).

EXAMPLE 27

N-methyl-N-(2-thienylmethyl)-2-{4-[3-(trifluoromethyl)-4,5,6,7-tetrahydro-1H-indazol-1-yl]phenyl}acetamide

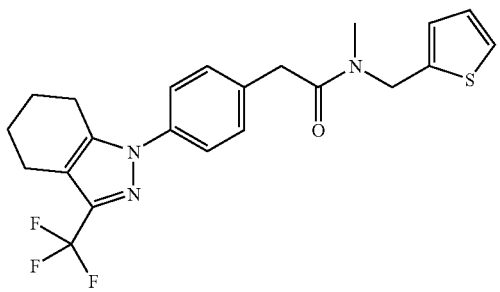

A solution of {4-[3-(trifluoromethyl)-4,5,6,7-tetrahydro-1H-indazol-1-yl]phenyl}acetic acid (65 mg, 0.2 mmol) in dichloromethane (2 ml) was treated in one portion with solid 1,1'-carbonyldiimidazole (33 g, 0.2 mmol). This mixture was shaken at room temperature for 15 minutes. Methylthiophen-2-yl methylamine (25 mg, 0.2 mmol) was then added and the shaking continued for 1 hour at room temperature. The reaction mixture was partitioned between dichloromethane and saturated sodium bicarbonate solution (3 ml). The organic layer was dried over sodium sulphate and evaporated under reduced pressure to give a yellow oil which was purified using mass directed auto-prep to give the title compound as a yellow oil (42 mg, 48%).

LC/mass spec (ES): Found 434 (ES+), retention time 3.54 mins. $C_{22}H_{22}F_3N_3OS$ requires 433.

$^1$H-NMR (400 MHz, CDCl$_3$): 1.82 (4H, m), 2.69 (4H, m), 2.97 & 3.01 (3H, s (rotomers)), 3.79 & 3.86 (2H, s, (rotomers)), 4.66 & 4.74 (2H, s (rotomers)), 6.89-6.99 (2H, m), 7.23 (1H, m), 7.36 (2H, m), 7.44 (2H, m).

EXAMPLE 28

{4-[3-(trifluoromethyl)-4,5,6,7-tetrahydro-1H-indazol-1-yl]phenyl}acetonitrile

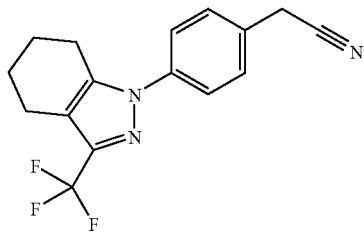

The title compound was prepared from (4-bromophenyl)acetonitrile and 3-(trifluoromethyl)-4,5,6,7-tetrahydro-1H-indazole using a similar procedure to that described for Example 7.

LC/mass spec (ES): Found 306 (ES+), retention time 3.34 mins. $C_{16}H_{14}F_3N_3$ requires 305.

$^1$H-NMR (400 MHz, CDCl$_3$): 1.83 (4H, m), 2.70 (4H, m), 3.82 (2H, s), 7.44 (2H, d, J=8 Hz), 7.53 (2H, m).

EXAMPLE 29

{4-[3-(trifluoromethyl)-4,5,6,7-tetrahydro-1H-indazol-1-yl]phenyl}methanol

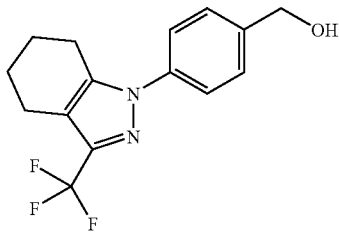

A mixture of 4-iodobenzylalcohol (1.23 g, 5.25 mmol), 3-(trifluoromethyl)-4,5,6,7-tetrahydro-1H-indazole (950 mg, 5 mmol), copper (I) iodide (10 mol %, 95 mg, 0.5 mmol), N,N-dimethylglycine (20 mol %, 103 mg, 1 mmol) and potassium carbonate (1.45 g, 10.5 mmol) in dimethylsulfoxide (30 ml) was stirred at 130° C. in an oil bath for 23 h. The reaction mix was cooled and partitioned between dichloromethane (30 ml) and brine (150 ml). The organic layer was removed filtered and the solvent removed under reduced pressure. The resulting product was purified by flash column chromatography on a Biotage 40+M column eluting from 0-60% ethyl acetate in pentane to give the title compound as a yellow oil (1.27 g, 86%).

LC/mass spec (ES): Found 297 (ES+), retention time 3.06 mins. $C_{15}H_{15}F_3N_2O$ requires 296.

$^1$H-NMR (400 MHz, CDCl$_3$): 1.76 (1H, t, J=6 Hz), 1.82 (4H, m), 2.69 (4H, m), 4.77 (2H, m), 7.48 (4H, m).

EXAMPLE 30

N-methyl-N-({4-[3-(trifluoromethyl)-4,5,6,7-tetrahydro-1H-indazol-1-yl]phenyl}methyl)acetamide

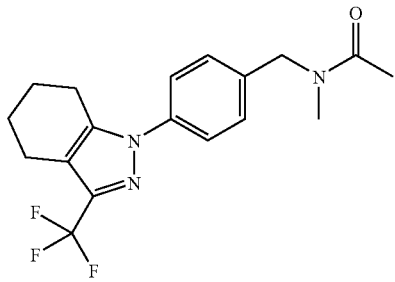

The title compound was prepared from N-[(4-bromophenyl)methyl]-N-methylacetamide and 3-(trifluoromethyl)-4,5,6,7-tetrahydro-1H-indazole using a similar procedure to that described for Example 1.

LC/mass spec (ES): Found 352 (ES+), retention time 3.13 mins. $C_{18}H_{20}F_3N_3O$ requires 351.

$^1$H-NMR (400 MHz, CDCl$_3$): 1.82 (4H, m), 2.18 (3H, m), 2.66 (4H, m), 2.94 & 2.96 (3H, s (rotomers)), 4.58 & 4.63 (2H, s (rotomers)), 7.26-7.35 (2H, m (rotomers), 7.42-7.52 (2H, m (rotomers)).

EXAMPLE 31

1-({4-[3-(trifluoromethyl)-4,5,6,7-tetrahydro-1H-indazol-1-yl]phenyl}methyl)-2-pyrrolidinone

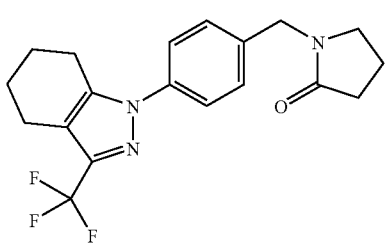

The title compound was prepared from 1-[(4-iodophenyl)methyl]-2-pyrrolidinone and 3-(trifluoromethyl)-4,5,6,7-tetrahydro-1H-indazole using a similar procedure to that described for Example 19.

LC/mass spec (ES): Found 364 (ES+), retention time 3.18 mins. $C_{19}H_{20}F_3N_3O$ requires 363.

$^1$H-NMR (400 MHz, CDCl$_3$): 1.82 (4H, m), 2.02 (2H, m), 2.45 (2H, m), 2.69 (4H, m), 3.26 (2H, m), 4.50 (2H, m), 7.34 (2H, d, J=8 Hz), 7.45 (2H, m).

EXAMPLE 32

N-methyl-N-({4-[3-(trifluoromethyl)-4,5,6,7-tetrahydro-1H-indazol-1-yl]phenyl}methyl)propanamide

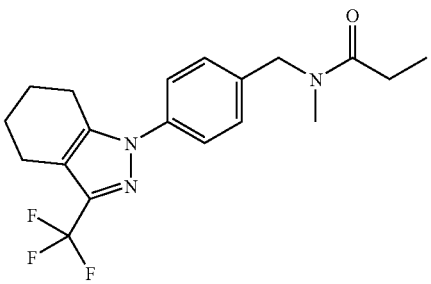

The title compound was prepared from 1-[4-(chloromethyl)phenyl]-3-(trifluoromethyl)-4,5,6,7-tetrahydro-1H-indazole and N-methylpropanamide using a similar procedure to that described for Description 15.

LC/mass spec (ES): Found 366 (ES+), retention time 3.30 mins. $C_{19}H_{22}F_3N_3O$ requires 365.

$^1$H-NMR (400 MHz, CDCl$_3$): 1.20 (3H, m), 1.80 (4H, m), 2.41 (2H, m), 2.68 (4H, m), 2.93 & 2.97 (3H, s (rotomers)), 4.58 & 4.64 (2H, s (rotomers)), 7.25-7.35 (2H, m), 7.42-7.51 (2H, m).

EXAMPLE 33

N-ethyl-N-({4-[3-(trifluoromethyl)-4,5,6,7-tetrahydro-1H-indazol-1-yl]phenyl}methyl)acetamide

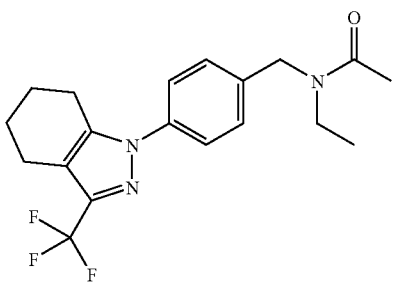

The title compound was prepared from 1-[4-(chloromethyl)phenyl]-3-(trifluoromethyl)-4,5,6,7-tetrahydro-1H-indazole and N-ethylacetamide using a similar procedure to that described for Description 15.

LC/mass spec (ES): Found 366 (ES+), retention time 3.28 mins. $C_{19}H_{22}F_3N_3O$ requires 365.

$^1$H-NMR (400 MHz, CDCl$_3$): 1.14 (3H, m), 1.82 (4H, m), 2.12 & 2.20 (3H, s (rotomers)), 2.68 (4H, m), 3.29 & 3.44 (2H, quart., J=7 Hz (rotomers)), 4.57 & 4.63 (2H, s, (rotomers)), 7.29 & 7.34 (2H, d, J=8 Hz (rotomers)), 7.42 & 7.50 (2H, d, J=8 Hz (rotomers)).

EXAMPLE 34

1-({4-[3-(trifluoromethyl)-4,5,6,7-tetrahydro-1H-indazol-1-yl]phenyl}methyl)-2-piperidinone

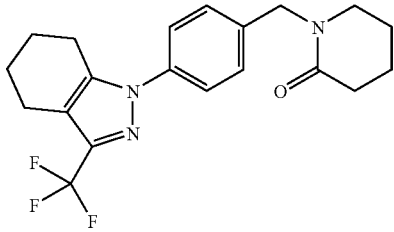

The title compound was prepared from 1-[4-(chloromethyl)phenyl]-3-(trifluoromethyl)-4,5,6,7-tetrahydro-1H-indazole and 2-piperidinone using a similar procedure to that described for Description 15.

LC/mass spec (ES): Found 378 (ES+), retention time 3.29 mins. $C_{20}H_{22}F_3N_3O$ requires 377.

$^1$H-NMR (400 MHz, CDCl$_3$): 1.79 (8H, m), 2.48 (2H, m), 2.68 (4H, m), 3.20 (2H, m), 4.64 (2H, s), 7.36 (2H, d, J=8 Hz), 7.43 (2H, m).

EXAMPLE 35

1-methyl-5-{4-[3-(trifluoromethyl)-4,5,6,7-tetrahydro-1H-indazol-1-yl]phenyl}-2-pyrrolidinone

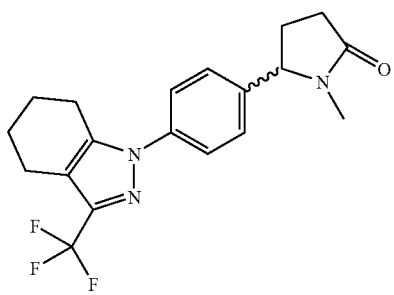

A mixture of 5-(4-bromophenyl)-1-methyl-2-pyrrolidinone (141 mg, 0.56 mmol), 3-(trifluoromethyl)-4,5,6,7-tetrahydro-1H-indazole (111 mg, 0.58 mmol), copper (I) iodide (10 mol %, 11 mg, 0.06 mmol), N,N-dimethylglycine (20 mol %, 12 mg, 0.12 mmol) and potassium carbonate (162 mg, 1.17 mmol) in dimethylsulfoxide (3 ml) was stirred at 180° C. in a microwave reactor for a total of 2 h. The reaction mix was filtered through a 5 g pre-packed silica column washing through with dichloromethane (20 ml), the filtrate was washed with water (50 ml) and the organic layer dried over sodium sulphate. The solvent was removed by rotary evaporation and the sample purified by mass directed auto prep. The final product was partitioned between dichloromethane (3 ml) and water (3 ml). The organic layer was separated and solvent removed by rotary evaporation to give the title compound as a brown oil (14 mg, 7%)

LC/mass spec (ES): Found 364 (ES+), retention time 3.14 mins. $C_{19}H_{20}F_3N_3O$ requires 363.

$^1$H-NMR (400 MHz, CDCl$_3$): 1.88 (5H, m), 2.44-2.65 (3H, m), 2.71 (7H, m), 4.58 (1H, m), 7.30 (2H, m), 7.52 (2H, m).

EXAMPLES 36-44

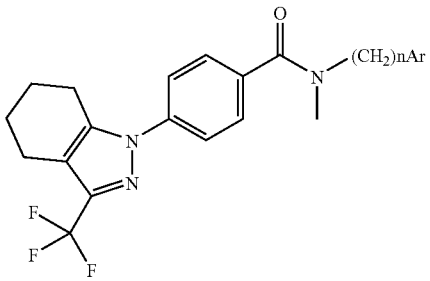

Typical procedure: To polymer supported 1-ethyl-3-(3-dimethylaminopropyl)carbodiimide (0.1 mmol, 0.068 g, 1.42 mmol/g) was added a solution of 1-hydroxy-7-azabenzotriazole (0.01 mmol, 0.8 ml (tetrahydrofuran:dichloromethane 1:1)) followed by the addition of 4-[3-(trifluoromethyl)-4,5,6,7-tetrahydro-1H-indazol-1-yl]benzoic acid (0.01 g, 0.05 mmol) in 1:3 N-methyl-2-pyrrolidinone:tetrahydrofuran then the addition of the amine (0.05 mmol) in dichloromethane (0.25 ml). The reaction was allowed to mix for 60 h. Following this was added polymer supported isocyanate (0.068 g, 0.1 mmol, 1.5 mmol/g) and polymer supported carbonate (0.068 g, 0.1 mmol, 1.5 mmol/g) and allowed to mix for a further 24 hours. The reaction mix was filtered and the solvent removed in the Genevac. All products were further purified by mass directed auto-prep.

| Example | n | Ar | Name | LC/mass spec (ES) |
|---|---|---|---|---|
| 36 | 3 | 1-imidazolyl | N-[3-(1H-imidazol-1-yl)propyl]-N-methyl-4-[3-(trifluoromethyl)-4,5,6,7-tetrahydro-1H-indazol-1-yl]benzamide | Found 432 (ES+), retention time 2.67 mins. $C_{22}H_{24}F_3N_5O$ requires 431. |
| 37 | 2 | 2-thienyl | N-methyl-N-[2-(2-thienyl)ethyl]-4-[3-(trifluoromethyl)-4,5,6,7-tetrahydro-1H-indazol-1-yl]benzamide | Found 434 (ES+), retention time 3.60 mins. $C_{22}H_{22}F_3N_3OS$ requires 433. |
| 38 | 2 | 1-(1,2,4-triazole) | N-methyl-N-[2-(1H-1,2,4-triazol-1-yl)ethyl]-4-[3-(trifluoromethyl)-4,5,6,7-tetrahydro- | Found 419 (ES+), retention time 3.01 mins. $C_{20}H_{21}F_3N_6O$ requires 418. |

-continued

| Example | n | Ar | Name | LC/mass spec (ES) |
|---|---|---|---|---|
| 39 | 1 | 2-(1,3-thiazole) | N-methyl-N-(1,3-thiazol-2-ylmethyl)-4-[3-(trifluoromethyl)-4,5,6,7-tetrahydro-1H-indazol-1-yl]benzamide | Found 421 (ES+), retention time 3.44 mins. $C_{20}H_{19}F_3N_4OS$ requires 420. |
| 40 | 2 | 2-(1-methylpyrrole) | N-methyl-N-[2-(1-methyl-1H-pyrrol-2-yl)ethyl]-4-[3-(trifluoromethyl)-4,5,6,7-tetrahydro-1H-indazol-1-yl]benzamide | Found 431 (ES+), retention time 3.49 mins. $C_{23}H_{25}F_3N_4O$ requires 430. |
| 41 | 1 | 2-thienyl | N-methyl-N-(2-thienylmethyl)-4-[3-(trifluoromethyl)-4,5,6,7-tetrahydro-1H-indazol-1-yl]benzamide | Found 420 (ES+), retention time 3.68 mins. $C_{21}H_{20}F_3N_3OS$ requires 419. |
| 42 | 1 | 3-pyridyl | N-methyl-N-(3-pyridinylmethyl)-4-[3-(trifluoromethyl)-4,5,6,7-tetrahydro-1H-indazol-1-yl]benzamide | Found 415 (ES+), retention time 2.79 mins. $C_{22}H_{21}F_3N_4O$ requires 414. |
| 43 | 1 | 2-furanyl | N-(2-furanylmethyl)-N-methyl-4-[3-(trifluoromethyl)-4,5,6,7-tetrahydro-1H-indazol-1-yl]benzamide | Found 404 (ES+), retention time 3.50 mins. $C_{21}H_{20}F_3N_3O_2$ requires 403. |
| 44 | 1 | 1-(4-F)phenyl | N-[(4-fluorophenyl)methyl]-N-methyl-4-[3-(trifluoromethyl)4,5,6,7-tetrahydro-1H-indazol-1-yl]benzamide | Found 432 (ES+), retention time 3.63 mins. $C_{23}H_{21}F_4N_3O$ requires 431. |

EXAMPLE 45

1-[4-(4-morpholinylcarbonyl)phenyl]-3-(trifluoromethyl)-4,5,6,7-tetrahydro-1H-indazole

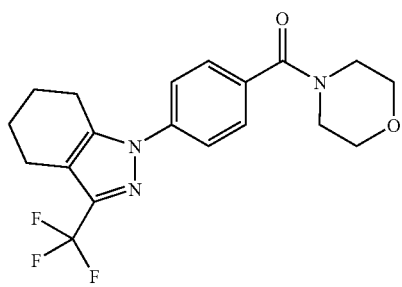

A mixture of 4-[(4-iodophenyl)carbonyl]morpholine (1.90 g, 6.0 mmol), 3-(trifluoromethyl)-4,5,6,7-tetrahydro-1H-indazole (1.14 g, 6.0 mmol), copper (I) oxide (10 mol %, 0.6 mmol, 86 mg), N,N-dimethylglycine (20 mol %, 1.2 mmol, 124 mg), and cesium carbonate (12.0 mmol, 3.91 g) in dimethylsulfoxide (16 ml) was stirred in an oilbath heated at 130° C. for 24 h under argon and then allowed to cool to room temperature. The reaction mixture was partitioned between dichloromethane (30 ml) and water (30 ml). The organic layer was separated and dried over sodium sulphate. The solvent was removed by rotary evaporation to give a dark brown residue that was added to a 20 g isolute pre-packed silica column and eluted from 0-50% ethyl acetate in petroleum ether to give the title compound as a brown gum (1.86 g, 82%).

LC/Mass Spec (ES): Found 380 (ES+), retention time 3.07 mins. $C_{19}H_{20}F_3N_3O_2$ requires 379.

$^1$H-NMR (400 MHz, CDCl3): 1.84 (4H, m), 2.71 (4H, m), 3.36-3.90 (8H, m), 7.53 (2H, m), 7.58 (2H, m).

EXAMPLE 46

N-({4-[3-(trifluoromethyl)-4,5,6,7-tetrahydro-1H-indazol-1-yl]phenyl}methyl)methanesulfonamide

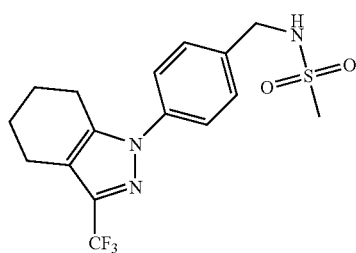

A mixture of ({4-[3-(trifluoromethyl)-4,5,6,7-tetrahydro-1H-indazol-1-yl]phenyl}methyl)amine (1.563 g, 5.29 mmol), triethylamine (1.48 ml, 10.58 mmol) in dichloromethane (40 ml) was stirred under argon in an ice bath. Methanesulfonyl chloride (1.213 g, 0.82 ml, 10.58 mmol) was added dropwise with stirring. The resulting mixture was allowed to stir at room temperature for 5 h. Then the reaction mixture was partitioned between dichloromethane and water. The organic layer was separated and dried over sodium sulphate. The desired product was isolated by column chromatography on silica using 10 to 70% ethyl acetate in n-pentane to give an oil which was then triturated with n-pentane to give the title compound as a white solid (1.602 g, 81%).

LC/Mass Spec (ES): Found 374 (ES+), retention time 3.12 mins. $C_{16}H_{18}F_3N_3O_2S$ requires 373.

1H-NMR (400 MHz, CDCl3): 1.82 (4H, m), 2.68 (4H, m), 2.92 (3H, s), 4.38 (2H, d, J=6 Hz), 4.70 (1H, m), 7.43-7.54 (4H, m).

EXAMPLES 47-48

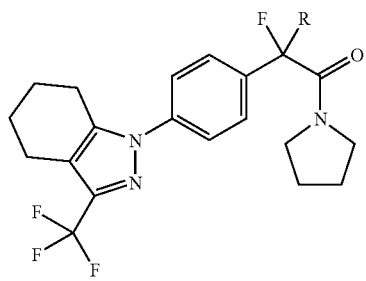

A solution of lithium diisopropylamide (2M in THF, 0.5 ml) in THF (5 ml) was cooled to −78° C. in a CO$_2$/methanol bath with stirring under argon. A solution of 1-{4-[2-oxo-2-(1-pyrrolidinyl)ethyl]phenyl}-3-(trifluoromethyl)-4,5,6,7-tetrahydro-1H-indazole (150 mg, 0.4 mmol) in THF (0.5 ml) was then added dropwise under argon. The resulting mix was stirred at −78° C. for 1 hour. Then a solution of 2-fluoro-3,3-dimethyl-2,3-dihydro-1,2-benzisothiazole 1,1-dioxide (189 mg, 0.88 mmol) in THF (5 ml) was added. The resulting mix was stirred at −78° C. for 1 hour and then allowed to warm up slowly to room temperature. The reaction mix was quenched with saturated aqueous ammonium chloride solution and partitioned between ethyl acetate and saturated aqueous ammonium chloride. The organic layer was dried over sodium sulphate and evaporated in vaccuo (i.e under reduced pressure) to give a brown oil (260 mg) which was purified by mass directed auto prep to separate the mono (example 47) and bis (example 48) fluorinated products.

EXAMPLE 49

N-methyl-N-({4-[3-(trifluoromethyl)-4,5,6,7-tetrahydro-1H-indazol-1-yl]phenyl}methyl)methanesulfonamide

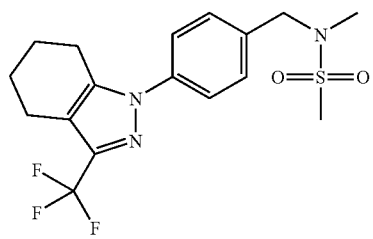

The title compound was prepared from 1-[4-(chloromethyl)phenyl]-3-(trifluoromethyl)-4,5,6,7-tetrahydro-1H-indazole and N-methyl methanesulfonamide using a similar procedure to that described for Description 15.

LC/Mass Spec (ES): Found 388 (ES+), retention time 3.35 mins. $C_{17}H_{20}F_3N_3O_2S$ requires 387.

$^1$H-NMR (400 MHz, CDCl$_3$): 1.83 (4H, m), 2.70 (4H, m), 2.79 (3H, s), 2.88 (3H, s), 4.36 (2H, s), 7.48 (4H, m).

EXAMPLE 50

1-(4-{[3-(trifluoromethyl)-4,5,6,7-tetrahydro-1H-indazol-1-yl]methyl}phenyl)-2-pyrrolidinone

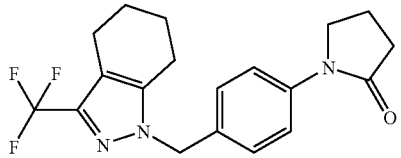

A solution of 4-{[3-(trifluoromethyl)-4,5,6,7-tetrahydro-1H-indazol-1-yl]methyl}aniline (166 mg, 0.56 mmol) in dichloromethane (4 ml) was treated with diisopropylethylamine (1.12 mmol, 146 mg) followed by 4-chlorobutyryl chloride (80 mg, 0.56 mmol). After stirring at room temperature for 15 minutes a solid suspension of sodium hydride (60% in mineral oil) (22 mg, 0.55 mmol) was added and stirring continued for 30 minutes. The dichloromethane was

| Ex | R | Name | LC/Mass Spec (ES) | 1H-NMR (400 MHz, CDCl$_3$) |
|---|---|---|---|---|
| 47 | H | 1-{4-[1-fluoro-2-oxo-2-(1-pyrrolidinyl)ethyl]phenyl}-3-(trifluoromethyl)-4,5,6,7-tetrahydro-1H-indazole | Found 396 (ES+), retention time 3.28 mins. $C_{20}H_{21}F_4N_3O$ requires 395. | 1.84 (8H, m), 2.70 (4H, m), 3.33 (1H, m), 3.45 (1H, m), 3.56 (2H, m), 5.92 & 6.04 (1H, m), 7.55 (2H, d, J = 8 Hz), 7.60 (2H, d, J = 8 Hz). |
| 48 | F | 1-{4-[1,1-difluoro-2-oxo-2-(1-pyrrolidinyl)ethyl]phenyl}-3-(trifluoromethyl)-4,5,6,7-tetrahydro-1H-indazole | Found 414 (ES+), retention time 3.61 mins. $C_{20}H_{20}F_5N_3O$ requires 413. | 1.87 (8H, m), 2.72 (4H, m), 3.50 (2H, m), 3.57 (2H, m), 7.61 (2H, d, J = 9 Hz), 7.71 (2H, d, J = 8 Hz). | removed by blowing with air and dimethylformamide added (3 ml) and stirring continued for 30 minutes. The reaction mix was partitioned between dichloromethane and water (2×5 ml). The organic layer was dried over sodium sulphate and evaporated under reduced pressure to give a yellow oil (190 mg) which was purified by mass directed auto prep to give the title compound as a yellow oil (39 mg, 19%).

LC/Mass Spec (ES): Found 364 (ES+), retention time 3.13 mins. $C_{19}H_{20}F_3N_3O$ requires 363.

$^1$H-NMR (400 MHz, CDCl$_3$): 1.65-1.81 (4H, m), 2.15 (2H, m), 2.43 (2H, m), 2.62 (4H, m), 3.84 (2H, m), 5.22 (2H, s), 7.15 (2H, d, J=9 Hz), 7.57 (2H, m).

EXAMPLE 51

N-methyl-N-({4-[3-(trifluoromethyl)-4,5,6,7-tetrahydro-1H-indazol-1-yl]phenyl}methyl)-1-pyrrolidinecarboxamide

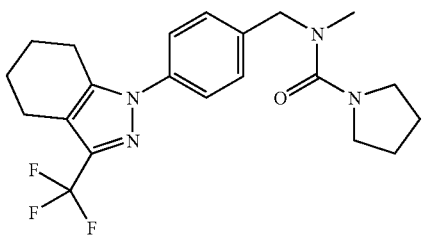

A mixture of N-[(4-bromophenyl)methyl]-N-methyl-1-pyrrolidinecarboxamide (250 mg, crude), 3-(trifluoromethyl)-4,5,6,7-tetrahydro-1H-indazole (152 mg, 0.8 mmol), N,N-dimethylglycine (20 mol %, 16.5 mg, 0.16 mmol), copper (I) iodide (10 mol %, 15 mg, 0.08 mmol) and potassium carbonate (1.6 mmol, 221 mg) in dimethylsulfoxide (4 ml) was stirred at 190° C. in a microwave reactor for 30 minutes. The reaction mix was treated with fresh N,N-dimethylglycine and copper (I) iodide and heated at 190° C. in a microwave reactor for a further 30 minutes. The reaction mix was partitioned between dichloromethane (5 ml) and water (5 ml). The organic layer was added to a 5 g isolute silica sep-pak column and eluted with ethyl acetate. The solvent was removed under reduced pressure and the residue purified by mass directed auto-prep (MDAP) to give the title compound as a brown oil (12 mg, 4%).

LC/Mass Spec (ES): Found 407 (ES+), retention time 3.50 mins. $C_{21}H_{25}F_3N_4O$ requires 406.

$^1$H-NMR (400 MHz, CDCl$_3$): 1.85 (8H, m), 2.69 (4H, m), 2.78 (3H, s), 3.39 (4H, m), 4.46 (2H, s), 7.39 (2H, d, J=9 Hz), 7.45 (2H, m).

EXAMPLE 52

5-{4-[3-(trifluoromethyl)-4,5,6,7-tetrahydro-1H-indazol-1-yl]phenyl}-2-pyrrolidinone

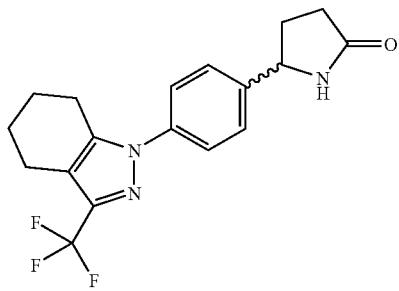

A mixture of 5-(4-bromophenyl)-2-pyrrolidinone (81 mg, 0.34 mmol; preparation described in WO00/21958), 3-(trifluoromethyl)-4,5,6,7-tetrahydro-1H-indazole (64 mg, 0.34 mmol) N,N-dimethylglycine (20 mol %, 7 mg, 0.07 mmol), copper (I) iodide (10 mol %, 6.5 mg, 0.034 mmol) and potassium carbonate (0.7 mmol, 97 mg) in dimethylsulfoxide (2 ml) was stirred at 190° C. in a microwave reactor for 30 minutes. The reaction mix was cooled and partitioned between dichloromethane (5 ml) and water (5 ml). The organic layer was added to a 5 g isolute silica sep-pak column and eluted with ethyl acetate. The solvent was removed under reduced pressure to give a dark oil (161 mg) which was further purified by mass directed auto-prep (MDAP) to give the title compound as a yellow oil (17 mg, 14%).

LC/Mass Spec (ES): Found 350 (ES+), retention time 2.99 mins. $C_{18}H_{18}F_3N_3O$ requires 349.

$^1$H-NMR (400 MHz, CDCl$_3$): 1.83 (4H, m), 1.97 (1H, m), 2.48 (2H, m), 2.52 (1H, m), 2.70 (4H, m), 4.83 (1H, t, J=7 Hz), 6.13 (1H, bs), 7.40 (2H, m), 7.51 (2H, m).

EXAMPLE 53-54

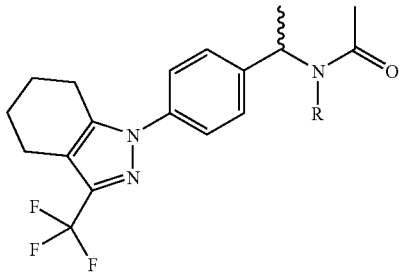

The title compounds were prepared from N-[1-(4-bromophenyl)ethyl]acetamide (Example 53) or N-[1-(4-bromophenyl)ethyl]-N-methylacetamide (Example 54) and 3-(trifluoromethyl)-4,5,6,7-tetrahydro-1H-indazole using a similar procedure to that used for example 51.

| Example | R | Name | LC/Mass Spec (ES) |
|---|---|---|---|
| 53 | H | N-(1-{4-[3-(trifluoromethyl)-4,5,6,7-tetrahydro-1H-indazol-1-yl]phenyl}ethyl)acetamide | Found 352 (ES+), retention time 3.08 mins. $C_{18}H_{20}F_3N_3O$ requires 351. |
| 54 | Me | N-methyl-N-(1-{4-[3-(trifluoromethyl)-4,5,6,7-tetrahydro-1H-indazol-1-yl]phenyl}ethyl)acetamide | Found 366 (ES+), retention time 3.31 mins. $C_{19}H_{22}F_3N_3O$ requires 365. |

EXAMPLE 55-56

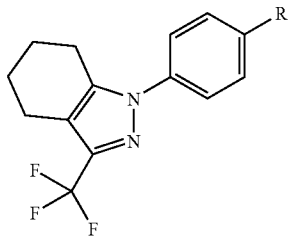

The title compounds was prepared from 1-acetyl-2-(4-bromophenyl)pyrrolidine (Example 55), 1-[2-(4-bromophenyl)ethyl]-2-pyrrolidinone (Example 56) and 3-(trifluoromethyl)-4,5,6,7-tetrahydro-1H-indazole using a similar procedure to that described for Example 52.

| Example | R | Name | LC/Mass Spec (ES) |
|---|---|---|---|
| 55 | | 1-[4-(1-acetyl-2-pyrrolidinyl)phenyl]-3-(trifluoromethyl)-4,5,6,7-tetrahydro-1H-indazole | Found 378 (ES+), retention time 3.23 mins. $C_{20}H_{22}F_3N_3O$ requires 377. |
| 56 | | 1-(2-{4-[3-(trifluoromethyl)-4,5,6,7-tetrahydro-1H-indazol-1-yl]phenyl}ethyl)-2-pyrrolidinone | Found 378 (ES+), retention time 3.30 mins. $C_{20}H_{22}F_3N_3O$ requires 377. |

EXAMPLE 57

1-{4-[(1,1-dioxido-2-isothiazolidinyl)methyl]phenyl}-3-(trifluoromethyl)-4,5,6,7-tetrahydro-1H-indazole

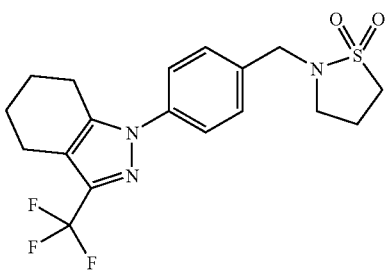

A mixture of 2-[(4-bromophenyl)methyl]isothiazolidine 1,1-dioxide (290 mg, 1.0 mmol), 3-(trifluoromethyl)-4,5,6,7-tetrahydro-1H-indazole (190 mg, 1.0 mmol), N,N-dimethylglycine (20 mol %, 21 mg, 0.2 mmol), copper (I) iodide (10 mol %, 19 mg, 0.1 mmol) and potassium carbonate (2 mmol, 276 mg) in dimethylsulfoxide (4 ml) was stirred at 190° C. in a microwave reactor for 30 minutes. The reaction mix was partitioned between dichloromethane (5 ml) and water (5 ml). The organic layer was added to a 5 g isolute silica sep-pak column and eluted with ethyl acetate. The solvent was removed under reduced pressure and the residue purified by mass directed auto-prep (MDAP) to give a greasy product which was partitioned between water and dichloromethane. The organic layer was dried over sodium sulphate and evaporated in air to give the title compound as a yellow oil (103 mg, 26%).

LC/Mass Spec (ES): Found 400 (ES+), retention time 3.31 mins. $C_{18}H_{20}F_3N_3O_2S$ requires 399.

$^1$H-NMR (400 MHz, CDCl$_3$): 1.83 (4H, m), 2.34 (2H, m), 2.69 (4H, m), 3.12 (2H, t, J=6 Hz), 3.23 (2H, t, J=8 Hz), 4.23 (2H, s), 7.47 (4H, m).

EXAMPLES 58-60

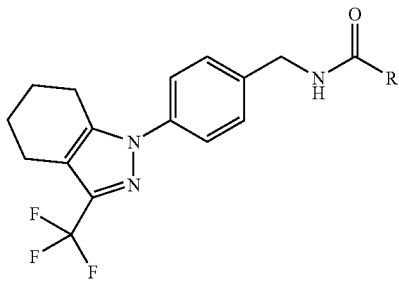

Typical procedure: A solution of ({4-[3-(trifluoromethyl)-4,5,6,7-tetrahydro-1H-indazol-1-yl]phenyl}methyl)amine (description 20, 0.2 mmol) in 5% dimethylformamide in dichloromethane (2 ml) was treated with triethylamine (2 equivalents, 0.05 ml) in a 15 ml sarstedt tube. The reaction mix was shaken for 20 minutes and then the appropriate acid chloride (0.05 ml) was added and the reaction mixtures shaken overnight. The reaction mixture was then quenched with water and separated between dichloromethane and brine. The organic layer was retained and the samples purified either on a 5 g pre-packed silica column eluting from 50% ethyl acetate in petroleum ether (examples 58 and 59) or by mass directed auto prep (MDAP, example 60). Relevant fractions were combined and the solvent removed by rotary evaporation to give the named products.

| Example | R | Name | LC/Mass Spec (ES) |
|---|---|---|---|
| 58 | iPr | 2-methyl-N-({4-[3-(trifluoromethyl)-4,5,6,7-tetrahydro-1H-indazol-1-yl]phenyl}methyl)propanamide | Found 366 (ES+), retention time 3.26 mins. $C_{19}H_{22}F_3N_3O$ requires 365. |
| 59 | nPr | N-({4-[3-(trifluoromethyl)-4,5,6,7-tetrahydro-1H-indazol-1-yl]phenyl}methyl)butanamide | Found 366 (ES+), retention time 3.17 mins. $C_{19}H_{22}F_3N_3O$ requires 365. |
| 60 | 2-thienyl | N-({4-[3-(trifluoromethyl)-4,5,6,7-tetrahydro-1H-indazol-1-yl]phenyl}methyl)-2-thiophenecarboxamide | Found 406 (ES+), retention time 3.43 mins. $C_{20}H_{18}F_3N_3OS$ requires 405. |

EXAMPLES 61-63

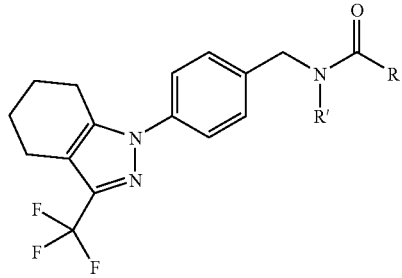

Typical procedure: The title compounds were prepared from 1-[4-(chloromethyl)phenyl]-3-(trifluoromethyl)-4,5,6,7-tetrahydro-1H-indazole (Description 17) and propanamide (example 61), acetamide (example 62) and 2-phenylacetamide (example 63) using a similar procedure to that described for description 15.

EXAMPLES 64-71

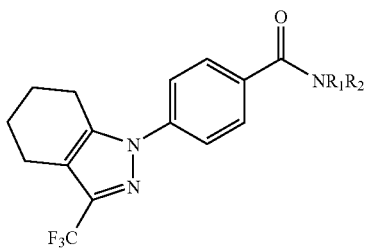

Typical Procedure: A mixture of 4-[3-(trifluoromethyl)-4,5,6,7-tetrahydro-1H-indazol-1-yl]benzoic acid (155 mg, 0.5 mmol), and 1,1'-carbonyldiimidazole (122 mg, 0.75 mmol) was dissolved in dichloromethane (2 ml) in a 15 ml plastic tube and shaken for 20 minutes. Then a solution of the secondary amine in dichloromethane (1 ml) was added in one portion (if the amine available as a HCl salt then triethylamine (51 mg, 0.5 mmol) was added). The reaction mixtures were

| Example | R | R' | Name | LC/Mass Spec (ES) |
|---|---|---|---|---|
| 61 | Et | H | N-({4-[3-(trifluoromethyl)-4,5,6,7-tetrahydro-1H-indazol-1-yl]phenyl}methyl)propanamide | Found 352 (ES+), retention time 3.06 mins. $C_{18}H_{20}F_3N_3O$ requires 351. |
| 62 | Me | H | N-({4-[3-(trifluoromethyl)-4,5,6,7-tetrahydro-1H-indazol-1-yl]phenyl}methyl)acetamide | Found 338 (ES+), retention time 2.90 mins. $C_{17}H_{18}F_3N_3O$ requires 337. |
| 63 | CH$_2$Ph | Me | N-methyl-2-phenyl-N-({4-[3-(trifluoromethyl)-4,5,6,7-tetrahydro-1H-indazol-1-yl]phenyl}methyl)acetamide | Found 428 (ES+), retention time 3.60 mins. $C_{24}H_{24}F_3N_3O$ requires 427. | shaken for 3 hours. Reaction mixture was washed with brine, the organic layer was retained and dried with sodium sulphate. All samples were purified by MDAP to give the named products.

| Example | NR1R2 | Name | LC/Mass Spec (ES) |
|---|---|---|---|
| 64 | N(Me)CH$_2$CH$_2$OH | N-(2-hydroxyethyl)-N-methyl-4-[3-(trifluoromethyl)-4,5,6,7-tetrahydro-1H-indazol-1-yl]benzamide | Found 368 (ES+), retention time 2.74 mins. C$_{18}$H$_{20}$F$_3$N$_3$O$_2$ requires 367. |
| 65 | N(Me)CH$_2$CH$_2$OMe | N-methyl-N-[2-(methyloxy)ethyl]-4-[3-(trifluoromethyl)-4,5,6,7-tetrahydro-1H-indazol-1-yl]benzamide | Found 382 (ES+), retention time 3.14 mins. C$_{19}$H$_{22}$F$_3$N$_3$O$_2$ requires 381. |
| 66 | N(Me)CH$_2$CH$_2$NHMe | N-methyl-N-[2-(methylamino)ethyl]-4-[3-(trifluoromethyl)-4,5,6,7-tetrahydro-1H-indazol-1-yl]benzamide formic acid salt | Found 381 (ES+), retention time 2.13 mins. C$_{19}$H$_{23}$F$_3$N$_4$O requires 380. |
| 67 | 1-(3-OH)pyrrolidinyl | 1-({4-[3-(trifluoromethyl)-4,5,6,7-tetrahydro-1H-indazol-1-yl]phenyl}carbonyl)-3-pyrrolidinol | Found 380 (ES+), retention time 2.78 mins. C$_{19}$H$_{20}$F$_3$N$_3$O$_2$ requires 379. |
| 68 | 1-(3-NHMe)pyrrolidinyl | N-methyl-1-({4-[3-(trifluoromethyl)-4,5,6,7-tetrahydro-1H-indazol-1-yl]phenyl}carbonyl)-3-pyrrolidinamine formic acid salt | Found 393 (ES+), retention time 1.92 mins. C$_{20}$H$_{23}$F$_3$N$_4$O requires 392. |
| 69 | 1-azetidinyl | 1-[4-(1-azetidinylcarbonyl)phenyl]-3-(trifluoromethyl)-4,5,6,7-tetrahydro-1H-indazole | Found 350 (ES+), retention time 3.08 mins. C$_{18}$H$_{18}$F$_3$N$_3$O requires 349. |
| 70 | 1-(3-OH)azetidinyl | 1-({4-[3-(trifluoromethyl)-4,5,6,7-tetrahydro-1H-indazol-1-yl]phenyl}carbonyl)-3-azetidinol | Found 366 (ES+), retention time 2.70 mins. C$_{18}$H$_{18}$F$_3$N$_3$O$_2$ requires 365. |
| 71 | 1-(3,3-difluoro)azetidinyl | (3,3-difluorocyclobutyl){4-[3-(trifluoromethyl)-4,5,6,7-tetrahydro-1H-indazol-1-yl]phenyl}methanone | Found 386 (ES+), retention time 3.39 mins. C$_{18}$H$_{16}$F$_5$N$_3$O requires 385. |

EXAMPLE 72

1-[4-(1H-imidazol-1-yl)phenyl]-3-(trifluoromethyl)-4,5,6,7-tetrahydro-1H-indazole

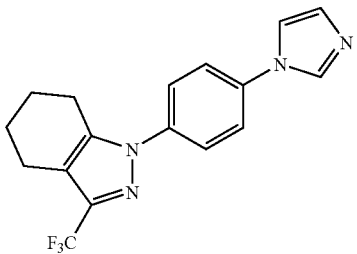

A mixture of 3-(trifluoromethyl)-4,5,6,7-tetrahydro-1H-indazole (152 mg, 0.8 mmol), potassium carbonate (232 mg, 1.68 mmol) and copper (I) iodide (1 mg, 0.005 mmol) was treated with a solution of trans-1,2-diaminocyclohexane (9 mg, 0.08 mmol) in dioxane followed by a solution of 1-(4-bromophenyl)imidazole (161 mg, 0.72 mmol) in dioxane (4 ml total volume). This mixture was heated at 180° C. in a microwave reactor for 1 hour. Further copper (I) iodide (1 mg) and trans-1,2-diaminocyclohexane (9 mg) was added and the reaction heated at 180° C. in a microwave reactor for a further hour. Again further copper (I) iodide (1 mg) and trans-1,2-diaminocyclohexane (9 mg) was added and the reaction heated at 180° C. in a microwave reactor for a further hour. The reaction mixture was added to a 5 g sep-pack column and eluted with ethyl acetate. The solvent was removed by rotary evaporation and the crude product further purified by MDAP. Further purified using a 5 g SCX column, eluting from 1M ammonia in methanol which was then evaporated off using rotary evaporation to give the title compound (42 mg, 18%).

LC/Mass Spec (ES): Found 333 (ES+), retention time 2.21 mins. $C_{17}H_{15}F_3N_4$ requires 332.

$^1$H-NMR (400 MHz, CDCl$_3$): 1.85 (4H, m), 2.73 (4H, m), 7.25 (1H, m), 7.32 (1H, m), 7.51 (2H, m), 7.63 (2H, m), 7.89 (1H, s).

EXAMPLES 73-74

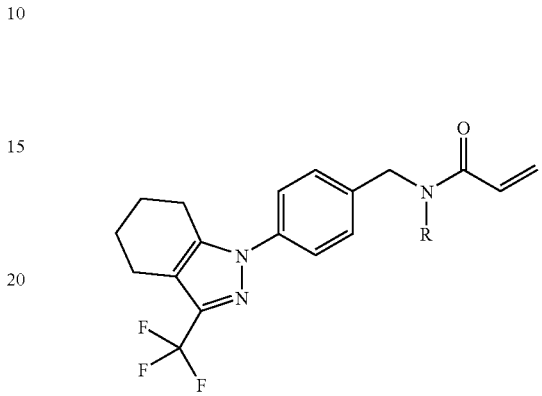

A solution of ({4-[3-(trifluoromethyl)-4,5,6,7-tetrahydro-1H-indazol-1-yl]phenyl}methyl)amine (436 mg, 1.48 mmol) in 10% dimethylformamide in dichloromethane (5 ml) was treated with triethylamine (2.96 mmol, 0.41 ml). The reaction mix was stirred for 5 minutes and then 2-propenoyl chloride (0.13 ml) was added dropwise and the reaction mixture stirred for a further 1.5 hours. The reaction mixture was then quenched with water and separated between dichloromethane and brine. The organic layer was retained and dried over sodium sulphate. The solvent was removed by rotary evaporation and the sample purified on a biotage 25+M column with 0-100% ethyl acetate/n-pentane solvent gradient. Combining relevant fractions and removing solvent by rotary evaporation gave the named products.

| Ex | R | Name | LC/Mass Spec (ES) | 1H-NMR (250 MHz, CDCl$_3$) |
|---|---|---|---|---|
| 73 | H | N-({4-[3-(trifluoromethyl)-4,5,6,7-tetrahydro-1H-indazol-1-yl]phenyl}methyl)-2-propenamide | Found 350 (ES+), retention time 3.06 mins. $C_{18}H_{18}F_3N_3O$ requires 349. | 1.81 (4 H, m), 2.665 (4 H, m), 4.52 (2 H, d, J = 6 Hz), 5.67 (1 H,dd, J = 10 Hz & 2 Hz), 6.07-6.20 (1 H, m), 6.33 (1 H, m), 6.46 (1 H, m), 7.37 (4 H, m). |
| 74 |  | N-(1-methylethenyl)-N-({4-[3-(trifluoromethyl)-4,5,6,7-tetrahydro-1H-indazol-1-yl]phenyl}methyl)-2-propenamide | Found 390 (ES+), retention time 3.61 mins. $C_{21}H_{22}F_3N_3O$ requires 389. | 1.81 (4 H, m), 1.89 (3 H, s), 2.68 (4 H, m),4.69 (1 H, s), 4.77 (2 H, s), 5.05 (1 H, d, J = 2 Hz), 5.68 (1 H, dd, J = 10 Hz & 2 Hz), 6.44 (1 H, m), 6.55-6.66 (1 H, m), 7.41 (4 H, s). |

EXAMPLE 75

N-methyl-N-({4-[3-(trifluoromethyl)-4,5,6,7-tetrahydro-1H-indazol-1-yl]phenyl}methyl)-2-propenamide

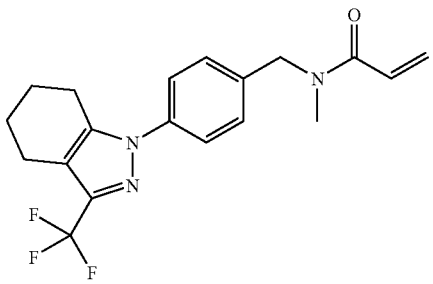

A stirred solution of N-({4-[3-(trifluoromethyl)-4,5,6,7-tetrahydro-1H-indazol-1-yl]phenyl}methyl)-2-propenamide (241 mg, 0.69 mmol) in dimethylformamide (5 ml) under argon was treated with sodium hydride (60% suspension in mineral oil, 28 mg, 0.7 mmol). The reaction mixture was stirred for 5 minutes then methyl iodide (0.05 ml) was added and the reaction mixture stirred for a further 1 hour. Reaction mixture was then quenched with 3 drops of water and 5 ml of 1M ammonia in methanol. Excess ammonia and methanol were removed by rotary evaporation. Reaction mixture was separated between ethyl acetate and brine. Organic layer was retained, dried over sodium sulphate and the solvent removed by rotary evaporation. Sample was purified by 5 g pre-pack silica column eluted with 50% ethyl acetate/petroleum ether. Relevant fractions were combined and the solvent removed by rotary evaporation to give the title compound as a yellow oil (66 mg, 26%).

LC/Mass Spec (ES): Found 364 (ES+), retention time 3.26 mins. $C_{19}H_{20}F_3N_3O$ requires 363.

$^1$H-NMR (250 MHz, CDCl$_3$): 1.82 (4H, bs), 2.68 (4H, bs), 3.02 (3H, m), 4.68 (2H, m), 5.68-5.80 (1H, m), 6.36-4.46 (1H, m), 6.52-6.71 (1H, m), 7.27-7.51 (4H, m).

EXAMPLES 76-77

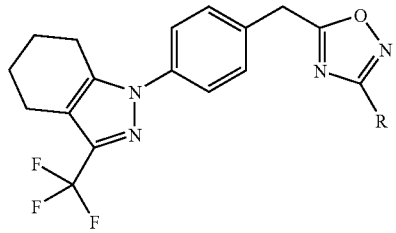

Typical procedure: A mixture of {4-[3-(trifluoromethyl)-4,5,6,7-tetrahydro-1H-indazol-1-yl]phenyl}acetic acid (90 mg, 0.28 mmol), and 1-hydroxybenzotriazole (45 mg, 0.33 mmol) were slurried in dry acetonitrile. 1-(3-dimethylaminopropyl)-3-ethylcarbodiimide hydrochloride (EDC) (61 mg, 0.32 mmol) was added in one portion and the reaction mixture stirred for 30 minutes at room temperature. The appropriate amidoxime was added in one portion and the reaction heated under reflux for 4 hours in the presence of 4 A molecular sieves. A further 0.5 equivalents of 1-(3-dimethylaminopropyl)-3-ethylcarbodiimide hydrochloride was added and the reflux continued for 4-6 hours. Reaction mixtures were evaporated to dry residue and separated between ethyl acetate and saturated aqueous sodium bicarbonate solution. The organic layer was retained and the solvent removed by rotary evaporation and the sample purified by MDAP. Relevant fractions were combined and the solvent removed by rotary evaporation to give the named products.

| Example | R | Name | LC/Mass Spec (ES) | 1H-NMR (250 MHz, CDCl$_3$) |
|---|---|---|---|---|
| 76 | Me | 1-{4-[(3-methyl-1,2,4-oxadiazol-5-yl)methyl]phenyl}-3-(trifluoromethyl)-4,5,6,7-tetrahydro-1H-indazole | Found 363 (ES+), retention time 3.45 mins. $C_{18}H_{17}F_3N_4O$ requires 362. | 1.83 (4H, m), 2.39 (3H, s), 2.69 (4H, m), 4.24 (2H, s), 7.43 (2H, m), 7.48 (2H, m). |
| 77 | cPr | 1-{4-[(3-cyclopropyl-1,2,4-oxadiazol-5-yl)methyl]phenyl}-3-(trifluoromethyl)-4,5,6,7-tetrahydro-1H-indazole | Found 389 (ES+), retention time 3.69 mins. $C_{20}H_{19}F_3N_3O$ requires 388. | 1.04 (4H, m), 1.82 (4H, m), 2.07 (1H, m), 2.69 (4H, m), 4.20 (2H, s), 7.41 (2H, m), 7.47 (2H, m). |

EXAMPLE 78

N-ethyl-4-[3-(trifluoromethyl)-4,5,6,7-tetrahydro-1H-indazol-1-yl]benzamide

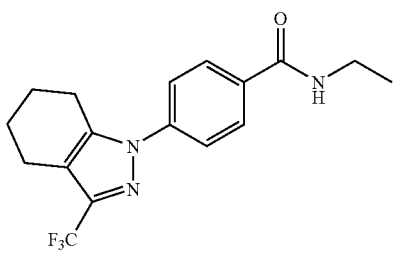

A suspension of 4-[3-(trifluoromethyl)-4,5,6,7-tetrahydro-1H-indazol-1-yl]benzoic acid (310 mg, 1.0 mmol) in dichloromethane (5 ml) was treated with 1,1'-carbonyldiimidazole (162 mg, 1.0 mmol) at room temperature under argon. This mix was stirred for 30 minutes and then treated with a 2M solution of ethylamine in tetrahydrofuran (0.5 ml). The whole mix was stirred at room temperature for 2 hours. The reaction mixture was washed with saturated aqueous sodium bicarbonate. The organic layer was separated, dried over sodium sulphate and reduced to minimum volume by rotary evaporation to give a beige solid (250 mg) which was purified by column chromatography on a 5 g pre-packed silica column, eluting from 0-50% ethyl acetate in petroleum ether to give the title compound as a colourless solid (128 mg, 38%).

LC/Mass Spec (ES): Found 338 (ES+), retention time 3.13 mins. $C_{17}H_{18}F_3N_3O$ requires 337.

$^1$H-NMR (400 MHz, CDCl$_3$): 1.28 (3H, t, J=7 Hz), 1.83 (4H, m), 2.68 (2H, bs), 2.74 (2H, bs), 3.53 (2H, m), 6.15 (1H, bs), 7.59 (2H, m), 7.89 (2H, m).

EXAMPLE 79-81

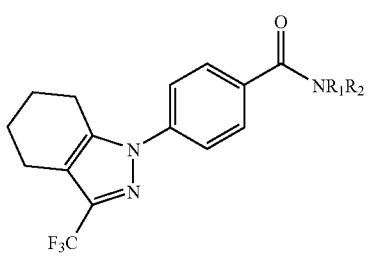

A solution of 4-[3-(trifluoromethyl)-4,5,6,7-tetrahydro-1H-indazol-1-yl]benzoic acid (MWt=310) in dichloromethane (2 ml) was treated with 1,1'-carbonyldiimidazole (1 equivalent, MWt=162) in one portion and stirred at room temperature for 15 minutes. Then the secondary amine (1.15 equivalents) was added and stirring continued for 1 hour. The reaction mix was added to a 5 g pre-packed silica column and eluted with 0-50% ethyl acetate in 40-60° C. petroleum ether. The product was optionally purified further by MDAP to give the named compounds.

| Example | NR1R2 | Name | LC/Mass Spec (ES) |
|---|---|---|---|
| 79 | N(Me)iPr | N-methyl-N-(1-methylethyl)-4-[3-(trifluoromethyl)-4,5,6,7-tetrahydro-1H-indazol-1-yl]benzamide | Found 366 (ES+), retention time 3.47 mins. $C_{19}H_{22}F_3N_3O$ requires 365. |
| 80 | 1-piperidinyl | 1-[4-(1-piperidinylcarbonyl)phenyl]-3-(trifluoromethyl)-4,5,6,7-tetrahydro-1H-indazole | Found 378 (ES+), retention time 3.54 mins. $C_{20}H_{22}F_3N_3O$ requires 377. |
| 81 | NEt$_2$ | N,N-diethyl-4-[3-(trifluoromethyl)-4,5,6,7-tetrahydro-1H-indazol-1-yl]benzamide | Found 366 (ES+), retention time 3.48 mins. $C_{19}H_{22}F_3N_3O$ requires 365. |

EXAMPLE 82

N-methyl-4-[3-(trifluoromethyl)-4,5,6,7-tetrahydro-1H-indazol-1-yl]benzamide

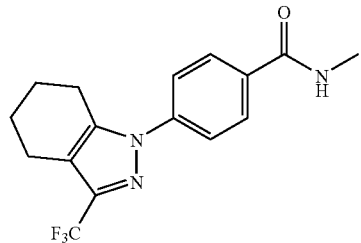

A solution of 4-[3-(trifluoromethyl)-4,5,6,7-tetrahydro-1H-indazol-1-yl]benzoic acid (87 mg, 0.28 mmol) and diisopropylethylamine (0.1 ml) in dichloromethane (3 ml) was treated with 1,1'-carbonyldiimidazole (46 mg, 0.28 mmol) in one portion and stirred at room temperature for 15 minutes. Then methylamine hydrochloride (22 mg, 0.33 mmol) was added and stirring continued for 1 hour. The reaction mix was added to a 5 g pre-packed silica column and eluted with 0-50% ethyl acetate in petroleum ether to give the title compound (28 mg, 31%).

LC/Mass Spec (ES): Found 324 (ES+), retention time 3.04 mins. $C_{16}H_{16}F_3N_3O$ requires 323.

$^1$H-NMR (400 MHz, CDCl$_3$): 1.83 (4H, m), 2.68 (2H, bs), 2.75 (2H, bs), 3.05 (3H, d, J=5 Hz), 6.17 (1H, m), 7.59 (2H, m), 7.87 (2H, m).

EXAMPLE 83

1-{4-[2-oxo-2-(2-phenyl-1-pyrrolidinyl)ethyl]phenyl}-3-(trifluoromethyl)-4,5,6,7-tetrahydro-1H-indazole

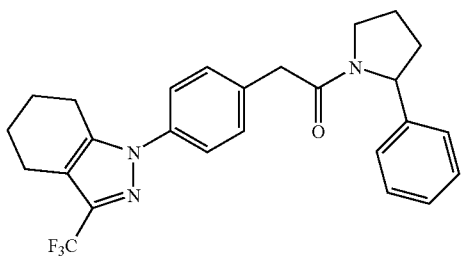

A solution of {4-[3-(trifluoromethyl)-4,5,6,7-tetrahydro-1H-indazol-1-yl]phenyl}acetic acid (65 mg, 0.2 mmol) in dichloromethane (2 ml) was treated with 1,1'-carbonyldiimidazole (32.5 mg, 0.2 mmol) in one portion at room temperature. Stirring was continued at room temperature for 15 minutes. Then 2-phenylpyrrolidine (29 mg, 0.2 mmol) was added and stirring continued for 1 hour. Most of the solvent was removed under reduced pressure and the crude product was further purified by MDAP to give the title compound (55 mg, 61%).

LC/Mass Spec (ES): Found 454 (ES+), retention time 3.61 mins. $C_{26}H_{26}F_3N_3O$ requires 453.

EXAMPLE 84

N-methyl-N-({4-[3-(trifluoromethyl)-4,5,6,7-tetrahydro-1H-indazol-1-yl]phenyl}methyl)benzamide

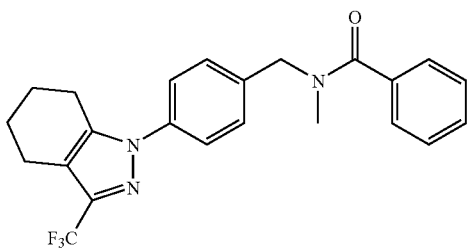

A solution of {4-[3-(trifluoromethyl)-4,5,6,7-tetrahydro-1H-indazol-1-yl]phenyl}methanol (286 mg, 0.97 mmol) was dissolved in dichloromethane (5 ml) and stirred under an atmosphere of argon in a methanol/ice bath. Triethylamine (106 mg, 1.05 mmol, 0.15 ml) was added in one portion and the reaction mixture stirred for a further 15 minutes. Methanesulfonyl chloride (115 mg, 1 mmol, 0.08 ml) was added dropwise over 10 minutes. The reaction mixture was stirred for a further 10 minutes at below 0° C., then allowed to return to room temperature. The reaction mixture was then separated between dichloromethane (5 ml) and water (30 ml). the organic layer was retained, dried using sodium sulphate and the solvent removed by rotary evaporation to give the crude mesylate (A) (299 mg).

N-methylbenzamide (20 mg, 0.14 mmol) was dissolved in dimethylformamide (1 ml) and shaken in a 15 ml plastic sarstedt tube. Sodium hydride (60% suspension in mineral oil, 6 mg, 0.15 mmol) was added in one portion and the reaction was shaken for 15 minutes. A solution of the mesylate (A) (50 mg, 0.13 mmol) in dimethylformamide (1 ml) was added dropwise over 10 minutes. The reaction mixture was shaken for a further 30 minutes. The reaction vessel was then flushed with argon and shaken for 3 days. The reaction mixture was separated between dichloromethane (30 ml) and water (20 ml) with brine (10 ml). The dichloromethane layer was washed with water (2×20 ml) and dried with sodium sulphate. Solvent was removed by rotary evaporation and the sample purified by MDAP. Relevany fraction were combined and the solvent removed by rotary evaporation to give the title compound (4 mg, 7%).

LC/Mass Spec (ES): Found 414 (ES+), retention time 3.57 mins. $C_{23}H_{22}F_3N_3O$ requires 413.

$^1$H-NMR (400 MHz, CDCl$_3$): 1.83 (4H, m), 2.70 (4H, m), 2.89 & 3.06 (3H, m, rotomers), 4.57 & 4.81 (2H, m, rotomers), 7.35-7.52 (9H, m).

EXAMPLE 85

1-[4-(1,3-oxazol-5-yl)phenyl]-3-(trifluoromethyl)-4,5,6,7-tetrahydro-1H-indazole

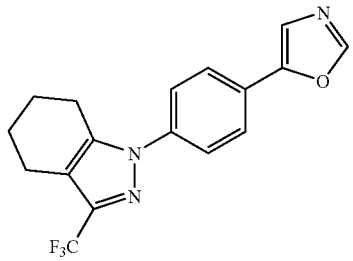

A mixture of 3-(trifluoromethyl)-4,5,6,7-tetrahydro-1H-indazole (152 mg, 0.8 mmol), 5-(4-bromophenyl)-1,3-oxazole (179 mg, 0.8 mmol), N,N-dimethylglycine (16 mg, 0.16 mmol), copper (I) iodide (16 mg, 0.08 mmol), potassium carbonate (235 mg, 1.7 mmol) in dimethylsulfoxide (3 ml) was heated in a microwave reactor at 180° C. for a total of 60 minutes. The reaction mixture was then filtered through a 5 g sep-pack column with 40 ml 1:1 ethyl acetate in petroleum ether. The solvent was removed by rotary evaporation and the residue partitioned between ethyl acetate (20 ml) and water (20 ml). The organic layer was retained and washed with brine (2×10 ml). The organic material was then purified by MDAP. The relevant fractions were combined and the solvent removed by rotary evaporation to give the named products. Product was then partitioned between dichloromethane (40 ml) and water (40 ml). The organic layer was retained and the solvent removed by rotary evaporation to give the title compound (80 mg, 30%).

LC/Mass Spec (ES): Found 334 (ES+), retention time 3.57 mins. $C_{17}H_{14}F_3N_3O$ requires 333.

$^1$H-NMR (400 MHz, CDCl$_3$): 1.83 (4H, m), 2.69 (2H, bs), 2.74 (2H, bs), 7.42 (1H, s), 7.58 (2H, m), 7.76 (2H, m), 7.96 (1H, m).

EXAMPLE 86

1-[4-(propyloxy)phenyl]-3-(trifluoromethyl)-4,5,6,7-tetrahydro-1H-indazole

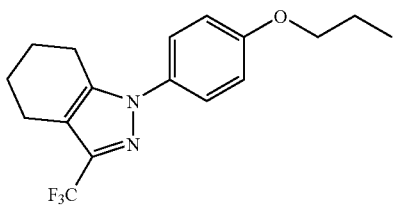

A mixture of 3-(trifluoromethyl)-4,5,6,7-tetrahydro-1H-indazole (152 mg, 0.8 mmol), 1-bromo-4-(propyloxy)benzene (177 mg, 0.8 mmol), N,N-dimethylglycine (16 mg, 0.16 mmol), copper (I) iodide (16 mg, 0.08 mmol), potassium carbonate (235 mg, 1.7 mmol) in dimethylsulfoxide (3 ml) was heated in a microwave reactor at 180° C. for a total of 50 minutes. Fresh N,N-dimethylglycine (16 mg, 0.16 mmol) and copper (I) iodide (16 mg, 0.08 mmol) was added and heating continued at 180° C. for a further 30 minutes. The reaction mixture was then filtered through a 5 g sep-pack column with 40 ml 1:1 ethyl acetate in petroleum ether. The solvent was removed by rotary evaporation and the residue partitioned between ethyl acetate (20 ml) and water (20 ml). The organic layer was retained and washed with brine (2×10 ml), then dried over sodium sulphate. The solvent was removed by rotary evaporation and the sample purified by MDAP. The relevant fractions were combined and the solvent removed by rotary evaporation to give the title compound (23 mg, 9%).

LC/Mass Spec (ES): Found 325 (ES+), retention time 4.01 mins. $C_{17}H_{19}F_3N_2O$ requires 324.

$^1$H-NMR (400 MHz, CDCl$_3$): 1.05 (3H, t, J=8 Hz), 1.83 (6H, m), 2.65 (4H, m), 3.95 (2H, t, J=7 Hz), 6.96 (2H, m), 7.36 (2H, m).

EXAMPLE 87

1-[4-(1-methyl-1H-imidazol-4-yl)phenyl]-3-(trifluoromethyl)-4,5,6,7-tetrahydro-1H-indazole

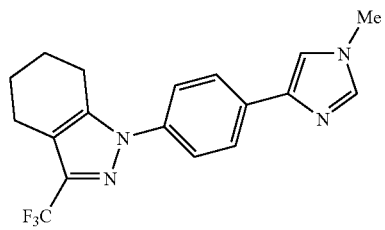

A mixture of copper (I) iodide (10 mol %, 5 mg, 0.02 mmol), 3-(trifluoromethyl)-4,5,6,7-tetrahydro-1H-indazole (50 mg, 0.26 mmol), potassium carbonate (73 mg, 0.52 mmol) in DMSO (2 ml) was stirred for 1 min, then 4-(4-bromophenyl)-1-methyl-1H-imidazole (62 mg, 0.26 mmol) (WO91/09855) and N,N-dimethylglycine (20 mol %, 5.4 mg) were then successively added. The reaction tube was quickly sealed and the contents were heated in a microwave reactor at 180° C. for 40 mins. The reaction mixture was partitioned between ethyl acetate and water, dried with sodium sulphate and solvent was removed by rotary evaporation and the sample purified by MDAP. The solvent was removed by rotary evaporation to give the title compound as a solid (15 mg, 16%).

LC/Mass Spec (ES): Found 347 (ES+), retention time 2.23 mins. C18H17F3N4 requires 346.

$^1$H-NMR (400 MHz, CDCl3): 1.82 (4H, m), 2.70 (4H, m), 3.75 (3H, s), 7.23 (1H, m), 7.48 (3H, d, J=8.8 Hz), 7.83 (2H, d, J=8.4 Hz).

EXAMPLE 88

N-({4-[3-(trifluoromethyl)-4,5,6,7-tetrahydro-1H-indazol-1-yl]phenyl}methyl)-2-propanesulfonamide

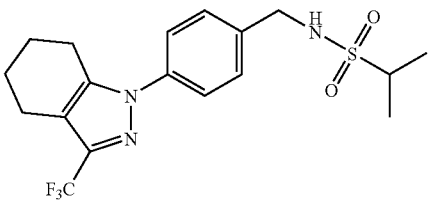

A mixture of ({4-[3-(trifluoromethyl)-4,5,6,7-tetrahydro-1H-indazol-1-yl]phenyl}methyl)amine (100 mg, 0.339 mmol), triethylamine (0.07 ml, 0.51 mmol) in DCM (10 ml) was stirred in an ice bath under argon. Then isopropylsulfonyl chloride was added (148 mg in total, 1 mmol) in DCM (1 ml) dropwise with stirring. The reaction mixture was allowed to stir at room temperature for 16 hr. Then the reaction mixture was washed with water (20 ml), separated the organic layer and dried with sodium sulphate. Solvent was removed by rotary evaporation and the sample purified by MDAP to give the title compound as an off white solid (51 mg, 37%).

LC/Mass Spec (ES): Found 402 (ES+), retention time 3.40 mins. C18H22F3N3O2S requires 401.

$^1$H-NMR (400 MHz, CDCl3): 1.4 (6H, d, J=6.8 Hz), 1.8 (4H, m), 2.68 (4H, m), 3.12 (1H, m), 4.36 (3H, m), 7.47 (4H, m).

EXAMPLE 89

N-({4-[3-(trifluoromethyl)-4,5,6,7-tetrahydro-1H-indazol-1-yl]phenyl}methyl)cyclopropanesulfonamide

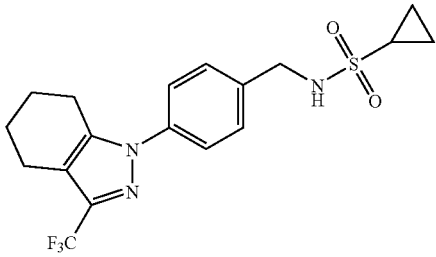

The title compound was prepared from ({4-[3-(trifluoromethyl)-4,5,6,7-tetrahydro-1H-indazol-1-yl]phenyl}methyl) amine and cyclopropanesulphonyl chloride using a similar procedure to that described for Example 88.

LC/Mass Spec (ES): Found 400 (ES+), retention time 3.35 mins. $C_{18}H_{20}F3N3O2S$ requires 399.

$^1$H-NMR (400 MHz, CDCl3): 0.9 (2H, m), 1.17 (2H, m), 1.80 (4H, m), 2.37 (1H, m), 2.70 (4H, m), 4.40 (2H, d, J=6 Hz), 4.62 (1H, m), 7.43-7.54 (4H, m).

EXAMPLE 90

N-({4-[3-(trifluoromethyl)-4,5,6,7-tetrahydro-1H-indazol-1-yl]phenyl}methyl)cyclopentanesulfonamide

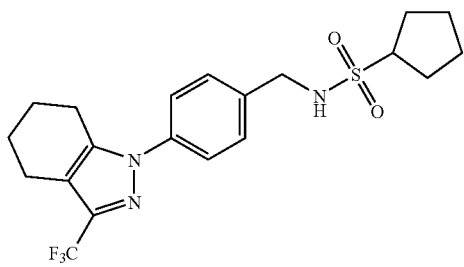

The title compound was prepared from ({4-[3-(trifluoromethyl)-4,5,6,7-tetrahydro-1H-indazol-1-yl]phenyl}methyl) amine and cyclopentanesulphonyl chloride using a similar procedure to that described for Example 88.

LC/Mass Spec (ES): Found 428 (ES+), retention time 3.41 mins. C20H24F3N3O2S requires 427.

$^1$H-NMR (400 MHz, CDCl3): 1.62 (2H, m), 1.80 (6H, m), 2.0 (4H, m), 2.68 (4H, m), 3.40 (1H, m), 4.38 (2H, m), 4.46 (1H, m), 7.42-7.52 (4H, m).

EXAMPLE 91

1-[4-(1-pyrrolidinylsulfonyl)phenyl]-3-(trifluoromethyl)-4,5,6,7-tetrahydro-1H-indazole

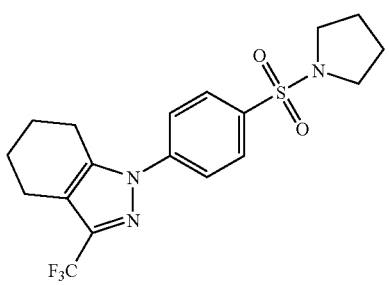

The title compound was prepared from 1-[(4-iodophenyl)sulfonyl]pyrrolidine and 3-(trifluoromethyl)-4,5,6,7-tetrahydro-1H-indazole using a similar procedure to that described for Example 87.

LC/Mass Spec (ES): Found 400 (ES+), retention time 3.59 mins. C18H20F3N3O2S requires 399.

$^1$H-NMR (400 MHz, CDCl3): 1.77 (4H, m), 1.84 (4H, m), 2.67 (2H, m), 2.76 (2H, m), 3.27 (4H, m), 7.69 (2H, m), 7.94 (2H, m).

EXAMPLES 92-96

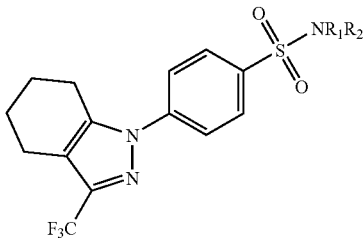

Typical Procedure: A mixture of copper (I) iodide (20 mol %, 20 mg), 3-(trifluoromethyl)-4,5,6,7-tetrahydro-1H-indazole (100 mg, 0.53 mmol), potassium carbonate (146 mg, 1.05 mmol) in DMSO (2 ml). The mixture was stirred for 1 min, then the 4-iodobenzenesulfonamide derivative (0.53 mmol) and N,N-dimethylglycine (20 mol %, 10 mg) were successively added. The reaction tube was quickly sealed and the contents were heated in a microwave reactor at 180° C. for 40 mins. The reaction mixture was partitioned between ethyl acetate and water, dried with sodium sulphate and solvent was removed by rotary evaporation and the sample purified by MDAP. The solvent was removed by rotary evaporation to give the named products.

| Example | NR1R2 | Name | LC/Mass Spec (ES) |
|---|---|---|---|
| 92 | Me-CH(Me)-NH- | N-(2-methylpropyl)-4-[3-(trifluoromethyl)-4,5,6,7-tetrahydro-1H-indazol-1-yl]benzenesulfonamide | Found 402 (ES+), retention time 3.67 mins. C18H22F3N3O2S requires 401. |
| 93 | morpholine | 1-[4-(4-morpholinylsulfonyl)phenyl]-3-(trifluoromethyl)-4,5,6,7-tetrahydro-1H-indazole | Found 416 (ES+), retention time 3.35 mins. C18H20F3N3O3S requires 415. |
| 94 | NH-CH2CH2-OMe | N-[2-(methyloxy)ethyl]-4-[3-(trifluoromethyl)-4,5,6,7-tetrahydro-1H-indazol-1-yl]benzenesulfonamide | Found 404 (ES+), retention time 3.30 mins. C17H20F3N3O3S requires 403. |
| 95 | NH-CH2CH2-pyrrolidinyl | N-[2-(1-pyrrolidinyl)ethyl]-4-[3-(trifluoromethyl)-4,5,6,7-tetrahydro-1H-indazol-1-yl]benzenesulfonamide | Found 443 (ES+), retention time 2.29 mins. C20H25F3N4O2S requires 442. |
| 96 | NH-CH2-(tetrahydrofuranyl) | N-(tetrahydro-2-furanylmethyl)-4-[3-(trifluoromethyl)-4,5,6,7-tetrahydro-1H-indazol-1-yl]benzenesulfonamide | Found 430 (ES+), retention time 3.39 mins. C19H22F3N3O3S requires 429. |

EXAMPLE 97

1-[4-(1H-imidazol-1-ylmethyl)phenyl]-3-(trifluoromethyl)-4,5,6,7-tetrahydro-1H-indazole

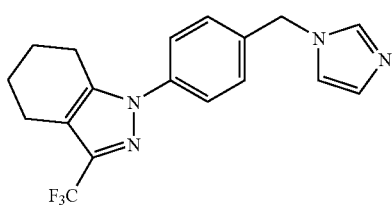

Sodium hydride (60% in mineral oil, 14.0 mg; 0.35 mmol) was added in one portion to a room temperature stirring solution of imidazole (11.5 mg; 0.17 mmol) in anhydrous DMF (1 mL). After stirring at this temperature for 1 hour, a solution of 1-[4-(chloromethyl)phenyl]-3-(trifluoromethyl)-4,5,6,7-tetrahydro-1H-indazole (61.2 mg; 0.19 mmol) in anhydrous DMF (0.4 mL) was added in one portion and the resulting mixture stirred at room temperature for a further 16 hours. The reaction was quenched with aqueous hydrochloric acid (0.2 M; 0.2 mL), and purified by SCX column chromatography, giving the title compound as a yellow oil (51.8 mg; 89%).

LC/Mass Spec (ES): Found 347 (ES+), retention time 2.18 mins. $C_{18}H_{17}F_3N_4$ requires 346.

$^1$H-NMR (400 MHz, CDCl$_3$): 1.77-1.95 (4H, m), 2.60-2.74 (4H, m), 5.18 (2H, s), 6.90-6.93 (1H, m), 7.12 (1H, app s), 7.22-7.29 (2H, m), 7.47-7.52 (2H, m), 7.56 (1H, app s).

EXAMPLES 98-99

The named examples were prepared from 1-[4-(chloromethyl)phenyl]-3-(trifluoromethyl)-4,5,6,7-tetrahydro-1H-indazole and the appropriate azole heterocycle in a manner similar to that described for example 97.

| Ex | Het | Name | LC/Mass Spec (ES) |
|---|---|---|---|
| 98 | 1,2,4-triazolyl | 1-[4-(1H-1,2,4-triazol-1-ylmethyl)phenyl]-3-(trifluoromethyl)-4,5,6,7-tetrahydro-1H-indazole | Found 348 (ES+), retention time 3.05 mins. $C_{17}H_{16}F_3N_5$ requires 347. |
| 99 | pyrazolyl | 1-[4-(1H-pyrazol-1-ylmethyl)phenyl]-3-(trifluoromethyl)-4,5,6,7-tetrahydro-1H-indazole | Found 347 (ES+), retention time 3.36 mins. $C_{18}H_{17}F_3N_4$ requires 346. |

EXAMPLE 102

1-{4-[(4-methyl-1H-pyrazol-1-yl)methyl]phenyl}-3-(trifluoromethyl)-4,5,6,7-tetrahydro-1H-indazole

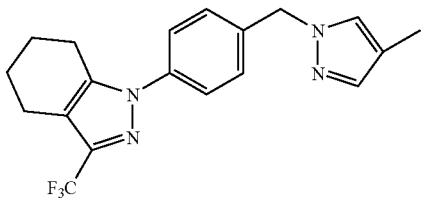

Sodium hydride (60% in mineral oil, 10.0 mg; 0.25 mmol) was added in one portion to a room temperature stirring solution of 4-methyl-1H-pyrazole (15.0 mg; 0.18 mmol) in anhydrous DMF (1 mL). After stirring at this temperature for 15 minutes, a solution of 1-[4-(chloromethyl)phenyl]-3-(trifluoromethyl)-4,5,6,7-tetrahydro-1H-indazole (52.0 mg; 0.16 mmol) in anhydrous DMF (1 mL) was added and the resulting mixture stirred at room temperature for a further 23 hours. The reaction was quenched with aqueous hydrochloric acid (2M; 1 mL), concentrated in vacuo and purified by MDAP, giving the title compound (35.6 mg; 60%).

LC/Mass Spec (ES): Found 361 (ES+), retention time 3.42 mins. $C_{19}H_{19}F_3N_4$ requires 360.

$^1$H-NMR (400 MHz, CDCl$_3$): 1.76-1.89 (4H, m), 2.08 (3H, s), 2.61-2.74 (4H, m), 5.29 (2H, s), 7.16 (1H, s), 7.23-7.31 (2H, m), 7.36 (1H, s), 7.42-7.48 (2H, m).

EXAMPLES 103-111

The named examples were prepared from 1-[4-(chloromethyl)phenyl]-3-(trifluoromethyl)-4,5,6,7-tetrahydro-1H-indazole and the appropriate azole heterocycle in a manner similar to that described for example 102.

| Ex | Het | Name | LC/Mass Spec (ES) |
|---|---|---|---|
| 103 | | 1-{4-[(3,5-dimethyl-1H-pyrazol-1-yl)methyl]phenyl}-3-(trifluoromethyl)-4,5,6,7-tetrahydro-1H-indazole | Found 375 (ES+), retention time 3.53 mins. $C_{20}H_{21}F_3N_4$ requires 374 |
| 104 | | 3-(trifluoromethyl)-1-(4-{[3-(trifluoromethyl)-1H-pyrazol-1-yl]methyl}phenyl)-4,5,6,7-tetrahydro-1H-indazole | Found 415 (ES+), retention time 3.75 mins. $C_{19}H_{16}F_6N_4$ requires 414 |
| 105 | | 3-(trifluoromethyl)-1-(4-{[5-(trifluoromethyl)-1H-pyrazol-1-yl]methyl}phenyl)-4,5,6,7-tetrahydro-1H-indazole | Found 415 (ES+), retention time 3.84 mins. $C_{19}H_{16}F_6N_4$ requires 414 |
| 106 | | 1-(4-{[5-methyl-3-(trifluoromethyl)-1H-pyrazol-1-yl[methyl}phenyl)-3-(trifluoromethyl)-4,5,6,7-tetrahydro-1H-indazole | Found 429 (ES+), retention time 3.85 mins. $C_{20}H_{18}F_6N_4$ requires 428 |
| 107 | | 1-(4-{[3-methyl-5-(trifluoromethyl)-1H-pyrazol-1-yl[methyl}phenyl)-3-(trifluoromethyl)-4,5,6,7-tetrahydro-1H-indazole | Found 429 (ES+), retention time 3.94 mins. $C_{20}H_{18}F_6N_4$ requires 428 |

-continued

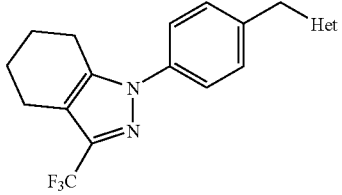

| Ex | Het | Name | LC/Mass Spec (ES) |
|---|---|---|---|
| 108 | (2-methyl-imidazolyl) | 1-{4-[(2-methyl-1H-imidazol-1-yl)methyl]phenyl}-3-(trifluoromethyl)-4,5,6,7-tetrahydro-1H-indazole Formic acid salt | Found 361 (ES+), retention time 1.98 mins. $C_{19}H_{19}F_3N_4$ requires 360 |
| 109 | (2-isopropyl-imidazolyl) | 1-(4-{[2-(1-methylethyl)-1H-imidazol-1-yl[methyl]phenyl)-3-(trifluoromethyl)-4,5,6,7-tetrahydro-1H-indazole Formic acid salt | Found 389 (ES+), retention time 2.28 mins. $C_{21}H_{23}F_3N_4$ requires 388 |
| 110 | (4-phenyl-imidazolyl) | 1-{4-[(4-phenyl-1H-imidazol-1-yl)methyl]phenyl}-3-(trifluoromethyl)-4,5,6,7-tetrahydro-1H-indazole Formic acid salt | Found 423 (ES+), retention time 2.69 mins. $C_{24}H_{21}F_3N_4$ requires 422 |
| 111 | (4-bromo-pyrazolyl) | 1-{4-[(4-bromo-1H-pyrazol-1-yl)methyl]phenyl}-3-(trifluoromethyl)-4,5,6,7-tetrahydro-1H-indazole | Found 425 ($^{79}$Br), 427 ($^{81}$Br) (ES+), retention time 3.70 mins. $C_{18}H_{16}^{79}BrF_3N_4$ requires 424, $C_{18}H_{16}^{81}BrF_3N_4$ requires 426, |

EXAMPLES 100-101

Example 100

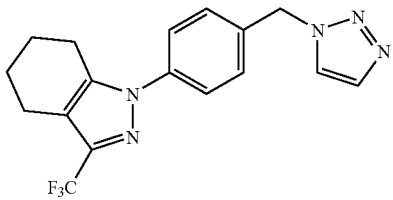

Example 101

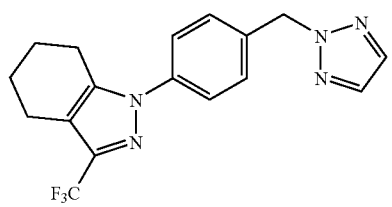

Sodium hydride (60% in mineral oil, 11.0 mg; 0.28 mmol) was added in one portion to a room temperature stirring solution of 1,2,3-triazole (11.3 mg; 0.16 mmol) in anhydrous DMF (1 mL). After stirring at this temperature for 1 hour, a solution of 1-[4-(chloromethyl)phenyl]-3-(trifluoromethyl)-4,5,6,7-tetrahydro-1H-indazole (61.2 mg; 0.19 mmol) in anhydrous DMF (0.4 mL) was added in one portion and the resulting mixture stirred at room temperature for a further 16 hours. The reaction was quenched with aqueous hydrochloric acid (0.2 M; 0.2 mL), and filtered through an SCX column. The filtrate was purified by MDAP, giving example 101 (11.7 mg; 21%). The SCX column was flushed with methanolic ammonia as part of the capture release SCX column chromatography, giving example 100 (9.1 mg; 16%);

| Example | Name | LC/Mass Spec (ES) | $^1$H-NMR (400 MHz, CDCl$_3$) |
|---|---|---|---|
| 100 | 1-[4-(1 H-1,2,3-triazol-1-ylmethyl)phenyl]-3-(trifluoromethyl)-4,5,6,7-tetrahydro-1 H-indazole | LC/Mass Spec (ES): found 348 (ES+), retention time 3.15 mins. $C_{17}H_{16}F_3N_5$ requires 347. | 1.75-1.89 (4 H, m), 2.62-2.74 (4 H, m), 5.63 (2 H, s), 7.49-7.54 (2 H, m), 7.51 (1 H, d (obscured), 7.75 (1 H, d, J = 1 Hz) |
| 101 | 1-[4-(2 H-1,2,3-triazol-2-ylmethyl)phenyl]-3-(trifluoromethyl)-4,5,6,7-tetrahydro-1 H-indazole | found 348 (ES+), retention time 3.38 mins. $C_{17}H_{16}F_3N_5$ requires 347. | 1.75-1.87 (4 H, m), 2.61-2.73 (4 H, m), 5.66 (2 H, s), 7.37-7.42 (2 H, m), 7.44-7.49 (2 H, m), 7.65 (2 H, s); |

EXAMPLE 112

(1-methyl-1H-imidazol-2-yl){4-[3-(trifluoromethyl)-4,5,6,7-tetrahydro-1H-indazol-1-yl]phenyl}methanone Formic Acid Salt

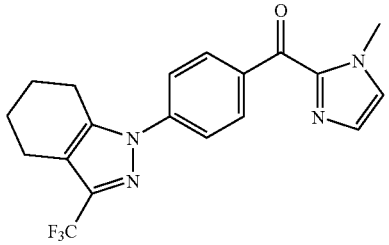

A stirring mixture of 3-(trifluoromethyl)-4,5,6,7-tetrahydro-1H-indazole (200 mg; 1.05 mmol), 4-bromoiodobenzene (297 mg; 1.05 mmol), $K_2CO_3$ (302 mg; 2.18 mmol), CuI (20 mg; 0.11 mmol) and N,N-dimethyl glycine (30 mg; 0.29 mmol) in DMSO (4 mL) was heated at 130° C. for 5 hours 30 minutes. The reaction mixture was partitioned between DCM and water, the organic phase filtered through silica (eluent—methanol), and concentrated in vacuo, giving a brown oil (411 mg). This was purified by column chromatography, giving a mixture of 1-(4-bromophenyl)-3-(trifluoromethyl)-4,5,6,7-tetrahydro-1H-indazole and 1-(4-iodophenyl)-3-(trifluoromethyl)-4,5,6,7-tetrahydro-1H-indazole (205 mg). Under an inert atmosphere of argon, 95 mg of this mixture was dissolved in anhydrous THF (2 mL), cooled to −78° C., and n-butyl lithium (2.5 M in hexanes, 330 µL; 0.82 mmol) was added dropwise over 2 minutes. After stirring for 1 hour, N,1-dimethyl-N-(methyloxy)-1H-imidazole-2-carboxamide (93 mg; 0.55 mmol) was added in one portion to the cold (−78° C.) mixture and the reaction stirred at this temperature for a further 40 minutes. The reaction was warmed to 0° C. and stirred at this temperature for 5 hours 20 minutes. Additional N,1-dimethyl-N-(methyloxy)-1H-imidazole-2-carboxamide (58 mg; 0.34 mmol) was added in one portion, and the reaction stirred at 0° C. for a further 1 hour. The reaction was quenched with aqueous hydrochloric acid (1M, 2 mL), and purified by SCX column chromatography, yielding a white solid (32 mg). This was further purified by MDAP, giving the title compound as white solid (1.14 mg; 0.29% [2 steps]).

LC/Mass Spec (ES): found 375 (ES+), retention time 3.44 mins. $C_{19}H_{17}F_3N_4O$ requires 374.

$^1$H-NMR (400 MHz, $CD_3OD$): 1.80-1.92 (4H, m), 2.68 (2H, br app s), 2.85 (2H, br app s), 7.20 (1H, d, J=1 Hz), 7.45 (1H, app s), 7.70-7.75 (2H, m), 8.28-8.35 (2H, m).

EXAMPLE 113

N-methyl-N-{4-[3-(trifluoromethyl)-4,5,6,7-tetrahydro-1H-indazol-1-yl]phenyl}-1-pyrrolidinecarboxamide

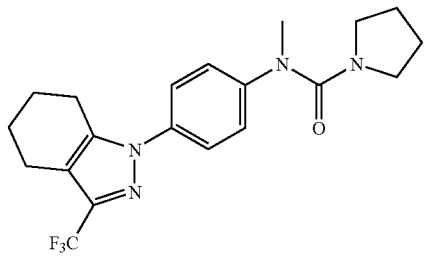

Under an inert atmosphere (Ar), NaH (60% in mineral oil, 3.8 mg; 95 µmol) was added in one portion to a stirring solution of N-{4-[3-(trifluoromethyl)-4,5,6,7-tetrahydro-1H-indazol-1-yl]phenyl}-1-pyrrolidinecarboxamide (17.7 mg; 44 µmol) in anhydrous DMF (1.5 mL). After stirring at room temperature for 1 hour, MeI (20 µL; 0.32 mmol) was added in one portion, and the reaction stirred at this temperature for 2 hours 10 minutes. The reaction was quenched with methanolic ammonia (1M, 1 mL), concentrated in vacuo and purified by column chromatography, giving the desired material as a yellow oil (15.4 mg; 84%).

LC/Mass Spec (ES): found 393 (ES+), retention time 3.46 mins. $C_{20}H_{23}F_3N_4O$ requires 392.

$^1$H-NMR (400 MHz, $CDCl_3$): 1.67-1.77 (4H, m), 1.77-1.88 (4H, m), 2.62-2.76 (4H, m), 3.04-3.18 (4H, m), 3.26 (3H, s), 7.15-7.23 (2H, m), 7.3

Example 36 requires use of [3-(1H-imidazol-1-yl)propyl]methylamine—Naidu et. al. Bioorganic & Medicinal Chemistry Letters (2004), 14(22), 5573-5577.

Example 38 requires use of N-methyl-2-(1H-1,2,4-triazol-1-yl)ethanamine—WO2004/014300.

Example 40 requires use of N-methyl-1-(1-methyl-1H-pyrrol-2-yl)methanamine—Raines et. al. Journal of Heterocyclic Chemistry 7(1), 223-5; 1970.

Biological Assays

The ability of the compounds of the invention to potentiate glutamate receptor-mediated response may be determined a) by using fluorescent calcium-indicator dyes such as FLUO4 and additionally b) by measuring glutamate-evoked current recorded from human GluR2 flip unedited HEK293 cells.

a) Calcium Influx Fluorescence Assay 384 well plates are prepared containing confluent monolayer of HEK 293 cells either stably expressing or transiently transfected with human GluR2 flip (unedited) AMPA receptor subunit. These cells form functional homotetrameric AMPA receptors. The tissue culture medium in the wells are discarded and the wells are each washed three times with standard buffer (80 µL) for the stable cell line (145 mM NaCl, 5 mM KCl, 1 mM $MgCl_2$, 2 mM $CaCl_2$, 20 mM N-[2-hydroxyethyl]-piperazine-N-[2-ethanesulfonic acid (HEPES), 5.5 mM glucose, pH 7.3) or with a Na-free buffer for the transient transfected cells (145 mM N-methyl-glucamine instead of NaCl). The plates are then incubated for 60 minutes in the dark with 2 µM FLUO4-AM dye (20 µL) (Molecular Probes, Netherlands) at room temperature to allow cell uptake of the FLUO-4AM, which is then converted to FLUO-4 by intracellular esterases which is unable to leave the cell. After incubation each well is washed three times with buffer (80 µL) (30 µL of buffer remained in each well after washing).

Compounds of the invention (or reference compounds such as cyclothiazide) are dissolved in dimethylsulfoxide (DMSO) at a stock concentration of 10 mM. These solutions are further diluted with DMSO using a Biomek FX (Beckman Coulter) in a 384 compound plate. Each dilution (1 µL) is transferred to another compound plate and buffer (50 µL) is added. An agonist stimulus (glutamate) plate is prepared by dissolving sodium glutamate in water to give a concentration of 100 mM. This solution is diluted with buffer to give a final concentration of 500 µM and dispensed into another 384-well plate (50 µL/well) using a Multidrop (Thermolabsystems).

The cell plate is then transferred into a fluorescence imaging plate based reader [such as the FLIPR384 (Molecular Devices)]. A baseline fluorescence reading is taken over a 10 to 240 second period, and then 10 µL from each plate containing a compound of the invention made up in standard buffer solution (in a concentration range from 100 µM to 10 pM) is added (to give a final concentration in the range 30 µM to 3 pM). The fluorescence is read over 5 minute period. 500 µM glutamate solution (10 µL) is added (to give a final concentration of 100 µM). The fluoresecence is then read over a 4 minute period. The activities of the compounds of the invention and reference compounds are determined by measuring peak fluorescence after the last addition. The activity is also expressed relative to the fluorescence increase induced by cyclothiazide at their maximum response (i.e. greater than 30 µM).

The assay described above is believed to have an effective limit of detection of a $pEC_{50}$ in the region of 3.5-4.0 due to the limitations of compound solubility. The $pEC_{50}$ result is generally considered to be accurate +/−0.3. Accordingly, a compound exhibiting a $pEC_{50}$ value within this range from such an assay may indeed have a reasonable affinity for the receptor, but equally it may also have a lower affinity, including a considerably lower affinity. For each compound, more than one reading was taken.

All the Example compounds were screened using the assay as described above and the average of the measurable pEC50s were taken. All compounds gave an average $pEC_{50}$ equal to or greater than 3.5 and demonstrated an activity of, on average at least 20% that of cyclothiazide (at its maximal response).

b) Whole Cell Voltage-Clamp Electrophysiology Assay

The ability of the compounds of the invention to potentiate AMPA-subtype glutamate receptor-mediated response are determined by measuring AMPA-evoked current recorded from rat cultured hippocampal neurons.

This assay involves the electrophysiological characterisation of AMPA receptor positive modulators using rat cultured hippocampal neurons. The extracellular recording solution contains: 145 mM NaCl, 2.5 mM KCl, 1.2 mM $MgCl_2$, 1.5 mM $CaCl_2$, 10 mM N-[2-hydroxyethyl]-piperazine-N-[2-ethanesulfonic acid (HEPES), 10 mM D-glucose, pH 7.3 with NaOH. The intracellular solution contains: 80 mM CsCl, 80 mM CsF, 10 mM N-[2-hydroxyethyl]-piperazine-N-[2-ethanesulfonic acid (HEPES), 10 mM ethylene glycol-bis(g-aminoethylether)-N,N,N',N,-tetra-acetic acid (EGTA), 14 mM MgATP, 14 mM DiTris Creatine Phosphate, 50 U/ml Creatine Phosphokinase pH 7.3 with CsOH. Recording electrodes are prepared from glass capillary tubes (Clark Electromedical GC120-F10) pulled into two equal lengths using a Zeitz Instruments DMZ Universal Puller, program 09, resulting in electrodes with a resistance of approximately 3-6 MOhms when measured in extracellular solution. Electrodes are back filled with internal recording solution. Positive pressure is applied to the electrode to prevent mixture of internal and external solutions and assist in formation of high resistance seal when the electrode makes contact with the cell membrane. Glass coverslip fragment, bearing rat cultured hippocampal neurons, is placed in the recording chamber positioned on the stage of an inverted microscope. A tube at the edge of the chamber is used to apply extracellular solution to the bath. Rapid solution exchange uses a fast step perfusion system (Biologic RSC160). Two outlet tubes attached together along their length are positioned close to a chosen cell so that the outflow from only one tube can pass directly over the cell surface. A motorized stepper could re-position the tubes such that the outflow from the second outlet tube flows over the cell allowing solution exchange at the cell membrane surface to occur within 10-20 ms. Excess bath solution is removed via a tube positioned at the edge of the chamber connected to a vacuum line.

A prospective cell is positioned in the centre of the microscope field of view. Recording electrode is positioned directly above the cell membrane surface. Using fine manipulator control (Luigs and Neumann, SM-6) the electrode is lowered, while monitoring the change in electrode resistance during delivery of a 5 mV depolarizing pulse, until a high resistance seal (gigaseal) is achieved. Whole cell configuration is achieved by removing by suction a small fragment of cell membrane immediately beneath the recording electrode tip. The cell membrane potential is held at −70 mV (voltage-clamped) via the electrode (Axopatch 200B Integrating patch clamp amplifier, pClamp software, Axon Instruments). Test solutions are applied using the fast application system using the following protocol and changes in inward current are recorded and stored for off-line analysis.

1) Control current—exchange from extracellular solution to extracellular solution+30 µM AMPA (2 s application time, 30 s interval between applications) repeated until measurements are stable.

2) Test current—exchange from extracellular solution+10 nM of compound of invention to extracellular solution+10 nM of compound of invention+30 µM AMPA (2 s application time, 30 s interval between applications) repeated until measurements are stable.

All experiments are performed at ambient temperature (20 to 22° C.).

The activity of a compound of the invention is determined by measuring the area under the curve (during 2 s period of application) for the 30 µM AMPA response in the presence of the compound of the invention and expressing it as % of potentiation of the 30 µM AMPA alone response (30 µM AMPA in the absence of the compound of the invention).

The range of mean responses at 10 nM increased 30 uM AMPA response by 14 to 79% and at 10 uM by 42 to 679%.

The invention claimed is:

1. A pharmaceutical composition comprising 1-[4-(1-pyrrolidinylcarbonyl)phenyl]-3-(trifluoromethyl)-4,5,6,7-tetrahydro-1H-indazole or a salt thereof, and a pharmaceutically acceptable carrier, diluent or excipient.

2. A method of treating schizophrenia in a human comprising administering an therapeutically effective amount of 1-[4-(1-pyrrolidinylcarbonyl)phenyl]-3-(trifluoromethyl)-4,5,6,7-tetrahydro-1H-indazole or a salt thereof, alone or combined with a pharmaceutically acceptable carrier, diluent or excipient.

3. The method of claim 2 comprising combining said compound or its salt with another antipsychotic drug.

4. A method of treating impairment of cognition in a human comprising administering an therapeutically effective amount of 1-[4-(1-pyrrolidinylcarbonyl)phenyl]-3-(trifluoromethyl)-4,5,6,7-tetrahydro-1H-indazole or a salt thereof, alone or combined with a pharmaceutically acceptable carrier, diluent or excipient.

* * * * *